United States Patent
Pu et al.

(10) Patent No.: US 12,296,027 B2
(45) Date of Patent: May 13, 2025

(54) MOLECULAR RENAL PROBES FOR DETECTING ACUTE KIDNEY INJURY

(71) Applicant: Nanyang Technological University, Singapore (SG)

(72) Inventors: Kanyi Pu, Singapore (SG); Jiaguo Huang, Singapore (SG)

(73) Assignee: Nanyang Technological University, Singapore (SG)

(*) Notice: Subject to any disclaimer, the term of this patent is extended or adjusted under 35 U.S.C. 154(b) by 893 days.

(21) Appl. No.: 17/420,666

(22) PCT Filed: Jan. 31, 2020

(86) PCT No.: PCT/SG2020/050049
§ 371 (c)(1),
(2) Date: Jul. 2, 2021

(87) PCT Pub. No.: WO2020/159448
PCT Pub. Date: Aug. 6, 2020

(65) Prior Publication Data
US 2022/0096662 A1    Mar. 31, 2022

(30) Foreign Application Priority Data
Feb. 1, 2019  (SG) .......................... 10201900965U

(51) Int. Cl.
| A61K 49/00 | (2006.01) |
| A61B 5/20 | (2006.01) |
| G01N 33/533 | (2006.01) |
| G01N 33/58 | (2006.01) |

(52) U.S. Cl.
CPC .......... *A61K 49/0032* (2013.01); *A61B 5/201* (2013.01); *A61K 49/0039* (2013.01); *G01N 33/533* (2013.01); *G01N 33/583* (2013.01); *G01N 2800/347* (2013.01)

(58) Field of Classification Search
None
See application file for complete search history.

(56) References Cited

U.S. PATENT DOCUMENTS

| 5,354,868 A * | 10/1994 | Harrington .......... C07H 19/052 536/53 |
| 2015/0328342 A1 * | 11/2015 | Della Ciana ........ C08B 37/0012 424/9.2 |
| 2016/0263249 A1 | 9/2016 | Frangioni et al. |
| 2018/0353626 A1 | 12/2018 | Teranishi et al. |
| 2019/0290787 A1 * | 9/2019 | Shabat ................. C07D 321/00 |

FOREIGN PATENT DOCUMENTS

| WO | WO-2017130191 A1 * | 8/2017 | ......... A61K 49/0013 |
| WO | 2018216013 A1 | 11/2018 | |

OTHER PUBLICATIONS

Redy-Keisar (Synthesis and use of QCy7-derived modular probes for the detection and imaging of biologically relevant analytes, Dec. 5, 2013, Nature Protocols, 9:27-36) (Year: 2013).*
Huang (Light-Emitting Agents for Noninvasive Assessment of Kidney Function, Jul. 20, 2017, Chemistry Open Reviews, 6(4):456-471) (Year: 2017).*
Hyun (Carbohydrate Microarrays Containing Glycosylated Fluorescent Probes for Assessment of Glycosidase Activities, Feb. 8, 2018, Organic Letters, 20:1240-1243) (Year: 2018).*
Richard (Latent Fluorophores Based on a Self-Immolative Linker Strategy and Suitable for Protease Sensing, 2008, Bioconjugate Chemistry, 19:1707-1718) (Year: 2008).*
Ho (Latent Fluorophores Based on a Self-Immolative Linker Strategy andSuitable for Protease Sensing, Mar. 13, 2007, ChemBioChem, 8:560-566) (Year: 2007).*
Karpkird (Synthesis and photostability of methoxycinnamic acid modified cyclodextrins, Apr. 3, 2010, Journal of Photochemistry and Photobiology A: Chemistry, 212:56-61) (Year: 2010).*
R. Hofmeister, et al., Toxicol. Lett. 1990, 50, 9-15.
Mehta, R.L., et al., The Lancet, 2015. 385(9987): p. 2616-2643.
Lassnigg, A., et al., Journal of the American Society of Nephrology, 2004. 15(6): p. 1597-1605.
Jablonski, K.L. and M. Chonchol, Nature Reviews Nephrology, 2013. 9(6): p. 318.
Hallan, S.I., et al., Journal of the American Society of Nephrology, 2009. 20(5): p. 1069-1077.
Cui, S., et al., Kidney international reports, 2016. 1(4): p. 324-326.
Laissy, J.-P., et al., Nephron Clinical Practice, 2006. 103(2): p. c50-c57.
Kalantarinia, K., Current drug targets, 2009. 10(12): p. 1184-1189.
Vivier, P.-H., et al., Radiology, 2011. 259(2): p. 462-470.
Cerdá, J., et al., Kidney international reports, 2017. 2(4): p. 530-543.

(Continued)

*Primary Examiner* — Michael G. Hartley
*Assistant Examiner* — Kaila A Craig
(74) *Attorney, Agent, or Firm* — Thomas Horstemeyer, LLP

(57) ABSTRACT

Disclosed herein are compounds or salts and/or solvates of formula I, II and III, where the compounds or salts and/or solvates have the following structures: $(X)_a$—Y—$(Z)_b$ I; II; or X'—Y' III; where X, Y, Z, X', Y', a, b, $R_4$, $R_6$ and $R_7$ are as defined herein.

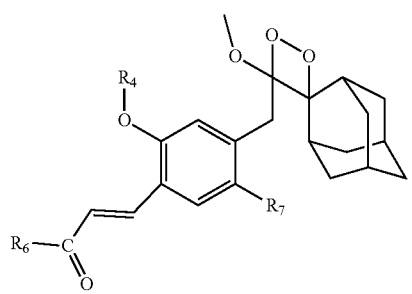

10 Claims, 53 Drawing Sheets

(56) References Cited

OTHER PUBLICATIONS

Malhotra, R. and E.D. Siew, Clinical Journal of the American Society of Nephrology, 2016: p. CJN. 01300216.
Liangos, O., et al., Journal of the American Society of Nephrology, 2007. 18(3): p. 904-912.
Harrison, D., et al., Journal of clinical pathology, 1989. 42(6): p. 624-628.
Vaidya, V.S., et al., Clinical and translational science, 2008. 1(3): p. 200-208.
Quesada, A., et al., PloS one, 2012. 7(7): p. e40402.
Mishra, J., et al., Journal of the American Society of Nephrology, 2003. 14(10): p. 2534-2543.
Alge, J.L., et al., Clinical Journal of the American Society of Nephrology, 2013. 8(2): p. 184-193.
Han, W.K., et al., Kidney international, 2002. 62(1): p. 237-244.
Kimmel, M., et al., Clinical Journal of the American Society of Nephrology, 2016: p. CJN. 10551015.
Nivy, R., et al., The Veterinary Journal, 2017. 220: p. 43-47.
Teppala, S., et al., Kidney and Blood Pressure Research, 2010. 33(1): p. 1-6.
Eijkenboom, J.J., et al., Intensive Care Med, 2005. 31(5): p. 664-7.
Murray, P.T., et al., Kidney international, 2014. 85(3): p. 513-521.
Baud, L. and R. Ardaillou, American Journal of Physiology-Renal Physiology, 1986. 251(5): p. F765-F776.
Kumar, S.V. and H.-J. Anders, Nature Reviews Nephrology, 2014. 10(10): p. 545.
Kim, S.R., et al., Medicine, 2016. 95(27).
Park, H.C., et al., BMC nephrology, 2012. 13(1): p. 93.
Bosomworth, M.P. et al., Nephrology, dialysis, transplantation: official publication of the European Dialysis and Transplant Association-European Renal Association, 1999. 14(3): p. 620-626.
Kim, S.Y. and A. Moon, Biomolecules & therapeutics, 2012. 20(3): p. 268.
Zou, A.-P. et al., Hypertension, 2001. 37(2): p. 547-553.
P. A. McCullough, J. Am. Coll. Cardiol. 2008, 51, 1419-1428.
A. D. Calvin, S. Misra, A. Pflueger, Nat. Rev. Nephrol. 2010, 6, 679-688.
M. Fähling et al., Nat. Rev. Nephrol. 2017, 13, 169-180.
A. Zuk, J. V. Bonventre, Annu. Rev. Med. 2016, 67, 293-307.
B. J. Barrett, P. S. Parfrey, N. Engl. J. Med. 2006, 354, 379-38.
F. Priem et al., Clin. Chem. 1999, 45, 567-568.
A. Lacquaniti et al., Radiology 2013, 267, 86-93.
C. Briguori et al., Circulation 2010, 121, 2117-2122.
J. W. Pickering, Z. H. Endre, Am. J. Physiol. Renal. Physiol. 2016, 311, F717-F721.
A. J. Shuhendler et al., Nat. Biotechnol. 2014, 32, 373-380.
Y. Jiang et al., Nat. Commun. 2019, 10, 2064.
J. Li, K. Pu, Chem. Soc. Rev. 2019, 48, 38-71.
Q. Miao, K. Pu, Adv. Mater. 2018, 30, 1801778.
X. Zhen et al., Angew. Chem. Int. Ed. 2018, 57, 7804-7808.
P. Cheng et al., Chem. Sci. 2018, 9, 6340-6347.
J. Zhang et al., Anal. Chem. 2018, 90, 9301-9307.
G. Hong, A. L. Antaris, H. Dai, Nat. Biomed. Eng. 2017, 1, 0010.
D. T. Quang, J. S. Kim, ?Chem. Rev. 2010, 110, 6280-6301.
Y. Yang et al., ?Chem. Rev. 2012, 113, 192-270.
J. Chan, S. C. Dodani, C. J. Chang, ?Nat. Chem. 2012, 4, 973-984.
Zhen et a; "Macrotheranostic Probe with Disease-activated Near-infrared Fluorescence, Photoacoustic and Photothermal Signals for Imaging-guided Therapy", Communication, Wiley VCH.
Green et al. "Near-Infrared Dioxetane Luminophores with Direct Chemiluminescence Emission Mode", J. Am. Chem. Soc. 2017, 139, 13243-13248.
Lv et al. "Visualization of oxidative injury in the mouse kidney using selective superoxide anion fluorescent probes", Chemical Science, 9:39:7577-7718, Oct. 21, 2018.
Cheng et al. "Near-infrared fluorescence probes to detect reactive oxygen species for keloid diagnosis", Chemical Science, 9:30:6317-6454, Aug. 14, 2018.
Redy-Keisar et al. "Synthesis and use of QCy7-derived modular probes for the detection and imaging of biologically relevant analytes", Nature Protools, 9:21, 2014.
Huang et al. "Light-Emitting Agents for Noninvasive Assessment of Kidney Function", ChemistryOpen, 6:456 471, 2017.
Huang et al., "Molecular optical imaging probes for early diagnosis of drug-induced acute kidney injury", Nature Materials, 18:1133-1143, Oct. 2019.
Huang et al., "ARenal-Clearable Duplex Optical Reporter for Real-Time Imaging of Contrast-Induced Acute Kidney Injury", Angew.Chem., 131:17960-17968, 2019.
Cheng et al., "Unimolecular Chemo-fluoro-luminescent Reporter for Crosstalk-Free Duplex Imaging of Hepatotoxicity", J. Am. Chem. Soc., 141:10581-10584, 2019.
P. Cheng et al., J. Am. Chem. Soc. 2019, 141, 10581-10584.
M. Andreucci et al., Int. J. Nephrol. Renovasc. Dis. 2016, 9, 205-221.
J. Huang et al., Chem. Sci. 2017, 8, 2652-2660.
J. J. Hu et al., J. Am. Chem. Soc. 2015, 137, 6837-6843.
N. Hananya et al., J. Am. Chem. Soc. 2016, 138, 13438-13446.
O. Green et al., ACS Cent. Sci. 2017, 3, 349-358.
S. Gnaim et al., Chem. Sci. 2019, 10, 2945-2955.
J. Cao et al., Chem. Sci. 2015, 6, 1979-1985.
A.P. Singh et al., Pharmacol. Rep. 2012, 64, 31-44.
Z. Wang, K. Ren, Ren. Fail. 2019, 41, 341-353.
C. Quintavalle et al., Cell Death Dis. 2011, 2, e155.
N. Kiss, P. Hamar, Biomed. Res. Int. 2016, 3763250.
Alobaidi, R. et al., Semin. Nephrol. 35, 2-11 (2015).
Kellum, J.A. & Prowle, J.R. Nat. Rev. Nephrol. 14, 217-230 (2018).
Willmann, J.K. et al., Nat. Rev. Drug Discov. 7, 591-607 (2008).
Lovell, J.F. et al., Nat. Mater. 10, 324-332 (2011).
Ntziachristos, V. et al., Nat. Biotechnol. 23, 313-320 (2005).
Grenier, N., Merville, P. & Combe, C. Nat. Rev. Nephrol. 12, 348-359 (2016).
So, M.K. et al., Nat. Biotechnol. 24, 339-343 (2006).
Smith, A.M. et al., Nat. Nanotechnol. 4, 710-711 (2009).
Ning, X. et al. Nat. Mater. 10, 602-607 (2011).
Park, S.M. et al., Nat. Rev. Mater. 2, 17014 (2017).
Ozer, J.S. et al. Nat. Biotechnol. 28, 486-494 (2010).
Sureshbabu, A. et al., Redox Biol. 4, 208-214 (2015).
Ware, L.B. et al., Shock 36, 12-17 (2011).
Naud, J.F. & Leblanc, M. Kidney Int. 3, 115-125 (2008).
Owens, E.A. et al., Acc. Chem. Res. 49, 1731-1740 (2016).
Dickinson, B.C. & Chang, C.J. Nat. Chem. Biol. 7, 504-511 (2011).
Asami, T. et al., Pediatr. Nephrol. 17, 560-565 (2002).
Hyun, H. et al. Nat. Med. 21, 192-197 (2015).
Dickey, D.T. et al. Cancer Chemother. Pharmacol. 62, 235-241 (2008).
Medicherla, S. et al. J. Inflamm. Res. 3, 9-16 (2010).
Ma, Q., Devarajan, S.R. & Devarajan, P. Ren. Fail. 38, 1476-1482 (2016).
Perse, M. & Veceric-Haler, Z. BioMed Res. Int. 1462802 (2018).
Pichler, R. et al., Am. J. Physiol. Renal. Physiol. 312, F716-731 (2017).
Wen, J. et al. Age 37, 112 (2015).
Galvan, D.L. et al. Kidney Int. 92, 1282-1287 (2017).
Ghosh, S. et al. Am. J. Physiol. Renal. Physiol. 296, F700-F708 (2009).
Grover, B. et al., J. Pharmacol. Exp. Ther. 308, 949-956 (2004).
Yang, P. et al. Toxicol. Sci. 131, 128-138 (2012).
J. Huang et al., Nat. Mater. 2019, 18, 1133-1143.
J. Huang et al., Bioconjugate Chem. 2016, 27, 2513-2526.
K. Xu et al., ChemBioChem 2007, 8, 453-458.
Y. Lv et al., Chem. Sci. 2018, 9, 7606-7613.
Y. Tanaka et al., Analytical Sciences 2012, 28, 33-38.
Z.-Q. Wang et al., Bioorganic & Medicinal Chemistry Letters 15 (2005) 2335-2338.
Kidney Int. 2012, 83, 72.
Int. J. Radiat. Biol. 1989, 55, 661.
Am. J. Physiol. Renal. Physiol. 2010, 298, F454.
Mol. Cell. Biochem. 2017, 434, 163.
Paragas, N., et al., Nature medicine, 2011. 17(2): p. 216.
Forootan, S.S. et al. Sci. Rep. 7, 16084 (2017).

(56) References Cited

OTHER PUBLICATIONS

Kidney Int. 2007, 72, 1474.
Am. J. Physiol. Renal. Physiol. 2012, 303, F437.
Inflamm. Res. 2017, 66, 399.
J. Am. Soc. Nephrol. 2016, 27, 3331.
J. Am. Soc. Nephrol. 2009, 20, 1323.
Kidney Int. 2008, 73, 578.
J. Pharmacol. Exp. Ther. 2012, 341,656.
Br. J. Radiol. 2001, 74, 1103.
Curr. Vasc. Pharmacol. 2017, 15, 174.
Clinical. Science. 2018, 132, 825.
Biomed. Pharmacother. 2018, 97, 1102.
Physiol. Rep. 2013, 1, e00163.
Proc. Natl. Acad. Sci. USA 2015, 112, 5231.
BMC. Complement. Altern. Med. 2017, 17, 544.
Ren. Fail. 2018, 40, 314.
BMC. Nephrol. 2017, 18, 101.
Nat. Biotechnol. 2010, 28, 463.
Toxicol Pathol. 2012, 40, 1049.
Biomarkers. 2011, 16, 553.
Toxicol Pathol. 2013, 41, 662.
Yu, Y. et al. Nat. Biotechnol. 28, 470-477 (2010).
Toxicol Pathol. 2014, 42, 591.
Vaidya, V.S. et al. Nat. Biotechnol. 28, 478-485 (2010).
Toxicol Sci. 2010, 116, 8.
Toxicol Rep, 2019, 6, 91.
J. Y. C. Soo, et al., Nat. Rev. Nephrol. 2018, 14, 378-393.
M. A. Perazella, S. G. Coca, Nat. Rev. Nephrol. 2013, 9, 484-490.
M. Darmon, et al., Intensive Care. Med. 2017, 43, 829-840.
K. Wang et al., J. Am. Soc. Nephrol. 2006, 17, 2900-2909.
Y. Wang, et al., Kidney International, 2000, 58(4), 1797-1804.
M. Jeansson, et al., J. Am. Soc. Nephrol. 2009. 20(1), 114-122.
G. L. Liu, et al., Exp. Ther. Med. 2017, 14, 3309-3313.
D. Robic, et al., Toxicology 1995, 103, 37-44.
M. Yu, et al., Angew. Chem. Int. Ed. 2016, 55, 2787-2791.
A. A. Burns, et al., Nano lett. 2008, 9, 442-448.
H. Huang, et al., Biomaterials 2016, 76, 25-32.
H. Kang, et al., Adv. Mater. 2016, 28, 8162-8168.
Z. Z. Liu, et al., Am. J. Physiol. Renal. Physiol. 2014, 306, F864-F872.
K. Liu, et al., PLoS One 2017, 12, e0182558.
S. Fishbane, Clin. J. Am. Soc. Nephrol. 2008, 3, 281-287.
L. S. Chawla, et al., N. Engl. J. Med. 2014, 371, 58-66.
J. G. Abuelo, et al., N. Engl. J. Med. 2007, 357, 797-805.
N. H. Lameire, et al., The Lancet, 2013, 382, 170-179.
Miao, Q. et al., Nat. Biotechnol. 2017, 35, 1102-1110.
Q. Miao, et al., Angew. Chem. Int. Ed., 2018, 57, 1256-1260.
R. C. Benson, H. A. Kues, J. Chem. Eng. Data 1977, 22, 379-383.
K. Gu, et al., J. Am. Chem. Soc. 2016, 138, 5334-5340.
Z. Qi, et al., Am. J. Physiol. Renal. Physiol. 2004, 286, F590-596.
W. Wang, et al., Am. J. Physiol. Renal. Physiol. 2007, 293, F1131-1136.
F. Dieterle, et al., Nat. Biotechnol. 2010, 28, 463-469.
C. M. Erley, et al., J. Am. Soc. Nephrol. 1997, 8, 1125-1132.
M. Colbay, et al., Exp. Toxicol. Pathol. 2010, 62, 81-89.
S. N. Heyman, et al., Invest. Radiol. 2010, 45, 188-195.
A. Pisani, et al., Biomed. Res. Int. 2013, 2013, 868321.
W. K. Han, et al., Clin. J. Am. Soc. Nephrol. 2009, 4, 873-882.
R. Galgamuwa, et al., J. Am. Soc. Nephrol 2016, 27, 3331-3344.
A. Otunctemur, et al., Ren. Fail., 2014, 36, 925-931.
D. P. Basile, et al., Compr. Physiol., 2012, 2, 1303-1353.
M. P. Iqbal, et al., J. Coll. Physicians Surg. Pak., 2008, 18(2), 74-77.
F. A. Pinho-Ribeiro, et al., J. Nutr. Biochem. 2016, 33, 8-14.
M. Hayyan, et al., Chem. Rev. 2016, 116, 3029-3085.
B. Zhivotovsky, et al., Cell Death Differ. 1999, 6, 644-651.
Antaris, A.L. et al. Nat. Mater. 15, 235-242 (2016).
H. S. Choi et al., Nat. Biotechnol. 2007, 25, 1165-1170.
ACS Nano 2013, 7(7), 5684-5693.
Nano Lett 2009, 9, 2354-2359.
S. Tang, et al., Small 2014, 10, 3139-3144.
Nano Lett 2009, 9(1), 442-448.
Eur. J. Drug. Metab. Pharmacokinet. 1995, 20, 307-313.
Kidney Int. 2002, 61, 1980-1985.
Nanoscale 2014, 6, 13501-13509.
Bioconjugate Chem. 2015, 26, 511-519.
ACS Nano 2015, 9, 3641-3653.
A. Ruggiero et al., Proc. Natl. Acad. Sci. U S A 2010, 107, 12369-12374.
J. Nucl. Med. Technol. 2008, 36(3), 162-168.
Nanoscale 2013, 5, 5930-5939.
Adv. Mater. 2008, 20, 225-230.
Acta. Radiol. 1980, 362, 131-134.
B. Du et al., Nat. Nanotechnol. 2017, 12, 1096-1102.
Angew. Chem. Int. Ed. Engl. 2011, 123, 3226-3230.
Biomed. Chromatogr. 1994, 8(5), 224-229.
Kidney Int. 2002, 61, 1980.
Abdom. Imaging 2006, 31,224.
Int. J. Nephrol. Renovasc. Dis. 2014, 7, 421.
Eur. Radiol. 2016, 26, 1597.
J. Vis. Exp. 2016, 109, e52409.
Resbcal. 2016, 4, 9.

* cited by examiner (a)

MRP$_D$

(b)

ADR

**Real-time *in vivo* NIRF imaging of gentamicin-induced AKI**

MOLECULAR RENAL PROBES FOR DETECTING ACUTE KIDNEY INJURY

CROSS-REFERENCE TO RELATED APPLICATION

This application is the 35 U.S.C. § 371 national stage application of PCT Application No. PCT/SG2020/050049, filed Jan. 31, 2020, where the PCT claims priority to and the benefit of, SG patent application Ser. No. 10201900965U, filed Feb. 1, 2019, both of which are herein incorporated by reference in their entireties.

FIELD OF INVENTION

The current invention relates to molecular probes that can be used in the fields of diagnosis.

The current invention also relates to intermediate compounds that can be used to form said molecular probes.

BACKGROUND

The listing or discussion of a prior-published document in this specification should not necessarily be taken as an acknowledgement that the document is part of the state of the art or is common general knowledge.

Acute kidney injury (AKI) is a life-threatening disorder characterised by a sudden decrease in kidney function, leading to an estimated mortality of 1.7 million deaths per year globally. Complications associated with AKI include chronic kidney disease (CKD), need for renal replacement therapy (RRT), end-stage renal disease (ESRD) and death. Importantly, the incidence of AKI has risen over the past decades. Particularly, early detection of kidney injury at the incipient stage can allow renoprotective intervention to be timely conducted to prevent AKI from progression into more severe complications.

The main etiologies of AKI include sepsis, ischemia/reperfusion, and nephrotoxin exposure. Among them, nephrotoxicity underlies up to 25% of AKI cases due to the use of clinically approved drugs. For example, the administration of contrast media is a common contributor to AKI, because contrast media are exclusively eliminated by the kidneys and often induce adverse effects including altered renal hemodynamics and tubular epithelial cell toxicity. As over 30 million doses of iodinated contrast media are administered annually for diagnostic imaging and interventional procedure, contrast-induced AKI (CIAKI) has become the third leading cause of hospital-acquired AKI. Therefore, CIAKI is a serious medical complication that demands timely preventive and therapeutic strategies.

The morbidity of drug-induced AKI can be reduced via a safer pharmacopeia and/or close monitoring of renal function during the use of known nephrotoxic drugs. Particularly, early detection of kidney injury at the incipient stage can allow renoprotective intervention to be timely conducted to prevent AKI from progression into severe complications including chronic kidney disease (CKD), renal replacement therapy (RRT), and death, and aid in kidney recovery. However, drug-induced AKI is deficiently evaluated in drug discovery due to the limitations of in vitro assays.

In relation to contrast agents, in vitro diagnostic methods have been used to monitor renal function upon administration of contrast media so as to prevent CIAKI. In clinic, CIAKI is diagnosed by an increase of >25% serum creatinine (sCr) within 48-72 h of administration of a contrast medium. However, as noted above, sCr is an insensitive indicator of late-stage kidney dysfunction because it only increases after a 50% decrease in glomerular filtration rate (GFR). Besides, blood and urinary biomarkers such as cystatin C, neutrophil gelatinase-associated lipocalin (NGAL) and kidney injury molecule-1 (KIM-1) are under preclinical/clinical trials for detection of CIAKI. However, detection of these biomarkers is limited by in vitro diagnostic methods based on static analysis, which are difficult for the longitudinal monitoring of dysregulation in kidneys.

Currently, the primary option for monitoring kidney dysfunction relies on the measurements of serum creatinine (sCr) and blood urea nitrogen (BUN). However, the level of sCr and BUN are insensitive and non-specific to kidney dysfunction as they can be affected by many non-renal factors, such as age, gender, muscle mass and many other anthropometric variables. Further, sCr is considered as a late indicator of renal impairment because the level of sCr increases only after a reduction of 50% in glomerular filtration rate (GFR). As such, this assessment is valid only when majority of kidney function is lost, thereby leading to a delay in diagnosis of kidney injury. Meanwhile, interventions and therapeutic opportunities are often lost within the so-called "creatinine-blind" range, which is characterised as the lag time between the onset of injury and the elevation in sCr concentration. A combination of proteinuria with estimated GFR (eGFR) has also been established to predict CKD progression. However, the different causes of CKD may result in different severity of proteinuria in each case, which can make accurate diagnosis difficult.

Identifying renal impairment often relies on renal biopsy in clinical practice, but this method is invasive and carries the risk of potential internal damage to the targeted or nearby organs. While single photon emission computed tomography (SPECT), contrast-enhanced computed tomography (CT), magnetic resonance imaging (MRI) and ultrasonography are used routinely for kidney imaging, they mainly detect anatomic and functional changes of organs and have little utility in detecting the early-stage molecular-level changes that underlie AKI. In addition, high energy radiation from some of the techniques mentioned above is potentially harmful to patients and the use of contrast agents associated with the high risk nephrotoxicity may cause further kidney damage.

Early recognition of kidney injury is essential to ensure timely preventive and therapeutic measures, and this has led to an interest in discovering and identifying serum and urine biomarkers for diagnosing renal cellular injury. Such potential biomarkers include enzymes (N-acetyl-β-D-glucosaminidase (NAG), glutathione s-transferase (GST), γ-glutamyl transpeptidase (GGT), alkaline phosphatases (ALP), and alanine aminopeptidase (AAP)), proinflammatory mediators (IL-18, neutrophil gelatinase-associated lipocalin (NGAL)), glomerular filtration markers (Cystatin C, Cys C), and other structural upregulated proteins (kidney injury molecule-1, KIM-1). Further, tissue inhibitor of metalloproteinases-2 (TIMP-2) and IGF-binding protein-7 (IG-FBP7) have emerged and are considered as a potential index for kidney injury risk stratification.

Although the quest for potential serum or urinary biomarkers of early diagnosis has intensified in the last decade, few biomarkers have been validated or implemented into routine kidney injury management in clinical practice. This is mainly due to:
   (i) the sensitivity and/or specificity of some biomarkers to adequately detect kidney injury are still controversial. Both urinary GGT and ALP have unsatisfactory discriminatory power for diagnosing AKI in some animal studies. In addition, no association between increased GGT levels and CKD has been suggested in cross-sectional studies;

(ii) some biomarkers not only originate from injured kidney cells, but are also expressed in extra-renal organs followed by excretion into urine, which may lead to an overestimation of biomarkers;

(iii) most studies have focused on identifying biomarkers, and not on exploring new techniques to detecting biomarkers and translating into clinical practice.

Existing techniques have been limited to measuring these biomarkers in the biofluid in vitro, which might not be precisely proportional to their expression at the site of injury in vivo. Although NGAL reporter mice have been generated for use in the real-time imaging of NGAL expression in kidneys, the model is limited to these genetically-altered mice and it is difficult to adapt this model into a universal approach. The lack of new techniques causes the absence of specific clinical recommendations for applying these emerging biomarkers in clinical practice.

Given the above, there remains a need to develop new compounds and methods to improve the early detection of kidney injury and/or kidney diseases. More importantly, such compounds and methods have to be safe, accurate, selective and sensitive in detecting signs of early AKI.

In addition, such compounds have to be robust and easy to handle so that they can be widely adopted for use in improving the diagnosis of patients with kidney injury and/or kidney diseases.

Reactive oxygen species (ROS) have been implicated in the pathogenesis of several renal diseases, including renal ischemic injury, drug-induced nephrotoxicity, renal graft rejection and acute glomerulonephritis. One-electron reduction of molecular oxygen yields the superoxide anion ($O_2^{*-}$) followed by production of hydrogen peroxide ($H_2O_2$) and hydroxyl radical ($OH^-$), which may cause cell damage in the kidney by lipid peroxidation, DNA breakdown, and protein damage. NAG, a high molecular weight (140 kDa) hydrolytic lysosomal enzyme found in kidney proximal tubules and normally secreted in very low concentrations, has been shown to be elevated dramatically in both AKI and CKD. Notably, plasma NAG cannot be filtered through the glomerulus and its increase in urine is caused exclusively by its secretion from proximal tubular cell lysosomes by proximal tubular cell injury. Moreover, NAG is excreted in the initial phrases of kidney injury. Therefore, it is considered to be an early sensitive indicator of kidney tubular injury. Additionally, the effector caspase such as caspase-3, is a member of the caspase enzyme family and an ideal apoptosis-imaging target as it plays a critical role in the initiation and execution of apoptosis.

SUMMARY OF INVENTION

Thus, in a first aspect of the invention, there is disclosed a compound of formula I:

$(X)_a$—Y—$(Z)_b$

I where:

X is selected from:

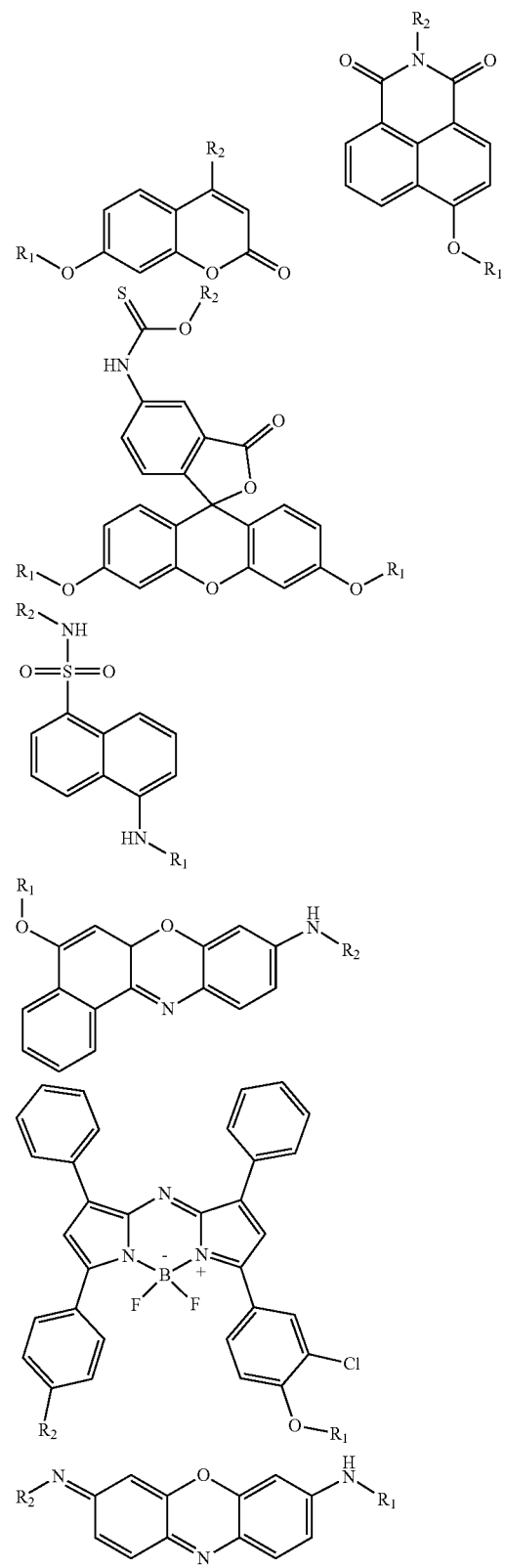

-continued
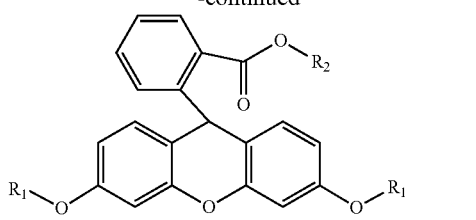
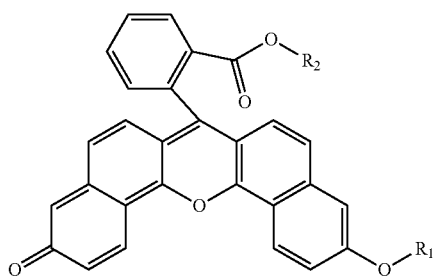
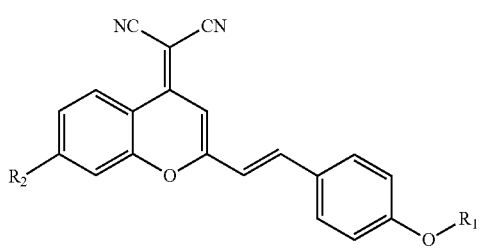
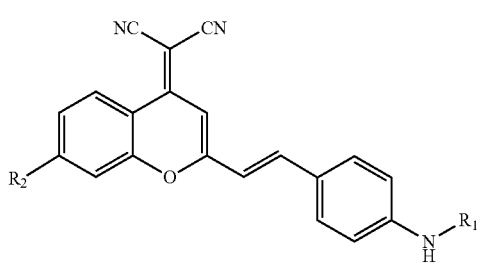
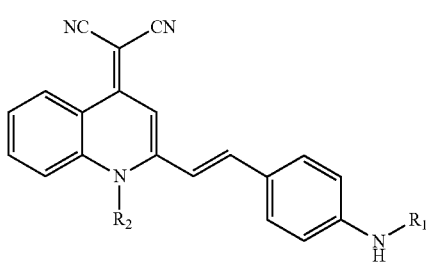
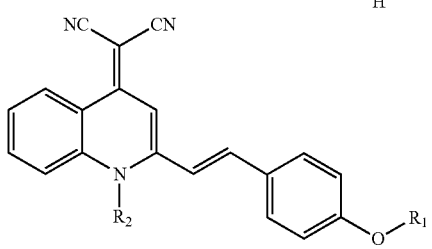
-continued
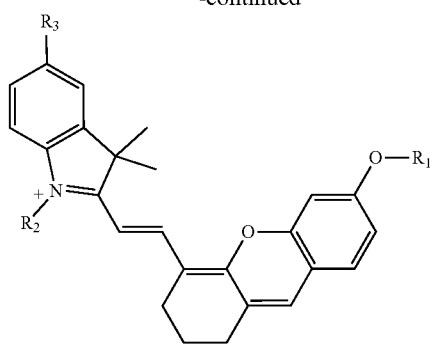
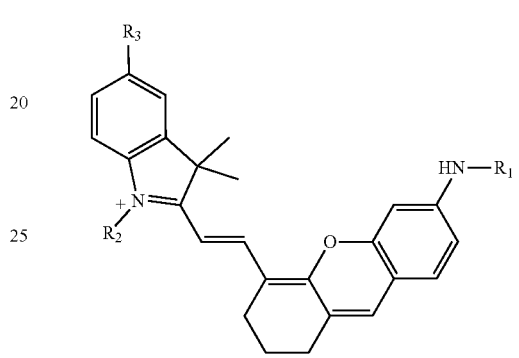
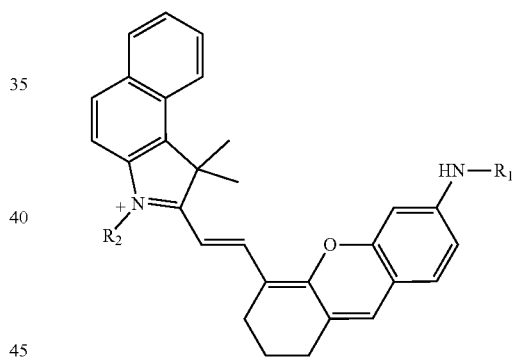
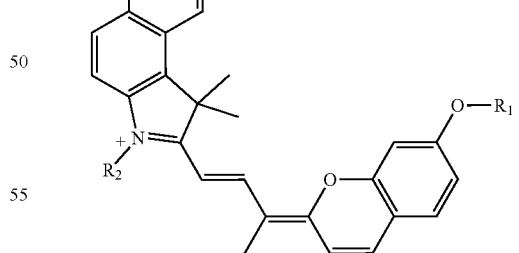
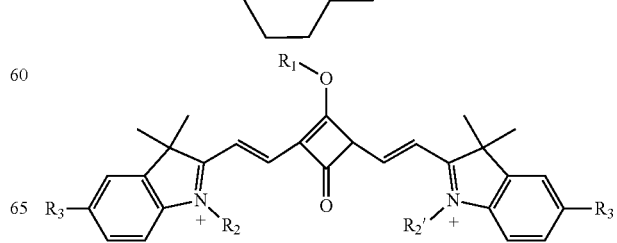

-continued

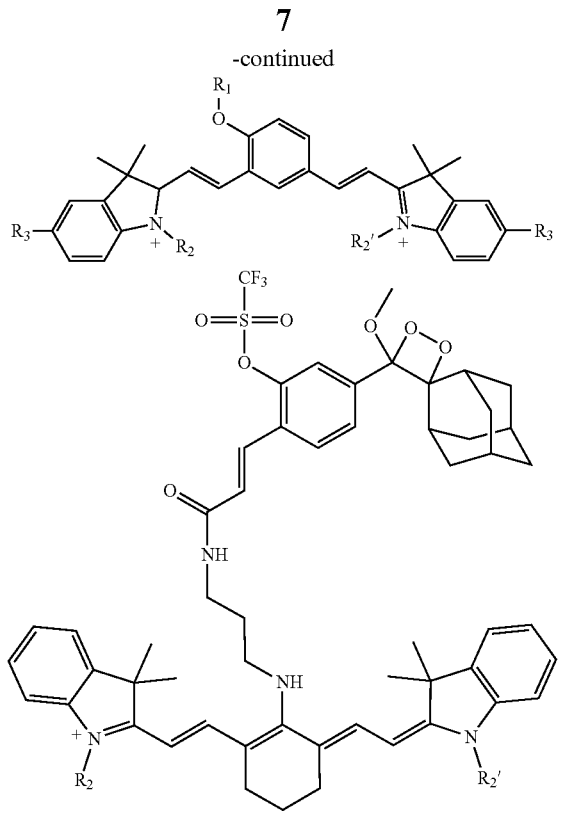

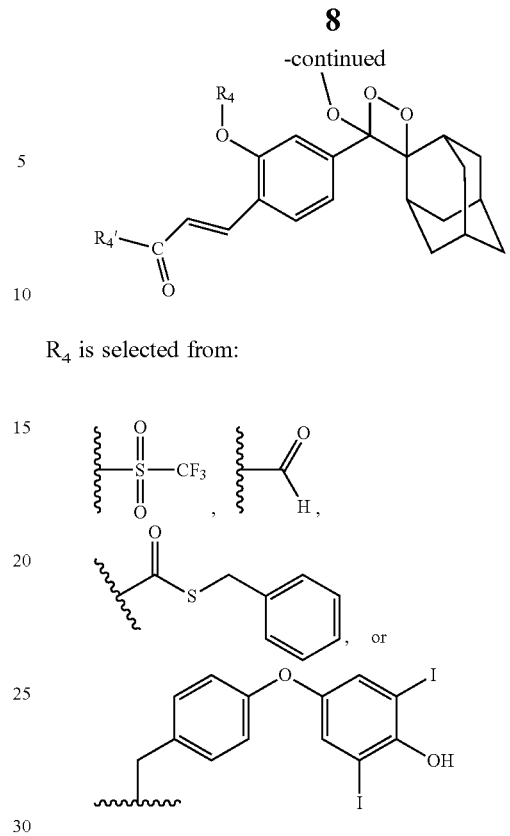

$R_4$ is selected from:

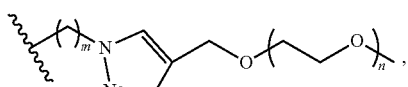

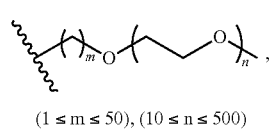

where the wavy line represents the point of attachment to the rest of the molecule;
$R_{4'}$ represents the point of attachment to Y;
each Y is selected from:

where $R_1$ represents a biomarker reactive moiety or a biomarker reactive moiety conjugated to a self-immolative moiety

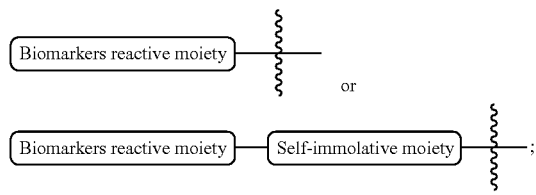

$R_2$ represents a point of attachment to Y and $R_{2'}$ represents another point of attachment to the same Y group or a point of attachment to a second Y group;
$R_3$ represents H, $SO_3H$ or COOH;
Z is selected from:

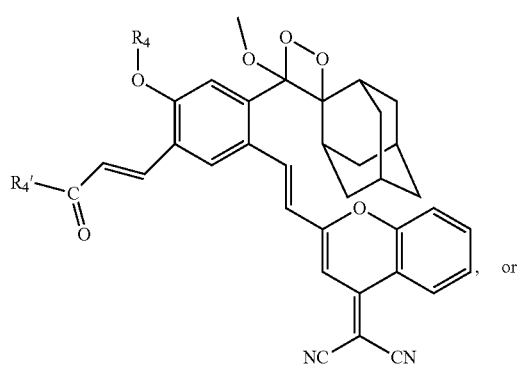

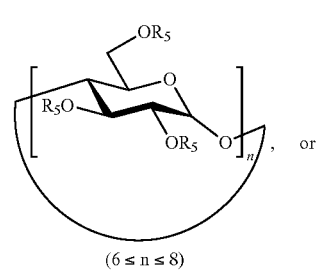

$(1 \leq m \leq 50), (10 \leq n \leq 500)$ where the wavy line represents the point of attachment to X or Z, $(1 \leq m \leq 50), (10 \leq n \leq 500)$ where the wavy line represents the point of attachment to X or Z, $(6 \leq n \leq 8)$ -continued

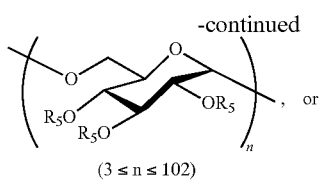

(3 ≤ n ≤ 102)

where each $R_5$ is independently selected from H, $CH_2CHOHCH_3$, $CH_2CCH$, and

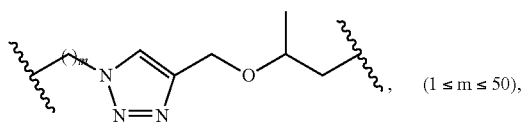 [SMILES: *CC(C)OCc1cn(C*)nn1]

(1 ≤ m ≤ 50), where the left-hand wavy line (adjacent to m) represents the point of attachment to X or Z and the right-hand wavy line represents the point of attachment to the rest of the molecule; a is 0 or 1 and b is 0 or 1, provided that:
at least one of a and b is 1; and
when a and b are both 1, Y is selected from:

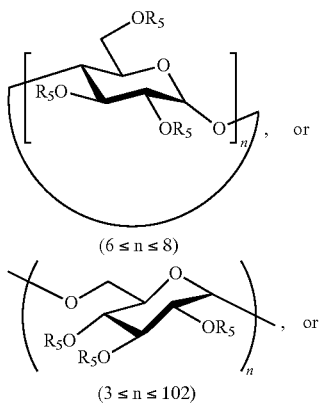

or pharmaceutically acceptable salts and/or solvates thereof, provided that when X is

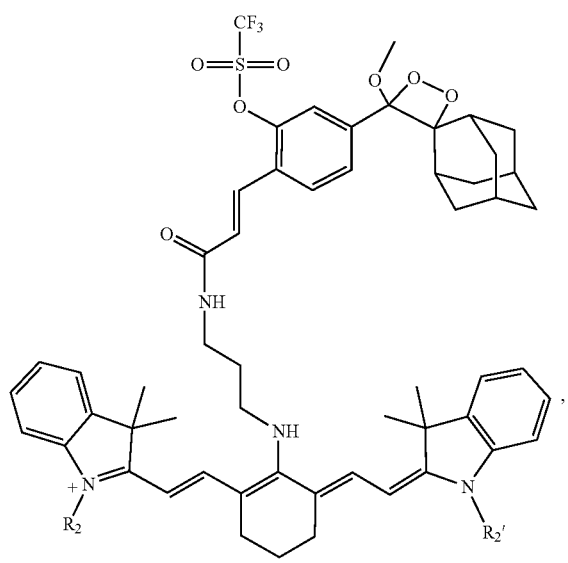

then Z is O.

In embodiments of the first aspect of the invention, the compound or salts and/or solvates thereof may be one in which:

(A) when $R_1$ is a biomarker reactive moiety or a biomarker reactive moiety conjugated to a self-immolative moiety, the biomarker reactive moiety may be selected from:

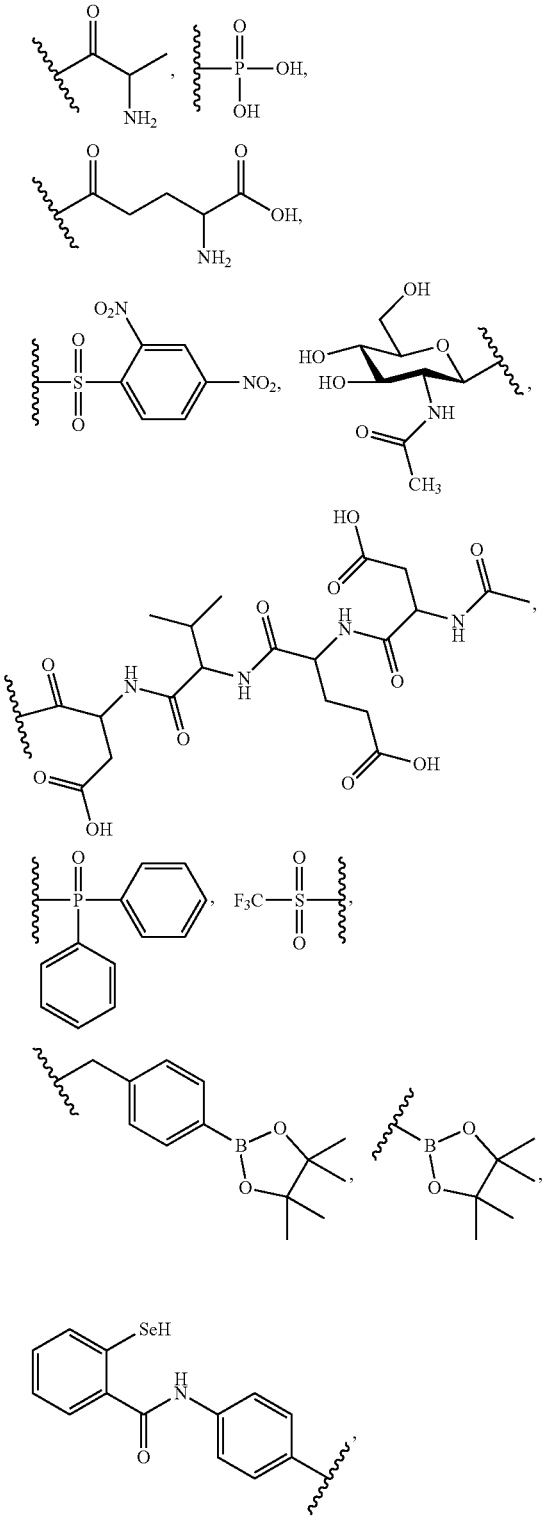

-continued

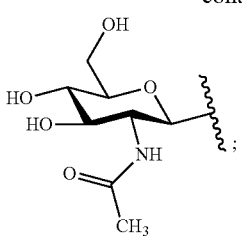

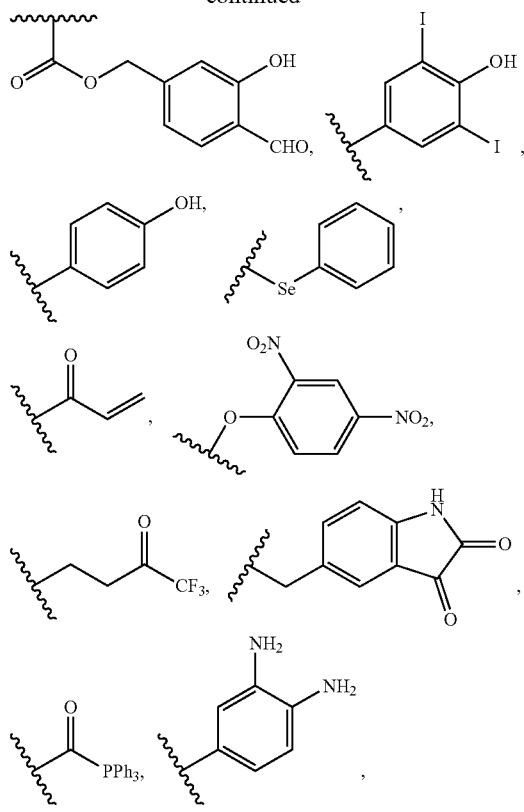

where the wavy line is the point of attachment to the rest of the molecule or, when present, the self-immolative linker, optionally wherein, when $R_1$ is a biomarker reactive moiety or a biomarker reactive moiety conjugated to a self-immolative moiety, the biomarker reactive moiety may be selected from:

-continued (B) when $R_1$ is a biomarker reactive moiety conjugated to a self-immolative moiety, the self immolative linker moiety may be selected from:

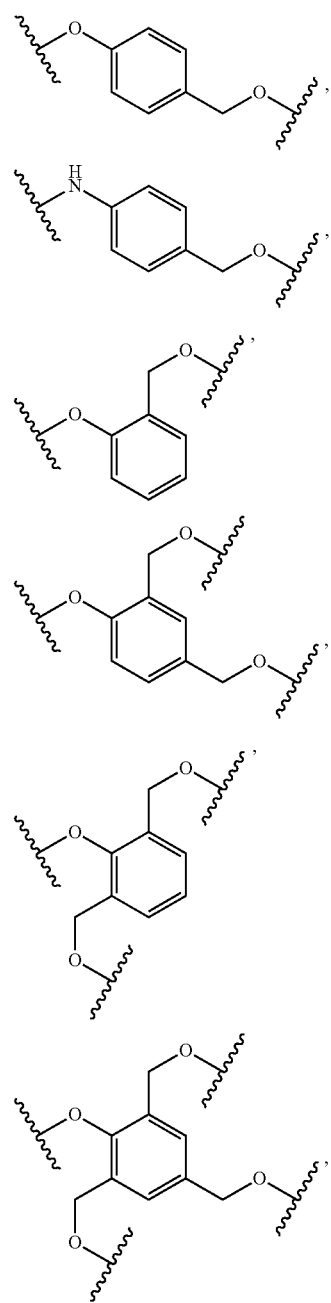

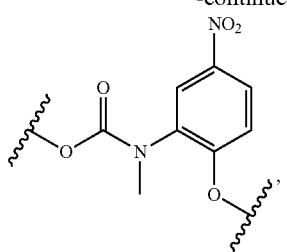

where the heteroatom directly bonded to the aromatic ring represents the point of attachment to Y and the other heteroatoms represent the point of attachment to a biomarker reactive moiety or are H, provided that at least one of the other heteroatoms is attached to a biomarker reactive moiety;

(C) X, when present, is selected from:

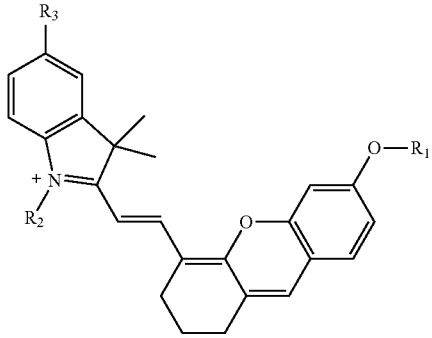

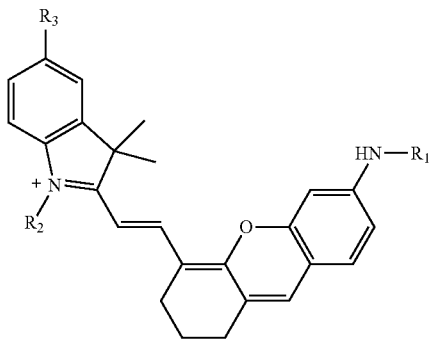

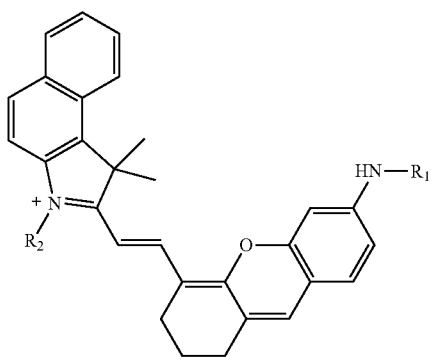

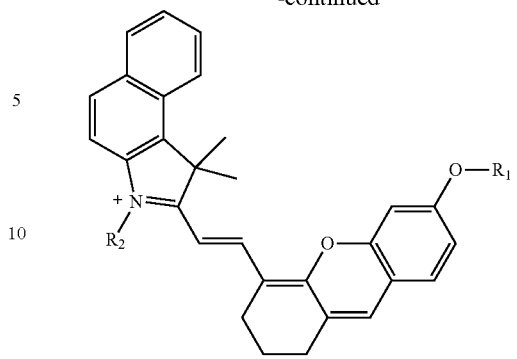

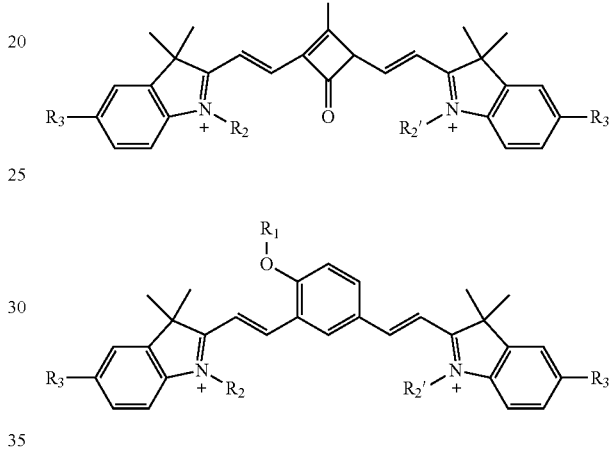

for example, when present X may be selected from:

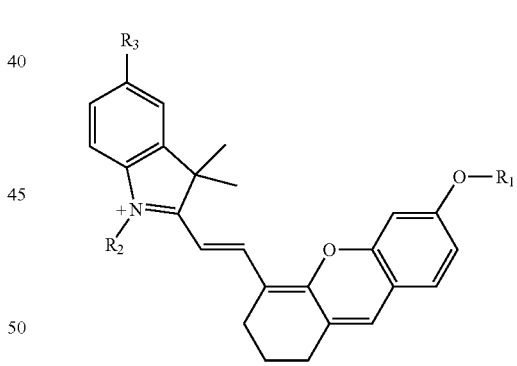

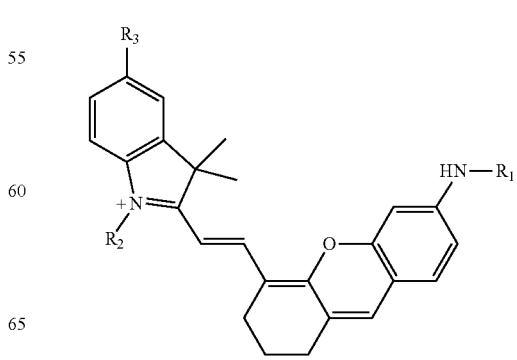

-continued

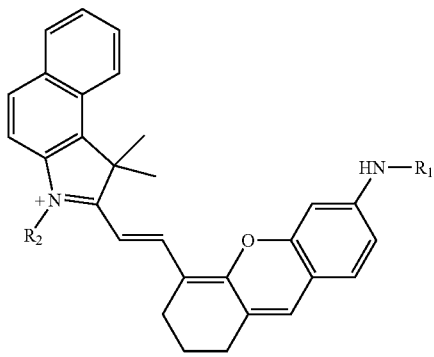

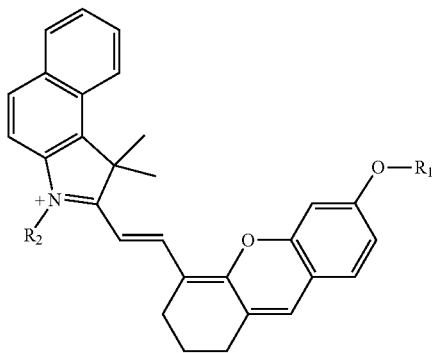

for example, X may be

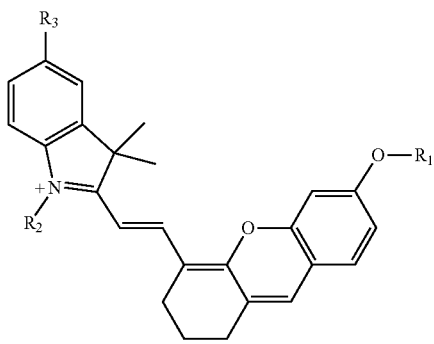

where R₃ is H;
(D) when present, Z may be:

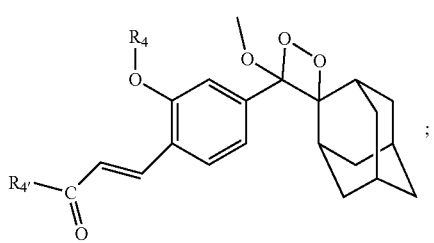

(E) R₄, when present, may be

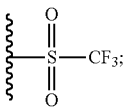

(F) each R₅, when present, may be independently selected from H, $CH_2CHOHCH_3$ and

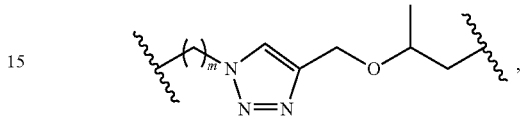

($1 \le m \le 50$), where the left-hand wavy line (adjacent to m) represents the point of attachment to X or Z and the right-hand wavy line represents the point of attachment to the rest of the molecule;
(G) whrere a and b may be 1 and Y may be

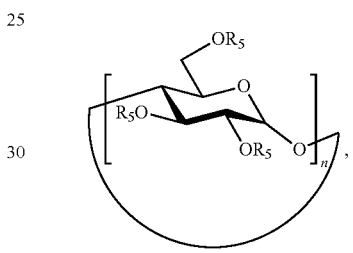

($6 \le n \le 8$).

Particular compounds of the first aspect of the invention that may be mentioned herein include those in which:
(a) a is 1, b is 0, X is

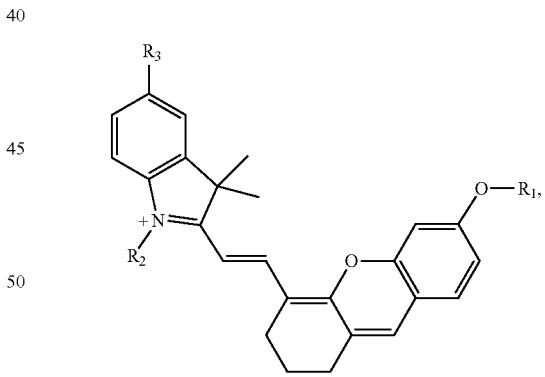

where $R_3$ is H, $R_1$ is a biomarker reactive moiety that is:

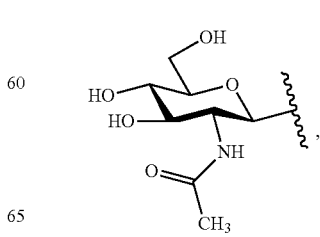

and Y is

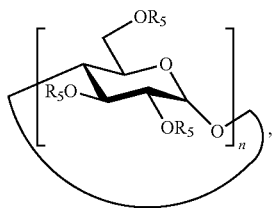

where n is 7; and (b) a is 1, b is 1, X is

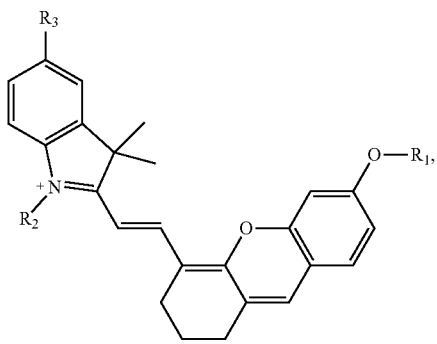

where $R_3$ is H, $R_1$ is a biomarker reactive moiety that is:

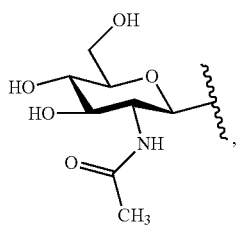

Z is

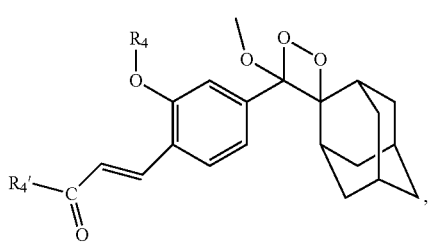

where $R_4$ is,

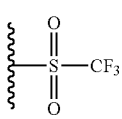

and Y is

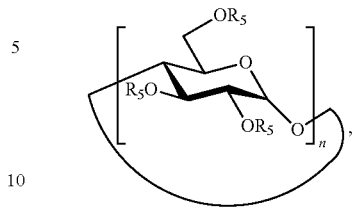

where n is 7.

In a second aspect of the invention, there is provided a compound according to formula II:

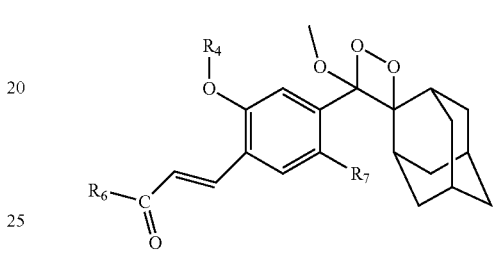

where:

$R_4$ is selected from:

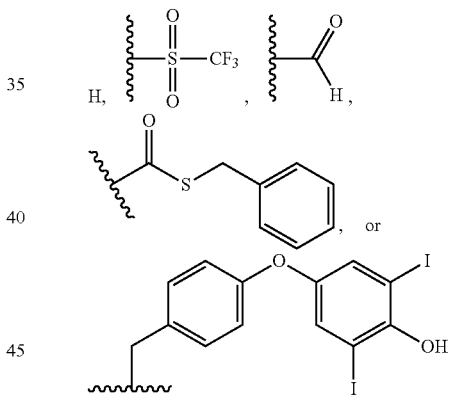

where the wavy line represents the point of attachment to the rest of the molecule;

$R_6$ is OH or $OC_1\text{-}C_6$ alkyl;

$R_7$ is:

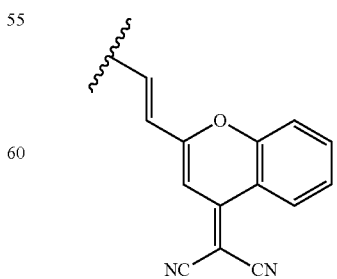

or pharmaceutically acceptable salts and/or solvates thereof.

In a third aspect of the invention, there is provided a compound of formula III:
$$X'—Y' \quad\quad III$$
where:
X' is selected from:
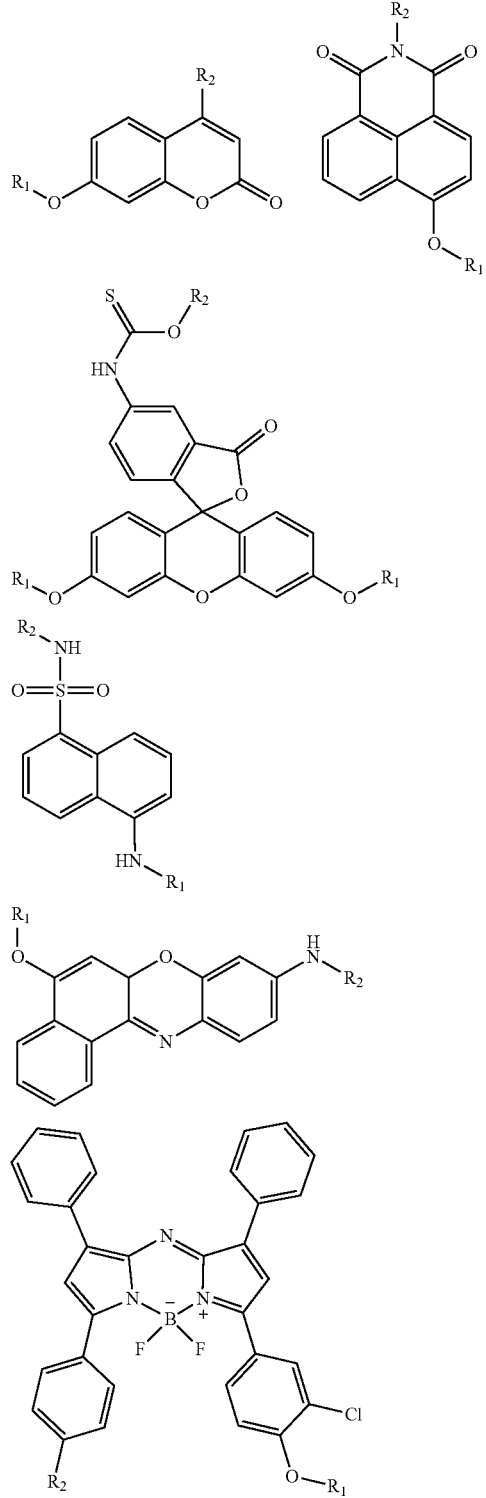
-continued
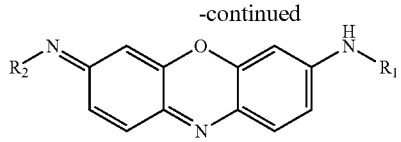
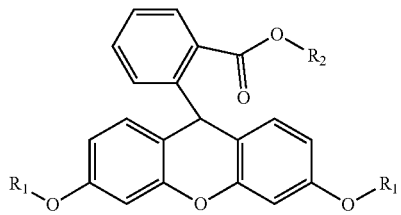
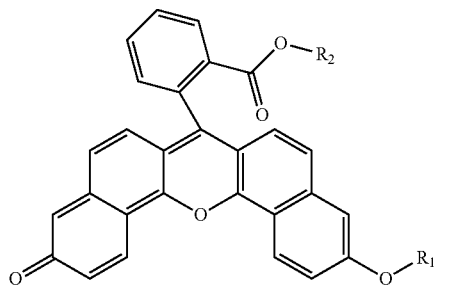
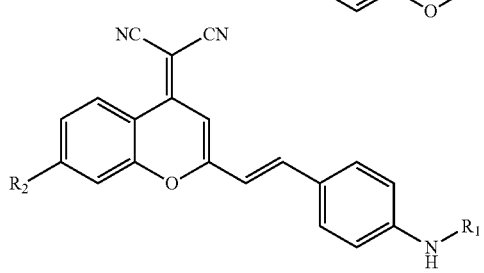
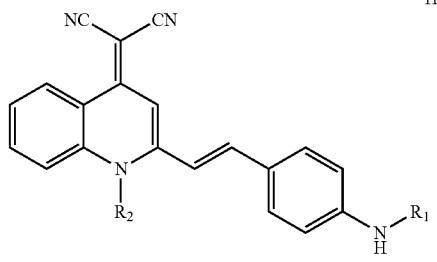
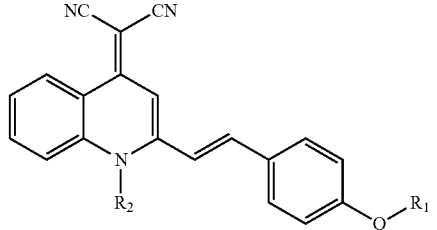

-continued where R₁ represents a biomarker reactive moiety or a biomarker reactive moiety conjugated to a self-immolative moiety one R₂ represents the point of attachment to Y' and the other R₂ represents Y";
R₃ represents H, SO₃H or COOK
Y' and Y" are selected from H, $C_mH_{2m+1}$ (1≤m≤50), (1≤m≤50)   (1≤m≤50)   (1≤m≤50)

where the wavy line represents the point of attachment to X', or pharmaceutically acceptable salts and/or solvates thereof.

In embodiments of the third aspect of the invention, the compound or salts and/or solvates thereof may be one in which:

(AA) when R₁ is a biomarker reactive moiety or a biomarker reactive moiety conjugated to a self-immolative moiety, the biomarker reactive moiety may be selected from:

23
-continued

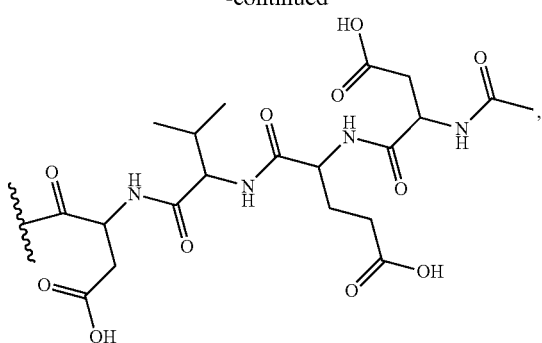

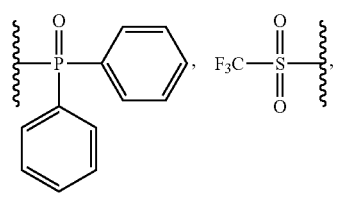

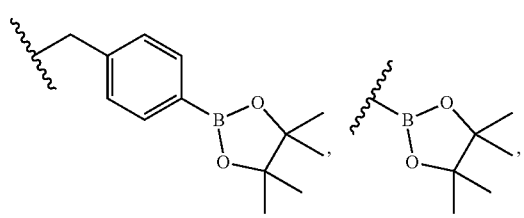

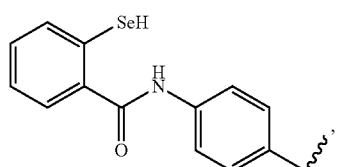

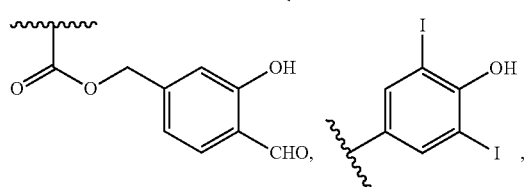

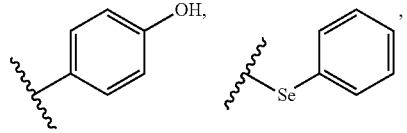

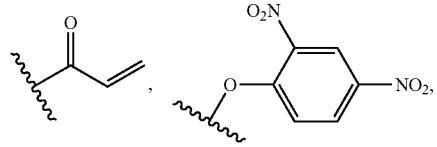

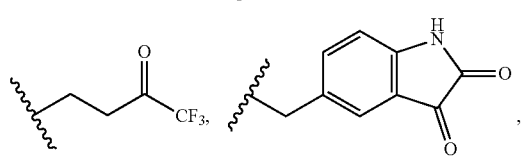

24
-continued

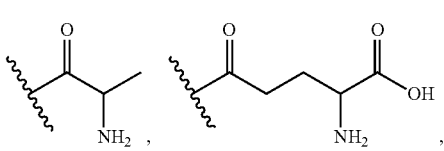

where the wavy line is the point of attachment to the rest of the molecule or, when present, the self-immolative linker, optionally wherein, when $R_1$ is a biomarker reactive moiety or a biomarker reactive moiety conjugated to a self-immolative moiety, the biomarker reactive moiety may be selected from:

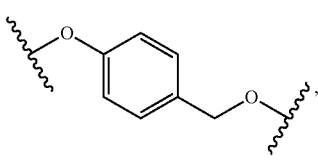

(AB) when $R_1$ is a biomarker reactive moiety conjugated to a self-immolative moiety, the self immolative linker moiety may be selected from:

-continued
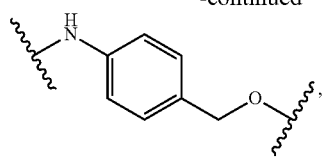
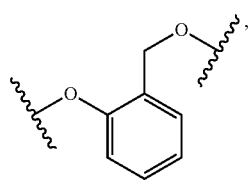
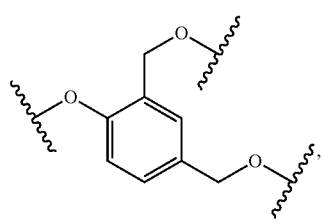
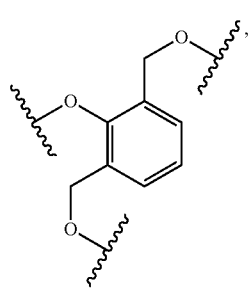
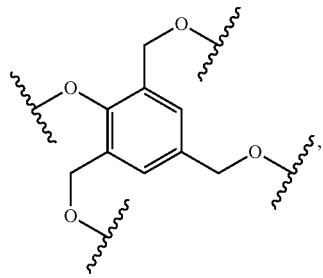
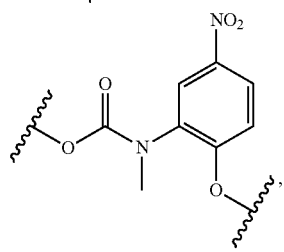
where the heteroatom directly bonded to the aromatic ring represents the point of attachment to Y and the other heteroatoms represent the point of attachment to a biomarker reactive moiety or are H, provided that at least one of the other heteroatoms is attached to a biomarker reactive moiety;
(AC) X', when present, is selected from:
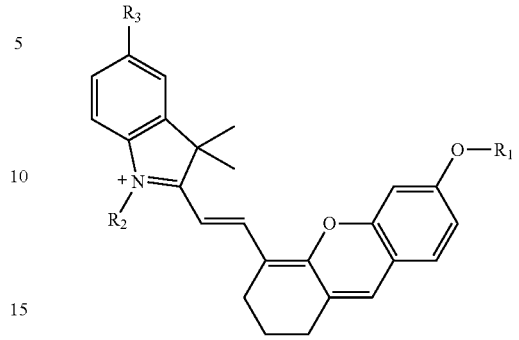
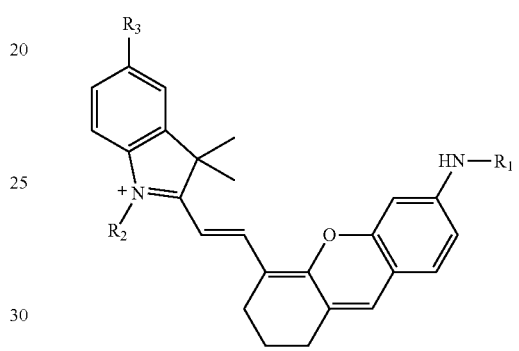
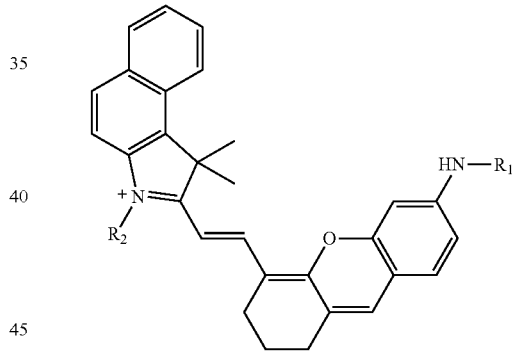
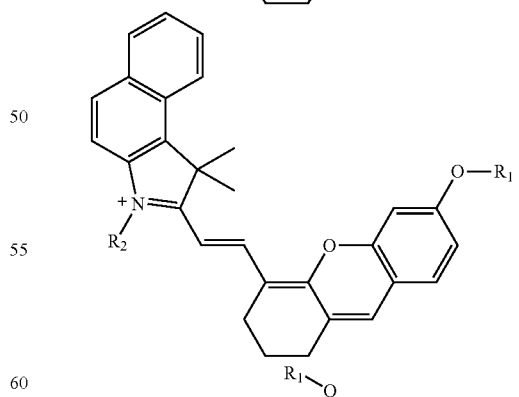
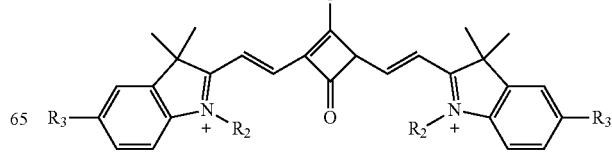

-continued

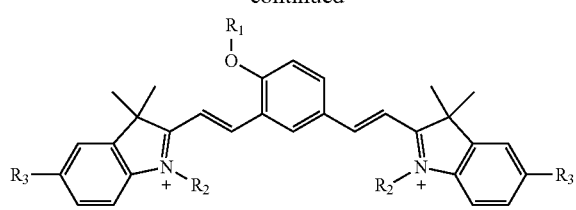

for example, when present X' may be selected from:

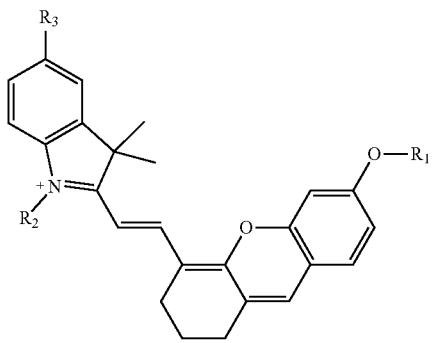

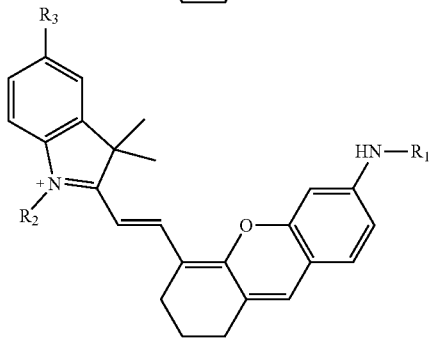

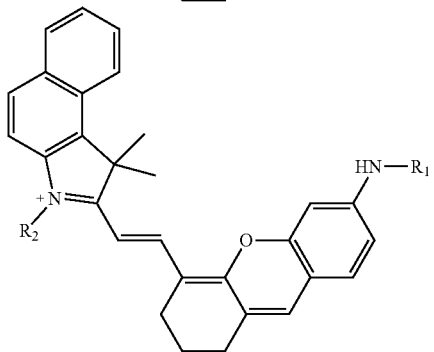

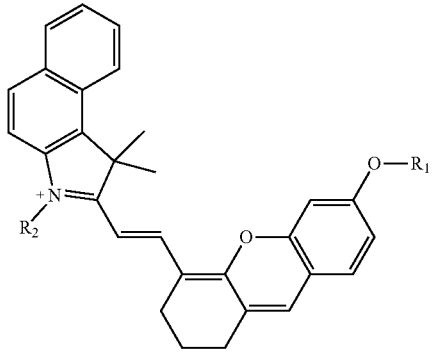

for example, X' may be

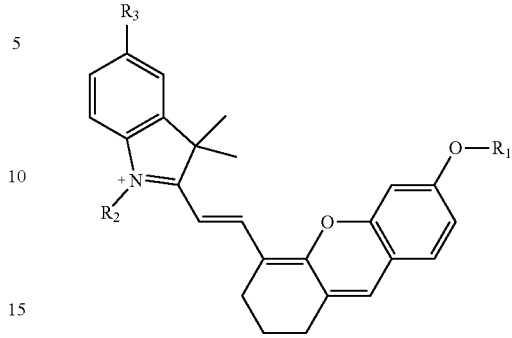

where $R_3$ is H.

In a fourth aspect of the invention, there is provided a use of a compound of formula I or a salt and/or solvate thereof as described in the first aspect of the invention or any technically sensible combination of its embodiments for the manufacture of a diagnostic agent for in vivo diagnosis of a kidney injury or a kidney disease.

In a fifth aspect of the invention, there is provided a compound of formula I or a salt and/or solvate thereof as described in the first aspect of the invention or any technically sensible combination of its embodiments for use in the in vivo diagnosis of a kidney injury or a kidney disease.

In a sixth aspect of the invention, there is provided a method of diagnosis of a kidney injury or a kidney disease, involving administering to a subject in need thereof a composition comprising a compound of formula I or a salt and/or solvate thereof as described in the first aspect of the invention or any technically sensible combination of its embodiments and detecting a signal, the detection of which indicates a kidney injury or a kidney disease in said subject.

In a seventh aspect of the invention, there is provided a method of in vitro diagnosis of a kidney injury or a kidney disease, using a compound of formula I or a salt and/or solvate thereof as described in the first aspect of the invention or any technically sensible combination of its embodiments, or a compound of formula III or a salt and/or solvate thereof as described in the third aspect of the invention or any technically sensible combination of its embodiments comprising the steps of:

(a) providing a sample for detection;
(b) adding a compound of formula I or a salt and/or solvate thereof, or a compound of formula III or a salt and/or solvate thereof to the sample, allowing said compound to incubate for a period of time; and
(c) detecting a signal from the sample, the detection of which indicates a kidney injury or a kidney disease.

$CsCO_3$, $CH_2Cl_2$, BrGlcNAc, 16 h; NaOMe, MeOH, 10 min, rt; (iv) DIPEA, Br-Ph-DVED, $CH_3CN$, 70° C., 4 h; TFA/$CH_2Cl_2$ (½), 30 min; (v) $CuSO_4 \cdot 5H_2O$, sodium ascorbate, propynyl-HPβCD, DMSO/$H_2O$ (1/1), 5 h, rt. (c) Syntheses of CP2, CP5 and CCD, (R: H or $CH_2CHOHCH_3$). (v) $CuSO_4 \cdot 5H_2O$, sodium ascorbate, propynyl-HPβCD, DMSO/$H_2O$ (1/1), 5 h, rt.

Figure 4:
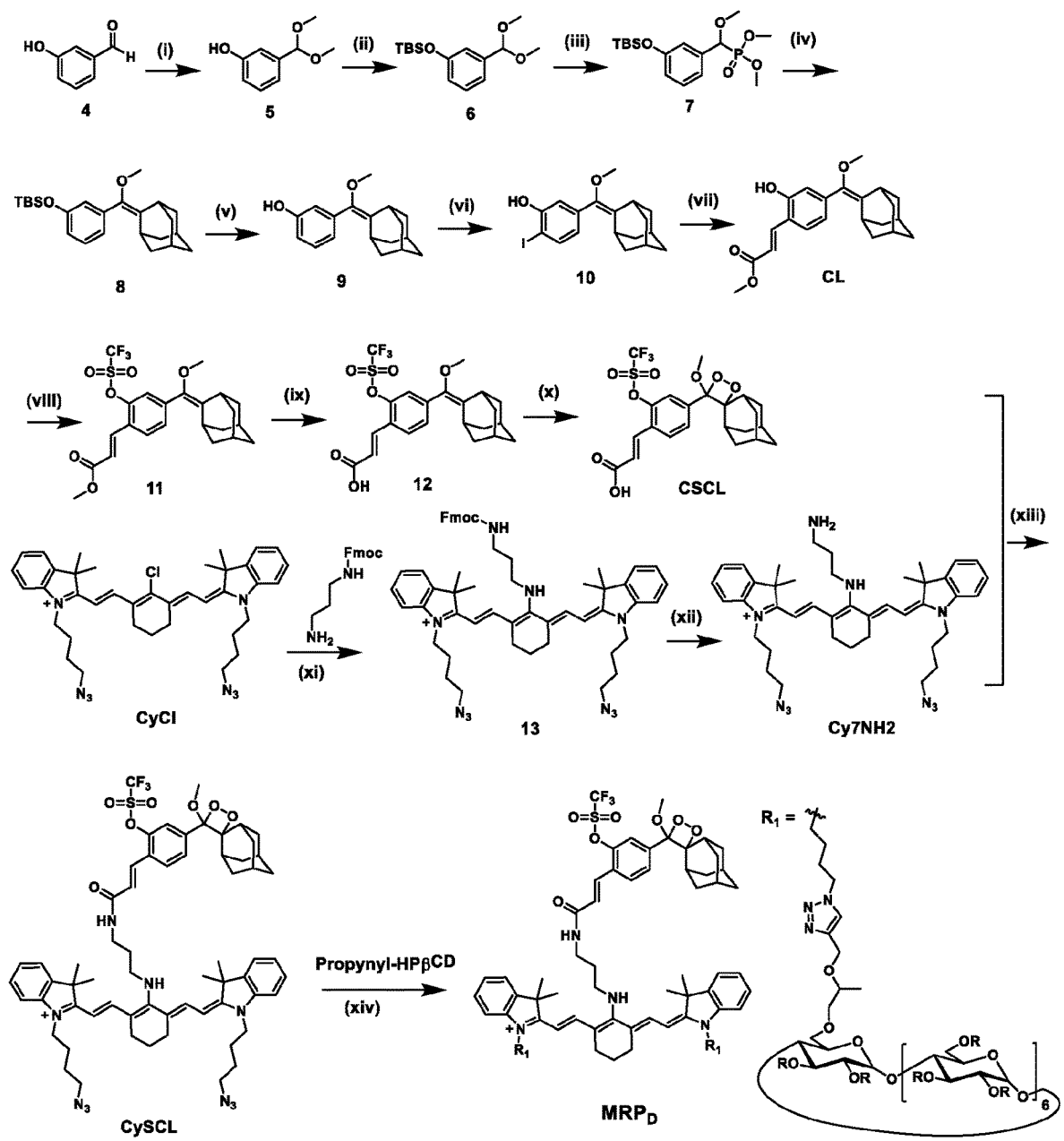

FIG. 4 Depicts the syntheses of $MRP_D$ (R: H or $CH_2CHOHCH_3$). Reagents and conditions: (i) $CH(OCH_3)_3$, $Bu_4NBr_3$, MeOH, 16 h, rt; (ii) TBS-Cl, imidazole, $CH_2Cl_2$, 16 h, rt; (iii) $P(OCH_3)_3$, $TiCl_4$, $CH_2Cl_2$, ice bath, 16 h; (iv) 2-adamantanone, LDA, THF, −78° C., 4 h; (v) TBAF, THF, 12 h; (vi) NIS, toluene, ice bath, 12 h; (vii) methyl acrylate, $Pd(OAc)_2$, P(O-tolyl)$_3$, $Et_3N$, MeCN, 12 h, 90° C.; (viii) $Tf_2O$, pyridine, $CH_2Cl_2$, −78 to 25° C., 2 h; (ix) NaOH, 60° C., 4 h; (x) methylene blue, $O_2$, $CH_2Cl_2$/MeOH, 2 h, ice bath; (xi) DMF, 60° C., 4 h; (xii) piperidine, $CH_2Cl_2$, 1 h; (xiii) HBTU, DIPEA, DMF, 4 h, rt; and (xiv) $CuSO_4 \cdot 5H_2O$, sodium ascorbate, propynyl-HPβCD, DMSO/$H_2O$ (1/1), 5 h, 0° C.

Figure 5:
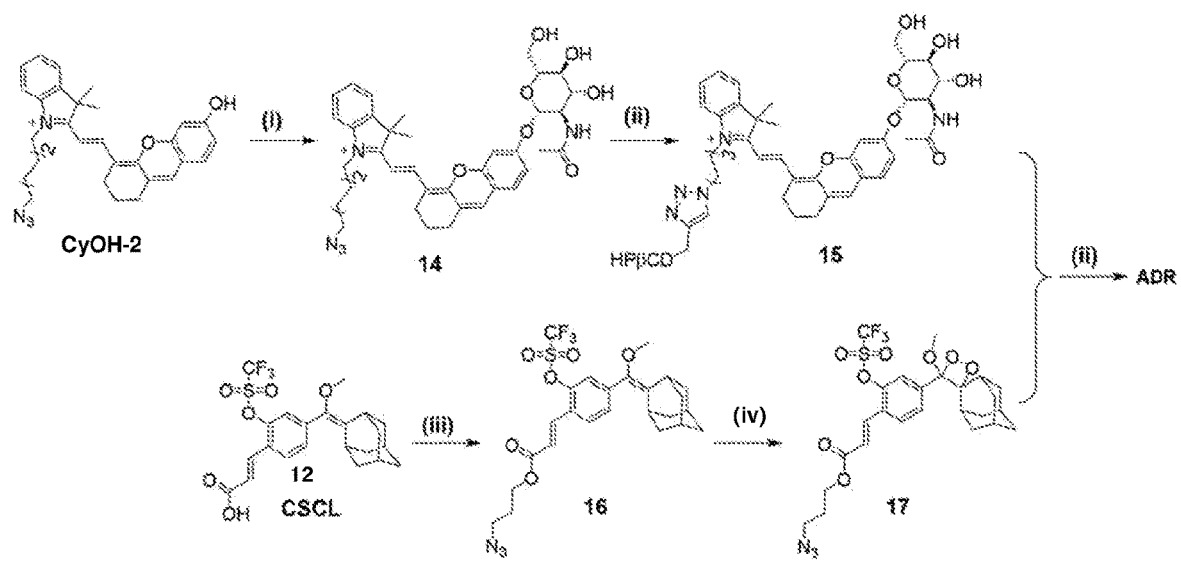

FIG. 5 Depicts the synthesis of ADR. Reagents and conditions: (i) $Cs_2CO_3$, $CH_2Cl_2$, BrGlcNAc, 16 h; NaOMe, MeOH, rt, 15 min; (ii) $CuSO_4 \cdot 5H_2O$, sodium ascorbate, propynyl-HPβCD, DMSO/$H_2O$, 2 h, rt; (iii) 1-ethyl-3-(3-dimethylaminopropyl) carbodiimide, 4-dimethylaminopyridine, 3-azido-1-propanol, rt, 24 h; and (iv) methylene blue, $O_2$, $CH_2Cl_2$/MeOH, 4 h, ice bath.

Figure 6:
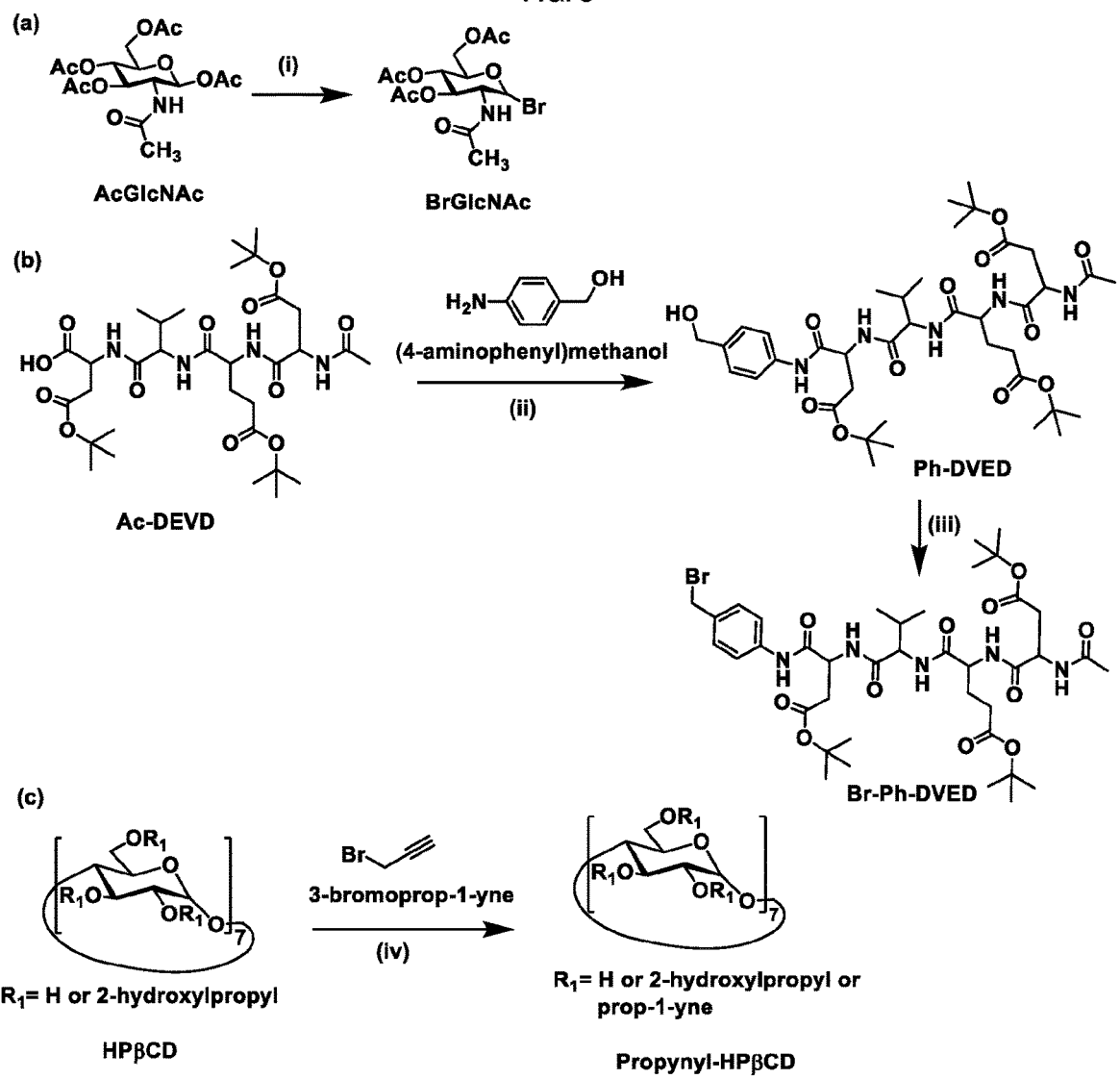

FIG. 6 Depicts the syntheses of chemical intermediates: (a) BrGlcNAc; (b) Br-Ph-DVED; and (c) propynyl-HPβCD. Reagents and conditions: (i) HBr/HOAc, ice bath, 8 h; (ii) EEDQ, THF, rt, 12 h; (iii) $CH_2Cl_2$, $PBr_3$, rt, 12 h; and (iv) tetra-tert-butylammonium iodide, NaH, DMF, rt, 20 h.

Figure 7:
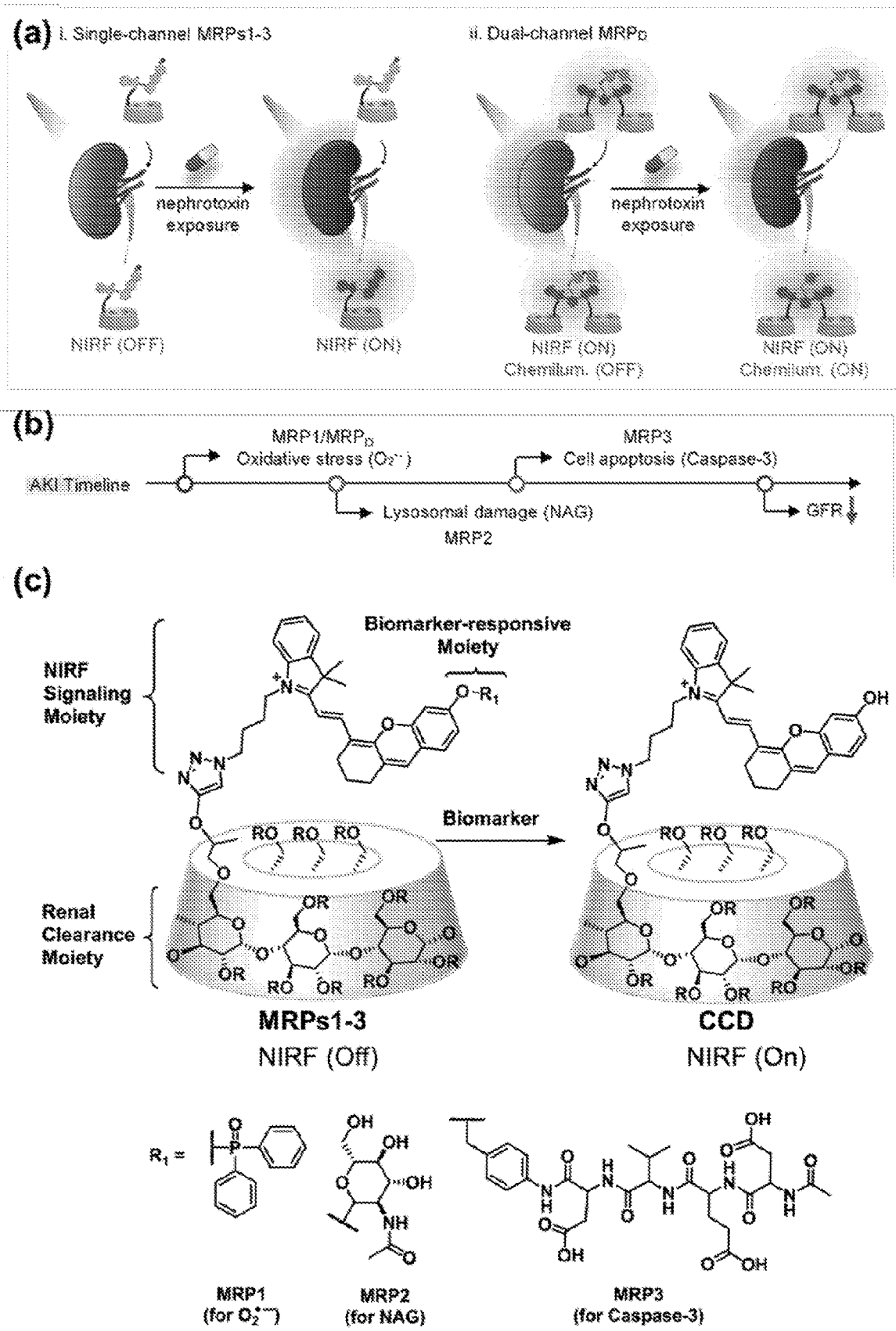

FIG. 7 Depicts: (a) schematic of real-time non-invasive imaging of drug-induced AKI using (i) single channel NIRF turn-on MRPs1-3 and (ii) the dual-channel chemiluminescent $MRP_D$; (b) timeline of AKI comparing the molecular events including oxidative stress, lysosomal damage and cell apoptosis with the decrease in glomerular filtration rate (GFR); and (c) chemical structures of MRPs1-3 and their activated form as CCD in response to their respective biomarkers ($O_2^{*-}$ for MRP1, NAG for MRP2, and caspase-3 for MRP3) (R=H or $CH_2CHOHCH_3$).

Figure 8:
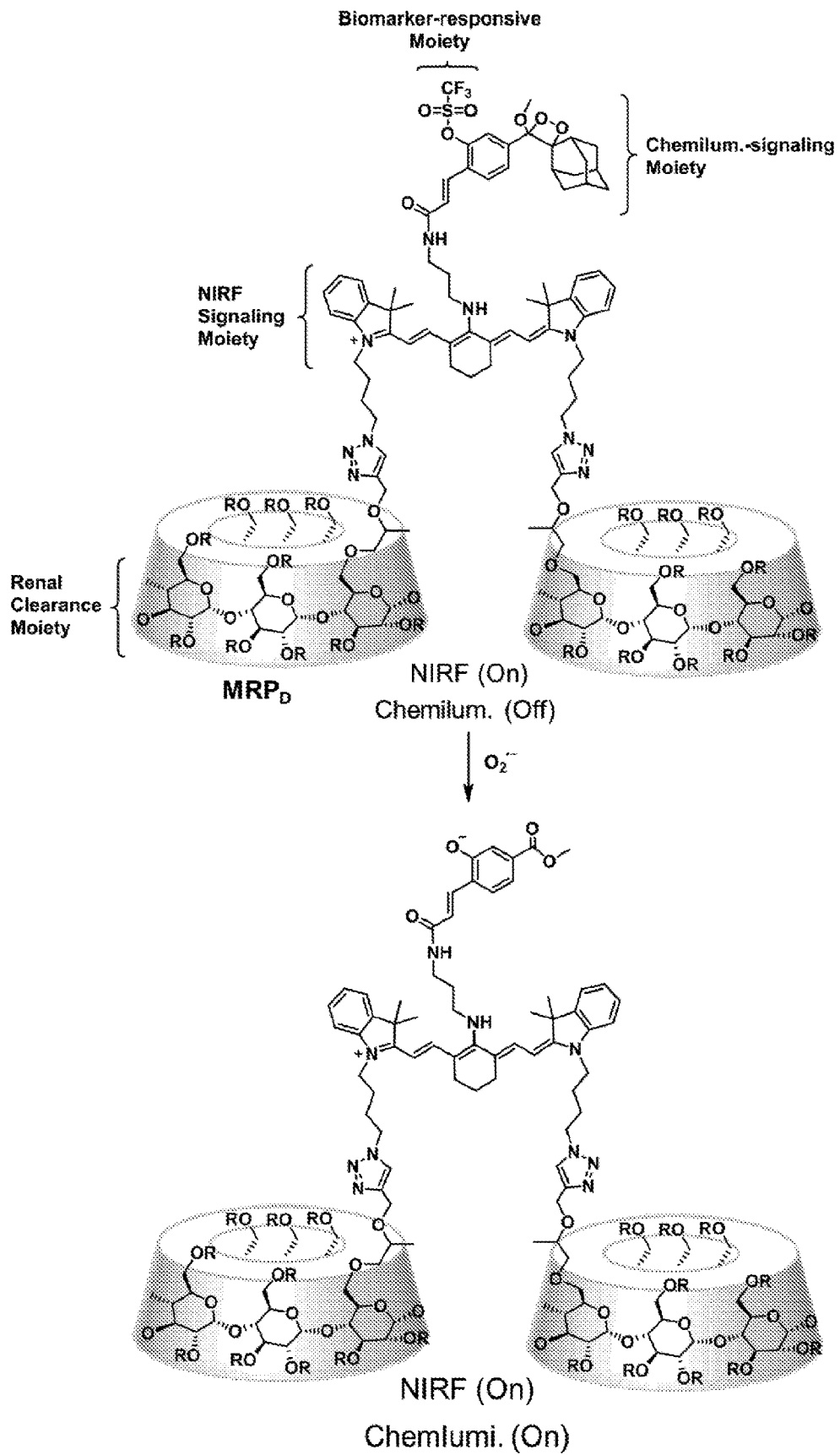

FIG. 8 Depicts the chemical structures of $MRP_D$ and its activated form in response to $O_2^{*-}$ (R=H or $CH_2CHOHCH_3$).

Figure 9:
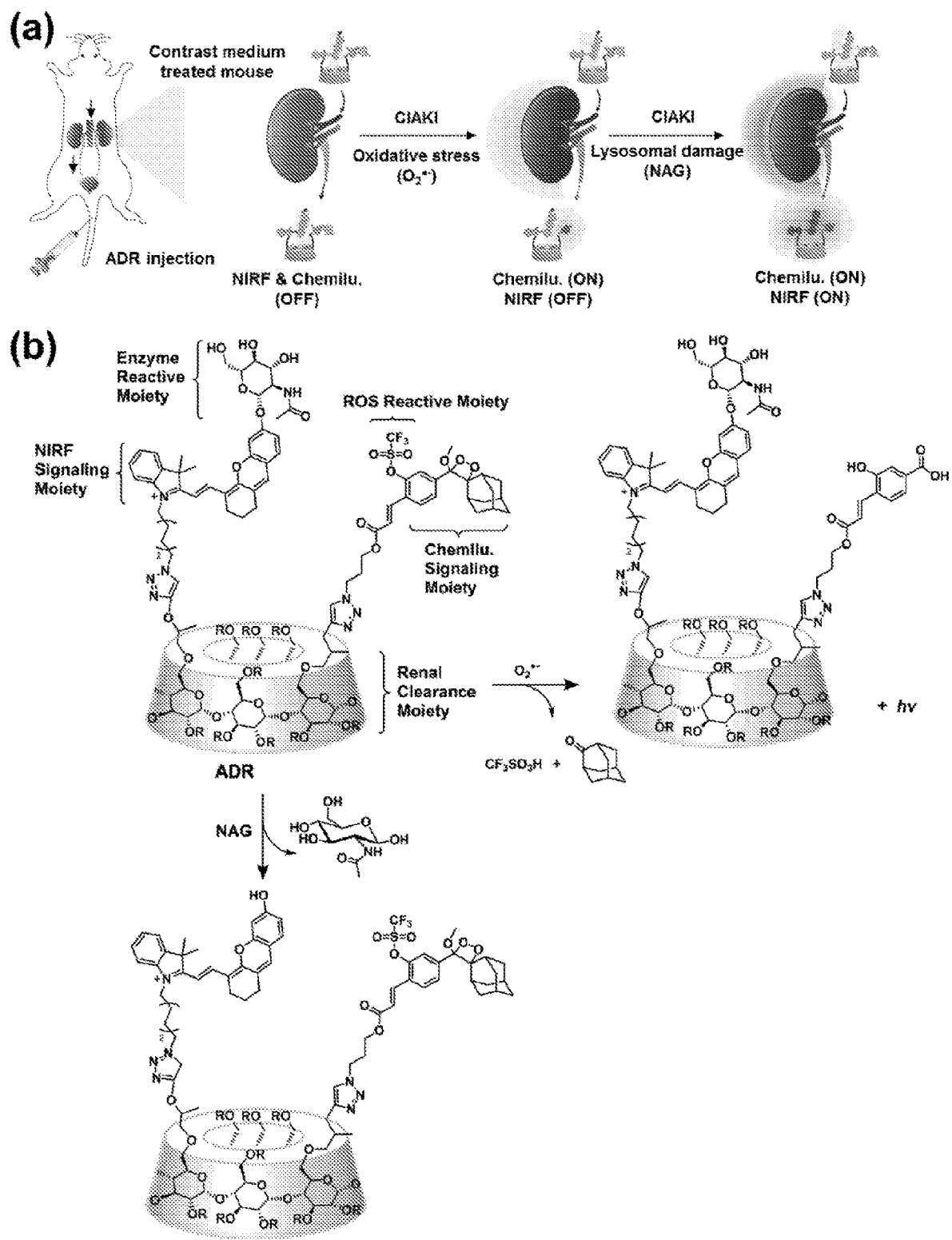

FIG. 9 Depicts: (a) schematic illustration of real-time duplex imaging and early detection of contrast-induced acute kidney injury (CIAKI) using ADR; and (b) chemical structures of ADR and its activated forms in response to oxidative stress ($O_2^{*-}$) and lysosomal damage (NAG), respectively (R=H, $CH_2CHOHCH_3$ or $CH_2CCH$).

Figure 10:
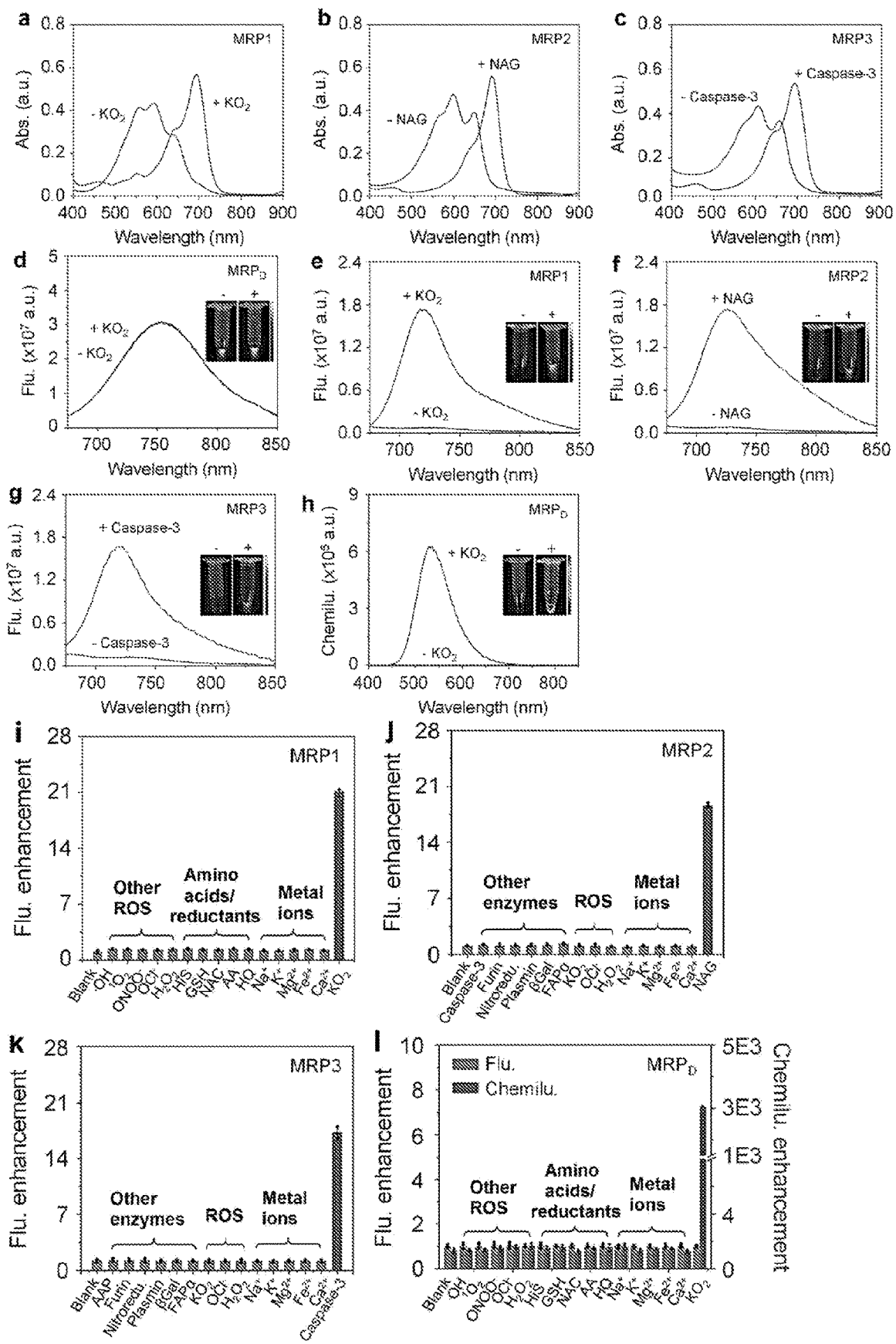

FIG. 10 Depicts in vitro evaluation of the MRPs sensing capabilities: (a-c) UV-Vis absorption; (e-g) fluorescence spectra of MRPs1-3 (30 μM) in the absence or presence of their respective biomarkers (60 μM $KO_2$, 40 mU NAG and 0.5 μg caspase-3, respectively) in PBS buffer (10 mM, pH 7.4) at 37° C. Fluorescence excitation at 675 nm. Inset: the corresponding fluorescence images acquired at 720 nm upon excitation at 675 nm with the IVIS spectrum imaging system; (d) fluorescence and (h) chemiluminescence spectra of $MRP_D$ (30 μM) in the absence or presence of $KO_2$ (60 μM) in PBS buffer (10 mM, pH 7.4) at 37° C. Fluorescence excitation at 640 nm. Inset: the corresponding fluorescence images acquired at 760 nm upon excitation at 640 nm and chemiluminescence images acquired under bioluminescence mode with the acquisition time of 1 s. The experiments (a-h) were repeated independently three times with similar results; (i-k) The NIRF changes of MRPs1-3 (30 μM) at 720 nm after incubation with indicated ROS (150 μM), enzymes, and other analytes (150 μM in PBS buffer (10 mM, pH 7.4) at 37° C.; and (l) NIRF (760 nm) and chemiluminescence changes (540 nm) of $MRP_D$ (30 μM) after incubation with indicated ROS (150 μM) and other analytes (150 μM) in PBS buffer (10 mM, pH 7.4) at 37° C. Fluorescence excitation at 640 nm and chemiluminescence acquired under bioluminescence mode with the acquisition time of 1 s. Data are the mean±SD. n=3 independent experiments. Hydroxyl radical (·OH), peroxynitrite ($ONOO^-$), histidine (His), glutathione (GSH), N-acetyl-L-cysteine (NAC), ascorbic acid (AA), hydroquinone (HQ), nitroreductase (Nitroredu.), β-galactosidase (βGal), fibroblast activation protein-alpha (FAPα), alanine aminopeptidase (AAP) are indicated accordingly.

Figure 11:
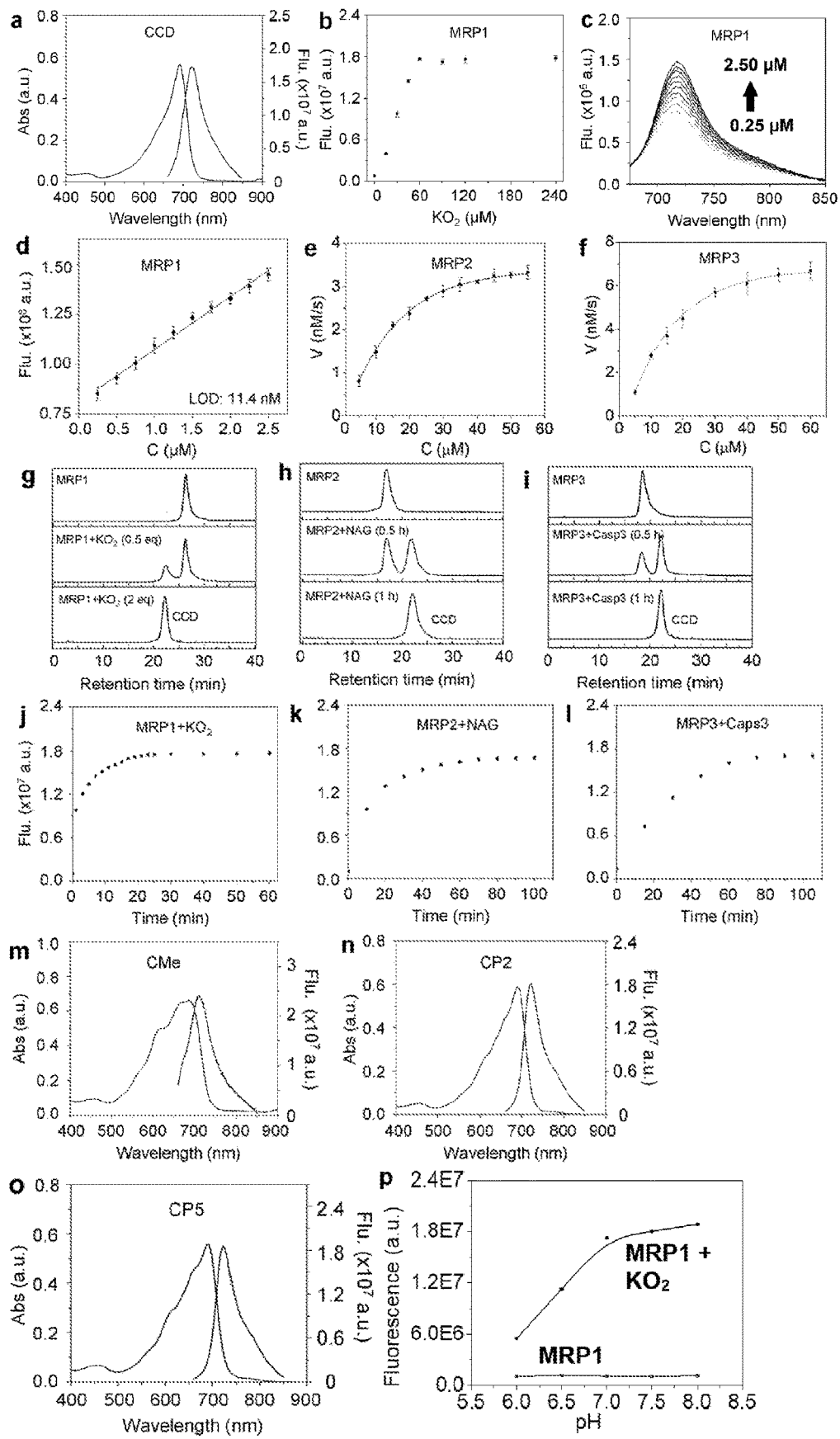

FIG. 11 Depicts optical and sensing characterisation of MRPs1-3 and the uncaged fluorophores: (a) absorption (dark) and fluorescence (red) spectra of CCD in PBS buffer (10 mM, pH 7.4) at 37° C.; (b) fluorescence intensities (720 nm) of MRP1 (30 μM) upon addition of $KO_2$ (15, 30, 60, 90, 120, 240 μM) in PBS buffer (10 mM, pH 7.4). Fluorescence excitation at 675 nm. Data are the mean±SD. n=3 independent experiments; (c) fluorescence spectra of MRP1 (30 μM) upon addition of $KO_2$ (0-2.5 μM) in PBS buffer (10 mM, pH 7.4). Fluorescence excitation at 675 nm. The experiments in (a) and (c) were repeated independently three times with similar results; (d) linear relationship between the fluorescence intensity of MRP1 (30 μM) at 720 nm and the concentration of $KO_2$ (0-2.5 μM). Fluorescence excitation at 675 nm. The limit of detection (LOD) was estimated to be as low as 11 nM (S/N=3). Data are the mean±SD. n=3 independent experiments; (e) steady-state kinetics of the enzymatic reaction between MRP2 (5, 10, 15, 20, 25, 30, 35, 40, 45, 50 or 55 μM) and NAG (40 mU). The initial velocity (v) was plotted against different concentrations of MRP2. Data are the mean±SD. n=3 independent experiments; (f) steady-state kinetics of the enzymatic reaction between MRP3 (5, 10, 15, 20, 30, 40, 50 or 60 μM) and caspase-3 (0.5 μg). The initial velocity (v) was plotted against different concentrations of MRP3. Data are the mean±SD. n=3 independent experiments; (g-i) evaluation of the sensing capability of MRPs1-3 through HPLC analysis of the incubation mixtures of MRPs1-3 (30 μM) in the absence and presence of their respective biomarkers (MRP1: 15 or 60 μM $KO_2$; MRP2: 40 mU NAG; and 0.5 μg casp-3 for MRP3 for 0.5 or 1 h) in PBS buffer (10 mM, pH 7.4) at 37° C.; (j-l) time course of fluorescence changes of MRPs1-3 (30 μM) at 720 nm in the presence of their respective biomarkers (60 μM $KO_2$, 40 mU NAG and 0.5 μg casp-3, respectively) in PBS buffer (10 mM, pH 7.4) at 37° C. Fluorescence excitation at 675 nm; (m-o) absorption (dark) and fluorescence (red) spectra of CMe (30 μM), CP2 (30 μM) and CP5 (30 μM) in PBS buffer (10 mM, pH 7.4) at 37° C. 10% DMSO/PBS buffer are co-solvents for CMe. The experiments in (g) to (o) were repeated independently three times with similar results; and (p) effect of pH on the fluorescence intensity of MRP1, and MRP1 (30 μM) with $KO_2$ (30 μM).

Figure 12:
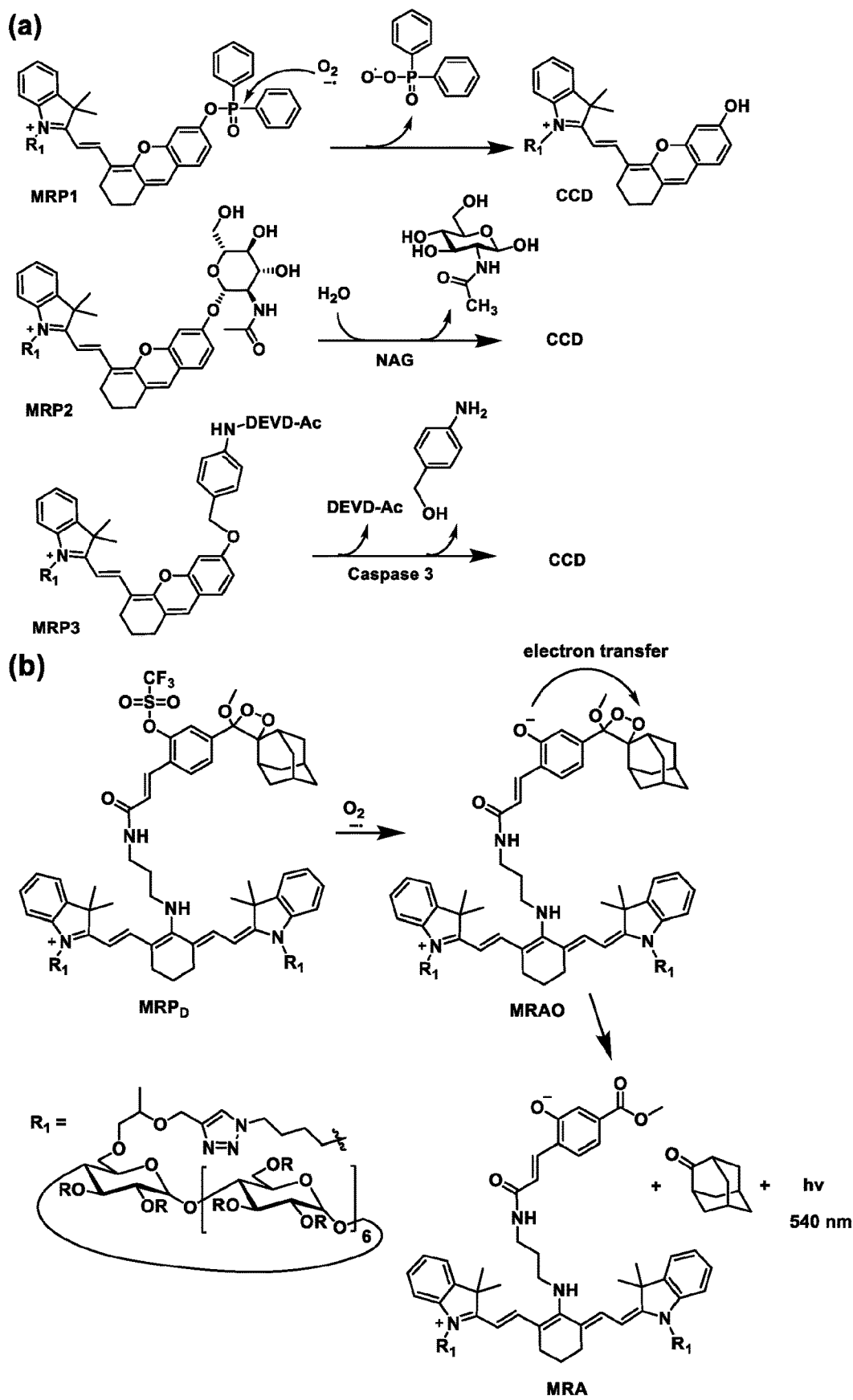

FIG. 12 Depict the proposed sensing mechanisms of: (a) MRP1, MRP2 and MRP3 for detection of superoxide anion, NAG, and caspase-3, respectively; and (b) $MRP_D$ for detection of superoxide anion (R: H or $CH_2CHOHCH_3$).

Figure 13:
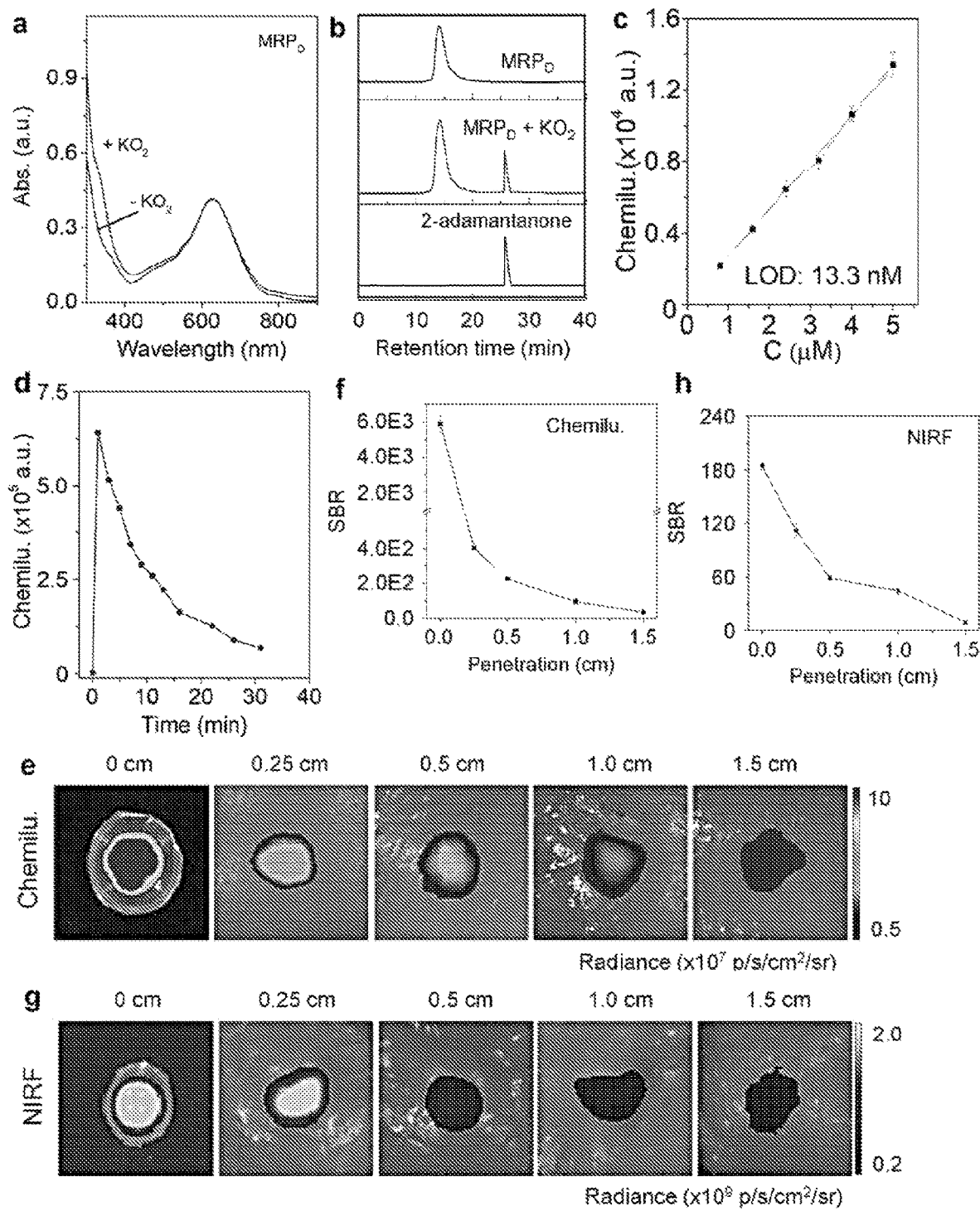

FIG. 13 Depicts the NIRF and chemiluminescence studies of $MRP_D$: (a) UV-Vis absorption of $MRP_D$ (30 μM) in the absence or presence of $KO_2$ (60 μM) in PBS buffer (10 mM, pH 7.4) at 37° C.; (b) HPLC analysis of the $MRP_D$ (30 μM) solutions in the absence and presence of $KO_2$ (60 μM) in PBS buffer (10 mM, pH 7.4) at 37° C. HPLC analysis of the pure 2-adamantanone is also indicated for comparison. The experiments in (a) and (b) were repeated independently three times with similar results; (c) linear relationship between the chemiluminescence intensities of $MRP_D$ (30 µM) and the concentration of $KO_2$ (0-5 µM). The limit of detection (LOD) was estimated to be as low as 13 nM (S/N=3). Data are the mean±SD. n=3 independent experiments; (d) chemiluminescence kinetic profiles of $MRP_D$ (30 µM) in the presence of $KO_2$ (60 µM) in PBS buffer (10 mM, pH 7.4) at 37° C. Tissue-penetration study of chemiluminescence and NIRF of $MRP_D$; (e) chemiluminescence imaging of the $MRP_D$ solutions (30 µM) after the addition of $KO_2$ (60 µM) through chicken tissues with different thickness. The experiments in (d) and (e) were repeated independently three times with similar results; (f) SBRs for chemiluminescence imaging of $MRP_D$ as a function of tissue depth. Data are the mean±SD. n=3 independent experiments; (g) NIRF imaging of the $MRP_D$ solutions through chicken tissues with different thickness. The experiments were repeated independently three times with similar results; and (h) SBRs for NIRF imaging of $MRP_D$ as a function of tissue depth. Chemiluminescence images were acquired using the IVIS spectrum imaging system under bioluminescence mode with open filter and the acquisition time of 180 s; NIRF images were obtained with the acquisition time of 0.1 s. Data are the mean±SD. n=3 independent experiments.

Figure 14:
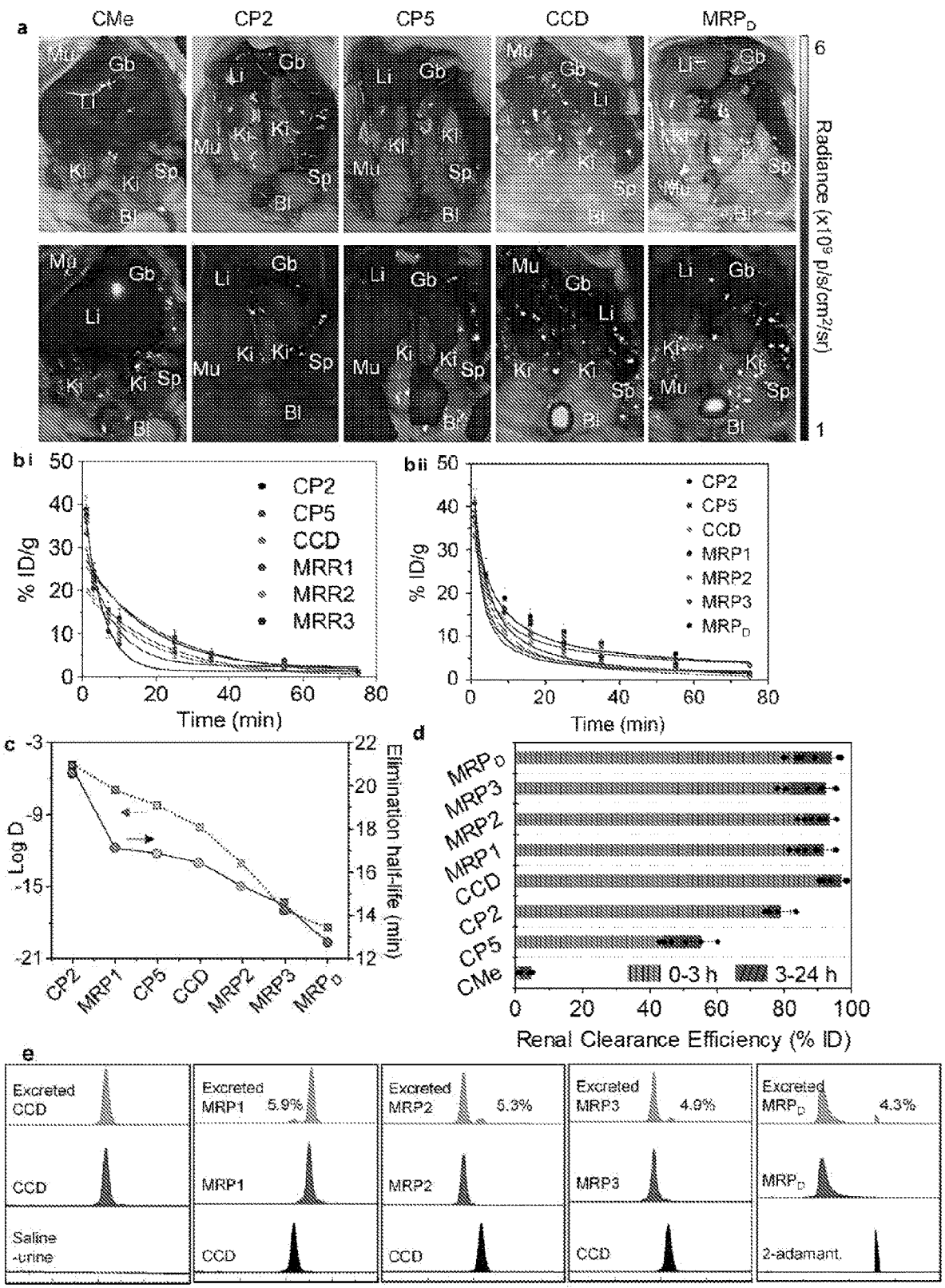

FIG. 14 Depicts renal clearance and in vivo stability studies of MRPs and the uncaged fluorophores: (a) NIRF images of the abdominal cavity of mice at t=60 min after intravenous injection of CMe, CP2, CP5, CCD or $MRP_D$. Bladder (Bl), gallbladder (Gb), kidneys (Ki), liver (Li), muscle (Mu), spleen (Sp). NIRF images acquired at 720 nm (760 nm for $MRP_D$) upon excitation at 675 nm (640 nm for $MRP_D$) with the IVIS spectrum imaging system; (bi) initial and (bii) subsequent studies on the blood concentration (% ID $g^{-1}$) decay of the uncaged fluorophores (CP2, CP5 and CCD) and MRPs after intravenous injection into living mice. Data are the mean±SD. n=3 independent mice; (c) correlation between elimination half-life and distribution coefficient (Log D) for the uncaged fluorophores (CP2, CP5 and CCD) and MRPs; (d) renal clearance efficiency of the uncaged fluorophores (CMe, CP2, CP5, and CCD) and MRPs at 0-3 h and 3-24 h after intravenous injection. Data are the mean±SD. n=3 independent mice; and (e) in vivo stability studies of CCD and MRPs through HPLC analysis of excreted components in the urine samples after intravenous injection. HPLC traces of the pure compounds (CCD, MRPs and 2-adamantanone) are also indicated for comparison. The experiments in (a) and (e) were repeated independently three times with similar results.

Figure 15:
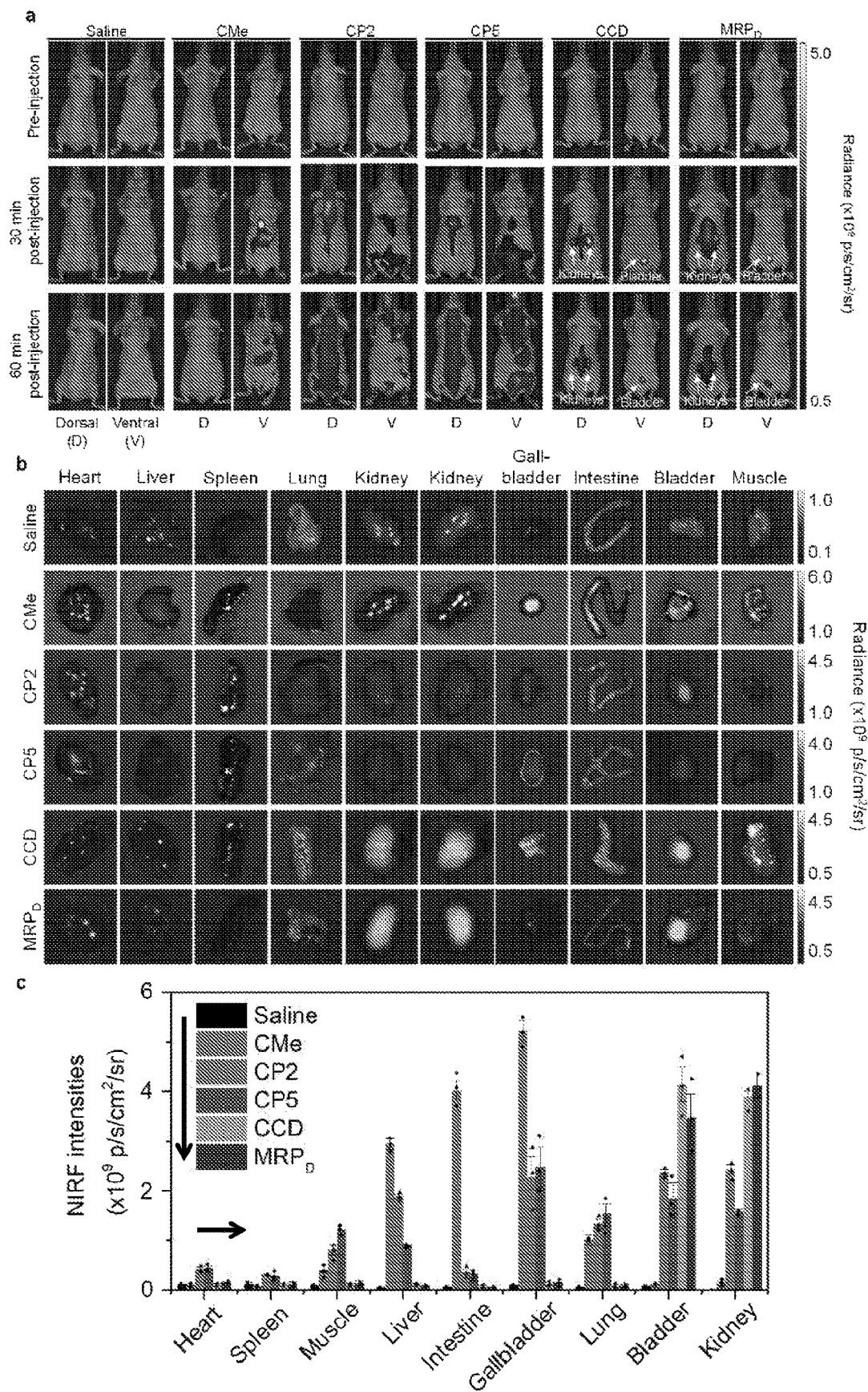

FIG. 15 Depicts the biodistribution studies of the uncaged fluorophores and $MRP_D$ in living mice: (a) representative NIRF images of both dorsal and ventral sides of living mice at 30 or 60 min after i.v injection of CMe, CP2, CP5, CCD (8 µmol $kg^{-1}$ body weight) and $MRP_D$ (32 µmol $kg^{-1}$ body weight), respectively. The white arrows in dorsal and ventral sides indicate the kidneys and the bladder, respectively; (b) ex vivo NIRF images of resected organs from mice at t=1 h post-injection of CMe, CP2, CP5, CCD or $MRP_D$. NIRF images acquired at 720 nm upon excitation at 675 nm with the IVIS spectrum imaging system. The experiments in (a) and (b) were repeated independently three times with similar results; and (c) ex vivo NIRF quantification of major organs of mice at t=1 h post-injection of saline, CMe, CP2, CP5, CCD or $MRP_D$ (from left to right of the charts for each organ) Data are the mean±SD. n=3 independent mice.

Figure 16:
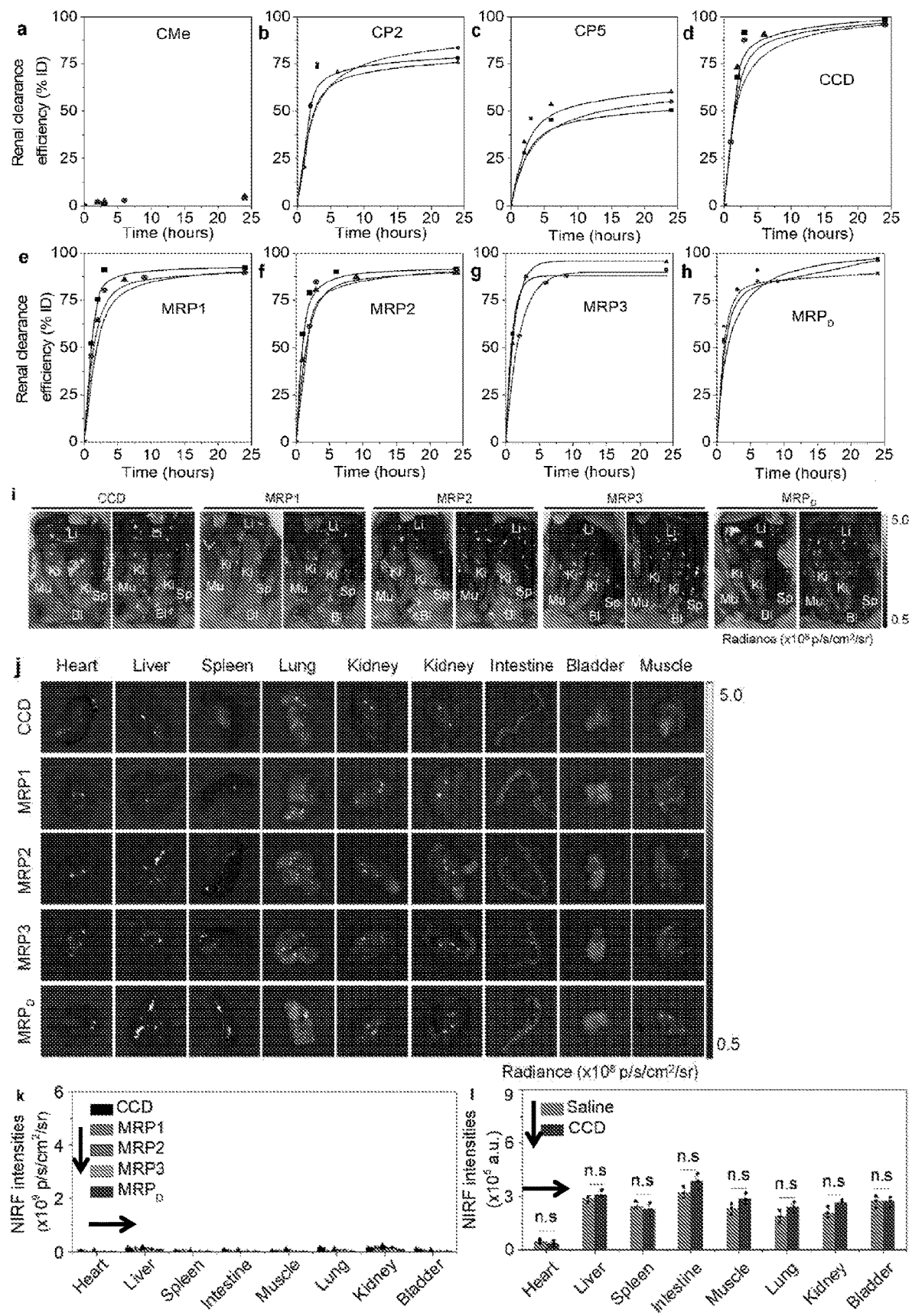

FIG. 16 Depicts renal clearance studies of the uncaged fluorophores and MRPs in living mice. Renal clearance efficiency as a function of time post-injection of (a) CMe, (b) CP2, (c) CP5, (d) CCD, (e) MRP1, (f) MRP2, (g) MRP3 (8 µmol $kg^{-1}$ body weight) or (h) $MRP_D$ (32 µmol $kg^{-1}$ body weight) into living mice (n=3 mice per injection group); (i) NIRF images of the abdominal cavity of mice at 24 h after i.v. injection of CCD, MRPs1-3 (8 µmol $kg^{-1}$ body weight), or $MRP_D$ (32 µmol $kg^{-1}$ body weight). Bladder (Bl), kidneys (Ki), liver (Li), muscle (Mu), spleen (Sp). The experiments were repeated independently three times with similar results; (j) ex vivo NIRF images of resected organs from mice at 24 h post-injection of CCD, MRPs1-3, or $MRP_D$. NIRF images acquired at 720 nm (760 nm for $MRP_D$) upon excitation at 675 nm (640 nm for $MRP_D$) with the IVIS spectrum imaging system. The experiments were repeated independently three times with similar results; (k) ex vivo NIRF quantification of major organs from mice at 24 h post-injection of CCD, MRPs1-3, or $MRP_D$. Data are the mean±SD. n=3 independent mice. No detectable NIRF signal was seen in any tissue 24 h after injection of CCD or MRPs. These results indicate that the HPβCD-substituted fluorophores are completely excreted renally after 24 h; and (l) fluorescence quantification of major organs from mice 24 h post-injection of saline or CCD (left and right of the charts, respectively for each organ). Fluorescence intensities (720 nm) were recorded on a fluorescence spectrophotometer after homogenisation of major organs in PBS buffer (10 mM, pH 7.4) and centrifugation to remove insoluble components. Fluorescence excitation at 675 nm. Data are the mean±SD. n=3 independent mice. Two-tailed student's t-test. Saline versus CCD group, n.s: not significant. Major organs from mice at 24 h post-injection of CCD had fluorescence intensities as low as those from the saline-injected mice, which further confirmed the complete renal excretion of CCD in mice after 24 h.

Figure 17:
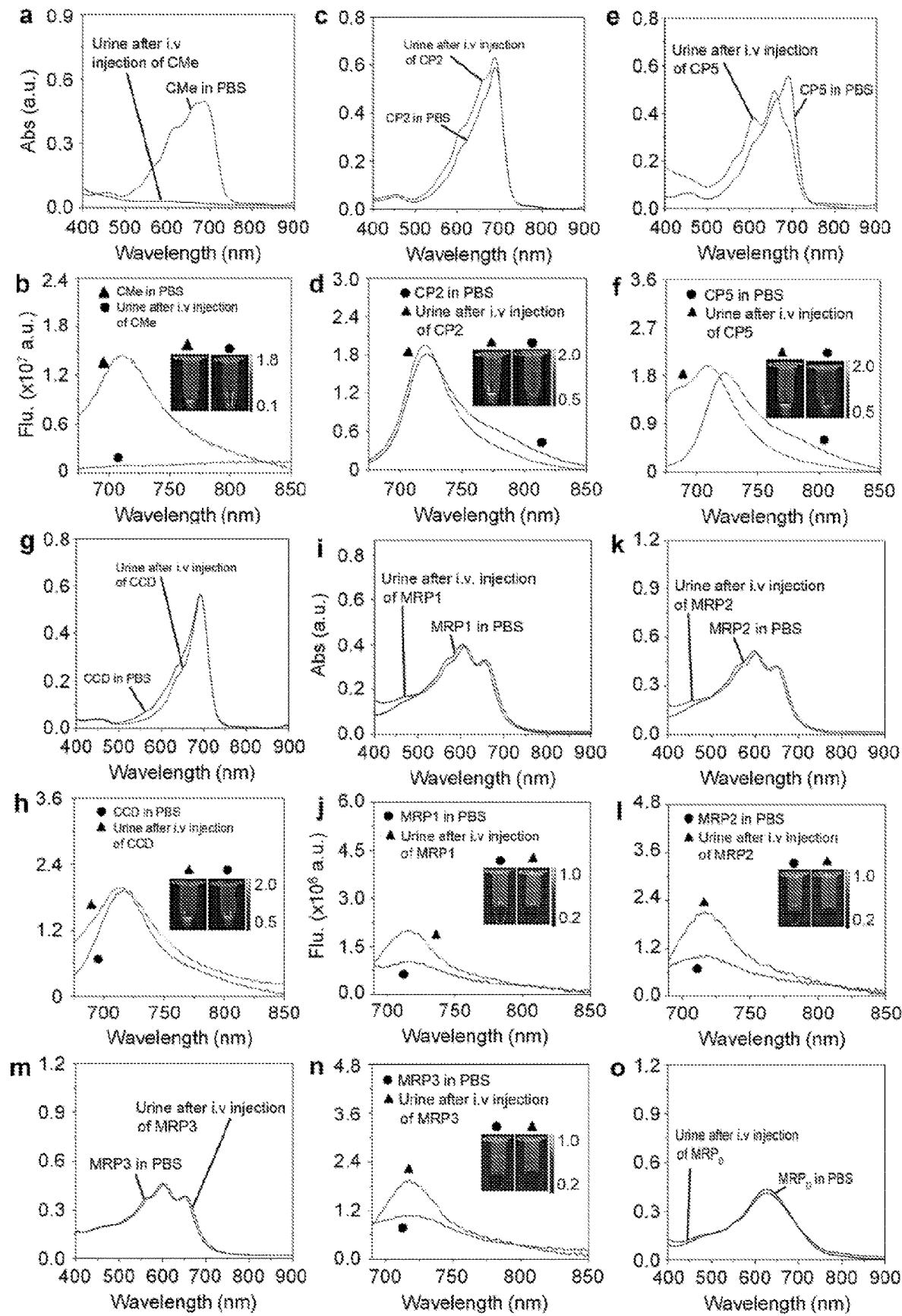

FIG. 17 Depicts in vivo stability studies of the uncaged fluorophores and MRPs using optical characterization. Absorption and fluorescence spectra of: (a, b) CMe; (c, d) CP2; (e, f) CP5; (g, h) CCD; (l, j) MRP1; (k, l) MRP2; (m, n) MRP3; and (o, p) $MRP_D$ in PBS buffer and the urine samples after i.v injection and excretion from living mice. Inset: the corresponding fluorescence images acquired at 720 nm upon excitation at 675 nm with the IVIS spectrum imaging system. The experiments were repeated independently three times with similar results.

Figure 18:
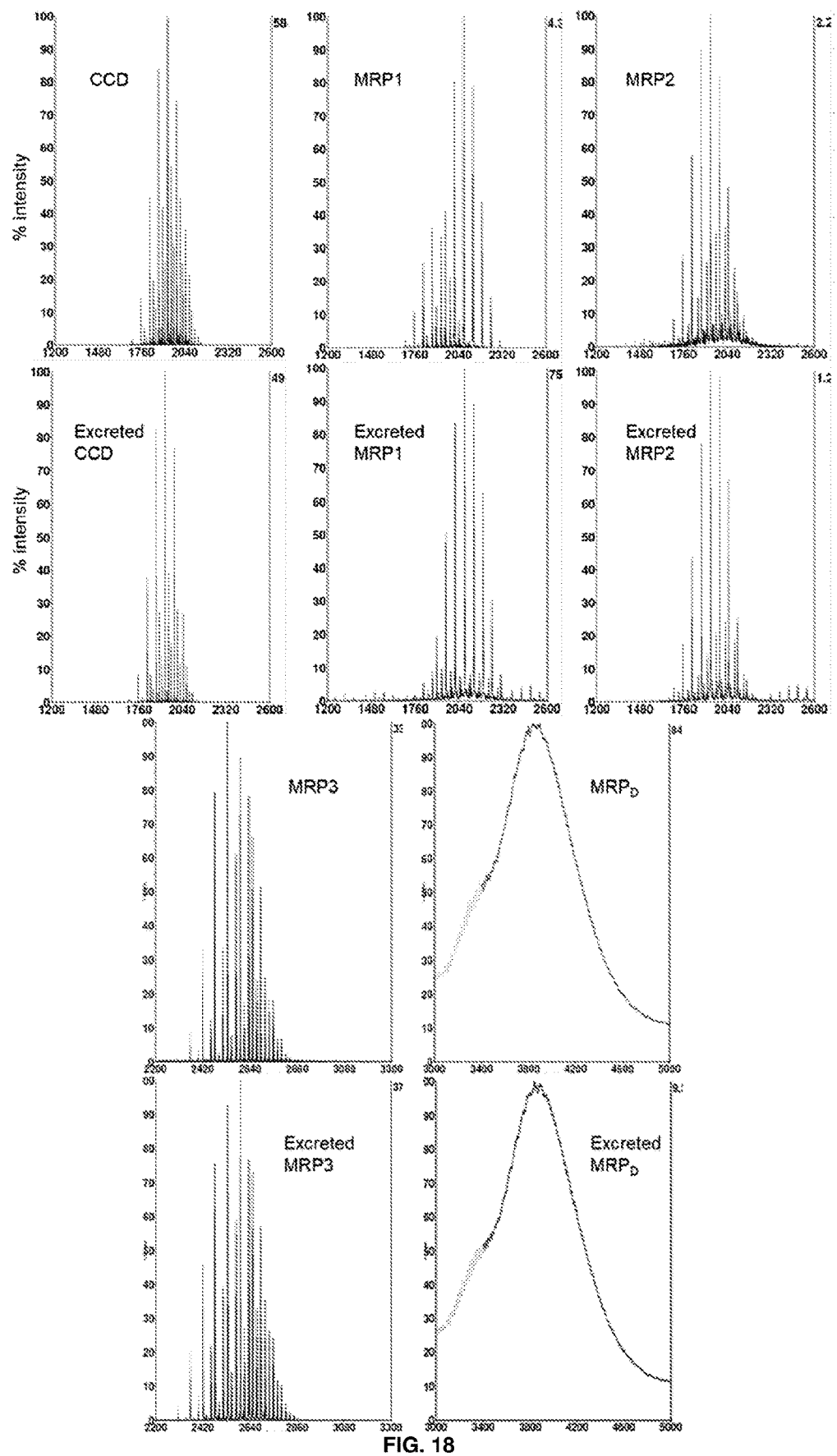

FIG. 18 Depicts in vivo stability studies of CCD and MRPs using MALDI-TOF mass spectrometry. In vivo stability studies of CCD and MRPs through MALDI-TOF mass analysis of the urine samples after i.v injection (8 µmol $kg^{-1}$ body weight for MRPs1-3 or 32 µmol $kg^{-1}$ body weight for $MRP_D$). MALDI-TOF mass analysis of the pure compounds (CCD and MRPs) in PBS are also indicated for comparison. Excreted CCD and MRPs had the identical mass range compared to that of the pure compounds in PBS. Note that the MALDI-TOF mass spectra of CCD and MRPs1-3 were performed in the reflector mode; the $MRP_D$ spectra were collected in linear mode because it cannot be obtained using the reflector mode. The experiments were repeated independently three times with similar results.

Figure 19:
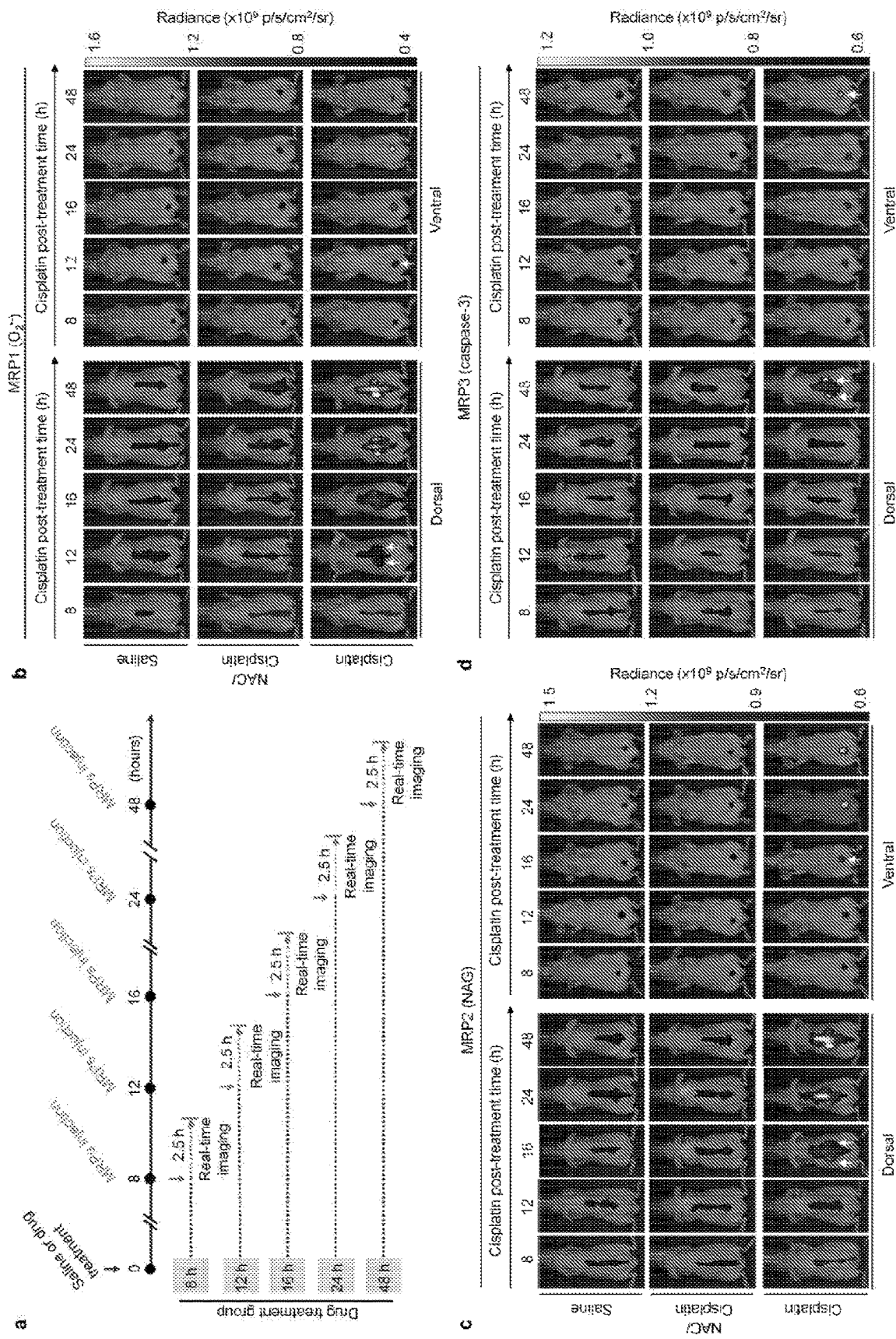
Figure 19:
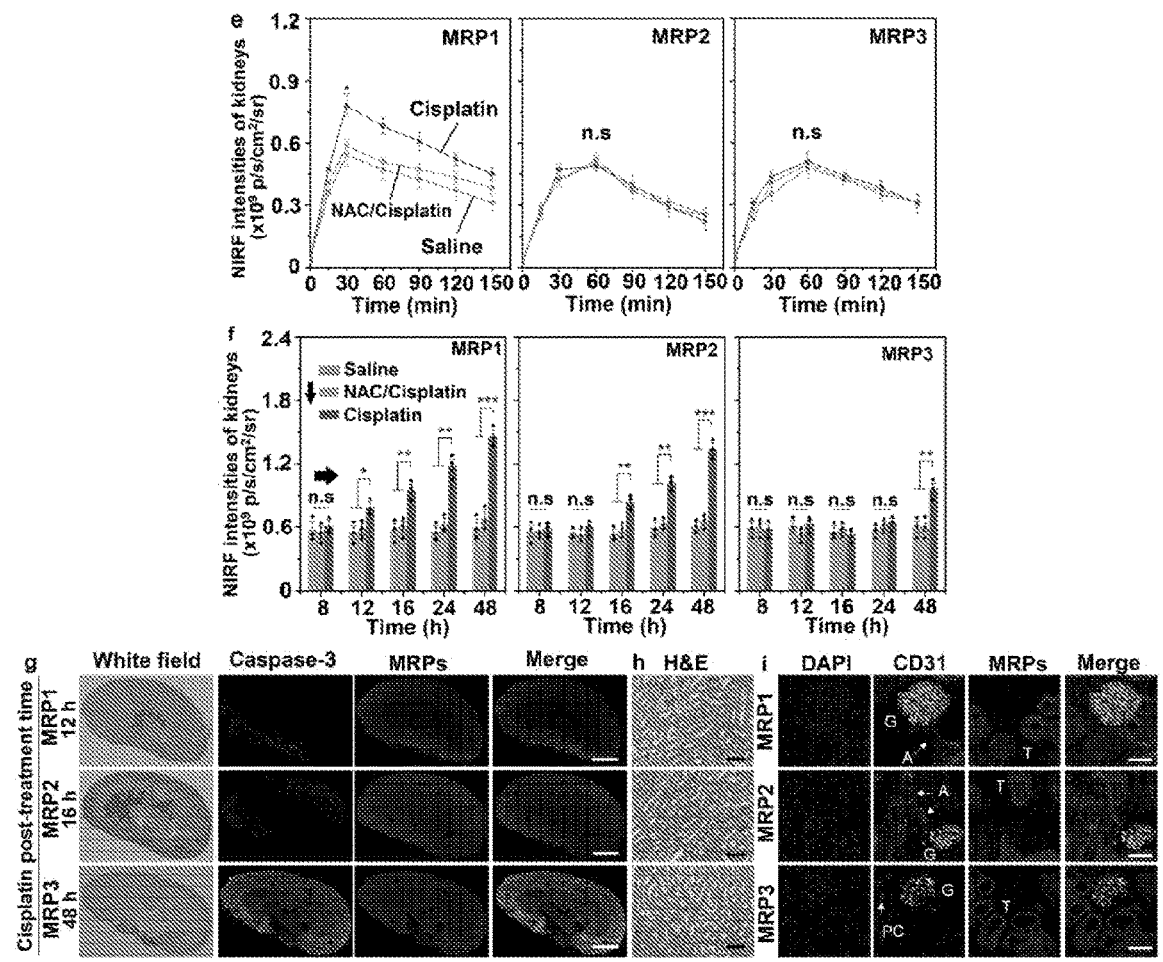

FIG. 19 Depicts real-time in vivo NIRF imaging of cisplatin-induced AKI: (a) schematic illustration of development of cisplatin (20 mg $kg^{-1}$ body weight)-induced AKI mouse model and NIRF imaging at different post-treatment timepoints; representative NIRF images of living mice after i.v injection of (b) MRP1, (c) MRP2, and (d) MRP3 at different post-treatment timepoints (8, 12, 16, 24 or 48 h). The white arrows indicate the kidneys and bladder in dorsal and ventral side, respectively; (e) the dynamic NIRF intensities of kidneys as a function of time post-injection of MRPs1-3 in living mice after treatment of cisplatin for 12 h. Data are the mean±SD. n=3 independent mice. Two-tailed student's t-test. Saline, NAC/cisplatin versus cisplatin-treated groups, n.s: not significant, *p<0.05; (f) NIRF intensities of kidneys in living mice t=30 min after i.v injection of MRP1 or 60 min after i.v injection of MRPs2-3 at the different post-treatment timepoints (8, 12, 16, 24 or 48 h). Data are the mean±SD, and represent mice treated with saline, NAC/cisplatin and cisplatin, respectively, from left to right of the charts of each timepoint. n=3 independent mice. Two-tailed student's t-test. Saline, NAC/cisplatin versus cisplatin-treated groups, n.s: not significant, *p<0.05, p<0.01, *p<0.001; and (g) representative confocal fluorescence microscopy images of the whole kidney slices from mice with i.v injection of MRP1, MRP2, and MRP3 at t=12, 16 and 48 h post-treatment of cisplatin, respectively. Scale bars, 2 mm; (h) representative photomicrographs of H&E staining in paraffin-embedded kidney sections from mice 12, 16, or 48 h after cisplatin treatment. Scale bar, 50 µm; and (i) representative confocal fluorescence microscopy images of regional kidney slices from mice with i.v injection of MRP1, MRP2, and MRP3 at t=12, 16, and 48 h post-treatment of cisplatin, respectively. Glomerulus (G), tubules (T), arteriole (A), peritubular capillaries (PC). Scale bars, 40 µm. The experiments in (b-d) and (g-i) were repeated independently three times with similar results.

Figure 20:
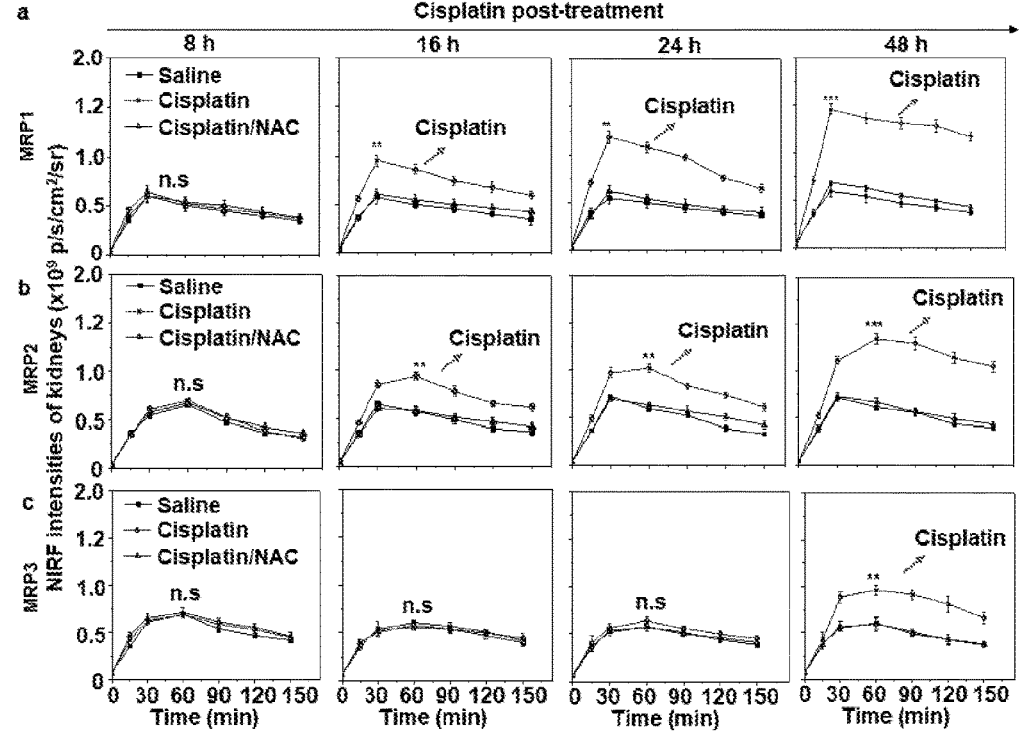

FIG. 20 Depicts the dynamic NIRF intensities of kidneys as a function of time post-injection of: (a-c) MRPs1-3 (8 µmol kg$^{-1}$ body weight) in living mice after treatment of cisplatin (20 mg kg$^{-1}$ body weight) for 8, 16, 24 or 48 h. Data are the mean±SD. n=3 independent mice. Two-tailed student's t-test. Saline, NAC/cisplatin versus cisplatin-treated groups, n.s: not significant, *p<0.05, p<0.01, *p<0.001.

Figure 21:
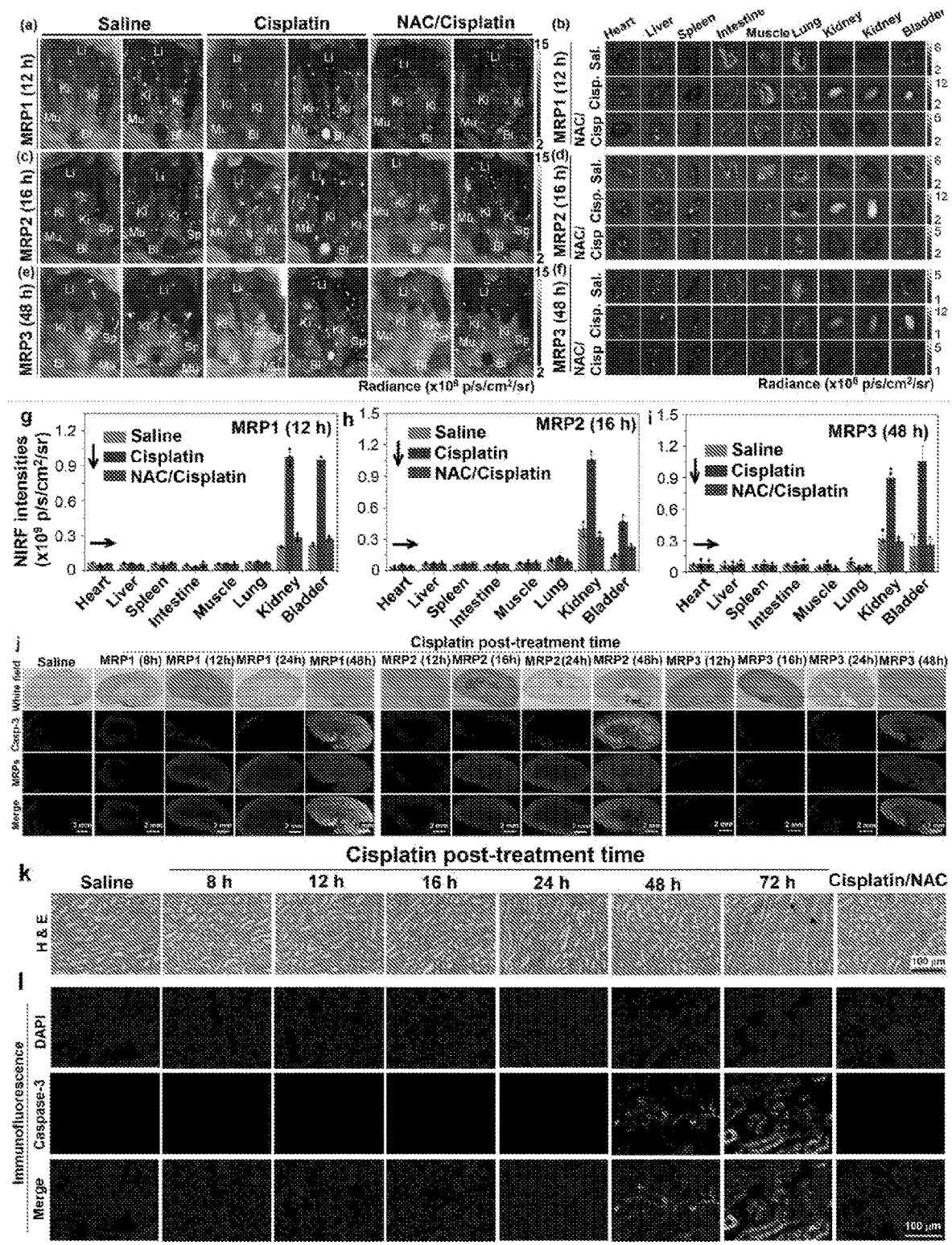

FIG. 21 Depicts ex vivo NIRF signal analysis of MRPs1-3 in the mouse model of cisplatin-induced AKI. Representative NIRF images of the abdominal cavity of mice with i.v injection of (a) MRP1, (c) MRP2, and (e) MRP3 (8 µmol kg$^{-1}$ body weight) after treatment of cisplatin (20 mg kg$^{-1}$ body weight) for 12, 16 and 48 h, respectively. The control groups were treated with saline (0.2 ml) or a nephroprotective antioxidant (NAC, 400 mg kg$^{-1}$ body weight, i.v injection) 30 min prior to cisplatin administration. Liver (Li), muscle (Mu), spleen (Sp), kidneys (Ki), bladder (Bl). The experiments were repeated independently three times with similar results; (b, d and f) ex vivo NIRF images and (g, h and i) signal quantification of resected organs from mice with i.v injection of MRP1 (b, g), MRP2 (d, h) or MRP3 (f, i) after treatment of cisplatin for 12, 16 and 48 h, respectively. NIRF images acquired at 720 nm upon excitation at 675 nm with the IVIS spectrum imaging system. Data are the mean±SD. n=3 independent mice. The bladder from cisplatin-treated mouse in the panel of d showed lower fluorescence intensity compare to that of in the panel of c due to urinary incontinence and bladder emptying after resection. For (g-i), the data represent mice treated with saline, NAC/cisplatin and cisplatin, respectively, from left to right of the charts of each organ; (j) confocal fluorescence microscopy images of the whole kidney slices from mice with i.v injection of saline, or MRP1 at t=8, 12, 24, or 48 h post-treatment of cisplatin, or MRP2 at t=12, 16, 24 or 48 h post-treatment of cisplatin, or MRP3 at t=12, 16, 24 or 48 h post-treatment of cisplatin. The green channel indicates signal from caspase-3 antibody staining, and the red channel indicates the signal from activated MRPs. (Scale bars=2 mm). The experiments were repeated independently three times with similar results. (k) Representative photomicrographs of H&E staining in paraffin embedded kidney sections from mice after treatment of cisplatin for 8, 12, 16, 24, 48 or 72 h, mice given saline (0.2 ml), or mice given a a nephroprotective antioxidant (NAC, 400 mg kg$^{-1}$ body weight, i.v injection) 30 min prior to cisplatin administration. The black arrow and triangle indicate loss of the brush border and hyaline casts, respectively. (Scale bar=100 µm). The experiments were repeated independently three times with similar results. (i) Confocal fluorescence microscopy images of kidney slices from mice after treatment of saline (0.2 ml), cisplatin for 8, 12, 16, 24, 48 or 72 h, or a nephroprotctive antioxidant (NAC, 400 mg kg$^{-1}$ body weight, i.v injection) 30 min prior to cisplatin administration. (Scale bar=100 µm). The blue and green signals come from DAPI and caspase-3 antibody staining, respectively. The experiments were repeated independently three times with similar results.

Figure 22:
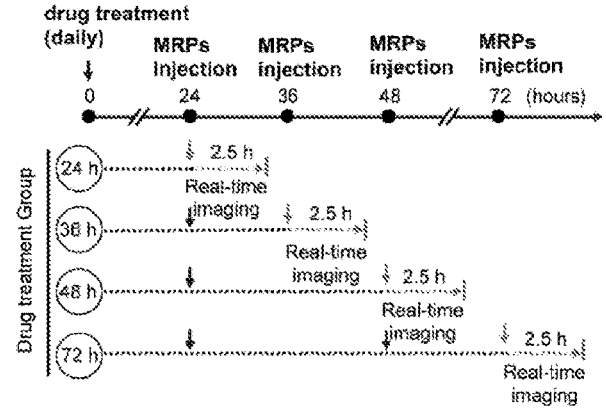
Figure 22:
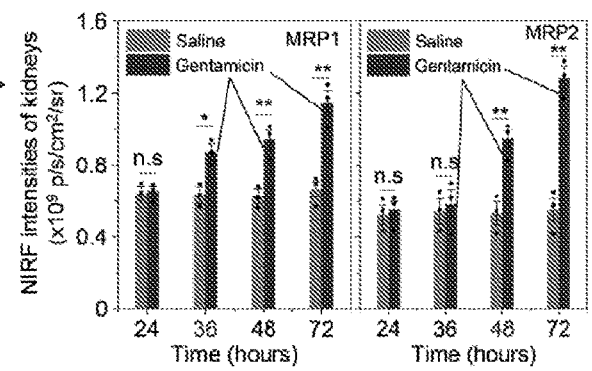
Figure 22:
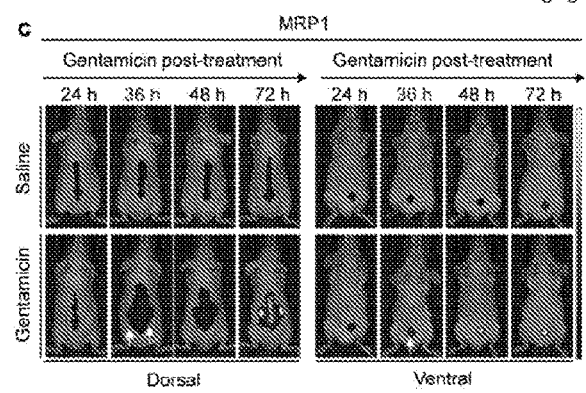
Figure 22:
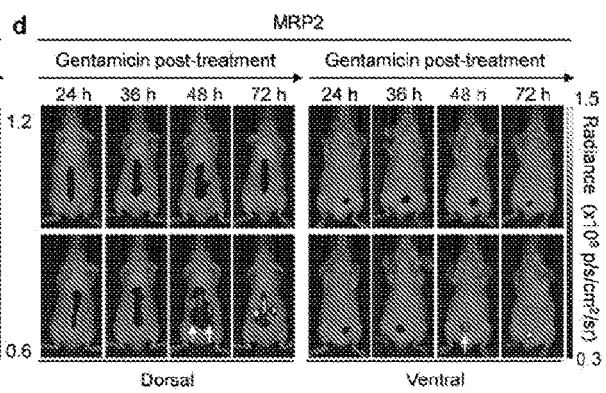
Figure 22:
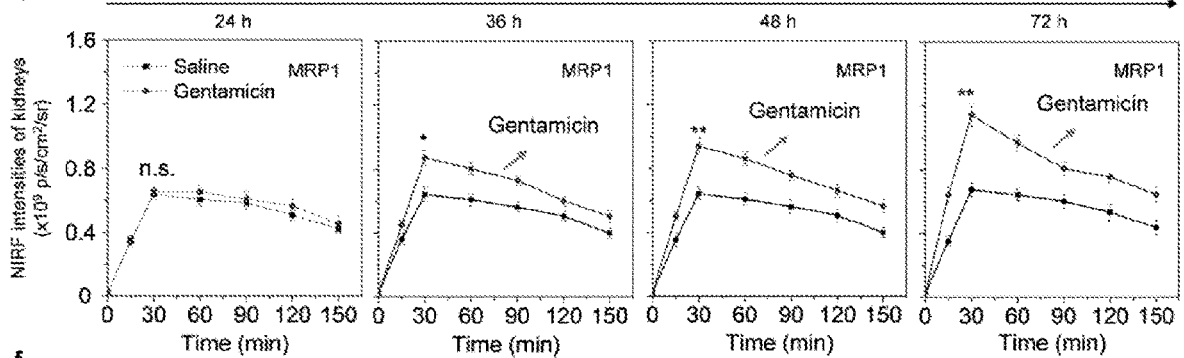
Figure 22:
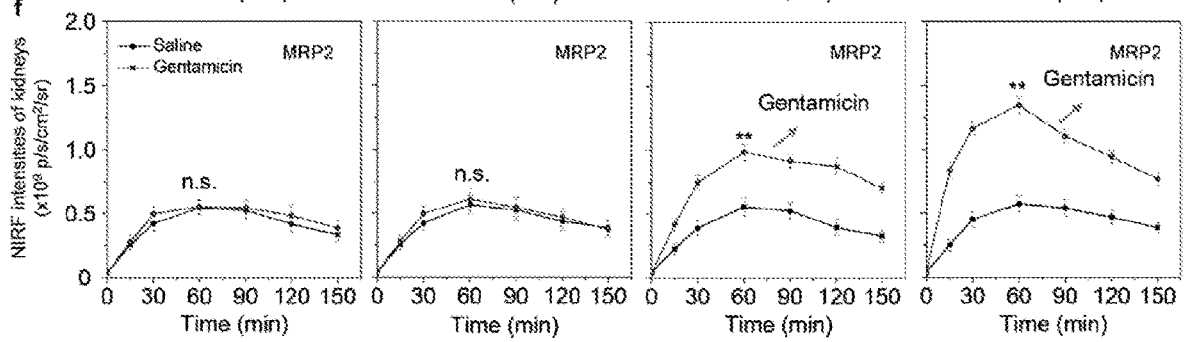

FIG. 22 Depicts real-time in vivo NIRF imaging of gentamicin-induced AKI in living mice: (a) schematic illustration of development of gentamicin-induced AKI model and NIRF imaging at different post-treatment timepoints. Gentamicin was intraperitoneally administered into living mice at 100 mg kg$^{-1}$ day$^{-1}$ (blue arrows indicate administration of gentamicin) followed by i.v injection of MRP1 or MRP2 (8 µmol kg$^{-1}$ body weight) at different timepoints post-treatment of gentamicin (24, 36, 48 or 72 h). The control groups were treated with saline (0.2 ml). Real-time NIRF imaging was conducted every 30 min for 2.5 h after i.v injection of MRP1 or MRP2; (b) NIRF intensities of kidneys in living mice at t=30 min after i.v injection of MRP1 or 60 min after i.v injection of MRP2 at different post-treatment timepoints (24, 36, 48 or 72 h). Data are the mean±SD, and represent mice treated with saline and gentamicin, respectively, for the left and right charts of each timepoint. n=3 independent mice. Two-tailed student's t-test. Saline versus gentamicin treated groups, n.s: not significant, *p<0.05, p<0.01, *p<0.001; representative NIRF images of living mice at t=30 min after i.v injection of (c) MRP1, or 60 min after i.v injection of (d) MRP2 at different post-treatment timepoints (24, 36, 48 or 72 h). MRP1 and MRP2 had the highest signals at 30 and 60 min post-injection, respectively. The white arrows indicate the kidneys and bladder in dorsal and ventral side, respectively. NIRF images acquired at 720 nm upon excitation at 675 nm with the IVIS spectrum imaging system. The experiments were repeated independently three times with similar results; dynamic NIRF intensities of kidneys as a function of time post-injection of (e) MRP1, and (f) MRP2 in living mice after treatment of gentamicin for 24, 36, 48 or 72 h. Data are the mean±SD. n=3 independent mice. Two-tailed student's t-test. Saline versus gentamicin treated groups, n.s: not significant, *p<0.05, p<0.01, *p<0.001.

Figure 23:
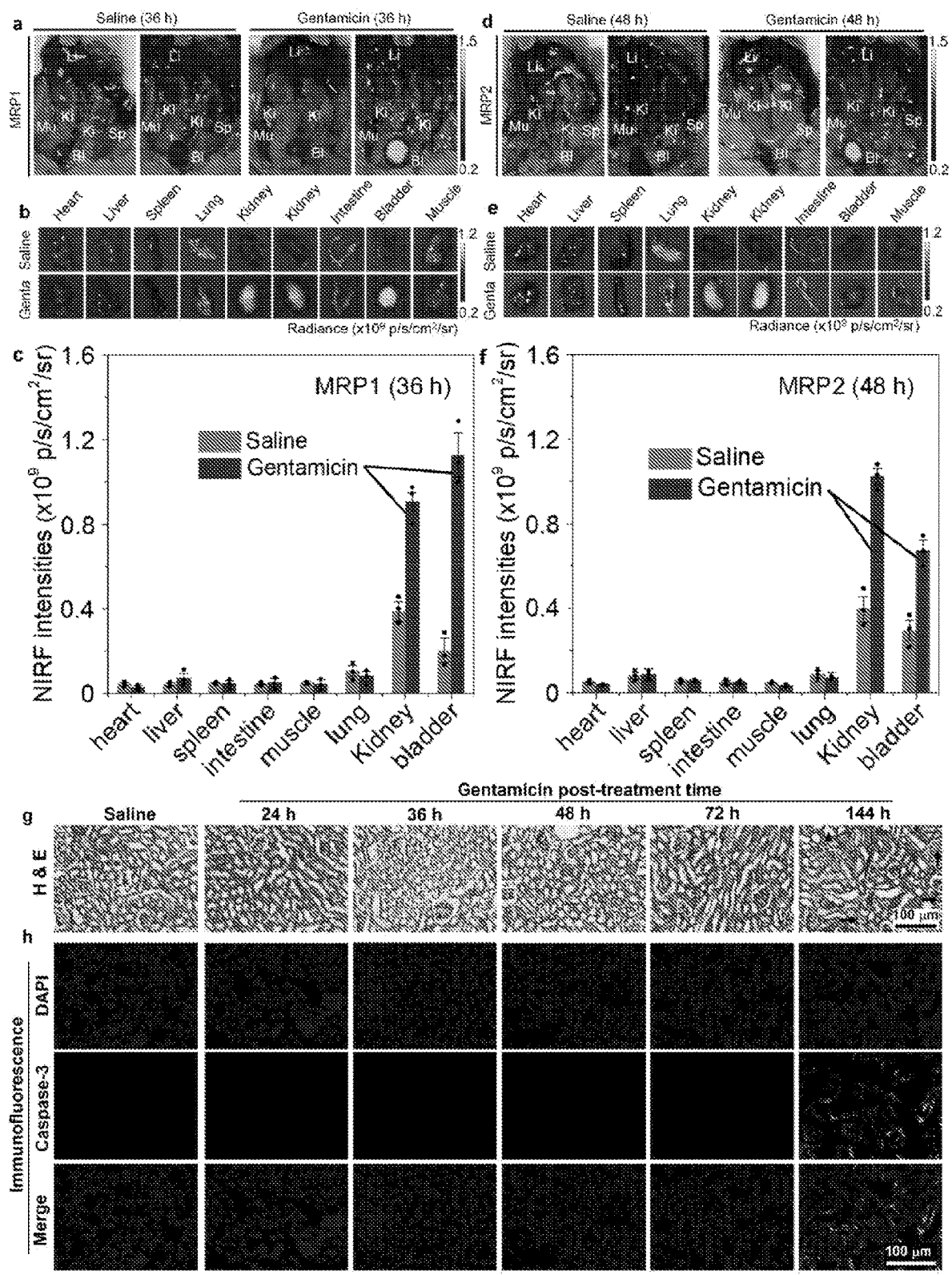

FIG. 23 Depicts ex vivo NIRF signal analysis of MRPs1-2 in the mouse model of gentamicin-induced AKI. Representative NIRF images of the abdominal cavity of mice with i.v injection of (a) MRP1, and (d) MRP2 (8 µmol kg$^{-1}$ body weight) after treatment of gentamicin (100 mg kg$^{-1}$ day$^{-1}$) for 36 and 48 h, respectively. The control groups were treated with saline (0.2 ml). Liver (Li), muscle (Mu), spleen (Sp), kidneys (Ki), bladder (Bl). The experiments were repeated independently three times with similar results; (b, e) ex vivo NIRF images, and (c, f) signal quantification of resected organs from mice with i.v injection of MRP1 (b, c) and MRP2 (e, f) after treatment of gentamicin for 36 and 48 h, respectively. The bladder from gentamicin-treated mouse in the panel of (e) showed lower fluorescence intensity than that in panel of (d) due to urinary incontinence and bladder emptying after resection. The NIRF images acquired at 720 nm upon excitation at 675 nm with the IVIS spectrum imaging system. Data are the mean±SD. n=3 independent mice. For (c) and (f), the data represent mice treated with saline and gentamicin, respectively, for the left and right charts of each organ; (g) representative photomicrographs of H&E staining in paraffin embedded kidney sections from mice after treatment of saline (0.2 ml), or after treatment of gentamicin for 24, 36, 48, 72 or 144 h. Green arrows and triangle indicate hyaline casts and tubular dilatation, respectively. (Scale bar=100 μm); and (h) confocal fluorescence microscopy images of kidney slices from mice after treatment of saline (0.2 ml), or mice after treatment of gentamicin for 24, 36, 48, 72 or 144 h. The blue and green signals come from DAPI and caspase-3 antibody staining, respectively (Scale bar=100 μm). The experiments were repeated independently three times with similar results.

Figure 24:
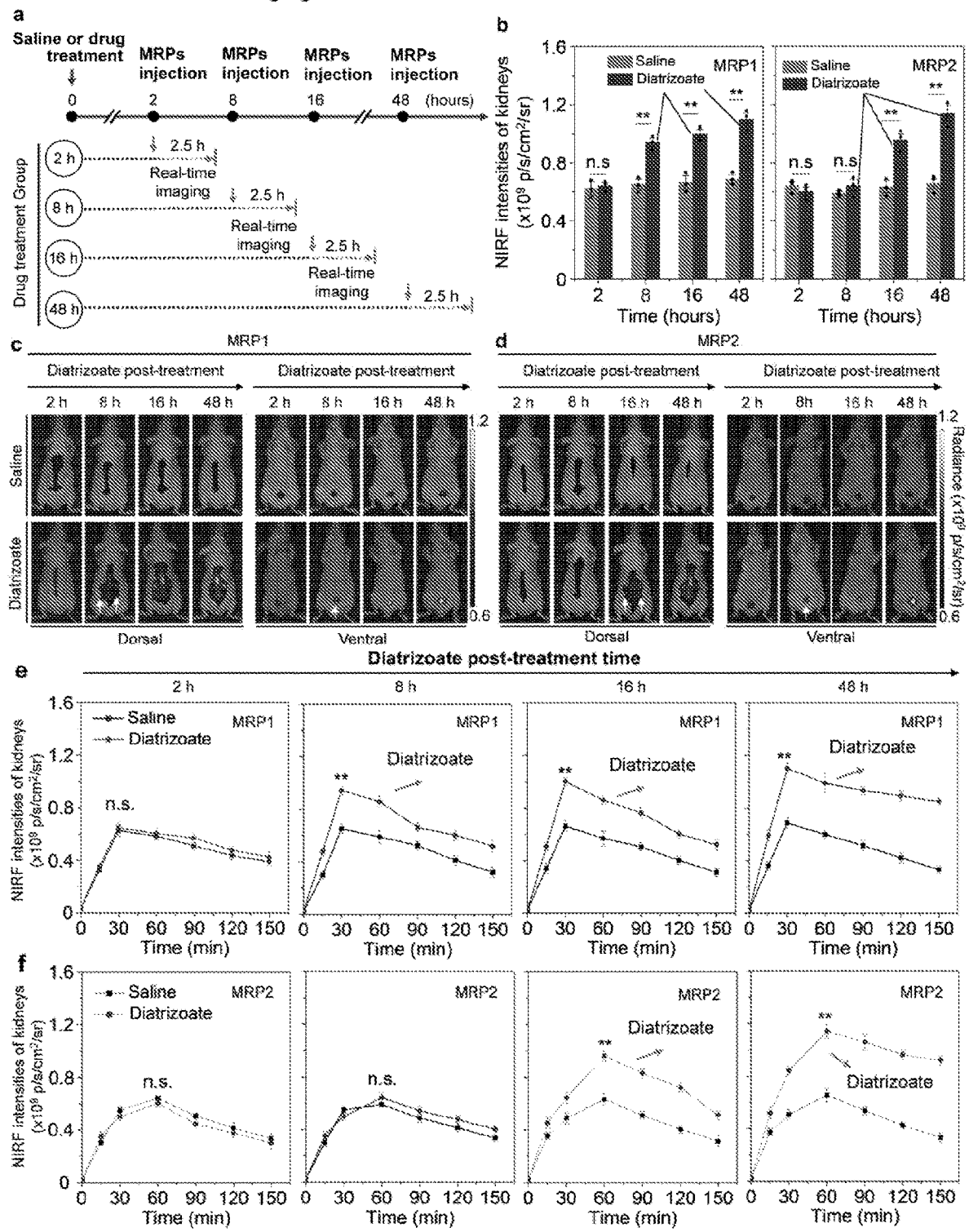

FIG. 24 Depicts real-time in vivo NIRF imaging of diatrizoate-induced AKI: (a) schematic illustration of development of diatrizoate-induced AKI model and NIRF imaging at different post-treatment timepoints. Diatrizoate was intravenously administered into living mice at a dosage of 1000 mg kg$^{-1}$ body weight followed by i.v injection of MRPs1-2 (8 μmol kg$^{-1}$ body weight) at different timepoints post-treatment of diatrizoate (2, 8, 16 or 48 h). The control groups were treated with saline (0.2 ml). Real-time NIRF imaging was conducted every 30 min for 2.5 h after i.v injection of MRP1 or MRP2; (b) NIRF intensities of kidneys in living mice at t=30 min after i.v injection of MRP1 or 60 min after i.v injection of MRP2 after different post-treatment timepoints (2, 8, 16 or 48 h). Data are the mean±SD, and represent mice treated with saline and diatrizoate, respectively, for the left and right charts of each timepoint. n=3 independent mice. Two-tailed student's t-test. Saline versus diatrizoate treated groups, n.s: not significant, *p<0.05, p<0.01, *p<0.001; representative NIRF images of living mice at t=30 min after i.v injection of (c) MRP1, and (d) 60 min after i.v injection of MRP2 after different post-treatment timepoints (2, 8, 16 or 48 h). MRP1 and MRP2 had the highest signals at 30 and 60 min post-injection, respectively. The white arrows indicate the kidneys and bladder on the dorsal and ventral side, respectively. NIRF images acquired at 720 nm upon excitation at 675 nm with the IVIS spectrum imaging system. The experiments were repeated independently three times with similar results; dynamic NIRF intensities of kidneys as a function of time post-injection of (e) MRP1, and (f) MRP2 in living mice after treatment of diatrizoate for 2, 8, 16 or 48 h. Data are the mean±SD. n=3 independent mice. Two-tailed student's t-test. Saline versus diatrizoate treated groups, n.s: not significant, *p<0.05, p<0.01, *p<0.001.

Figure 25:
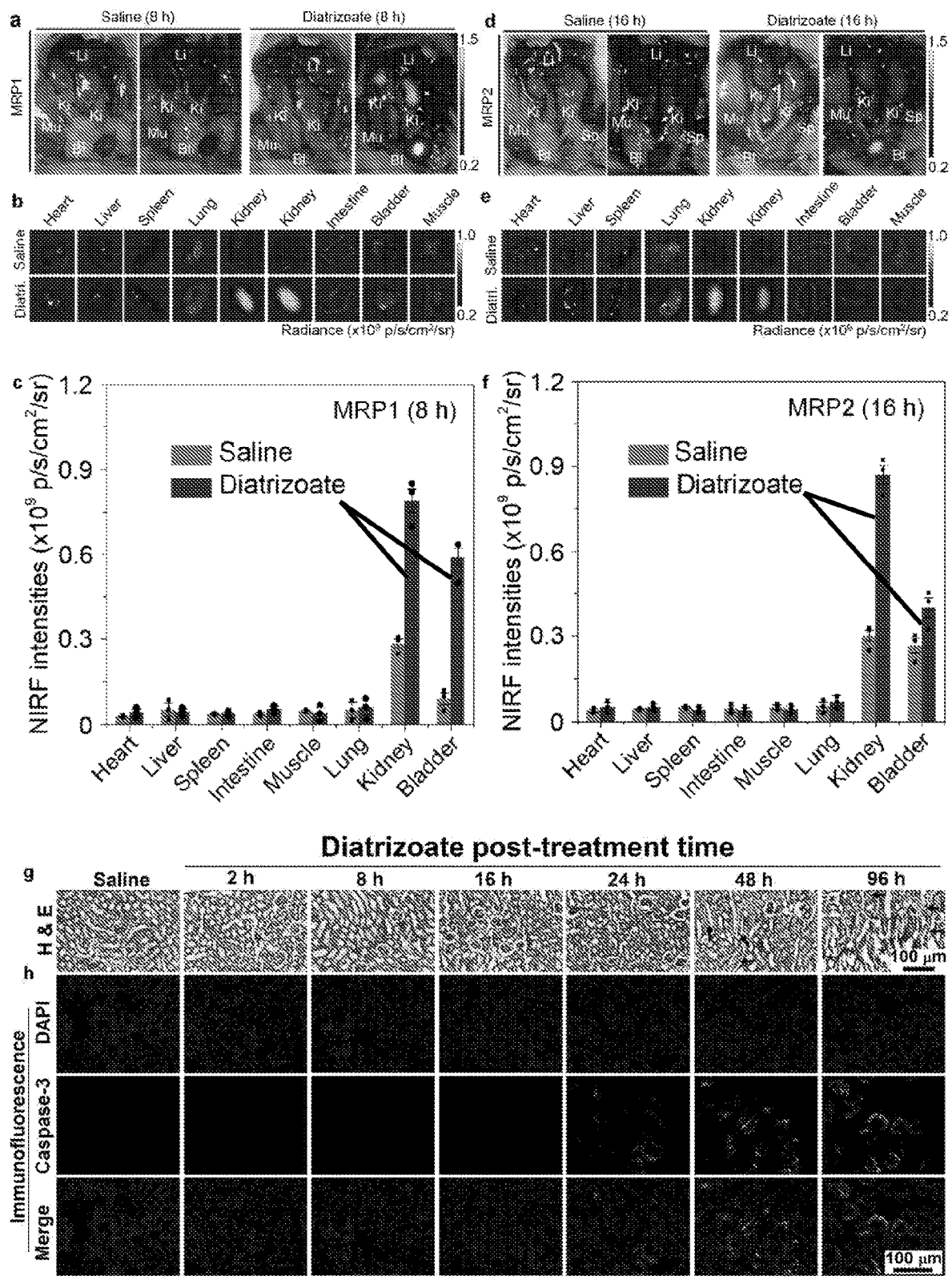

FIG. 25 Depicts ex vivo NIRF signal analysis of MRPs1-2 in the mouse model of diatrizoate-induced AKI. NIRF images of the abdominal cavity of mice with i.v injection of (a) MRP1, and (d) and MRP2 (8 μmol kg$^{-1}$ body weight) after treatment of diatrizoate (1 g kg$^{-1}$ body weight) for 8 and 16 h, respectively. The control groups were treated with saline (0.2 ml). Liver (Li), muscle (Mu), spleen (Sp), kidneys (Ki), bladder (Bl). The experiments were repeated independently three times with similar results; (b, e) ex vivo NIRF images, and (c, f) signal quantification of resected organs from mice with i.v injection of (b, c) MRP1, and (e, f) MRP2 after treatment of diatrizoate for 8 and 16 h, respectively. The bladder from diatrizoate-treated mouse in the panel of e showed lower fluorescence intensity compared to panel d due to urinary incontinence and bladder emptying after resection. NIRF images acquired at 720 nm upon excitation at 675 nm with the IVIS spectrum imaging system. Data are the mean±SD. n=3 independent mice. For (c) and (f), the data represent mice treated with saline and diatrizoate, respectively, for the left and right charts of each organ; (g) representative photomicrographs of H&E staining in paraffin embedded kidney sections from mice after treatment of saline (0.2 ml), or after treatment of diatrizoate for 2, 8, 16, 24, 48 or 96 h. Green arrows and red asterisks indicate hyaline casts and tubular dilatation, respectively. (Scale bar=100 μm); and (h) confocal fluorescence microscopy images of kidney slices from mice after treatment of saline (0.2 ml), or after treatment of diatrizoate for 2, 8, 16, 24, 48 or 96 h. The blue and green signals come from DAPI and caspase-3 antibody staining, respectively (Scale bar=100 μm). The experiments were repeated independently three times with similar results.

Figure 26:
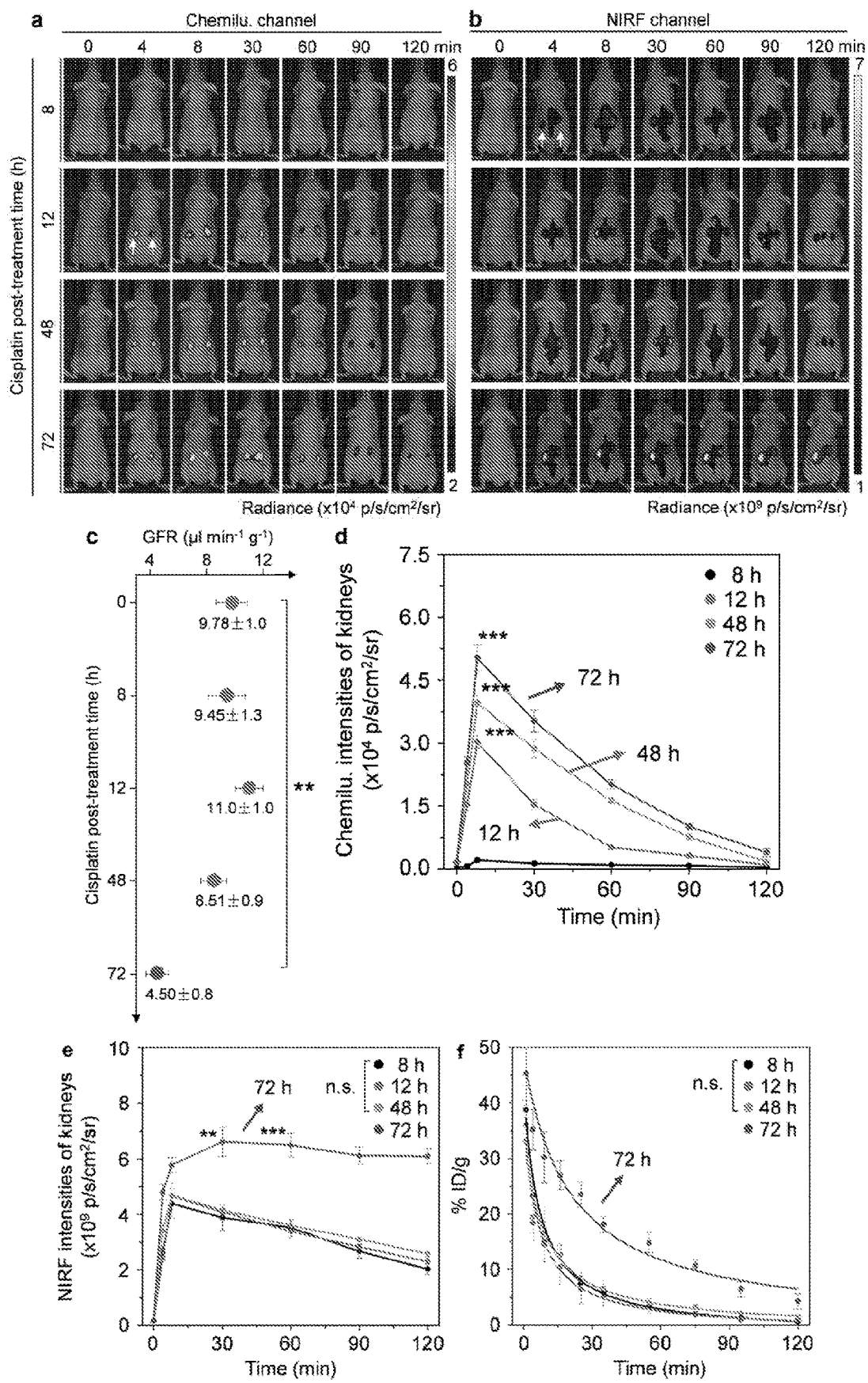

FIG. 26 Depicts real-time in vivo dual-channel imaging of cisplatin-induced AKI: (a) representative chemiluminescence, and (b) NIRF images of living mice with i.v injection of $MRP_D$ after treatment of cisplatin (20 mg kg$^{-1}$ body weight) for 8, 12, 48 or 72 h. The experiments were repeated independently three times with similar results; (c) GFR of living mice at t=8, 12, 48, or 72 h post-treatment of cisplatin, or saline, measured by the standard FITC-Inulin method. Data are the mean±SD. n=3 independent mice. Two-tailed student's t-test. Pre-treatment versus 8, 12, 48 h post-treatment groups, not significant; Pre-treatment versus 72 h post-treatment group, p<0.01; (d) the dynamic chemiluminescence, and (e) NIRF intensities of kidneys as a function of time post-injection of $MRP_D$ in living mice after treatment of cisplatin for 8, 12, 48 or 72 h. Data are the mean±SD. n=3 independent mice. Two-tailed student's t-test. 8 h post-treatment versus 12, 48, or 72 h post-treatment groups, n.s: not significant, p<0.01, ***p<0.001; and (f) blood concentration (% ID g$^{-1}$) decay of $MRP_D$ in the living mice at t=8, 12, 48 or 72 h post-treatment of cisplatin. Data are the mean±SD. n=3 independent mice. Two-tailed student's t-test. 8 h post-treatment versus 12, or 48 h post-treatment groups, n.s: not significant.

Figure 27:
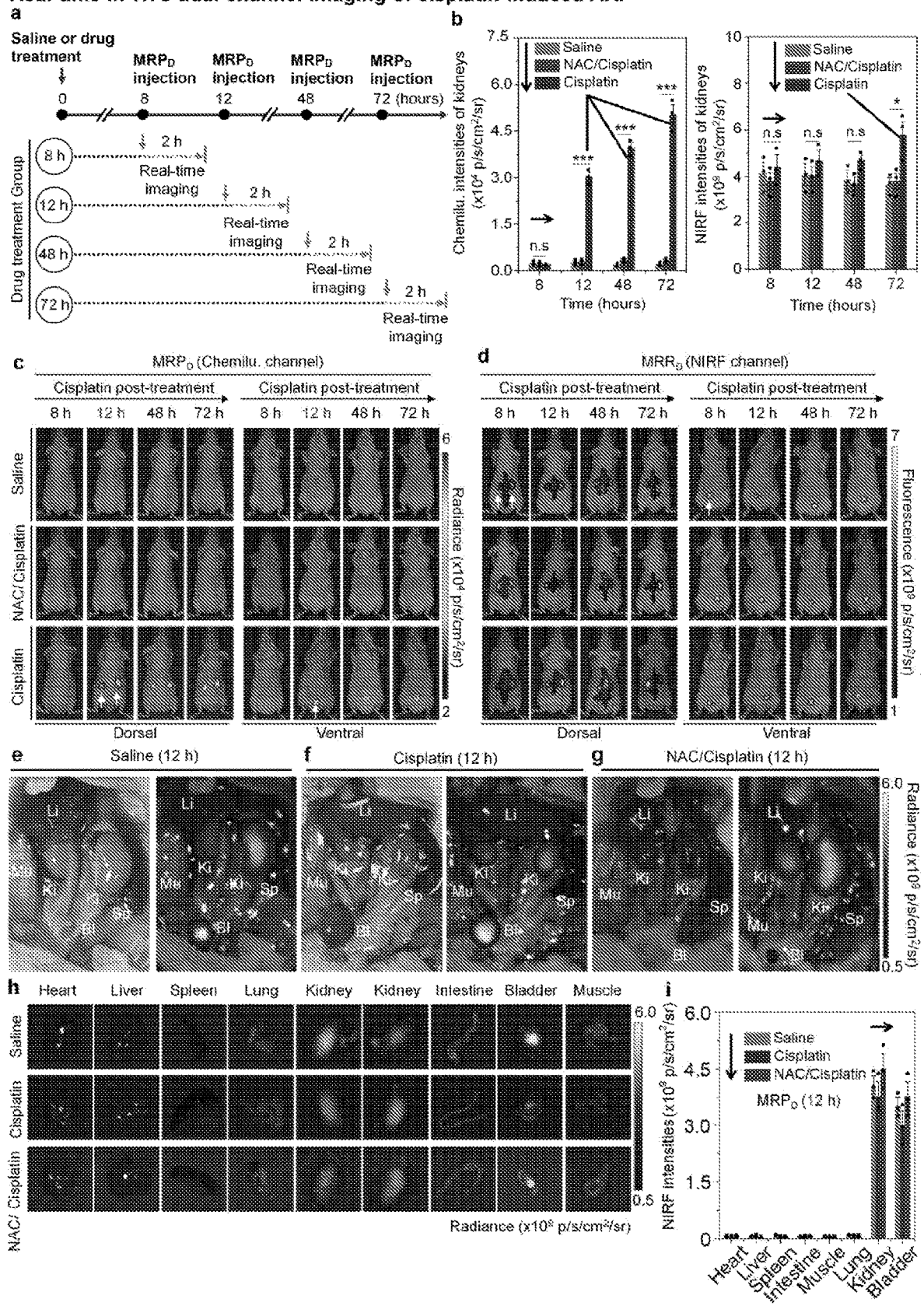

FIG. 27 Depicts real-time in vivo dual-channel imaging of cisplatin-induced AKI using $MRP_D$: (a) schematic illustration of development of cisplatin-induced AKI model and dual-channel imaging at different post-treatment timepoints. Cisplatin was intraperitoneally administered into living mice at a nephrotoxic dosage (20 mg kg$^{-1}$ body weight), followed by i.v injection of $MRP_D$ (32 μmol kg$^{-1}$ body weight) at different timepoints post-treatment of cisplatin (8, 12, 48 or 72 h). The control groups were treated with saline (0.2 ml) or a nephroprotective antioxidant (NAC, 400 mg kg$^{-1}$ body weight, i.v injection) 30 min prior to cisplatin administration. Real-time dual-channel imaging was conducted every 30 min for 2 h after i.v injection of $MRP_D$; (b) chemiluminescence and NIRF intensities of kidneys in living mice at t=8 min after i.v injection of $MRP_D$ at different post-treatment timepoints (8, 12, 48 or 72 h). Data are the mean±SD, and represent mice treated with saline, NAC/cisplatin and cisplatin, respectively, for the left to right charts of each timepoint. n=3 independent mice. Two-tailed student's t-test. Saline, NAC/cisplatin versus cisplatin-treated groups, n.s: not significant, *p<0.05, p<0.01, *p<0.001; (c) representative chemiluminescence, and (d) NIRF images of living mice at t=8 min after i.v injection of $MRP_D$ at different post-treatment timepoints (8, 12, 48 or 72 h). $MRP_D$ has the highest signal at 8 min post-injection. The white arrows indicate the kidneys and bladder in dorsal and ventral side, respectively. NIRF images acquired at 760 nm upon excitation at 640 nm with the IVIS spectrum imaging system, and chemiluminescence images acquired under bioluminescence mode with the acquisition time of 180 s. The experiments were repeated independently three times with similar results; and (e-g) NIRF images of the abdominal cavity of mice with i.v injection of $MRP_D$ at t=12 h post-treatment of cisplatin. The control groups were treated with saline (0.2 ml) or a nephroprotective antioxidant (NAC, 400 mg $kg^{-1}$ body weight, i.v injection) 30 min prior to cisplatin administration. Liver (Li), muscle (Mu), spleen (Sp), kidneys (Ki), bladder (Bl). The experiments were repeated independently three times with similar results; (h) ex vivo NIRF images, and (i) signal quantification of resected organs from mice with i.v injection of $MRP_D$ at t=12 h post-treatment of cisplatin, or mice given saline (0.2 ml) or a nephroprotective antioxidant (NAC, 400 mg $kg^{-1}$ body weight, i.v injection) 30 min prior to cisplatin administration. For (i), the data represent mice treated with saline, cisplatin and NAC/cisplatin, respectively, from left to right of the charts for each timepoint The bladder from the NAC/cisplatin co-treated mouse in the panel of (g) showed lower fluorescence intensity compared to panel (e) due to urinary incontinence and bladder emptying after resection. NIRF images acquired at 760 nm upon excitation at 640 nm with the IVIS spectrum imaging system. Data are the mean±SD. n=3 independent mice. Similar NIRF intensities of resected kidneys were observed between control and cisplatin-treated groups because the kidney filtration capacity did not decrease at 12 h post-treatment of cisplatin.

Figure 28:
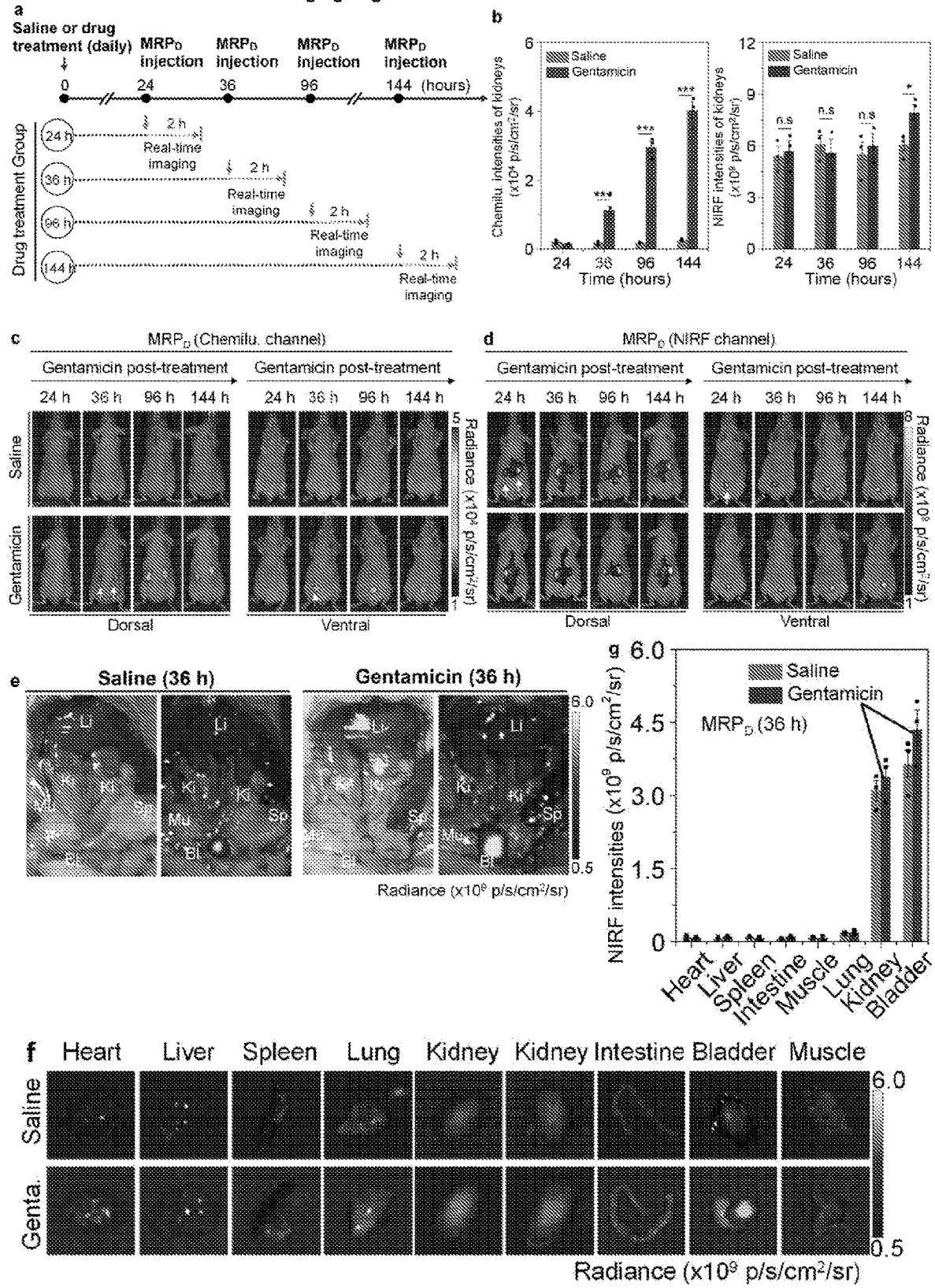

FIG. 28 Depicts real-time in vivo dual-channel imaging of gentamicin-induced AKI: (a) schematic illustration of development of gentamicin-induced AKI model and dual-channel imaging at different post-treatment timepoints. Gentamicin was intraperitoneally administered into living mice at 100 mg $kg^{-1}$ $day^{-1}$ followed by i.v injection of $MRP_D$ (32 μmol $kg^{-1}$ body weight) at different timepoints post-treatment of gentamicin (24, 36, 96 or 144 h). The control groups were treated with saline (0.2 ml). Real-time dual-channel imaging was conducted every 30 min for 2 h after i.v injection of $MRP_D$; (b) chemiluminescence and NIRF intensities of kidneys in living mice at t=8 min after i.v. injection of $MRP_D$ at different post-treatment timepoints (24, 36, 96 or 144 h). Data are the mean±SD, and represent mice treated with saline and gentamicin, respectively, for the left and right charts of each timepoint. n=3 independent mice. Two-tailed student's t-test. Saline versus gentamicin treated groups, n.s: not significant, *p<0.05, p<0.01, *p<0.001; (c) representative chemiluminescence, and (d) NIRF images of living mice at t=8 min after i.v. injection of $MRP_D$ at different post-treatment timepoints (24, 36, 96 or 144 h). $MRP_D$ has the highest signal at 8 min post-injection. The white arrows indicate the kidneys and bladder in dorsal and ventral side, respectively. NIRF images acquired at 760 nm upon excitation at 640 nm with the IVIS spectrum imaging system, and chemiluminescence images acquired under bioluminescence mode with the acquisition time of 180 s. The experiments were repeated independently three times with similar results; (e) NIRF images of the abdominal cavity of mice with i.v injection of $MRP_D$ at t=36 h post-treatment of gentamicin. The control groups were treated with saline (0.2 ml). Liver (Li), muscle (Mu), spleen (Sp), kidneys (Ki), bladder (Bl). The experiments were repeated independently three times with similar results; (f) ex vivo NIRF images, and (g) signal quantification of resected organs from mice with i.v injection of $MRP_D$ at t=36 h post-treatment of saline or gentamicin. The bladder from saline-treated mouse in the panel of (f) showed lower fluorescence intensity compare to that of in the panel of (e) due to urinary incontinence and bladder emptying after resection. NIRF images acquired at 760 nm upon excitation at 640 nm with the IVIS spectrum imaging system. Data are the mean±SD, and represent mice treated with saline and gentamicin, respectively, for the left and right charts of each organ. n=3 independent mice. Similar NIRF intensities of resected kidneys were observed between control and gentamicin-treated groups because the kidney filtration capability did not decline at 36 h post-treatment of gentamicin.

Figure 29:
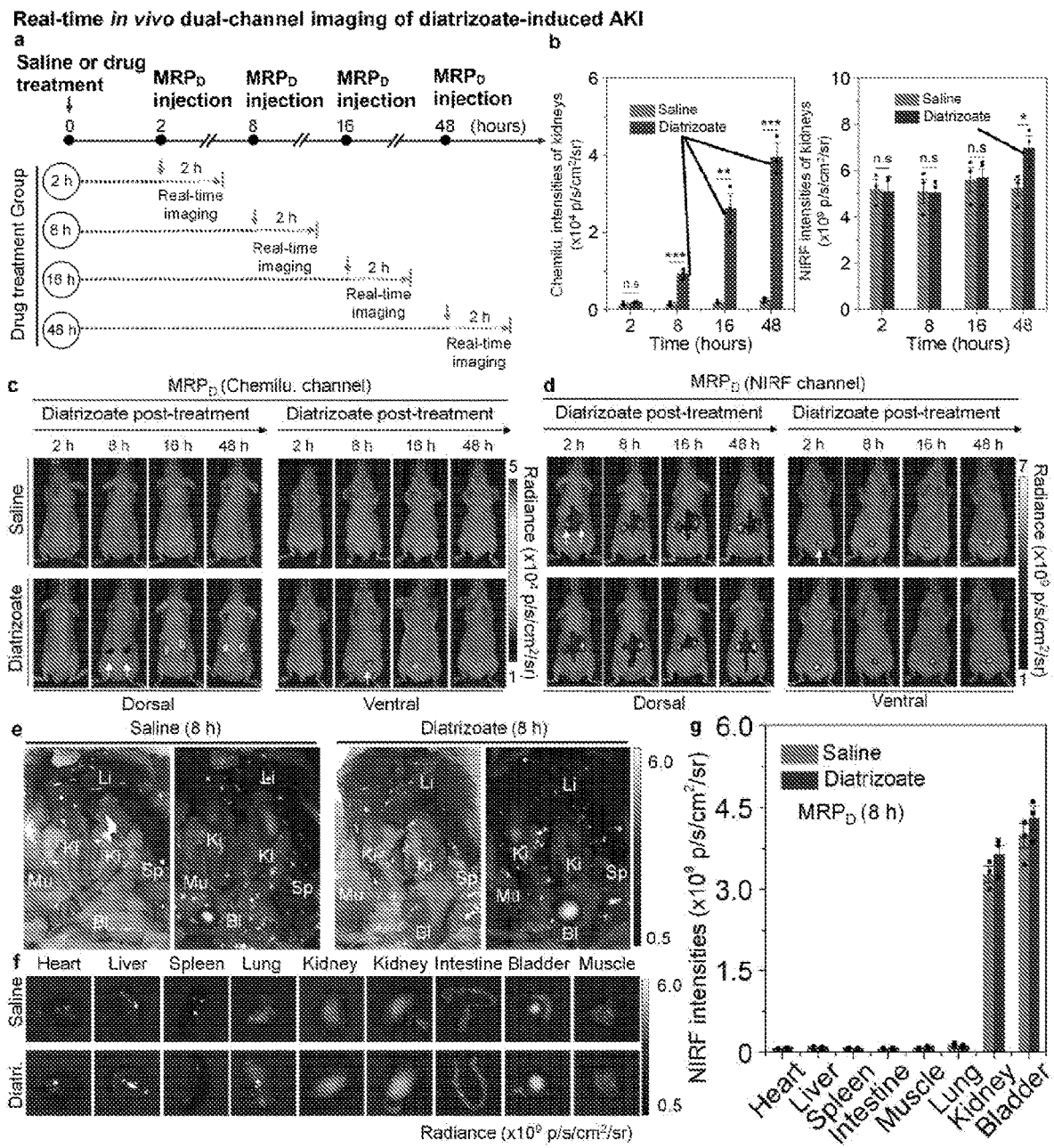

FIG. 29 Depicts real-time in vivo dual-channel imaging of diatrizoate-induced AKI: (a) schematic illustration of development of diatrizoate-induced AKI model and dual-channel imaging at different post-treatment timepoints. Diatrizoate was intravenously administered into living mice at a dosage of 1000 mg $kg^{-1}$ body weight, followed by i.v injection of $MRP_D$ (32 μmol $kg^{-1}$ body weight) at different timepoints post-treatment of diatrizoate (2, 8, 16 or 48 h). The control groups were treated with saline (0.2 ml). Real-time dual-channel imaging was conducted every 30-min for 2 h after i.v injection of $MRP_D$; (b) chemiluminescence and NIRF intensities of kidneys in living mice at t=8 min after i.v. injection of $MRP_D$ at different post-treatment timepoints (2, 8, 16 or 48 h). Data are the mean±SD, and represent mice treated with saline and diatrizoate, respectively, for the left and right charts of each timepoint. n=3 independent mice. Two-tailed student's t-test. Saline versus diatrizoate treated groups, n.s: not significant, *p<0.05, p<0.01, *p<0.001; (c) representative chemiluminescence, and (d) NIRF images of living mice at t=8 min post-injection of $MRP_D$ after different post-treatment timepoints (2, 8, 16 or 48 h). $MRP_D$ has the highest signal at 8 min post-injection. The white arrows indicate the kidneys and bladder in dorsal and ventral side. NIRF images acquired at 760 nm upon excitation at 640 nm with the IVIS spectrum imaging system, and chemiluminescence images acquired under bioluminescence mode with the acquisition time of 180 s. The experiments were repeated independently three times with similar results; (e) NIRF images of the abdominal cavity of mice with i.v of $MRP_D$ at t=8 h post-treatment of diatrizoate. The control groups were treated with saline (0.2 ml). Liver (Li), muscle (Mu), spleen (Sp), kidneys (Ki), bladder (Bl). The experiments were repeated independently three times with similar results; (f) ex vivo NIRF images, and (g) signal quantification of resected organs from mice with i.v injection of $MRP_D$ at t=8 h post-treatment of saline or diatrizoate. NIRF images acquired at 760 nm upon excitation at 640 nm with the IVIS spectrum imaging system. Data are the mean±SD, and represent mice treated with saline and diatrizoate, respectively, for the left and right charts of each organ. n=3 independent mice. Similar NIRF intensities of resected kidneys were observed between control and diatrizoate-treated groups because the kidney filtration capability did not decline at 8 h post-treatment of diatrizoate.

Figure 30:
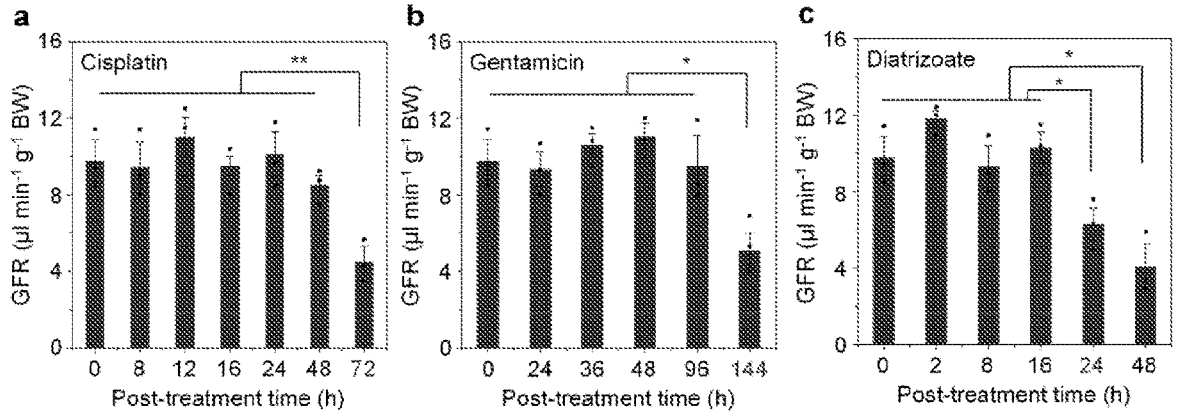

FIG. 30 Depicts the determination of GFR in the mouse models of drug-induced AKI: (a) GFR of living mice at t=8, 12, 16, 24, 48, or 72 h post-treatment of cisplatin (20 mg $kg^{-1}$ body weight); (b) at t=24, 36, 48, 96, or 144 h post-treatment of gentamicin (100 mg $kg^{-1}$ $day^{-1}$ body weight); and (c) at t=2, 8, 16, 24, or 48 h post-treatment of diatrizoate (1000 mg kg body weight), or saline (0.2 ml) treated mice, measured by the standard FITC-Inulin method. Data are the mean±SD. n=3 independent mice. Two-tailed student's t-test. For cisplatin, pre-treatment, 8, 12, 16, 24 and 48 h post-treatment versus 72 h post-treatment groups; for gentamicin, pre-treatment, 24, 36, 48 and 96 h post-treatment versus 144 h post-treatment groups; for diatrizoate, pre-treatment, 2, 8, 16 h post-treatment versus 24 h or 48 h post-treatment groups. n.s: not significant, *p<0.05, **p<0.01.

Figure 31:
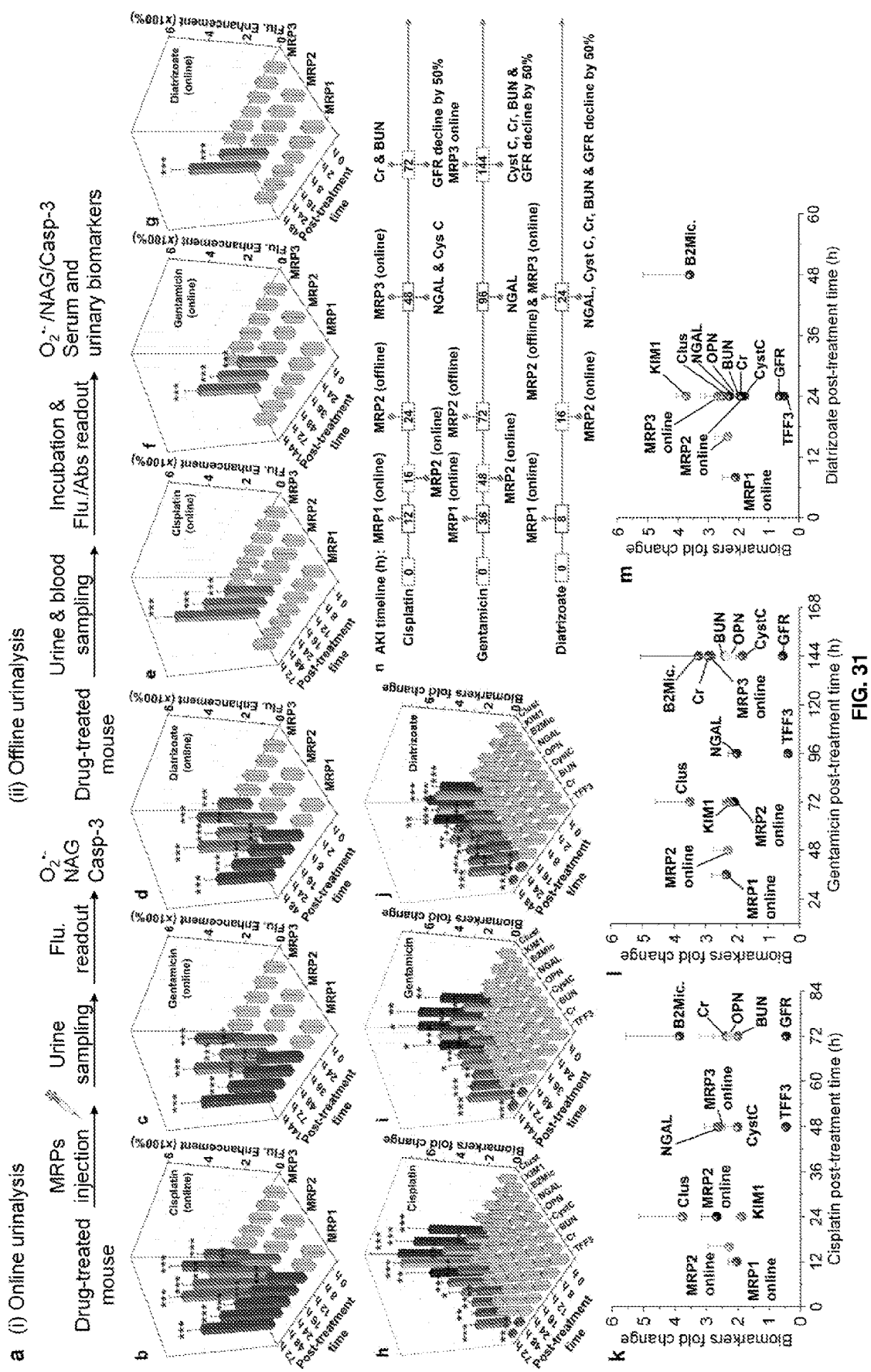

FIG. 31 Depicts in vitro diagnosis of drug-induced AKI in living mice: (a) schematic illustration of the workflows for optical urinalysis of drug-induced AKI in living mice. (i) Online urinalysis: fluorescence readouts of excreted MRPs1-3 in the urine from drug-treated living mice after i.v injection of MRPs1-3 at different timepoints post-treatment of drug. (ii) Offline urinalysis: fluorescence readouts of MRPs1-3 after incubation with urine samples collected from drug-treated living mice at different timepoints post-treatment of drug. The commercial assays were used to measure Cr, BUN, and Cystatin C in the blood as well as NGAL, TFF3, OPN, β2-microglobulinin, KIM-1 and clusterin in the urine samples collected from drug-treated living mice at different timepoints post-treatment of drug; (b-d) fluorescence enhancement of excreted MRPs1-3 in the urine from drug-treated living mice after i.v injection of MRPs1-3 at different timepoints post-treatment of drug; (e-g) fluorescence enhancement of MRPs1-3 after incubation with the urine samples collected from drug-treated living mice at different timepoints post-treatment of drug. Data are the mean±SD. n=9 independent experiments for (b-d) and (e-g). Two-tailed student's t-test. Pre-treatment versus post-treatment groups, *p<0.05, p<0.01, *p<0.001; (h-j) fold change in urinary and serum biomarkers at different timepoints post-treatment of drug. Data are the mean±SD. n=5 independent experiments for Cr, BUN, Cyst C, NGAL and KIM-1, n=6 independent experiments for TFF3, OPN, β2-Microglobulin and clusterin. Two-tailed student's t-test. Pre-treatment versus post-treatment groups, *p<0.05, p<0.01, *p<0.001; (k-m) optimised timeline comparing MRPs (online and offline urinalysis) to the clinical methods and FDA qualified urinary biomarkers for detection of drug-induced AKI. Data are the mean±SD. n=5 independent experiments for Cr, BUN, Cyst C, NGAL and KIM-1, n=6 independent experiments for TFF3, OPN, β2-Microglobulin and clusterin; and (n) initial timeline comparing MRPs (online and offline urinalysis) to the clinical methods for detection of drug-induced AKI.

Figure 32:
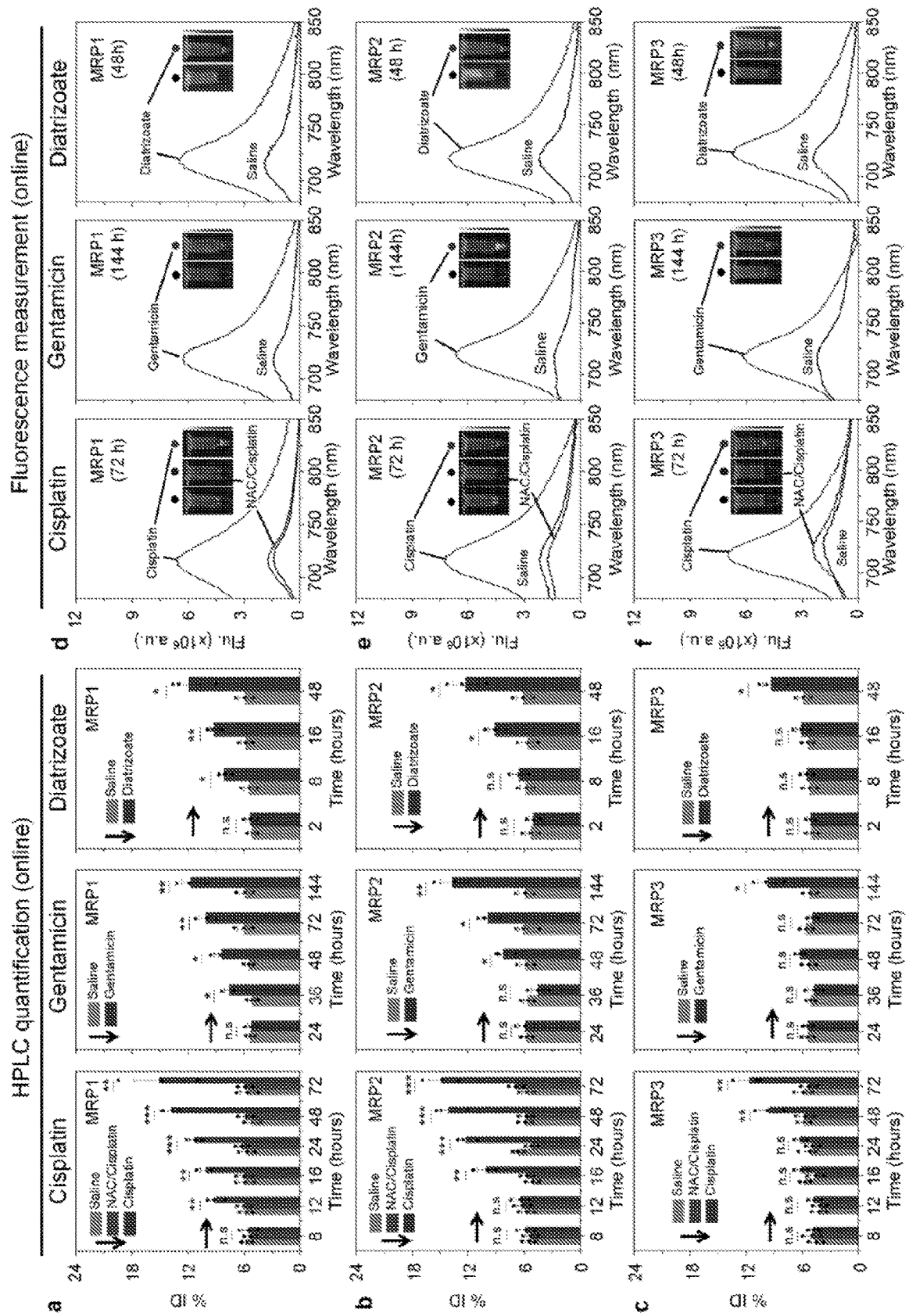

FIG. 32 Depicts quantification of excreted MRPs1-3 in the mouse models of drug-induced AKI: (a-c) HPLC quantification of activated MRPs1-3 in the urine from living mice with i.v injection of MRPs1-3 (8 μmol kg$^{-1}$ body weight) at different timepoints post-treatment of drugs (cisplatin: 20 mg kg$^{-1}$ body weight; gentamicin: 100 mg kg$^{-1}$ day$^{-1}$ body weight; or diatrizoate: 1000 mg kg$^{-1}$ body weight) Data are the mean±SD, and represent mice treated with saline and the respective drugs, respectively, from left to right of the charts for each timepoint. n=3 independent mice. Two-tailed student's t-test. saline versus drug post-treatment groups, n.s: not significant, *p<0.05, p<0.01, *p<0.001; and (d-f) fluorescence spectra of excreted MRPs1-3 in the urine samples from living mice with i.v injection of MRPs1-3 after treatment of drug (cisplatin: 20 mg kg$^{-1}$ body weight; gentamicin: 100 mg kg$^{-1}$ day$^{-1}$ body weight; or diatrizoate: 1000 mg kg$^{-1}$ body weight). Fluorescence excitation at 675 nm. Inset: the corresponding fluorescence images acquired at 720 nm upon excitation at 675 nm with the IVIS spectrum imaging system. The experiments were repeated independently three times with similar results.

Figure 33:
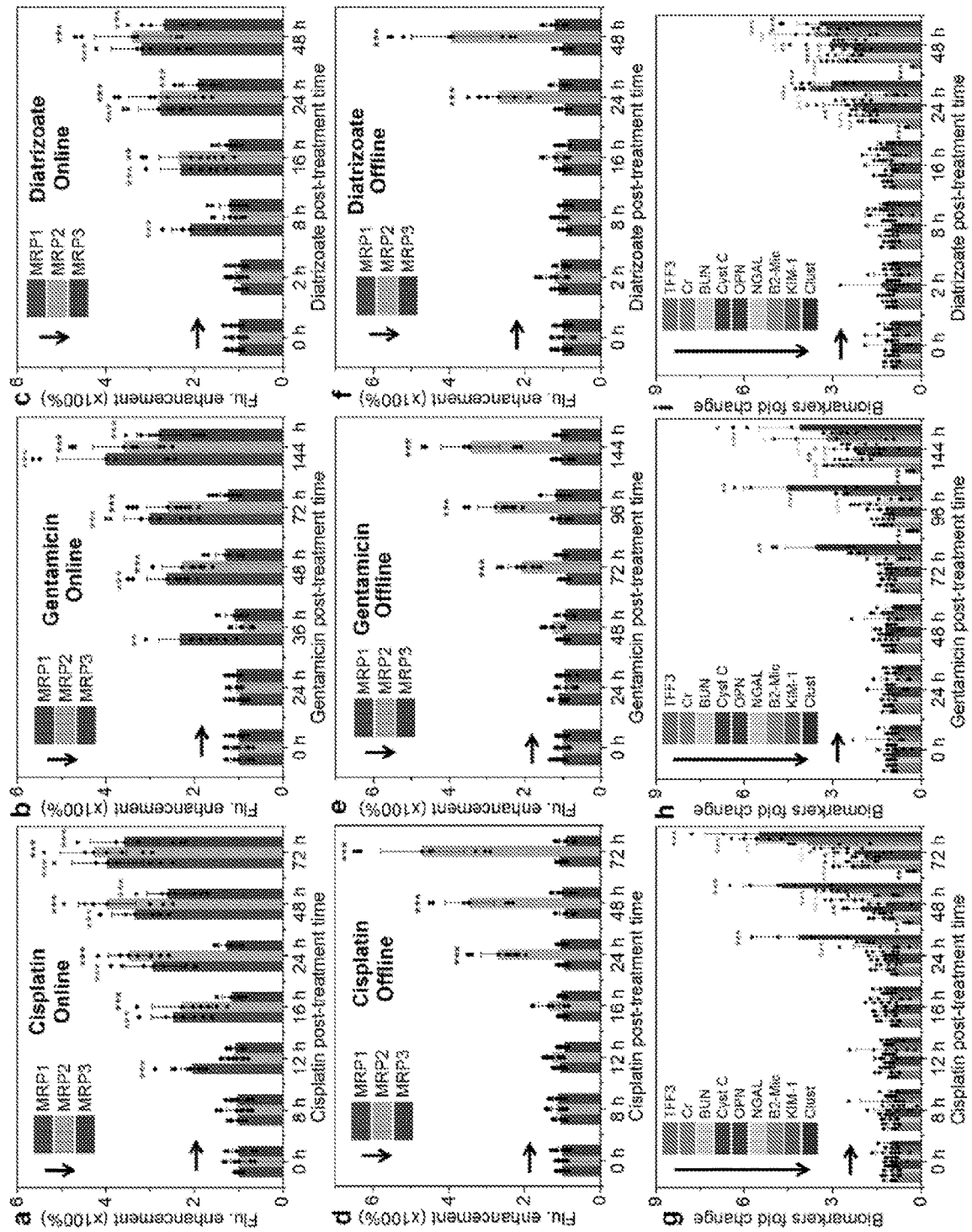

FIG. 33 Depicts in vitro diagnosis of drug-induced AKI in living mice: (a-c) fluorescence enhancement of excreted MRPs1-3 in the urine from drug-treated living mice after i.v injection of MRPs1-3 at different timepoints post-treatment of drug. Data are the mean±SD. n=9 independent experiments. Two-tailed student's t-test. Pre-treatment versus post-treatment groups, *p<0.05, p<0.01, *p<0.001; (d-f) fluorescence enhancement of MRPs1-3 after incubation with the urine samples collected from drug-treated living mice at different timepoints post-treatment of drug. Data are the mean±SD. n=9 independent experiments. Two-tailed student's t-test. Pre-treatment versus post-treatment groups, *p<0.05, p<0.01, *p<0.001. For (a-f), the data represent mice treated with MRP1, MRP2 and MRP3, respectively, from left to right of the charts for each timepoint; and (g-i) fold change in urinary and serum biomarkers at different timepoints post-treatment of drug. Data are the mean±SD. n=5 independent experiments for Cr, BUN, Cyst C, NGAL and KIM-1, n=6 independent experiments for TFF3, OPN, β2-Microglobulin and clusterin. Two-tailed student's t-test. Pre-treatment versus post-treatment groups, *p<0.05, p<0.01, *p<0.001. In online urinalysis, the first statistically significant NIRF enhancement was respectively observed at 12 (2.0-fold), 36 (2.3-fold), and 8 h (2.1-fold) post-treatment of cisplatin, gentamicin, and diatrizoate for excreted MRP1, 16 (2.3-fold), 48 (2.3-fold) and 16 h (2.4-fold) for MRP2, and 48 (2.6-fold), 144 (2.8-fold) and 24 h (1.9-fold) for MRP3. In offline urinalysis, the first statistically significant NIRF enhancement was observed at 24 (2.7-fold), 72 (2.1-fold) and 24 (2.7-fold) for cisplatin-, gentamicin-, and diatrizoate-treated mice, respectively, showing the different timeline for detection of drug induced-AKI dependent on the drugs. This was ascribed to the different molecular mechanisms of the drugs that lead to tubular toxicity. The figure is a further representation of FIG. 31 which represents each data point as dot plots to indicate the distribution of the data. For (g-i), the data represent the respective biomarkers from left to right, which are in exact sequence as those listed in the legend from top to bottom.

Figure 34:
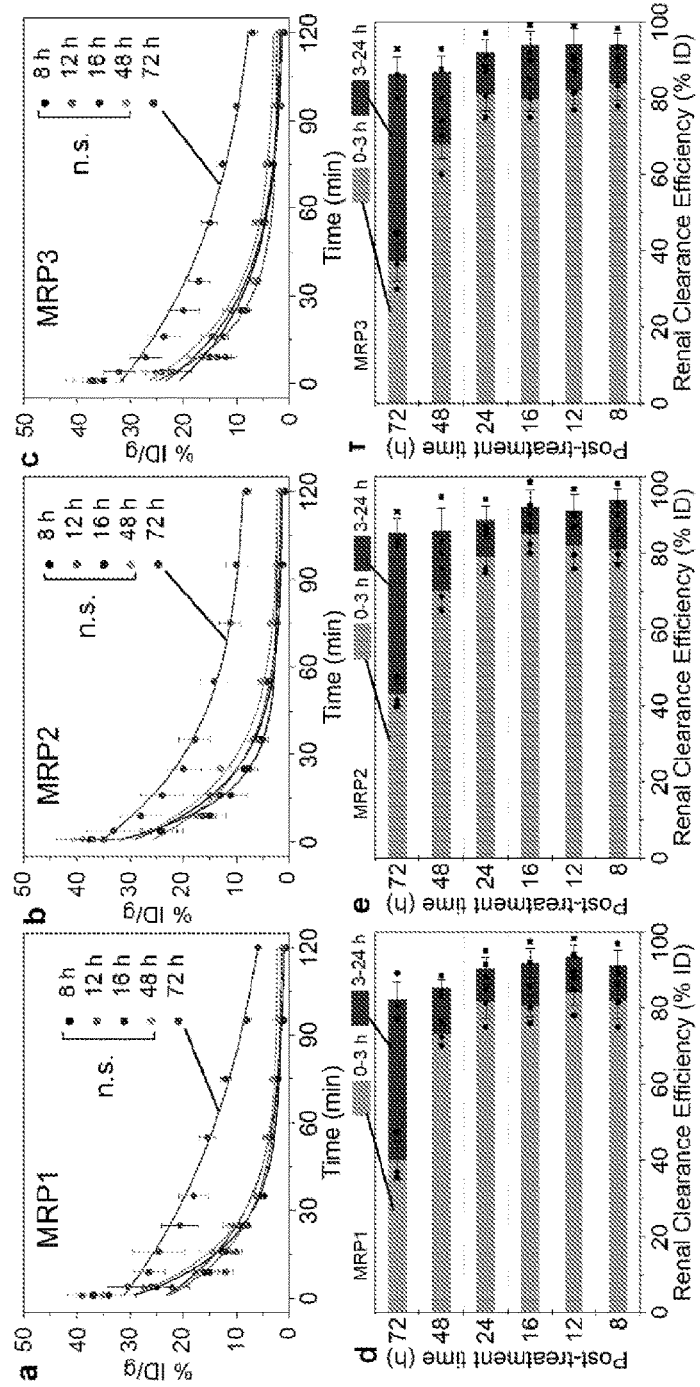

FIG. 34 Depicts pharmacokinetics and renal clearance efficiency for MRPs1-3 in cisplatin-induced AKI model: (a-c) blood concentration (% ID g$^{-1}$) decay of (a) MRP1, (b) MRP2, and (c) MRP3 in the living mice after intravenous injection of MRPs1-3 (8 μmol kg$^{-1}$ body weight) at t=8, 12, 16, 48 or 72 h post-treatment of cisplatin (20 mg kg$^{-1}$ body weight). Data are the mean±SD. n=3 independent mice. Two-tailed student's t-test. 8 h post-treatment versus 12, 16, 48 h post-treatment groups, n.s: not significant; (d-f) renal clearance efficiency of (d) MRP1, (e) MRP2, and (f) MRP3 at 0-3 h and 3-24 h after intravenous injection of MRPs1-3 (8 μmol kg$^{-1}$ body weight) in the living mice at t=8, 12, 16, 24, 48 or 72 h post-treatment of cisplatin (20 mg kg$^{-1}$ body weight). Data are the mean±SD. n=3 independent mice. Note that the blood elimination half-lives ($t_{1/2β}$) of MRP1 in the mice after cisplatin treatment for 8, 12, and 48 h were similar (~6.3 min), but increase to 42.3 min in the mice after cisplatin treatment for 72 h. This was ascribed to the significantly decreased GFR at 72 h post-treatment (FIG. 26c). This was further confirmed by the renal clearance data. The renal clearance efficiency of MRP1 in the mice after cisplatin treatment for 72 h were only 40% ID at t=3 h post-injection, which were ~80% ID (t=3 h post-injection) in the mice after cisplatin treatment for 8, 12, and 48 h. Similar results were observed for MRP2 and MRP3.

Figure 35:
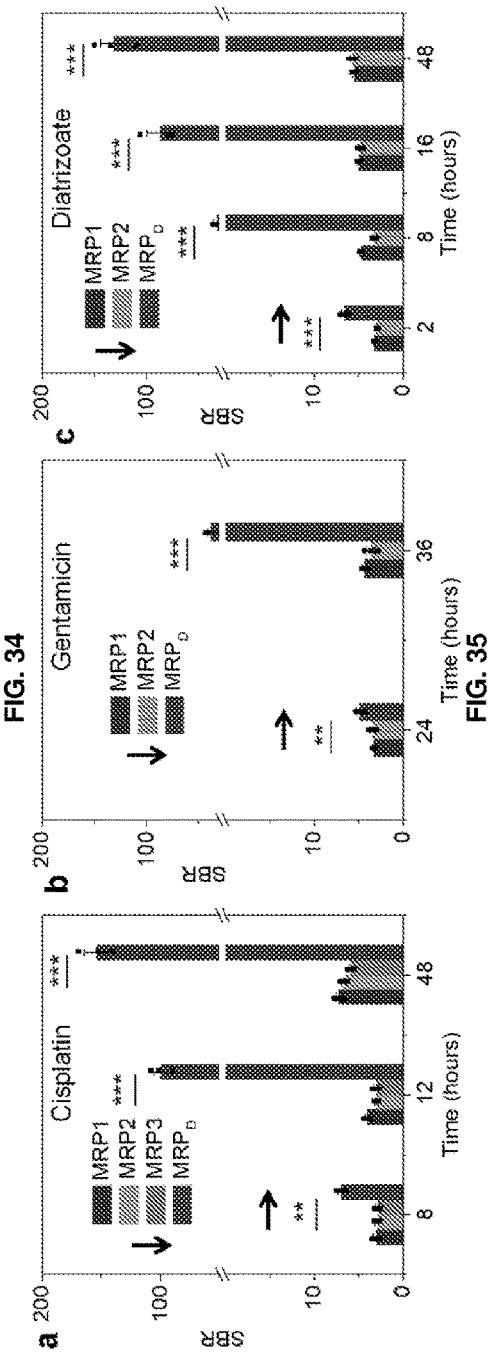

FIG. 35 Depicts comparison of SBRs between NIRF and chemiluminescence imaging in the mouse models of drug-induced AKI: (a-c) SBRs for NIRF (MRPs1-3) and chemiluminescence (MRP$_D$) imaging of kidneys in living mice as a function of post-treatment time of (a) cisplatin, (b) gentamicin and (c) diatrizoate. The SBRs were calculated at 30 min post-injection of MRP1, or 60 min post-treatment of MRP2 and MRP3 for NIRF imaging, or at 8 min post-injection of $MRP_D$ for chemiluminescence imaging. At these imaging timepoints, the signals are the highest. Data are the mean±SD, and represent the respective MRPs from left to right, which are in exact sequence as those listed in the legend from top to bottom. n=3 independent mice. One-way analysis of variance with Tukey's post hoc test. $MRP_D$ versus MRP1, MRP2, and MRP3 groups, n.s: not significant, *p<0.05, p<0.01, *p<0.001.

Figure 36:
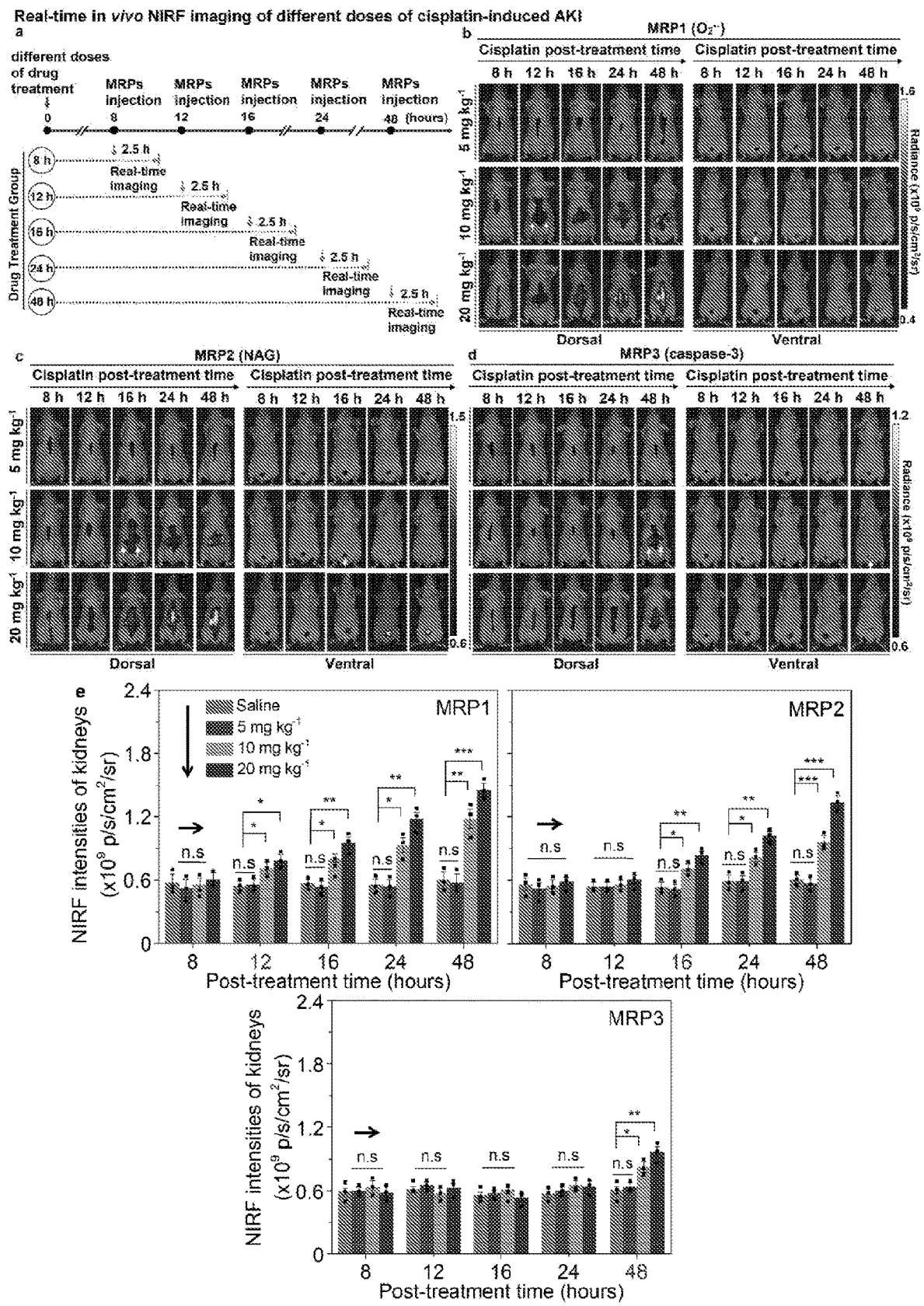

FIG. 36 Depicts real-time in vivo NIRF imaging of different doses of cisplatin induced AKI in living mice: (a) schematic illustration of development of AKI model using different doses of cisplatin and NIRF imaging at different post-treatment timepoints. Cisplatin was intraperitoneally administered into living mice at 5, 10 or 20 mg kg$^{-1}$ followed by i.v injection of MRP1, MRP2, or MRP3 (8 μmol kg$^{-1}$ body weight) at different timepoints post-treatment of cisplatin (8, 12, 16, 24 or 48 h). Real-time NIRF imaging was conducted every 30 min for 2.5 h after i.v injection of MRP1, MRP2 or MRP3. Representative NIRF images of living mice at t=30 min after i.v injection of (b) MRP1, (c) 60 min after i.v injection of MRP2, and (d) MRP3 at different post-treatment timepoints (8, 12, 16, 24 or 48 h). MRP1, MRP2 and MRP3 had the highest signals at 30, 60 and 60 min post-injection, respectively. The white arrows indicate the kidneys and bladder in dorsal and ventral side, respectively. NIRF images acquired at 720 nm upon excitation at 675 nm with the IVIS spectrum imaging system. The experiments were repeated independently three times with similar results; and (e) NIRF intensities of kidneys in living mice at t=30 min after i.v injection of MRP1 or 60 min after i.v injection of MRP2 and MRP3 at different post-treatment timepoints (8, 12, 16, 24 or 48 h). Data are the mean±SD, and represent mice treated with saline, 5 mg kg$^{-1}$, 10 mg kg$^{-1}$ and 20 mg kg$^{-1}$ of MRP, respectively, from the left to right charts of each timepoint. n=3 independent mice. Two-tailed student's t-test. Saline versus 5 mg, 10 mg, or 20 mg cisplatin treated groups, n.s: not significant, *p<0.05, p<0.01, *p<0.001. The signals of MRPs1-3 for 5 mg kg$^{-1}$ cisplatin-treated mice were as low as the background of saline-treated control mice at all post-treatment timepoints, due to the fact such a low dosage of cisplatin is below the nephrotoxicity level (L. S. Chawla, et al., N. Engl. J. Med. 2014, 371, 58-66; J. G. Abuelo, et al., N. Engl. J. Med. 2007, 357, 797-805). For 10 mg kg$^{-1}$ cisplatin-treated mice, the earliest timepoints of signal increase were observed at 12, 16 and 48 h post-treatment of cisplatin for MRP1, MRP2 and MRP3, respectively, which were the same as those for 20 mg kg$^{-1}$ of cisplatin-treated mice. However, the signals of kidneys in 10 mg kg$^{-1}$ cisplatin-treated mice were lower (9%-29%) than those of 20 mg kg$^{-1}$ cisplatin-treated mice at each post-treatment timepoints. This is consistent with the literatures that animals develop different severity of AKI depending on the dosage of cisplatin injection.

Figure 37:
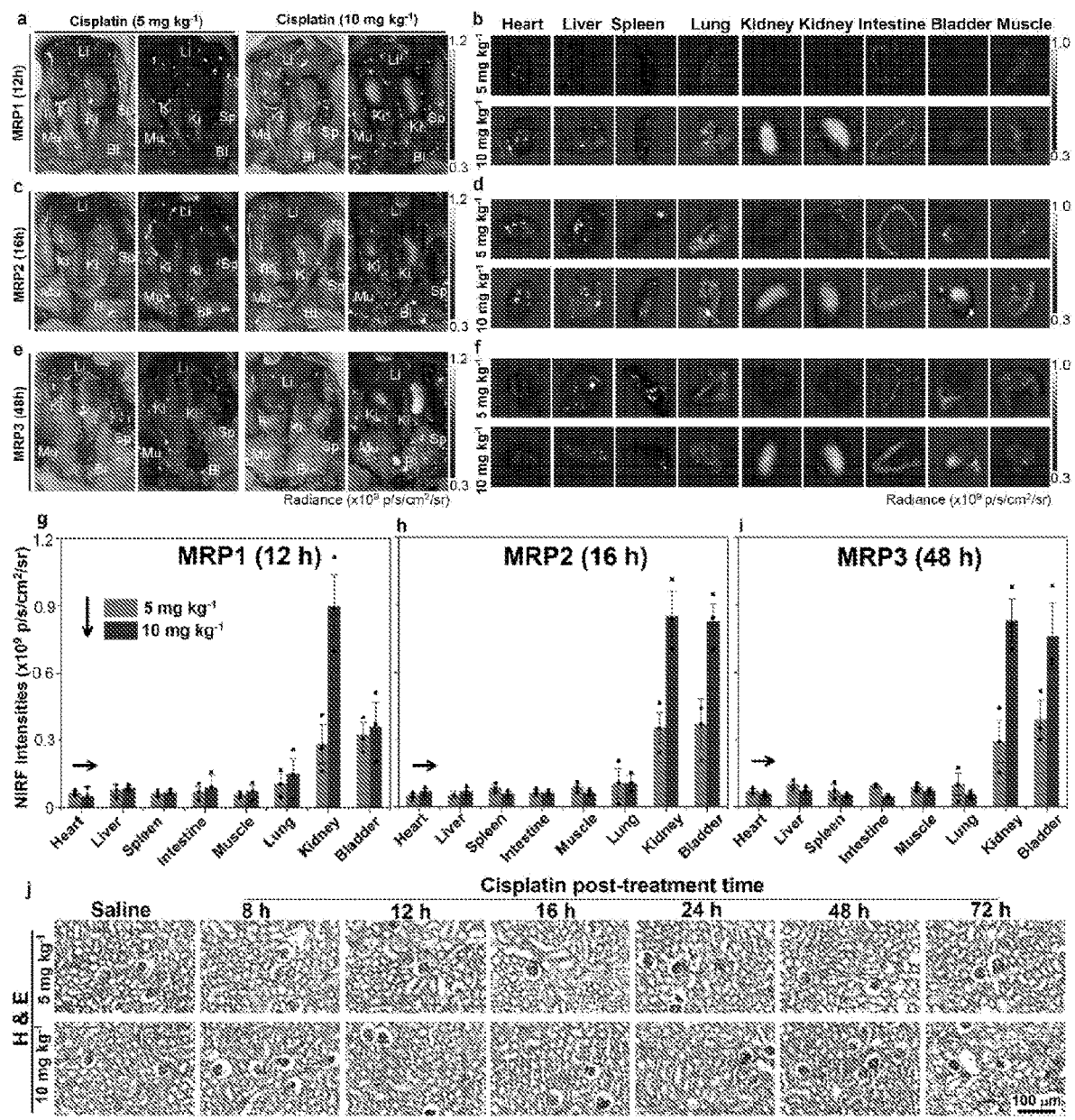

FIG. 37 Depicts ex vivo NIRF signal analysis of MRPs1-3 in the mouse model of different doses of cisplatin induced AKI. Representative NIRF images of the abdominal cavity of mice with i.v injection of (a) MRP1, (c) MRP2, and (e) MRP3 (8 μmol kg$^{-1}$ body weight) after treatment of cisplatin (5 or 10 mg kg$^{-1}$) for 12, 16 and 48 h, respectively. Liver (Li), muscle (Mu), spleen (Sp), kidneys (Ki), bladder (Bl). The experiments were repeated independently three times with similar results; (b, d and f) ex vivo NIRF images, and (g, h and i) signal quantification of resected organs from mice with i.v injection of (b, g) MRP1, (d, h) MRP2, and (f, i) MRP3 after treatment of cisplatin for 12, 16 and 48 h, respectively. The bladder from cisplatin-treated mouse in the panel of (a and c) showed lower fluorescence intensity than that in panel of (e) due to urinary incontinence and bladder emptying after resection. The NIRF images acquired at 720 nm upon excitation at 675 nm with the IVIS spectrum imaging system. Data are the mean±SD. n=3 independent mice. For (g-i), the data represent mice treated with 5 mg kg$^{-1}$ and 10 mg kg$^{-1}$ of MRP, respectively, for the left and right charts of each organ; and (j) representative photomicrographs of H&E staining in paraffin embedded kidney sections from mice after treatment of saline (0.2 ml), or after treatment of cisplatin (5 or 10 mg kg$^{-1}$) for 8, 12, 16, 24, 48 or 72 h. Green arrows and triangle indicate loss of brush border and hyaline casts, respectively. (Scale bar=100 μm). The experiments were repeated independently three times with similar results. The H&E staining also showed normal tubular morphology at 48 h post-treatment of cisplatin (10 mg kg$^{-1}$), but tubular damage at 72 h post-treatment of cisplatin, demonstrating the increases of MRPs signals were prior to the histological changes even for a low dose of cisplatin treatment. Note that such a low dosage of cisplatin (5 mg kg$^{-1}$) is below the nephrotoxicity level. Ex vivo NIRF images and signal quantification of resected organs from mice after treatment of cisplatin (20 mg kg$^{-1}$) are shown in FIG. 21.

Figure 38:
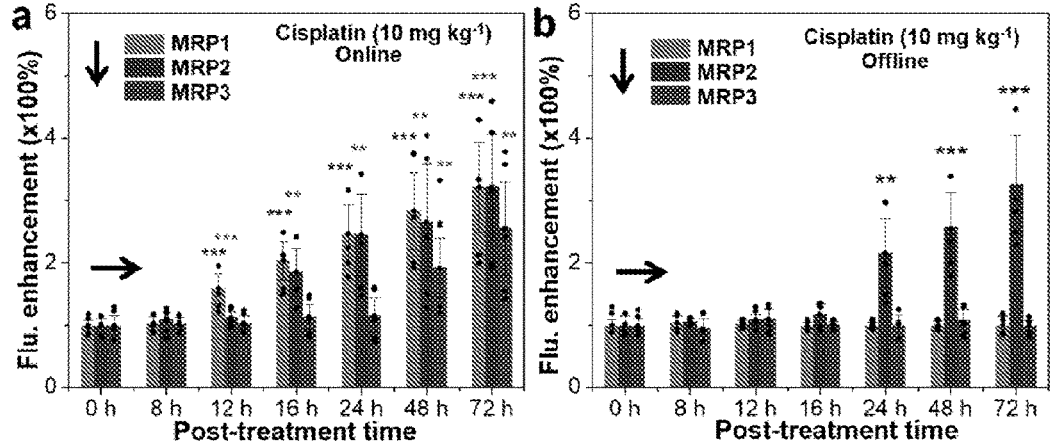

FIG. 38 Depicts online and offline urinalysis in mouse model of a low dose of cisplatin (10 mg kg$^{-1}$) induced AKI: (a) fluorescence enhancement of excreted MRPs1-3 in the urine from drug-treated living mice after i.v injection of MRPs1-3 at different timepoints post-treatment of cisplatin (10 mg kg$^{-1}$). Data are the mean±SD. n=6 independent experiments. Two-tailed student's t-test. Pre-treatment versus post-treatment groups, *p<0.05, p<0.01, *p<0.001; and (b) fluorescence enhancement of MRPs1-3 after incubation with the urine samples collected from cisplatin-treated (10 mg kg$^{-1}$) living mice at different post-treatment timepoints. Fluorescence intensities acquired at 720 nm upon excitation at 675 nm. Data are the mean±SD. n=6 independent experiments. Two-tailed student's t-test. Pre-treatment versus post-treatment groups, *p<0.05, p<0.01, *p<0.001. In the online method, the first statistically significant NIRF enhancement was respectively observed at 12 (2.0-fold), 36 (1.8-fold), and 8 h (1.9-fold) post-treatment of cisplatin for MRP1, MRP2 and MRP3. In offline urinalysis, the earliest timepoints for MRP2 to detect the upregulation of NAG in offline urinalysis were 24 h (2.2-fold) for cisplatin-treated mice. For (a and b), the data represent mice treated with MRP1, MRP2 and MRP3, respectively, from left to right of the charts for each timepoint.

Figure 39:
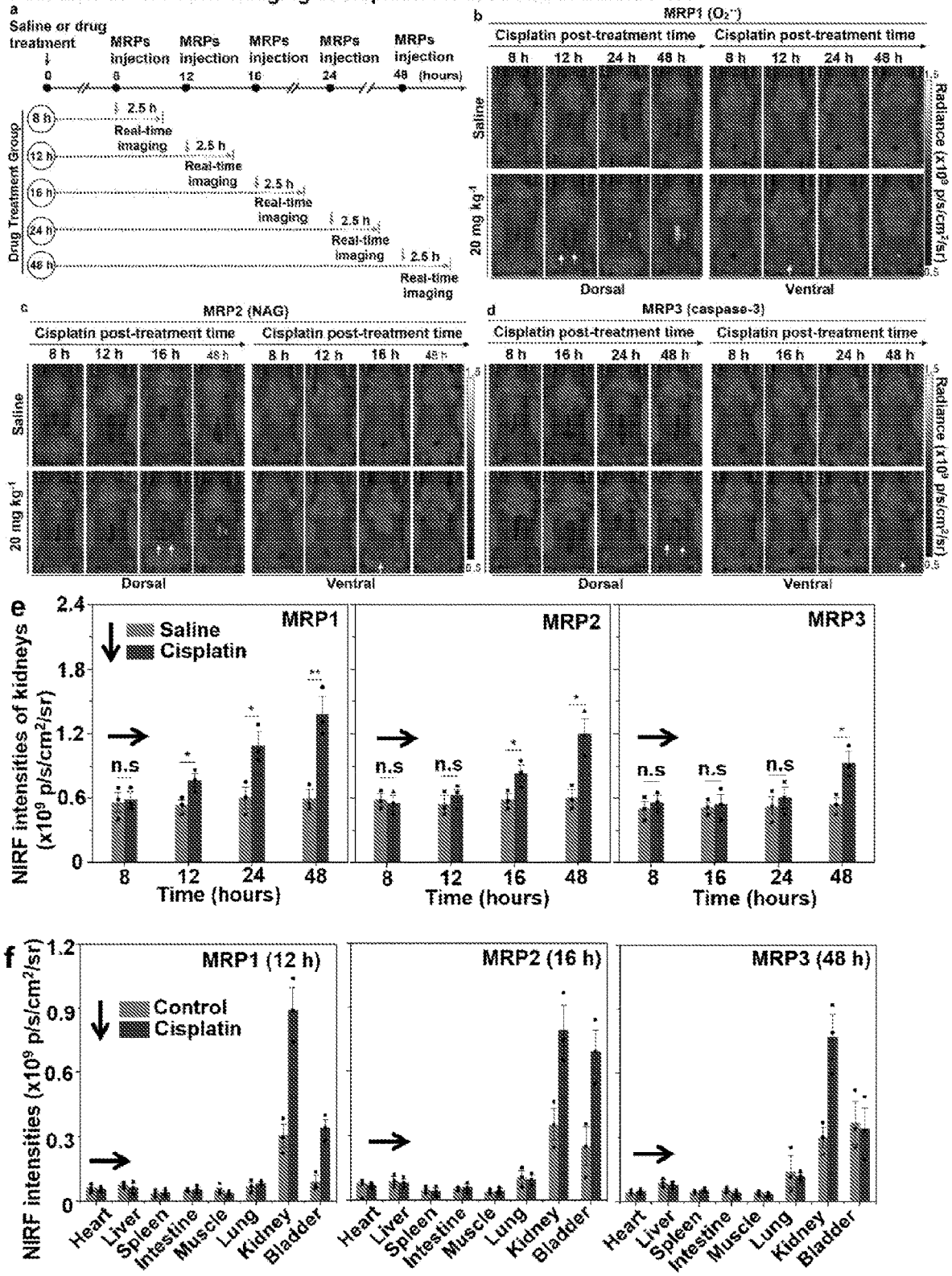
Figure 39:
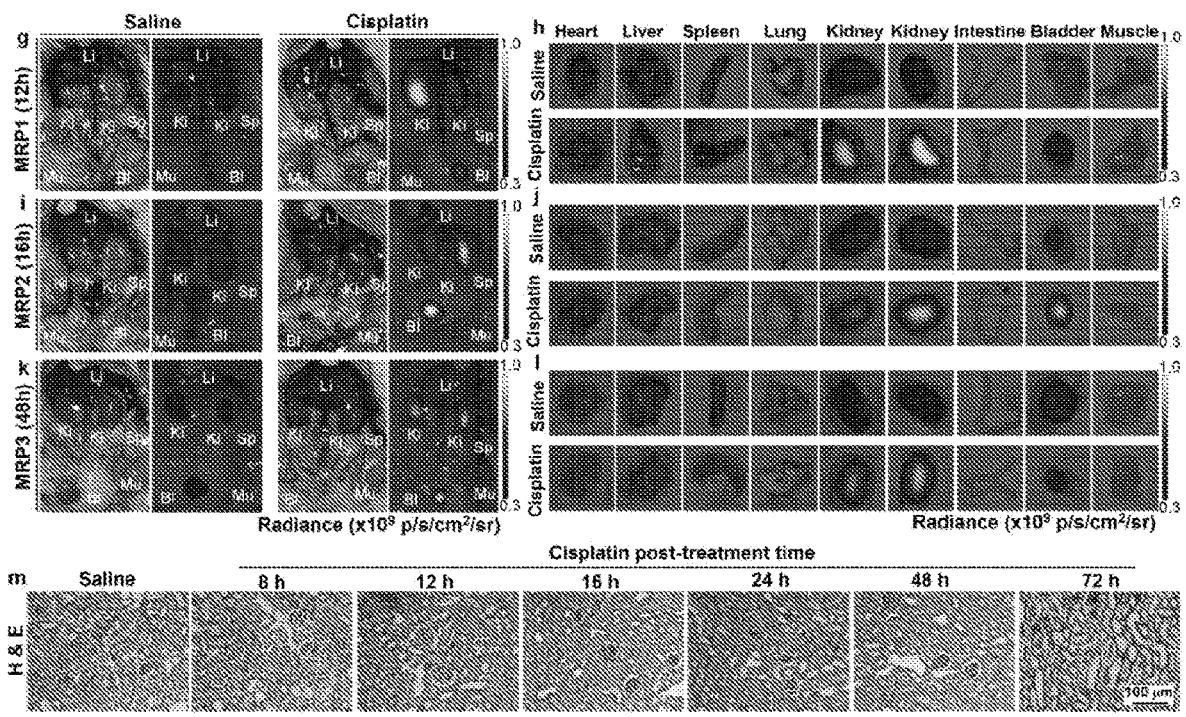

FIG. 39 Depicts real-time in vivo NIRF imaging of cisplatin-induced AKI in living Balb/c mice: (a) schematic illustration of development of cisplatin-induced AKI model and NIRF imaging at different post-treatment timepoints. Cisplatin was intraperitoneally administered into living mice at 20 mg kg$^{-1}$ followed by i.v injection of MRP1, MRP2, or MRP3 (8 μmol kg$^{-1}$ body weight) at different timepoints post-treatment of cisplatin (8, 12, 16, 24 or 48 h). Real-time NIRF imaging was conducted every 30 min for 2.5 h after i.v injection of MRP1, MRP2 or MRP3; representative NIRF images of living mice at t=30 min after i.v injection of (b) MRP1, (c) 60 min after i.v injection of MRP2, and (d) MRP3 at different post-treatment timepoints (8, 12, 16, 24 or 48 h). The white arrows indicate the kidneys and bladder in dorsal and ventral side, respectively. NIRF images acquired at 720 nm upon excitation at 675 nm with the IVIS spectrum imaging system (IVIS Lumina III). The experiments were repeated independently three times with similar results; (e)

NIRF intensities of kidneys in living mice at t=30 min after i.v injection of MRP1 or 60 min after i.v injection of MRP2 and MRP3 at different post-treatment timepoints (8, 12, 16, 24 or 48 h). Data are the mean±SD, and represent mice treated with saline and cisplatin, respectively, for the left and right charts of each timepoint. n=3 independent mice. Two-tailed student's t-test. Saline versus cisplatin treated groups, n.s: not significant, *p<0.05, p<0.01, *p<0.001; (f) signal quantification of resected organs from mice with i.v injection of (h) MRP1, (j) MRP2, and (l) MRP3 after treatment of cisplatin for 12, 16 and 48 h, respectively. Data in (f) represent the control mice and mice treated with cisplatin, respectively, for the left and right charts of each timepoint; representative NIRF images of the abdominal cavity of mice and resected organs from mice with i.v injection of (g) MRP1, (i) MRP2, and (k) MRP3 (8 µmol kg$^{-1}$ body weight) after treatment of cisplatin (20 mg kg$^{-1}$) for 12, 16 and 48 h, respectively. Liver (Li), muscle (Mu), spleen (Sp), kidneys (Ki), bladder (Bl). The bladder from cisplatin-treated mouse in the panel of h and l showed lower fluorescence intensity than that in panel of j due to urinary incontinence and bladder emptying after resection. The NIRF images acquired at 720 nm upon excitation at 675 nm with the IVIS spectrum imaging system. (IVIS Lumina III). Data are the mean±SD. n=3 independent mice; and (m) representative photomicrographs of H&E staining in paraffin embedded kidney sections from mice after treatment of saline (0.2 ml), or after treatment of cisplatin (20 mg kg$^{-1}$) for 8, 12, 16, 24, 48 or 72 h. Green arrows and triangle indicate hyaline casts and tubular dilatation. (Scale bar=100 µm). The experiments were repeated independently three times with similar results. The results from Balb/c mouse model of cisplatin-induced AKI revealed the earliest timepoints of signal increase were at 12, 16 and 48 h post-treatment of cisplatin for MRP1, MRP2 and MRP3, respectively; and the H&E staining showed normal tubular morphology at 48 h post-treatment of cisplatin, but tubular dilatation and hyaline casts at 72 h post-treatment of cisplatin. These observations were similar to those in NCr mice (FIG. 19 and FIG. 21). Thereby, these results validated that MRPs1-3 can detect drug-induced AKI in different mouse strains.

Figure 40:
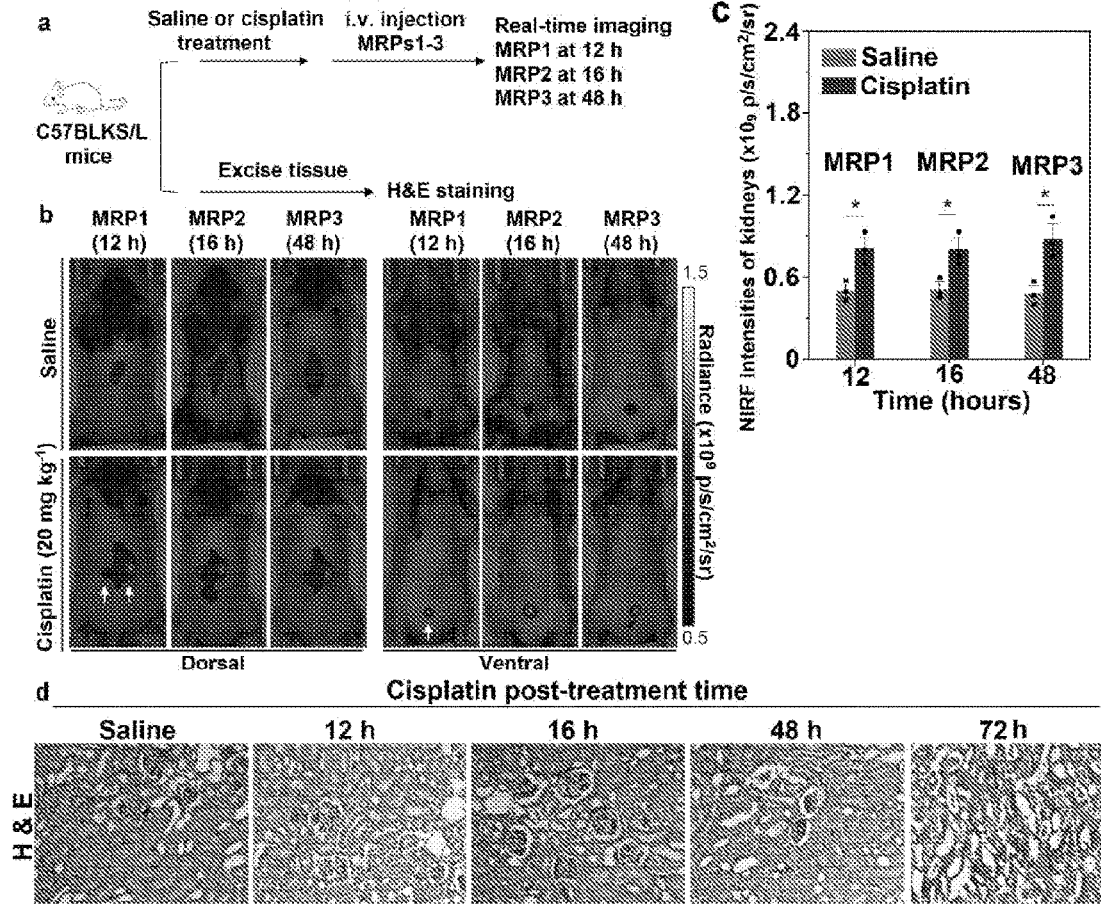

FIG. 40 Depicts real-time in vivo NIRF imaging of cisplatin-induced AKI in C57BLKS/J mice: (a) schematic illustration of development of cisplatin-induced AKI model and NIRF imaging at different post-treatment timepoints for MRPs1-3. Kidneys were resected after euthanasia for Hematoxylin-Eosin staining; (b) representative NIRF images of living mice at t=30 min after i.v injection of MRP1 or 60 min after i.v injection of MRP2 and MRP3 at 12, 16, or 48 h post-treatment of cisplatin, respectively. The white arrows indicate the kidneys and bladder in dorsal and ventral side, respectively. NIRF images acquired at 720 nm upon excitation at 675 nm with the IVIS spectrum imaging system (IVIS Lumina III). The experiments were repeated independently three times with similar results; (c) NIRF intensities of kidneys in living mice at t=30 min after i.v injection of MRP1 or 60 min after i.v injection of MRP2 and MRP3 at 12, 16, or 48 h post-treatment of cisplatin, respectively. Data are the mean±SD, and represent mice treated with saline and cisplatin, respectively, for the left and right charts of each MRP. n=3 independent mice. Two-tailed student's t-test. Saline versus cisplatin treated groups, n.s: not significant, *p<0.05; and (d) representative photomicrographs of H&E staining in paraffin embedded kidney sections from C57BLKS/J mice after treatment of saline (0.2 ml), or cisplatin (20 mg kg$^{-1}$) for 12, 16, or 48 h. The experiments were repeated independently three times with similar results. Green triangles indicate hyaline casts in the tubules. The results from C57BLKS/L mouse model of cisplatin-induced AKI revealed the earliest timepoints of signal increase were at 12, 16 and 48 h post-treatment of cisplatin for MRP1, MRP2 and MRP3, respectively; and the H&E staining showed normal tubular morphology at 48 h post-treatment of cisplatin, but hyaline casts at 72 h post-treatment of cisplatin. These observations were similar to those in NCr mice (FIG. 19 and FIG. 21). Thereby, these results validated that MRPs1-3 can detect drug-induced AKI in different mouse strains.

Figure 41:
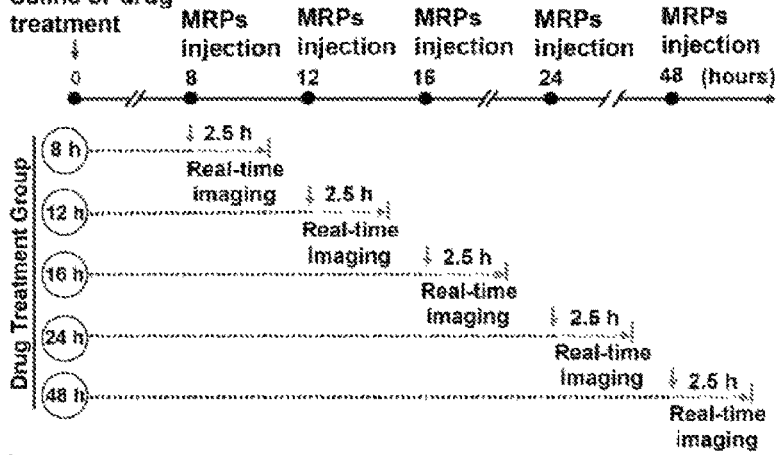
Figure 41:
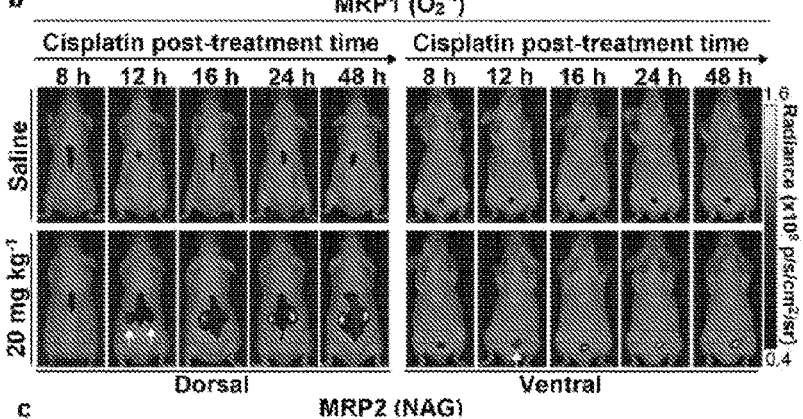
Figure 41:
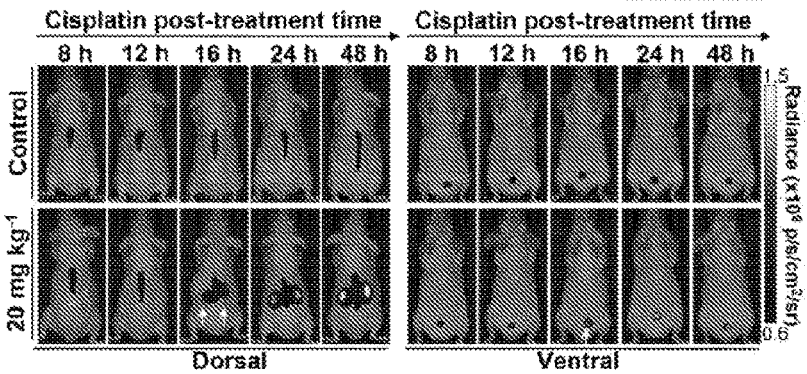
Figure 41:
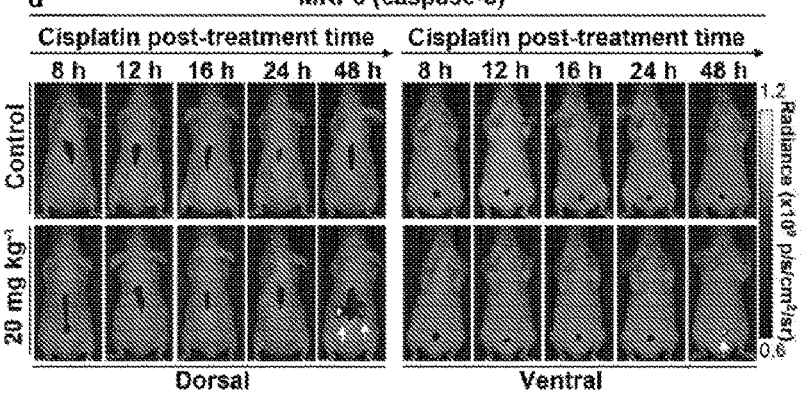
Figure 41:
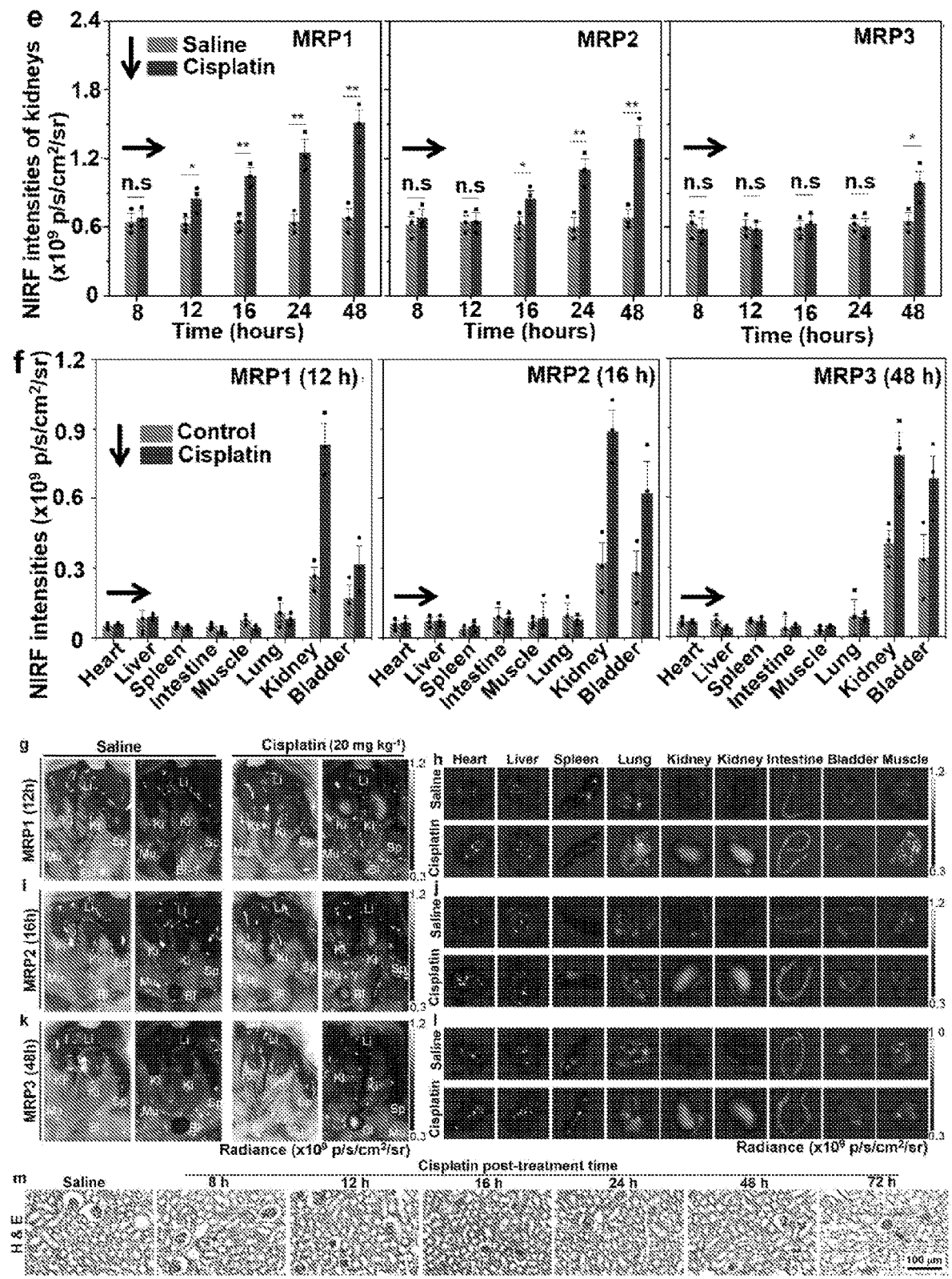

FIG. 41 Depicts real-time in vivo NIRF imaging of cisplatin-induced AKI in living aged mice (25-weeks): (a) schematic illustration of development of cisplatin-induced AKI model and NIRF imaging at different post-treatment timepoints. Cisplatin was intraperitoneally administered into living mice at 20 mg kg$^{-1}$ followed by i.v injection of MRP1, MRP2, or MRP3 (8 µmol kg$^{-1}$ body weight) at different timepoints post-treatment of cisplatin (8, 12, 16, 24 or 48 h). Real-time NIRF imaging was conducted every 30 min for 2.5 h after i.v injection of MRP1, MRP2 or MRP3; representative NIRF images of living mice at t=30 min after i.v injection of (b) MRP1, (c) 60 min after i.v injection of MRP2, and (d) MRP3 at different post-treatment timepoints (8, 12, 16, 24 or 48 h). MRP1, MRP2 and MRP3 had the highest signals at 30, 60 and 60 min post-injection, respectively. The white arrows indicate the kidneys and bladder in dorsal and ventral side, respectively. NIRF images acquired at 720 nm upon excitation at 675 nm with the IVIS spectrum imaging system. The experiments were repeated independently three times with similar results; (e) NIRF intensities of kidneys in living mice at t=30 min after i.v injection of MRP1 or 60 min after i.v injection of MRP2 and MRP3 at different post-treatment timepoints (8, 12, 16, 24 or 48 h). Data are the mean±SD, and represent mice treated with saline and cisplatin, respectively, for the left and right charts of each timepoint. n=3 independent mice. Two-tailed student's t-test. Saline versus cisplatin treated groups, n.s: not significant, *p<0.05, **p<0.01; (f) signal quantification of resected organs from mice with i.v injection of (h) MRP1, (j) MRP2 and (l) MRP3 after treatment of cisplatin for 12, 16 and 48 h, respectively. Data are the mean±SD. n=3 independent mice. Data in (f) represent the control mice and mice treated with cisplatin, respectively, for the left and right charts of each timepoint. Representative NIRF images of the abdominal cavity of mice and resected organs from mice with i.v injection of (g) MRP1, (i) MRP2, and (k) MRP3 (8 µmol kg$^{-1}$ body weight) after treatment of cisplatin (20 mg kg$^{-1}$) for 12, 16 and 48 h, respectively. Liver (Li), muscle (Mu), spleen (Sp), kidneys (Ki), bladder (Bl). The bladder from cisplatin-treated mouse in the panel of (g) showed lower fluorescence intensity than that in panel of (h) due to urinary incontinence and bladder emptying after resection. The NIRF images acquired at 720 nm upon excitation at 675 nm with the IVIS spectrum imaging system. The experiments were repeated independently three times with similar results; and (m) representative photomicrographs of H&E staining in paraffin embedded kidney sections from mice after treatment of saline (0.2 ml), or after treatment of cisplatin (20 mg kg$^{-1}$) for 8, 12, 16, 24, 48 or 72 h. Green arrow and triangles indicate loss of brush border and sloughed cells in the tubular lumen, respectively (Scale bar=100 µm). The experiments were repeated independently three times with similar results. Similar to the results for relatively young NCr mice (8-weeks), the earliest timepoints of signal increase were 12, 16 and 48 h post-treatment of cisplatin for MRP1, MRP2 and MRP3, respectively. However, the signals of kidneys in aged mice at each post-treatment timepoints is slightly higher (3%-10%) than those in young mice. This was caused by the altered inflammatory response and antioxidant signaling in the kidneys of aged mice.

Figure 42:
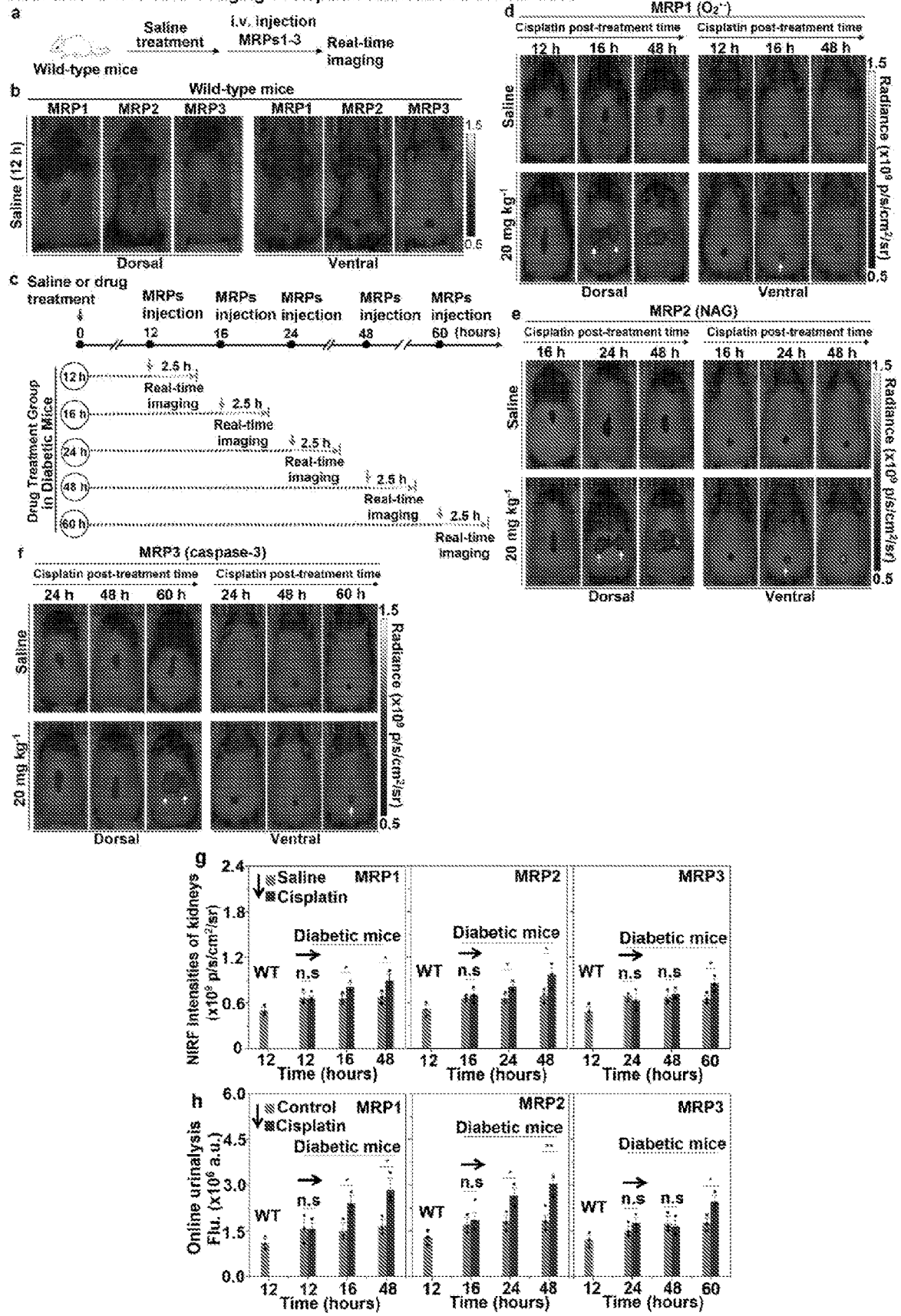

FIG. 42 Depicts real-time in vivo NIRF imaging of cisplatin-induced AKI in CKD mice: (a) schematic illustration of NIRF imaging in healthy wild-type (WT) mice; (b) representative NIRF images of living C57BLKS/J mice at t=30 min after i.v injection of MRP1 or 60 min after i.v injection of MRP2 and MRP3 at 12 h post-treatment of saline. The experiments were repeated independently three times with similar results; (c) schematic illustration of development of cisplatin-induced AKI model in type 2 diabetic BKS-db mice and NIRF imaging at different post-treatment timepoints. Cisplatin was intraperitoneally administered into living mice at 20 mg $kg^{-1}$ followed by i.v injection of MRP1, MRP2, or MRP3 (8 µmol $kg^{-1}$ body weight) at different timepoints post-treatment of cisplatin (12, 16, 24, 48 or 60 h). Real-time NIRF imaging was conducted every 30 min for 2.5 h after i.v injection of MRP1, MRP2 or MRP3; representative NIRF images of living mice at t=30 min after i.v injection of (d) MRP1, (e) 60 min after i.v injection of MRP2, and (f) MRP3 at different post-treatment timepoints (12, 16, 24, 48 or 60 h). MRP1, MRP2 and MRP3 had the highest signals at 30, 60 and 60 min post-injection, respectively. The white arrows indicate the kidneys and bladder in dorsal and ventral side, respectively. NIRF images acquired at 720 nm upon excitation at 675 nm with the IVIS spectrum imaging system (IVIS Lumina III). The experiments were repeated independently three times with similar results; (g) NIRF intensities of kidneys in living mice at t=30 min after i.v injection of MRP1 or 60 min after i.v injection of MRP2 and MRP3 at different post-treatment timepoints (12, 16, 24, 48 or 60 h). Data are the mean±SD, and represent mice treated with saline and cisplatin, respectively, for the left and right charts of each timepoint. n=3 independent mice. Two-tailed student's t-test. Saline versus cisplatin treated groups, n.s: not significant, *p<0.05; and (h) fluorescence readouts of excreted MRPs1-3 in the urine from saline-treated wild-type mice, saline-treated diabetic mice or cisplatin-treated diabetic mice after i.v injection of MRPs1-3 (8 µmol $kg^{-1}$ body weight) at different post-treatment timepoints (online urinalysis). Fluorescence intensities were acquired at 720 nm upon excitation at 675 nm. Data are the mean±SD, and represent control mice and mice treated with cisplatin, respectively, for the left and right charts of each timepoint. n=3 independent mice. Two-tailed student's t-test. Saline versus cisplatin treated groups, n.s: not significant, *p<0.05, **p<0.01.

Figure 43:
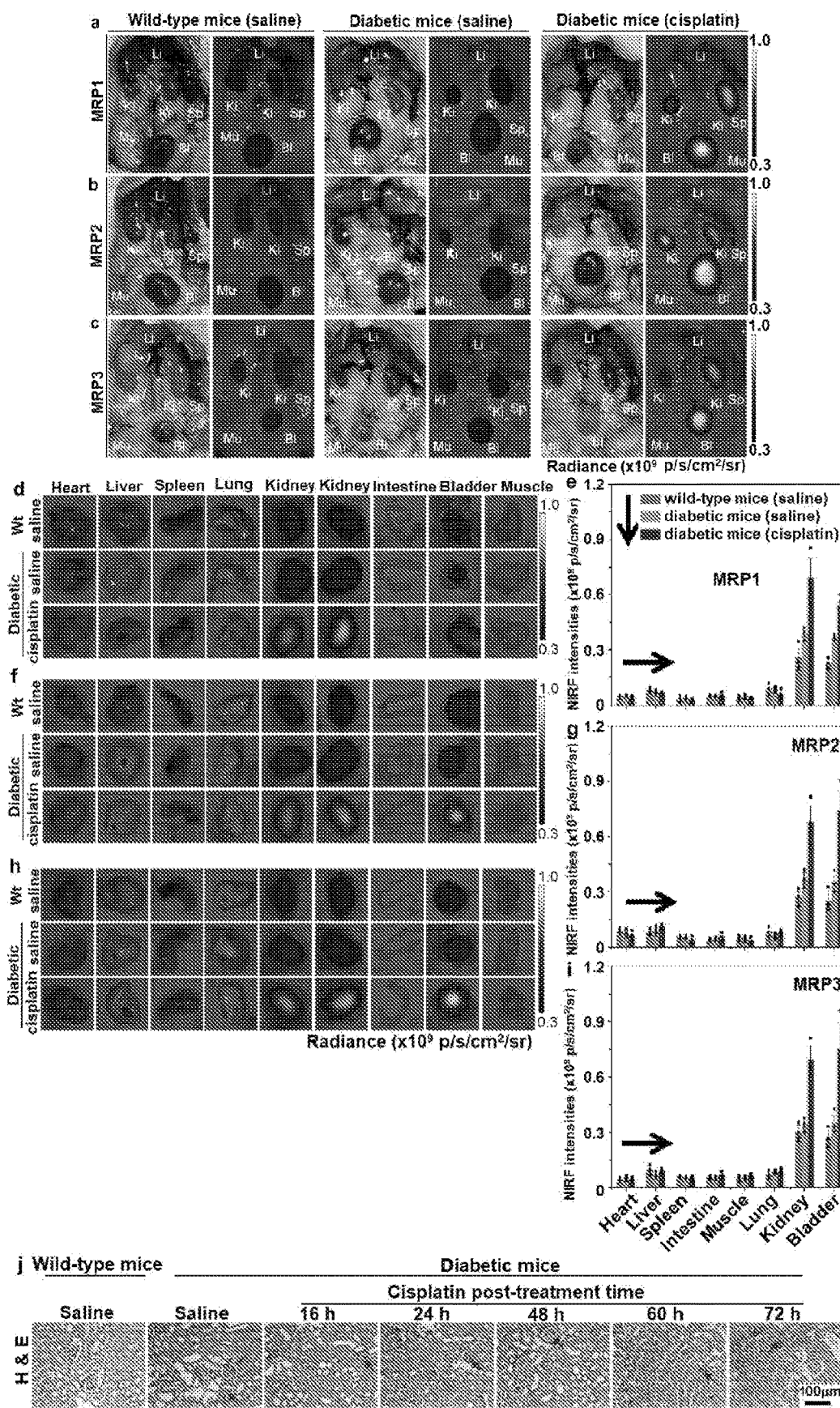

FIG. 43 Depicts ex vivo NIRF signal analysis of MRPs1-3 in CKD mouse model of cisplatin induced AKI: representative NIRF images of the abdominal cavity of mice with i.v injection of (a) MRP1, (b) MRP2, and (c) MRP3 (8 µmol $kg^{-1}$ body weight) after treatment of saline or cisplatin (20 mg $kg^{-1}$) for 16, 24 and 60 h, respectively. Liver (Li), muscle (Mu), spleen (Sp), kidneys (Ki), bladder (Bl). The experiments were repeated independently three times with similar results; (d, f and h) ex vivo NIRF images, and (e, g and i) signal quantification of resected organs from mice with i.v injection of (d) MRP1, (f) MRP2, and (h) MRP3 after treatment of cisplatin for 16, 24 and 60 h, respectively. The NIRF images acquired at 720 nm upon excitation at 675 nm with the IVIS spectrum imaging system (IVIS Lumina III). Data are the mean±SD. n=3 independent mice; (j) representative photomicrographs of H&E staining in paraffin embedded kidney sections from healthy wild-type mice or diabetic mice after treatment of saline (0.2 ml), or cisplatin (20 mg $kg^{-1}$) for 16, 24, 48, 60 or 72 h. Red arrows and green triangle indicate expansion of the mesangial matrix and thickened glomerular basement membranes, respectively. Green arrows indicate hyaline casts (Scale bar=100 µm). The experiments were repeated independently three times with similar results. For (e), (g) and (i), the data represent wild-type mice treated with saline, diabetic mice treated saline and diabetic mice treated with cisplatin, respectively, from the left to right chart of each organ.

Figure 44:
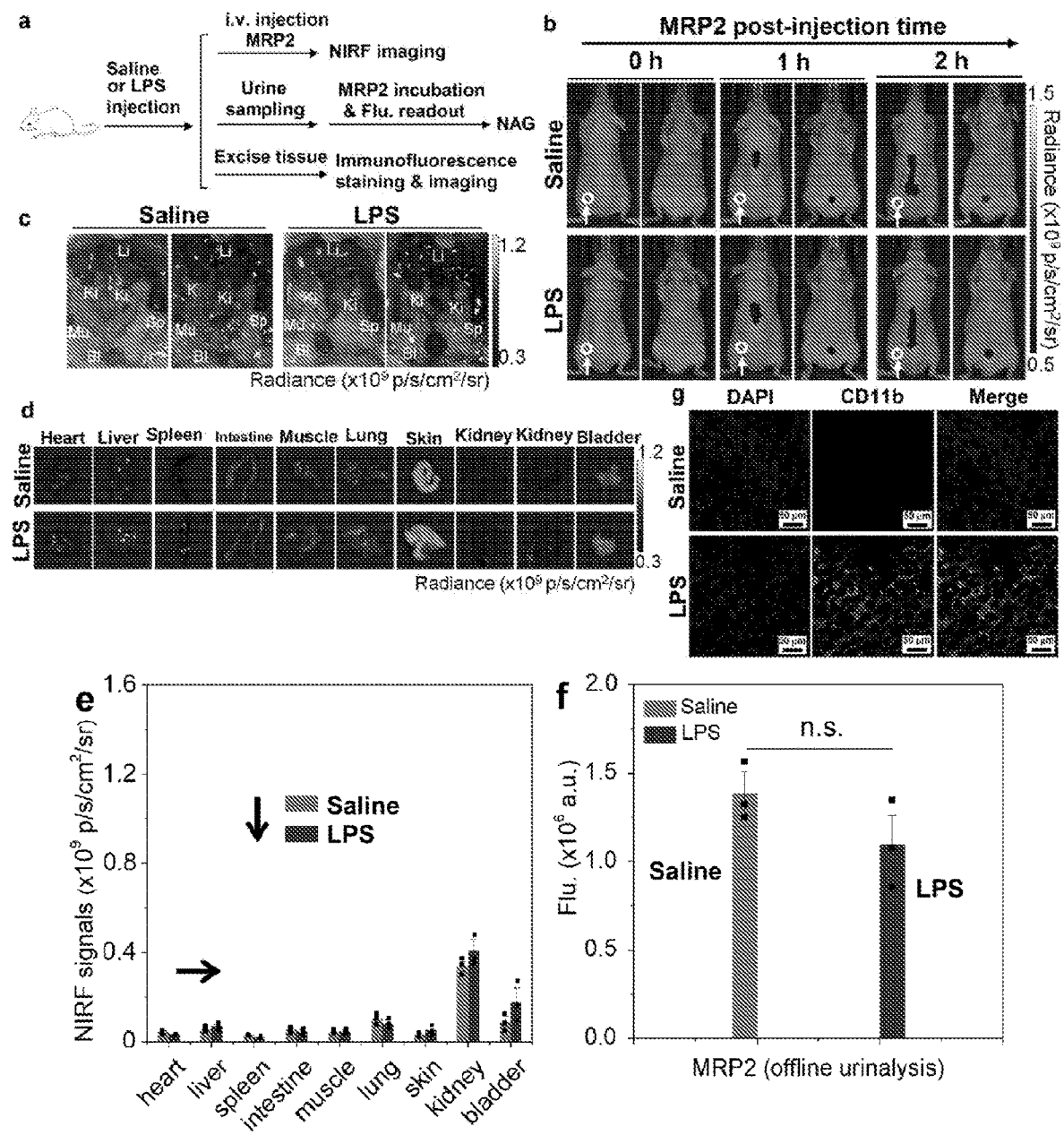

FIG. 44 Depicts specificity studies in living mice with local skin inflammation: (a) schematic illustration of development of LPS-induced local skin inflammation and NIRF imaging and optical urinalysis. Real-time NIRF imaging was conducted after treatment with saline (15 µl) or LPS (5 µg in 15 µl PBS; intradermal injection into the skin on the left thigh) followed by i.v injection of MRP2 (8 µmol $kg^{-1}$ body weight). Fluorescence readouts of MRP2 after incubation with the urine samples collected from saline or LPS-treated living mice. Sections of skin from the injection sites were resected after euthanasia for immunofluorescence staining; (b) representative NIRF images of living mice at 1 or 2 h post-injection of MRP2 after 4 h treatment of saline or LPS. The white arrows and circles indicate the LPS injection sites on the left thigh. NIRF images acquired for 0.1 s at 720 nm upon excitation at 675 nm with the IVIS spectrum imaging system; (c) NIRF images of the abdominal cavity of mice at 2 h post-injection of MRP2 after 4 h treatment of saline or LPS. Liver (Li), muscle (Mu), spleen (Sp), kidneys (Ki), and bladder (Bl). The bladder from saline-treated mouse in the panel of c and d showed low fluorescence intensity compared to LPS-treated mouse due to urinary incontinence and bladder emptying after resection. The experiments were repeated independently three times with similar results; (d) ex vivo NIRF images, and (e) signal quantification of resected organs from mice at 2 h post-injection of MRP2 after 4 h treatment of saline or LPS. NIRF images acquired for 0.1 s at 720 nm upon excitation at 675 nm with the IVIS spectrum imaging system. Data are the mean±SD, and represent mice treated with saline and LPS, respectively, for the left and right charts of each organ. n=3 independent mice; (f) fluorescence readouts of MRP2 after incubation with the urine samples collected from the living mice at 4 h post-treatment of saline or LPS. Fluorescence intensities were acquired at 720 nm upon excitation at 675 nm. Data are the mean±SD, and represent mice treated with saline and LPS, respectively, for the left and right charts of each organ. n=3 independent mice. Two-tailed student's t-test. Saline versus LPS treated groups, n.s: not significant; and (g) representative immunofluorescence-stained skin section obtained from saline-treated mice and LPS-treated mice. Skin slices were stained with anti-CD11b antibody. Blue fluorescence indicates the signal from DAPI, and green fluorescence indicates the signal from anti-CD11b antibody staining. (Scale bar=50 µm). The experiments were repeated independently three times with similar results. Strong green fluorescence corresponding to anti-CD11b staining was observed in the skin slide of LPS-treated mice, indicating local inflammation induced by LPS. Note that such a low dosage of LPS cannot induce organ injury (N. H. Lameire, et al., The Lancet, 2013, 382, 170-179).

Figure 45:
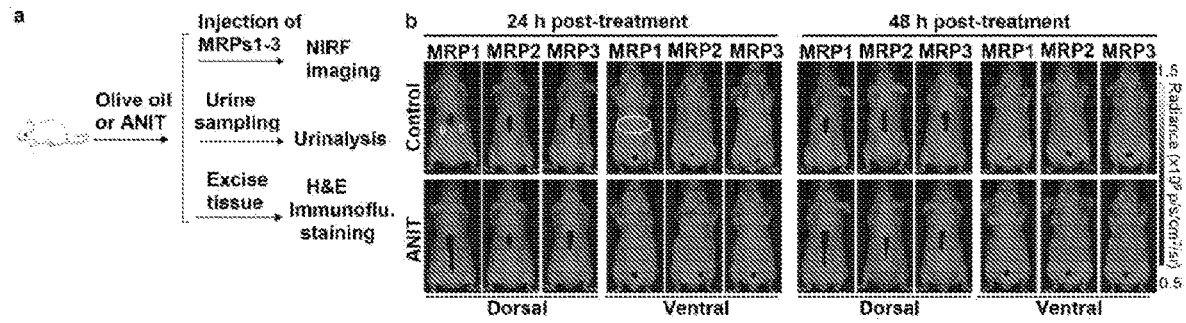
Figure 45:
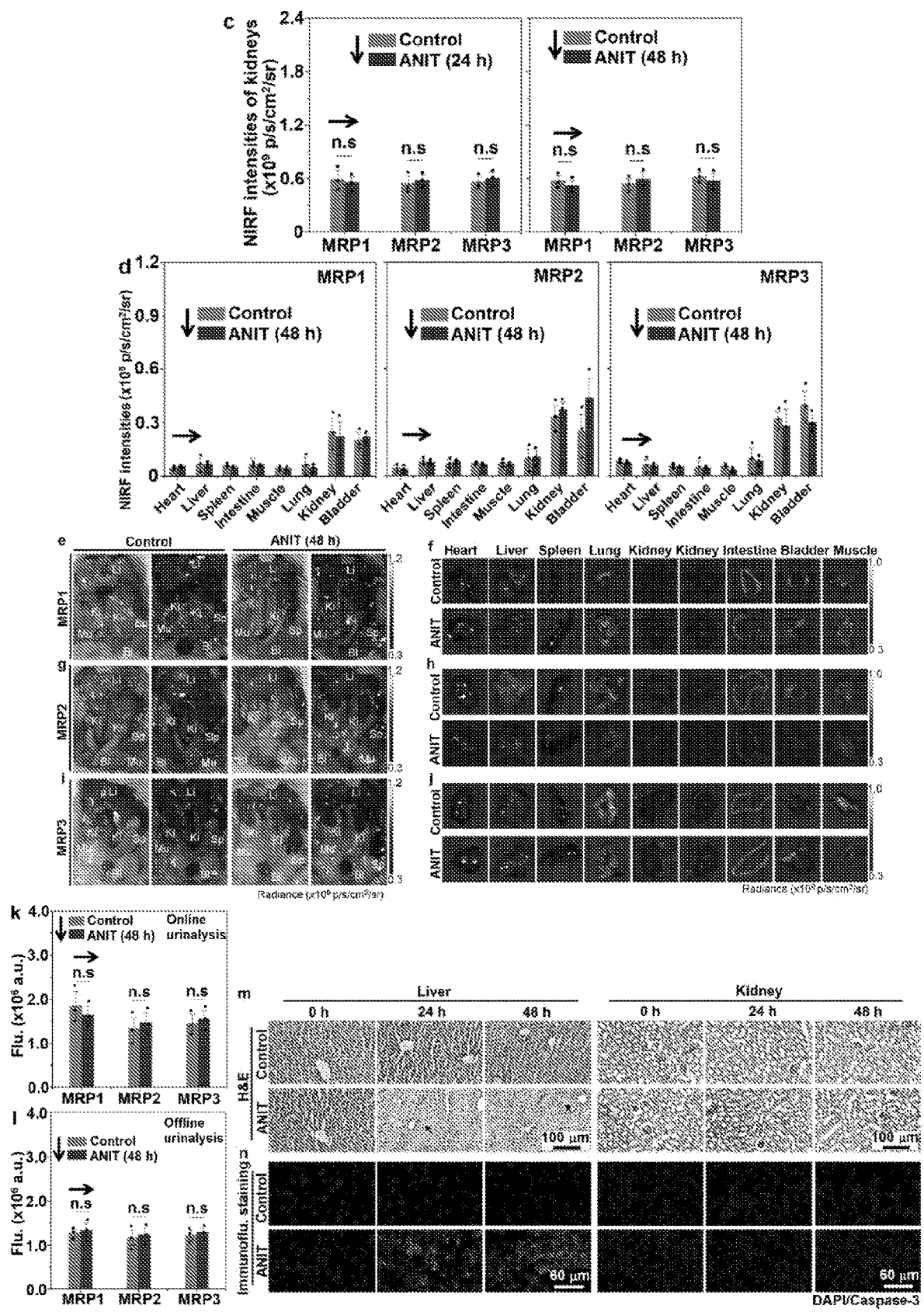

FIG. 45 Depicts real-time in vivo NIRF imaging of ANIT-induced liver injury in living mice: (a) schematic illustration of development of ANIT-induced liver injury and NIRF imaging and optical urinalysis. Real-time NIRF imaging was conducted after treatment with olive oil (0.2 ml, control group) or ANIT (dissolved in olive oil, 75 mg kg$^{-1}$ body weight, intragastrically injection) followed by i.v injection of MRPs1-3 (8 μmol kg$^{-1}$ body weight). Fluorescence readouts of excreted MRPs1-3 in the urine from control or ANIT-treated living mice after i.v injection of MRPs1-3 at 48 h post-treatment of ANIT (online urinalysis) or fluorescence readouts of MRPs1-3 after incubation with the urine samples collected from control or ANIT-treated living mice (offline urinalysis). Liver and kidneys were resected after euthanasia for Hematoxylin-Eosin and immunofluorescence staining; (b) representative NIRF images of living mice at 30 min post-injection of MRP1 or 60 min post-injection of MRP2 and MRP3 after 24 h or 48 h treatment of olive oil or ANIT. The white circles indicate the kidney and liver sites in dorsal and ventral side, respectively. NIRF images acquired for 0.1 s at 720 nm upon excitation at 675 nm with the IVIS spectrum imaging system. The experiments were repeated independently three times with similar results; (c) NIRF intensities of kidneys in living mice at t=30 min after i.v injection of MRP1 or 60 min after i.v injection of MRP2 and MRP3 at different post-treatment timepoints (24 or 48 h). Data are the mean±SD, and represent the control mice and mice treated with ANIT, respectively, for the left and right charts of each MRP. n=3 independent mice. Two-tailed student's t-test. Saline versus ANIT treated groups, n.s: not significant; (d) signal quantification of resected organs from mice with i.v injection of (f) MRP1, (h) MRP2, and (j) MRP3 after treatment of olive oil or ANIT for 48 h, respectively. Data are the mean±SD, and represent the control mice and mice treated with ANIT, respectively, for the left and right charts of each organ. n=3 independent mice; representative NIRF images of the abdominal cavity of mice at 2 h post-injection of (e) MRP1, (g) MRP2, and (i) MRP3 after 48 h treatment of olive oil or ANIT. Liver (Li), muscle (Mu), spleen (Sp), kidneys (Ki), and bladder (Bl). The experiments were repeated independently three times with similar results. Ex vivo NIRF images of resected organs from mice at 2 h post-injection of (f) MRP1, (h) MRP2, and (j) MRP3 after 48 h treatment of olive oil or ANIT. NIRF images acquired for 0.1 s at 720 nm upon excitation at 675 nm with the IVIS spectrum imaging system. Intensity values are the mean±s.d. for n=3 mice; (k) fluorescence readouts of excreted MRPs1-3 in the urine from control or ANIT-treated living mice after i.v injection of MRPs1-3 (8 μmol kg$^{-1}$ body weight) at 48 h post-treatment of ANIT (online urinalysis). Data represent the control mice and mice treated with ANIT, respectively, for the left and right charts of each MRP; (l) fluorescence readouts of MRPs1-3 after incubation with the urine samples collected from control or ANIT-treated living mice at 48 h post-treatment of ANIT (offline urinalysis). Fluorescence intensities were acquired at 720 nm upon excitation at 675 nm. Data are the mean±SD, and represent the control mice and mice treated with ANIT, respectively, for the left and right charts of each MRP. n=3 independent mice. Two-tailed student's t-test. Saline versus ANIT treated groups, n.s: not significant; (m) representative photomicrographs of H&E staining in paraffin embedded liver and kidney sections from control and ANIT-treated mice. Black arrows indicate hepatocyte necrosis. Renal structures were preserved in ANIT-treated mice. (Scale bar=100 μm). The experiments were repeated independently three times with similar results; and (n) confocal fluorescence microscopy images of liver and kidney slices from control and ANIT-treated mice (Scale bar=60 μm). The blue and green signals come from DAPI and caspase-3 antibody staining, respectively. The experiments were repeated independently three times with similar results. Note that ANIT does not cause kidney injury (Miao, Q. et al., Nat. Biotechnol. 2017, 35, 1102-1110). The signals of kidneys and liver from ANIT-treated mice were as low as the background of the control mice after post-treatment of ANIT for 24 h or 48 h. Similarly, no significant difference between control and ANIT-treated mice was observed for both MRP-based online and offline urinalysis. This should be ascribed to the facts that MRPs1-3 do not accumulate in liver and ANIT does not cause kidney injury. H&E staining indicated the liver damage but normal renal morphology for ANIT-treated mice, and immunofluorescence staining further confirmed that the caspase-3 signal was only detectable in liver but not in kidneys.

Figure 46:
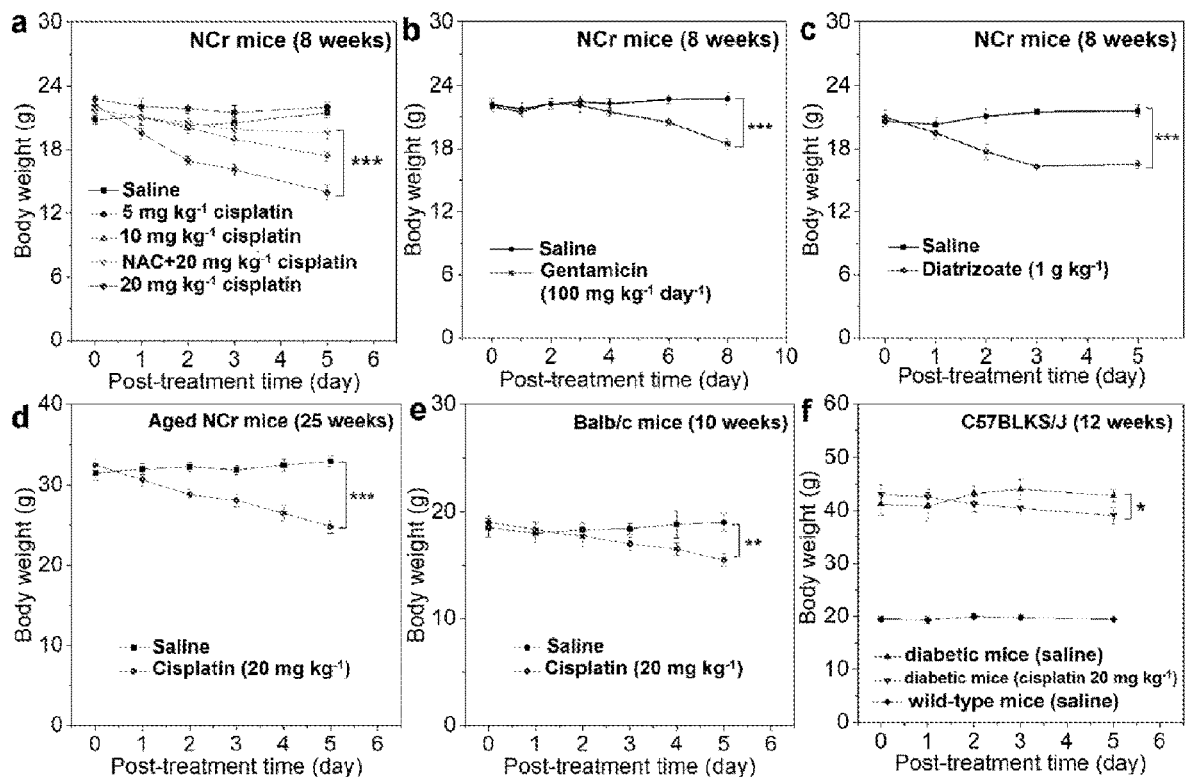

FIG. 46 Depicts the change of body weight in the mouse models of drug-induced AKI: (a) body weight of living NCr nude mice at t=0, 1, 2, 3, 4, or 5 days post-treatment of saline, cisplatin (5, 10, or 20 mg kg$^{-1}$ body weight), or NAC (400 mg kg$^{-1}$ body weight) 30 min prior to cisplatin (20 mg kg$^{-1}$ body weight) administration. Data are the mean±SD. n=3 independent mice. Two-tailed student's t-test. Saline versus cisplatin treated group at day 5, *p<0.001; (b) body weight of living NCr nude mice at t=0, 1, 2, 3, 4, 6, or 8 days post-treatment of saline or gentamicin (100 mg kg$^{-1}$ day$^{-1}$ body weight). Data are the mean±SD. n=3 independent mice. Two-tailed student's t-test. Saline versus gentamicin treated group at day 8, *p<0.001; (c) body weight of living NCr nude mice at t=0, 1, 2, 3, or 5 days post-treatment of saline or diatrizoate (1000 mg kg$^{-1}$ body weight). Data are the mean±SD. n=3 independent mice. Two-tailed student's t-test. Saline versus diatrizoate treated group at day 5, *p<0.001; (d) body weight of living aged NCr nude mice (25 weeks) at t=0, 1, 2, 3, 4, or 5 days post-treatment of saline or cisplatin (20 mg kg$^{-1}$ body weight). Data are the mean±SD. n=3 independent mice. Two-tailed student's t-test. Saline versus cisplatin treated group at day 5, *p<0.001; and (e) body weight of living Balb/c mice at t=0, 1, 2, 3, 4, or 5 days post-treatment of saline or cisplatin (20 mg kg$^{-1}$ body weight). Data are the mean±SD. n=3 independent mice. Two-tailed student's t-test. Saline versus cisplatin treated group at day 5, **p<0.01. (f) Body weight of living C57BLKS/J mice at t=0, 1, 2, 3, 4, or 5 days post-treatment of saline or cisplatin (20 mg kg$^{-1}$ body weight). Data are the mean±SD. n=3 independent mice. Two-tailed student's t-test. Saline versus cisplatin treated group at day 5, *p<0.05. Note that neither premature deaths nor adverse clinical signs in behaviors were observed in saline-treated group. Control mice and the low dose (5 mg kg$^{-1}$) of cisplatin treated group had a mean body weight gain of 2%-5%. Mice of the cisplatin-treated group at 10 mg kg$^{-1}$ and 20 mg kg$^{-1}$ had a mean body weight loss of approximately 20% and 36% by day 5, respectively, while loss of approximately 9% was observed for NAC-cisplatin co-treated group. Similar results in gentamicin-treated, diatrizoate-treated mice and other strains of mice were also recorded.

Figure 47:
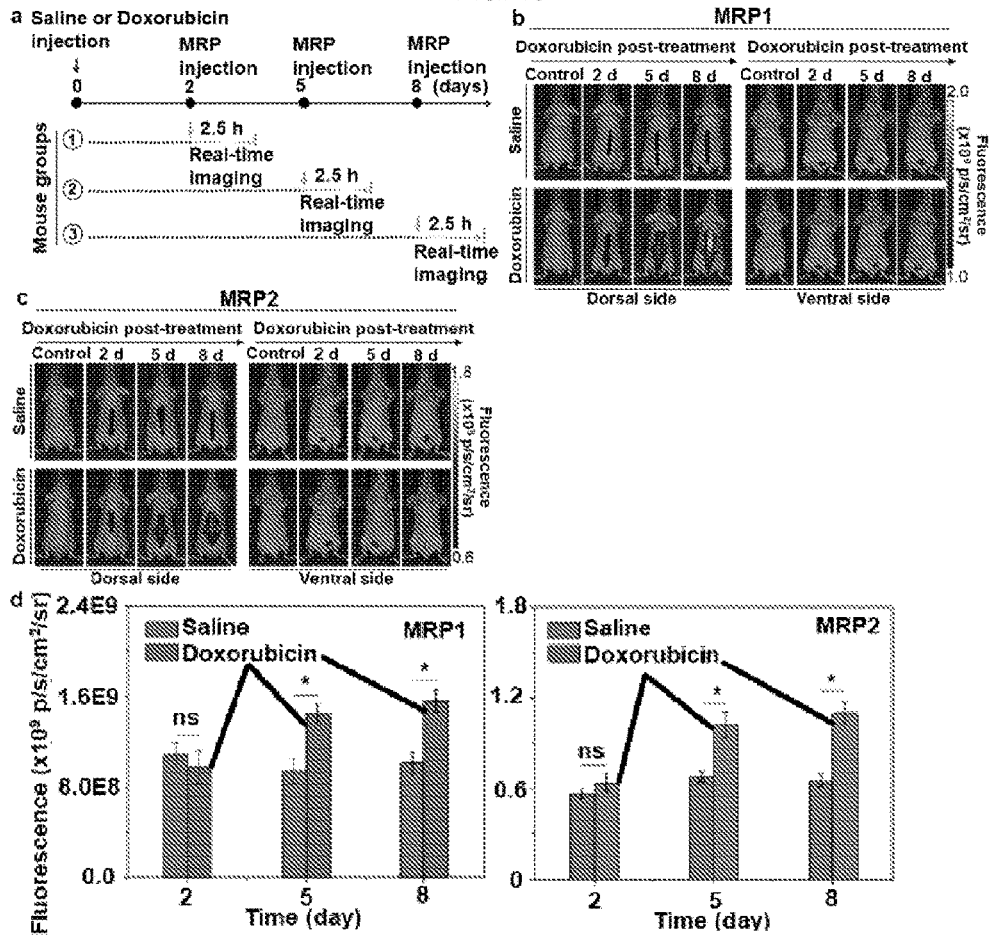
Figure 47:
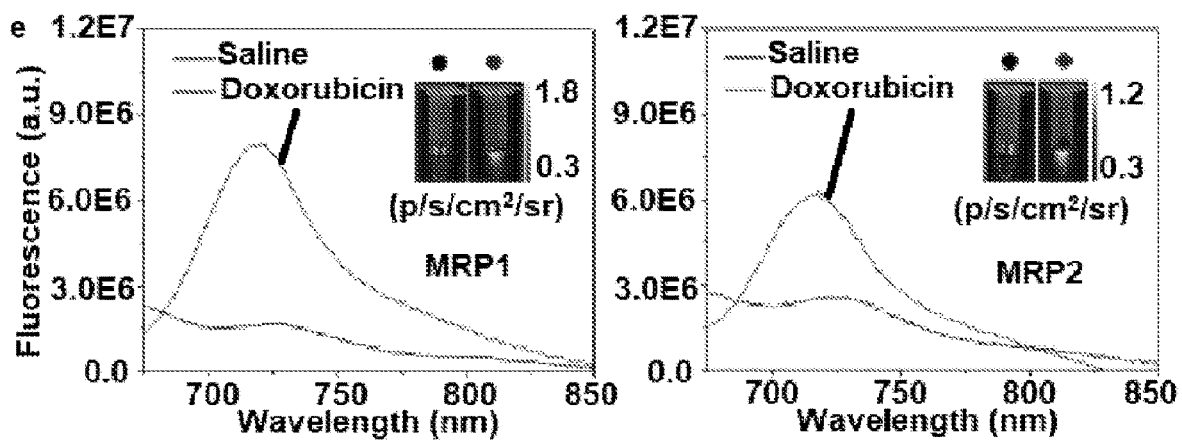

FIG. 47 Depicts real time in vivo fluorescence imaging for the early detection of DOX-induced kidney injury on mice: (a) schematic illustration of development of DOX-induced kidney injury model and real-time imaging at different post-treatment timepoints; (b and c) fluorescence images of the kidneys and bladder in living mice treated intravenously with saline and DOX (9 mg kg$^{-1}$), followed by an i.v. injection of (b) MRP1 and (c) MRP2, respectively. Representative images were acquired for 0.1 s at 720 nm after 30 min intravenously injection of MRP1 (40 mg kg$^{-1}$) or after 60 min intravenously injection of MRP2 (40 mg kg$^{-1}$) into mice at pre-treatment, day 0, day 2, day 5 and day 8 post-treatment of DOX (from left to right in panel (b) and (c)). Excitation: 650 nm. n=3 mice per time point treatment group; (d) average signal intensities in the kidney region of mice at day 0, day 2, day 5 and day 8 post-treatment of DOX after 30 min i.v. injection of MRP1 or 60 min i.v. injection of MRP2 (in panel a and b) (Intensities values are the mean±s.d. for n=3 mice.). *Statistically significant difference in the fluorescence intensities between saline and gentamicin group (*p<0.05, p<0.01, *p<0.001); (e) fluorescence spectra of urine samples recovered from mice at day 5 post-treatment of saline and DOX; followed by an i.v. injection of MRP1 (left panel) or MRP2 (right panel). Inset: the fluorescence images of urine samples were acquired at 720 nm upon excitation at 650 nm. The data represent mice treated with saline and doxorubicin, respectively, for the left and right charts of each timepoint.

Figure 48:
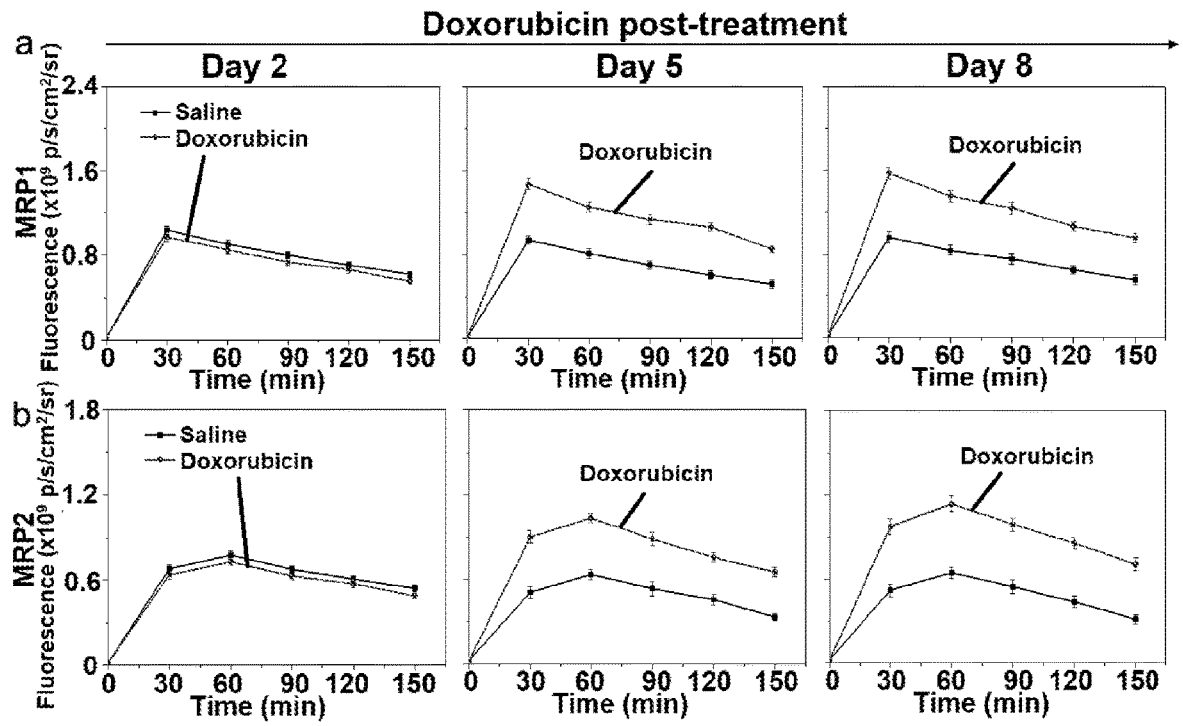

FIG. 48 Depicts the average signal intensities in the kidney region of mice at different time points after i.v. injection of: (a) MRP1; and (b) MRP2 in the group of day 0, day 2, day 5 and day 8 post-treatment of DOX, respectively.

Figure 49:
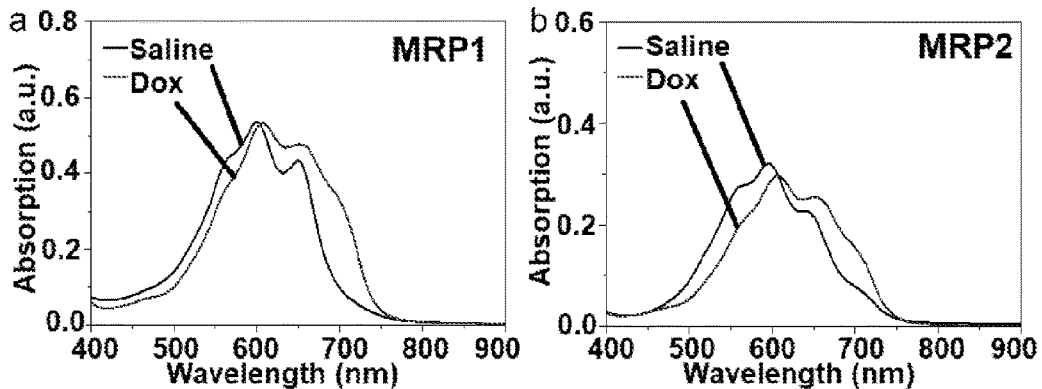

FIG. 49 Depicts the UV/Vis absorption spectra of urine sampling from mice after 5 days treated with saline or DOX, followed by an i.v. injection of: (a) MRP1; and (b) MRP2.

Figure 50:
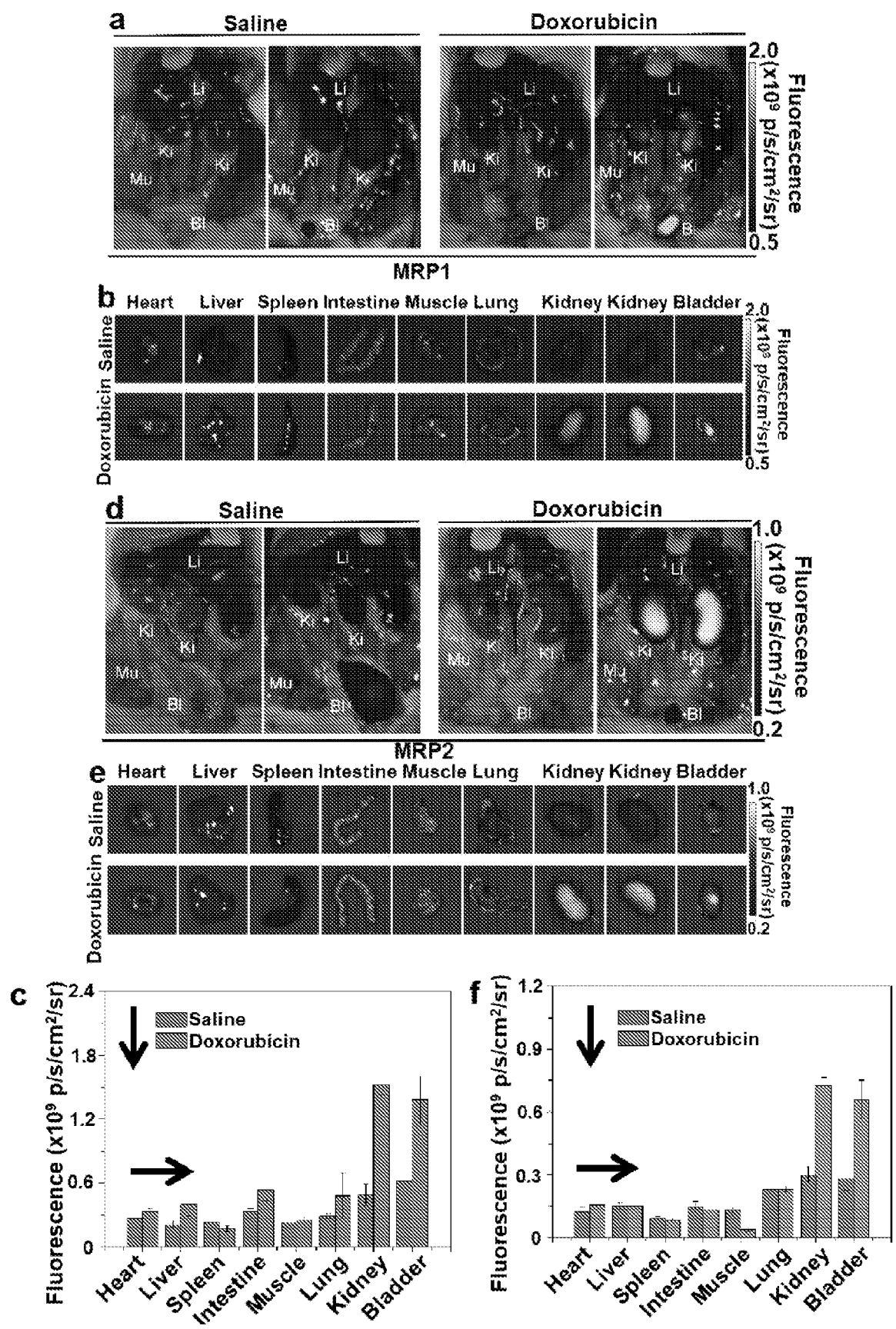

FIG. 50 Depicts fluorescence images of abdominal cavity of mice after day 5 treatment of saline or DOX, followed by an intravenous injection of MRP1 and MRP2, respectively: (a) fluorescence images of abdominal cavity of mice injected with MRP1. Mice treated with saline displayed very weak fluorescence signal in kidney and bladder. In contrast, mice treated with DOX exhibited strong fluorescence signal in both kidney and bladder; (b) ex vivo NIR fluorescence images of resected organs were obtained at 1 h post-injection of MRP1 intravenously into mice; and (c) ex vivo fluorescence quantification of resected organs (in panel b) of mice 1 h after systemic administration of MRP1 via tail vein injection. Values are the mean±s.d. for n=3 mice. The data represent mice treated with saline and doxorubicin, respectively, for the left and right charts of each organ; (f) fluorescence images of abdominal cavity of mice injected with MRP2. Mice treated with saline displayed very weak fluorescence signal in kidney and bladder. In contrast, mice treated with DOX exhibited strong fluorescence signal in both kidney and bladder. The data represent mice treated with saline and doxorubicin, respectively, for the left and right charts of each organ; (d) ex vivo NIR fluorescence images of resected organs were obtained at 1 h post-injection of MRP2 intravenously into mice; and (e) ex vivo fluorescence quantification of resected organs (in panel e) of mice 1 h after systemic administration of MRP2 via tail vein injection. Values are the mean±s.d. for n=3 mice.

Figure 51:
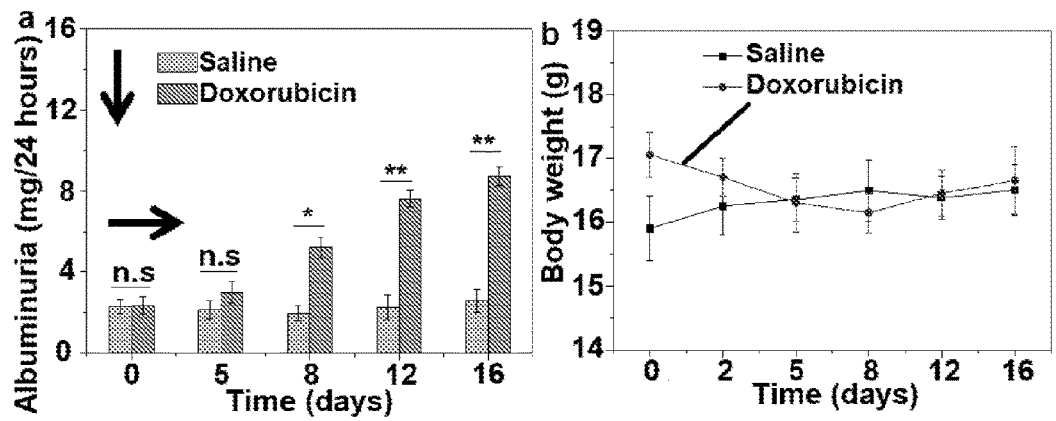

FIG. 51 Depicts: (a) mean albuminuria over 24 hours measured at day 0, 5, 8, 12 and 16 after DOX administration. DOX administered mice had a significant increase of albuminuria level at day 8, while in control mice urinary albumin stayed constant throughout the study. The data represent mice treated with saline and doxorubicin, respectively, for the left and right charts of each timepoint; and (b) mean change in body weight of mice up to 16 days after DOX administration. Mice of the DOX treated group had a mean body weight loss of approximately 6% by day 8, followed by a mean body weight gain of 3% by day 16, while control mice had a mean body weight gain of 4%.

Figure 52:
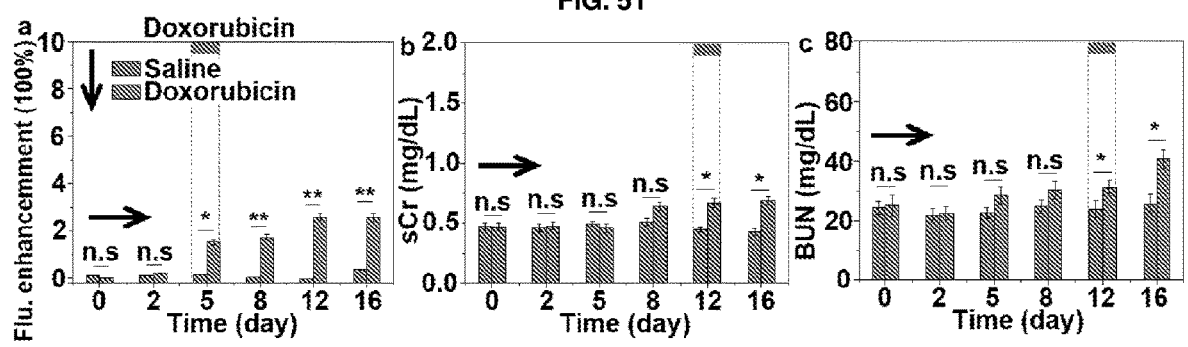

FIG. 52 Depicts: (a) in vitro liquid biopsy for the early detection of kidney injury on CKD mice using MRP2. Comparison of fluorescence enhancement of MRP2 with (b) sCr; and (c) BUN in the time course study. For (a-c), the data represent mice treated with saline and doxorubicin, respectively, for the left and right charts of each timepoint.

Figure 53:
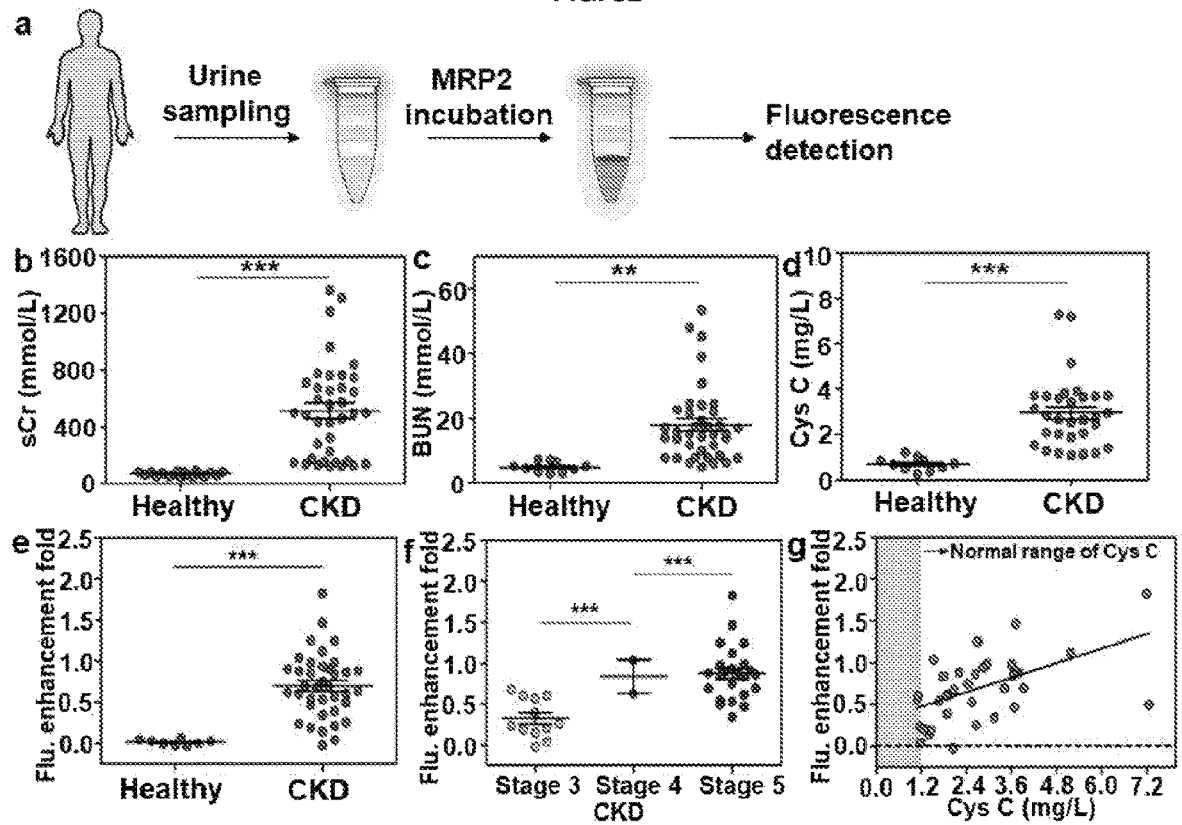

FIG. 53 Depicts in vitro diagnosis of CKD in patients: (a) schematic illustration of measurements of urine samples from CKD patients; (b, c and d) comparison of the concentrations of sCr, BUN and Cys C between CKD patients and healthy volunteers; (e) comparison of urinary biomarker NAG between CKD patients and healthy volunteers through the fluorescence enhancement of MRP2; (f) comparison of the fluorescence enhancement of MRP2 between different CKD stages; and (g) correlation between urinary biomarker NAG and Cys C.

Figure 54:
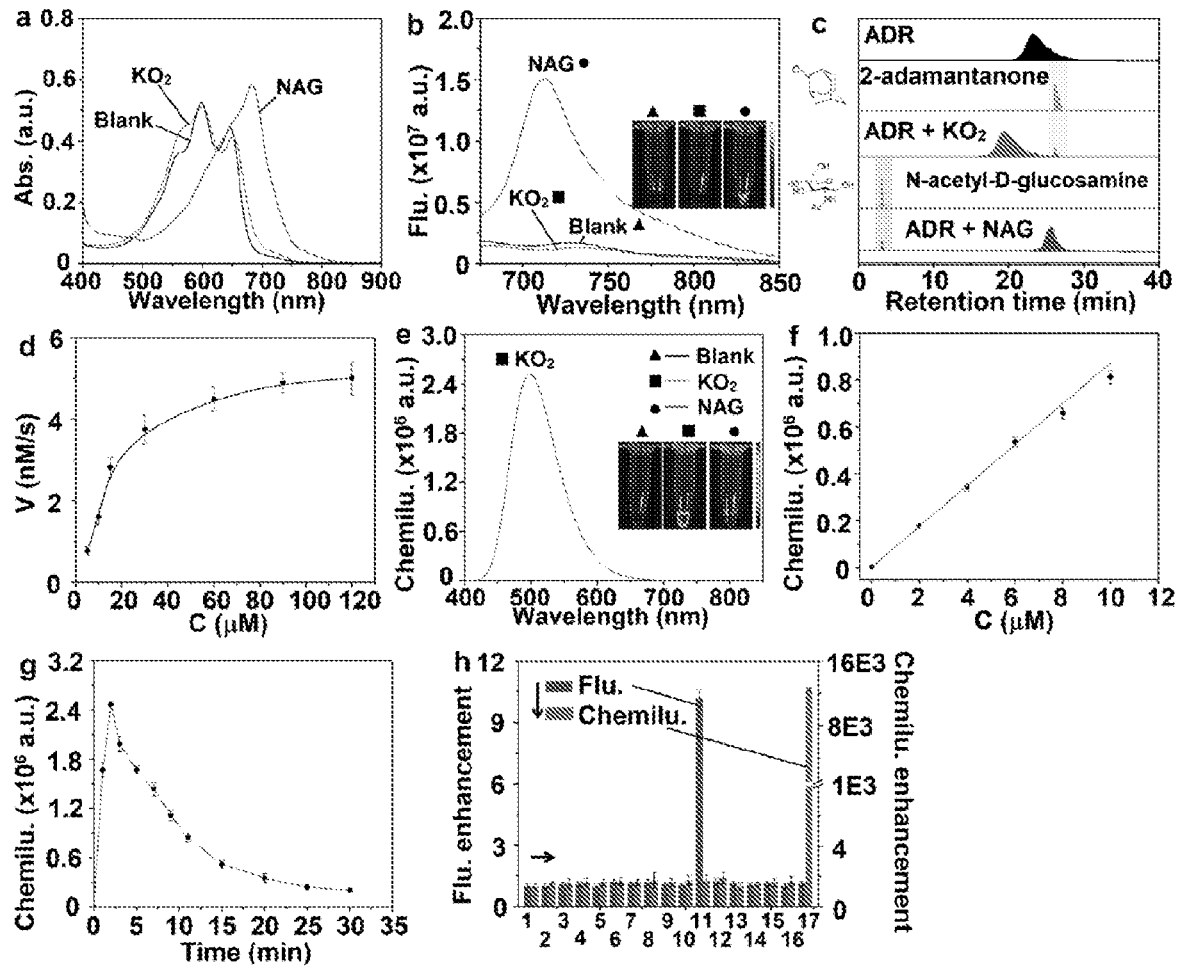

FIG. 54 Depicts in vitro detection of $O_2^{*-}$ and NAG using ADR: (a) UV-Vis absorption, and (b) fluorescence spectra of ADR (30 µM) in the absence or presence of $KO_2$ (60 µM) or NAG (40 mU) in PBS (10 mM, pH 7.4) at 37° C. Inset: the corresponding fluorescence images acquired at 720 nm upon excitation at 675 nm with IVIS spectrum imaging system; (c) HPLC traces of ADR (30 µM) in the absence or presence of $KO_2$ (60 µM) or NAG (40 mU), and the traces of pure 2-admantanone as well as N-acetyl-β-D-glucosamine for comparison; (d) steady-state kinetics of the enzymatic reaction between ADR (5, 10, 15, 30, 60, 90 or 120 µM) and NAG (40 mU); (e) chemiluminescence spectra of ADR (30 µM) in the absence or presence of $KO_2$ (60 µM) or NAG (40 mU) in PBS (10 mM, pH 7.4) at 37° C. Inset: the corresponding chemiluminescence images acquired under bioluminescence mode of IVIS spectrum imaging system with the acquisition time of 1 s; (f) chemiluminescence intensities of ADR (30 µM) as a function of the concentration of $KO_2$ (0-15 µM); (g) chemiluminescence kinetic profiles of ADR (30 µM) in the presence of $KO_2$ (60 µM) in PBS (10 mM, pH 7.4); and (h) NIRF and chemiluminescence changes of ADR (30 µM) at 720 nm and 520 nm, respectively, after incubation with indicated ROS (150 µM), enzymes, and metal ions (150 µM) in PBS (10 mM, pH 7.4) at 37° C. 1, blank; 2, hydroxyl radical; 3, singlet oxygen; 4, peroxynitrite; 5, hypochlorite anion; 6, hydrogen peroxide; 7, furin; 8, plasmin; 9, 8-galactosidase; 10, fibroblast activation protein-alpha; 11, NAG; 12, $Na^+$; 13, $K^+$; 14, $Mg^{2+}$; 15, $Fe^{2+}$; 16, $Ca^{2+}$; 17, $KO_2$. Data in (d) and (f-h) are the mean±SD. n=3 independent experiments.

Figure 55:
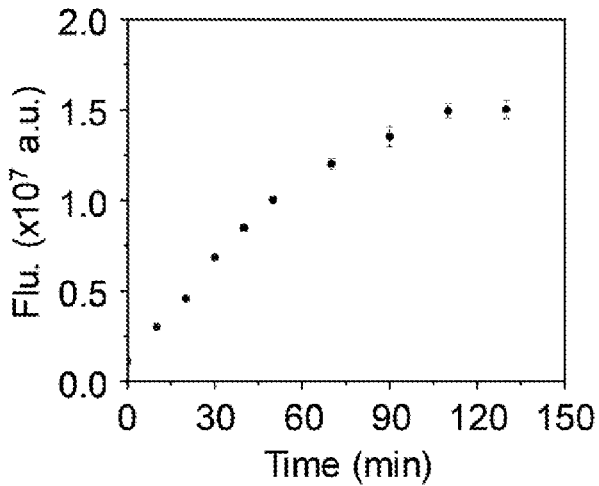

FIG. 55 Depicts the time course of fluorescence changes of ADR (30 µM) at 720 nm in the presence of NAG (40 mU) in PBS buffer (10 mM, pH 7.4) at 37° C. Fluorescence excitation at 675 nm.

Figure 56:
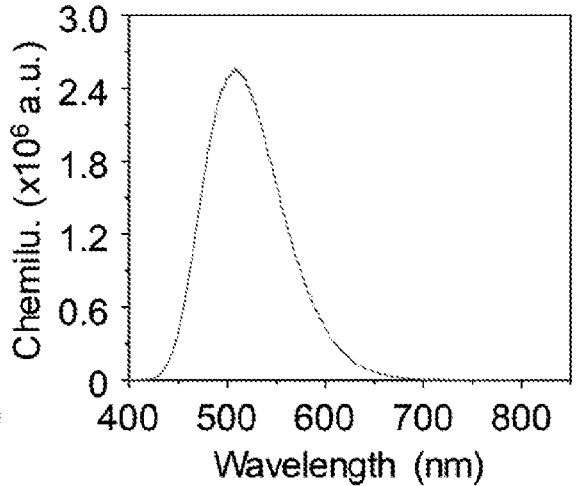

FIG. 56 Depicts the chemiluminescence spectrum in the presence of both NAG and $O_2^{*-}$. ADR (30 µM) was pre-incubated with NAG (40 mU) in PBS buffer (10 mM, pH 7.4) for 120 minutes before addition of $KO_2$ (60 µM). The chemiluminescence maximum was the same as the phenoxy-dioxetane substrate itself at 520 nm, indicating no energy transfer between the chemiluminescent moiety and the NIR moiety.

Figure 57:
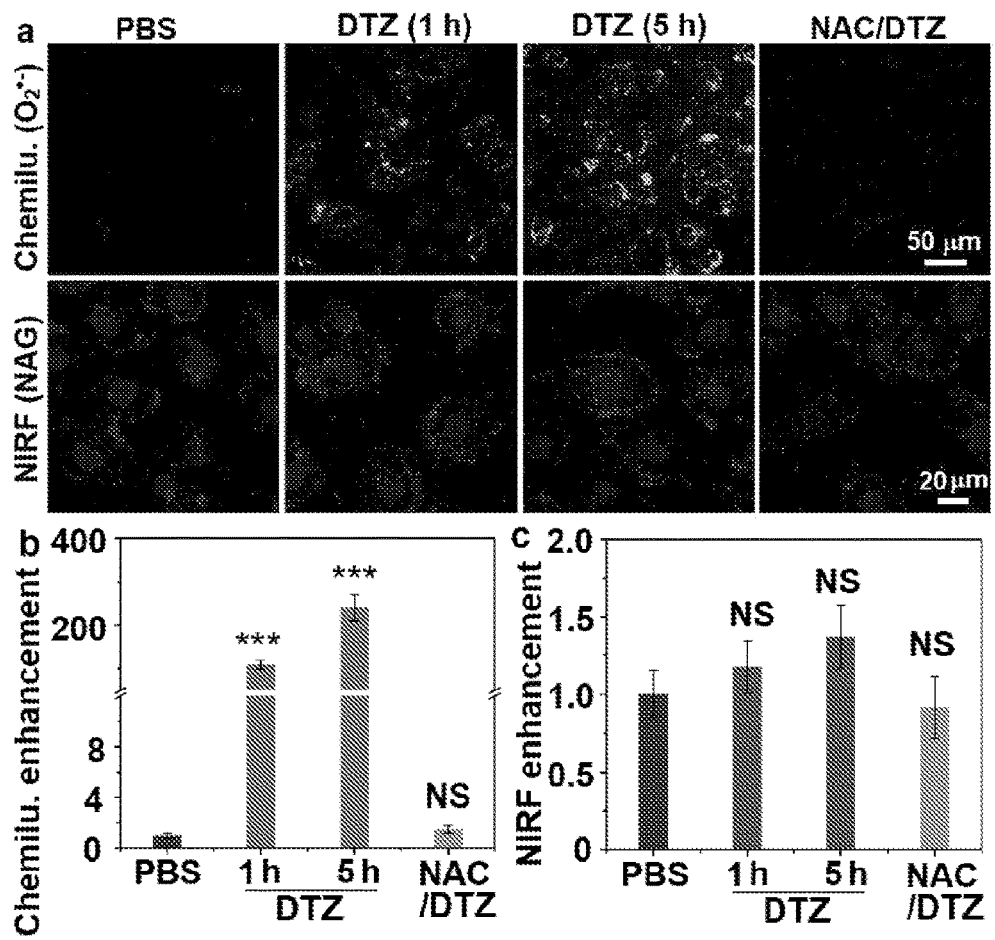

FIG. 57 Depicts in vitro chemiluminescence and NIRF imaging of ADR in HK2 cells: (a) chemiluminescence and NIRF images of cells with different pre-treatments before incubation with ADR (10 µM) for 15 min and 30 min, respectively. From left to right: untreated cells, cells treated with DTZ (100 mg/ml) (1 h and 5 h), and cells pre-treated with NAC (1 h) before co-incubation with DTZ (100 mg/ml) and NAC (100 mM) for 5 h. Blue fluorescence was from cell nucleus stained with DAPI, and green and red fluorescence indicated the signals from ADR; (b) mean chemiluminescence and (c) NIRF intensity enhancement of HK2 cell images in the panel (a). The values relative to the control groups. NS: not significant; ***p<0.001 (n=3). The NIRF intensity of DTZ-treated cells remained nearly the same as the control. This was due to the fact that although treatment of DTZ induced the release of NAG from lysosomes, the total amount of NAG remained the same in the static cellular condition. Nevertheless, these results confirmed the feasibility of ADR to image $O_2^{*-}$ and NAG in living cells.

Figure 58:
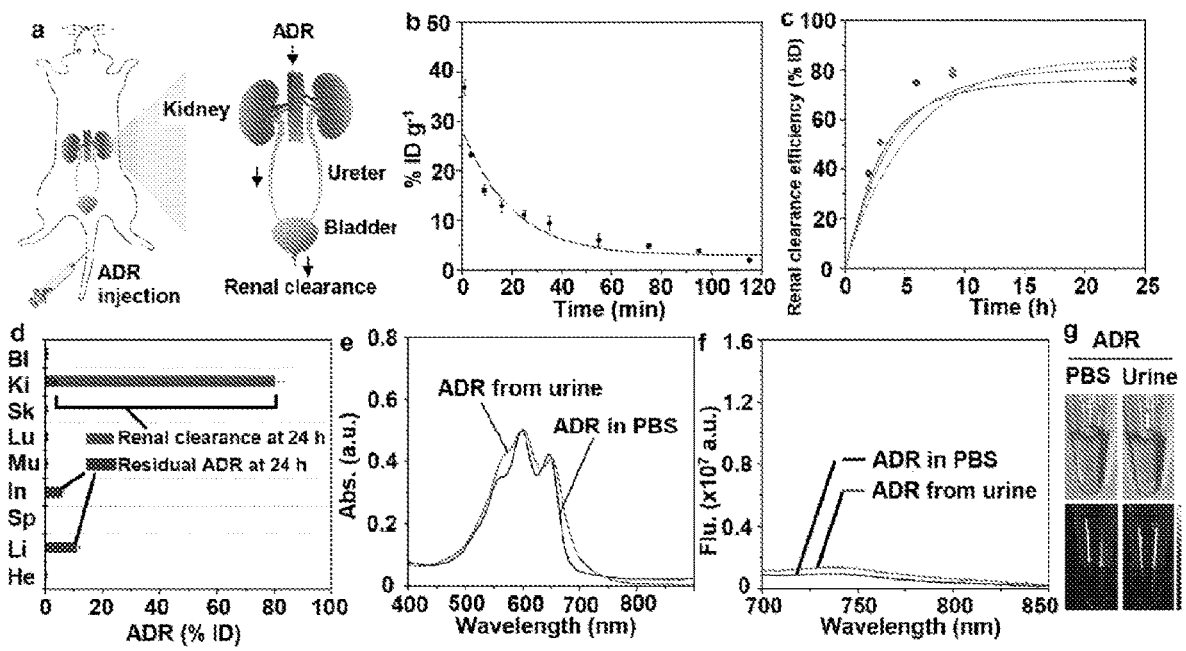

FIG. 58 Depicts renal clearance and in vivo stability studies of ADR: (a) schematic illustration of the excretion of ADR through the urinary tract; (b) blood concentration (% ID $g^{-1}$) decay of ADR after i.v. injection into living mice; (c) renal clearance efficiency as a function of time post-injection of ADR (30 μmol kg-1 body weight) in living mice, three lines represent the measurements in three independent mice; (d) HPLC analysis of ADR excreted from kidneys into urine (red bar) and residual ADR in major organs of mice (black bar) after 24 h injection of ADR. Major organs were homogenised in PBS and centrifuged to remove insoluble components. The supernatant containing extracted probes were analysed by HPLC assay. Heart (He), liver (Li), spleen (Sp), intestine (In), muscle (Mu), lung (Lu), skin (Sk), kidneys (Ki), bladder (Bl); (e-f) in vivo stability studies of ADR using optical characterization; (e) absorption and (f) fluorescence spectra of ADR in PBS and the urine samples after 24 h i.v injection of ADR and excretion from living mice; and (g) white light and NIRF images of ADR in PBS and ADR in the urine excreted from living mice after 24 h i.v. injection of ADR. The corresponding NIRF images acquired at 720 nm upon excitation at 675 nm with IVIS spectrum imaging system. Data in (b) and (d) are the mean±SD. n=3 independent experiments.

Figure 59:
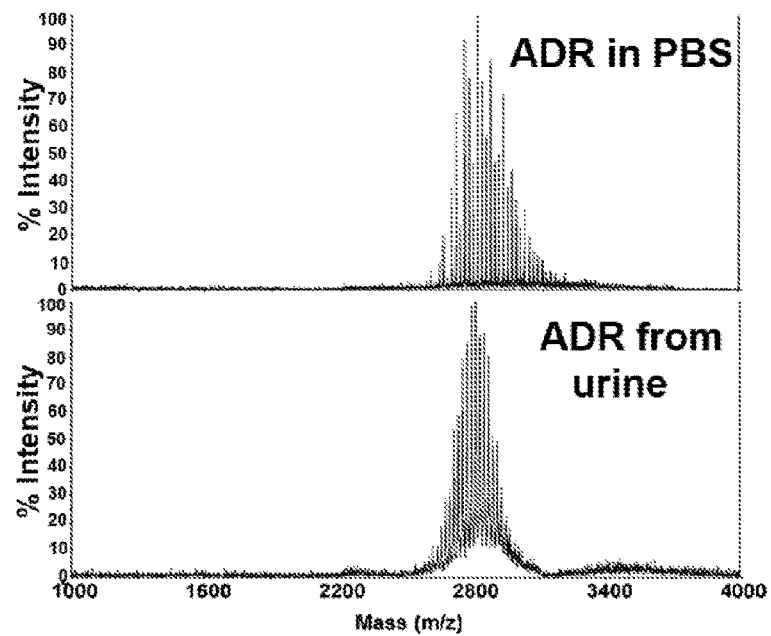

FIG. 59 Depicts in vivo stability studies of ADR using MALDI-TOF mass spectrometry. In vivo stability studies of ADR through MALDI-TOF mass analysis of the urine samples after 24 h i.v injection of ADR (30 μmol $kg^{-1}$ body weight). MALDI-TOF mass analysis of the pure compound ADR in PBS are also presented for comparison. Excreted ADR had almost identical mass range compared to that of the pure compounds in PBS. Note that the MALDI-TOF mass spectra of ADR were performed in the reflector mode.

Figure 60:
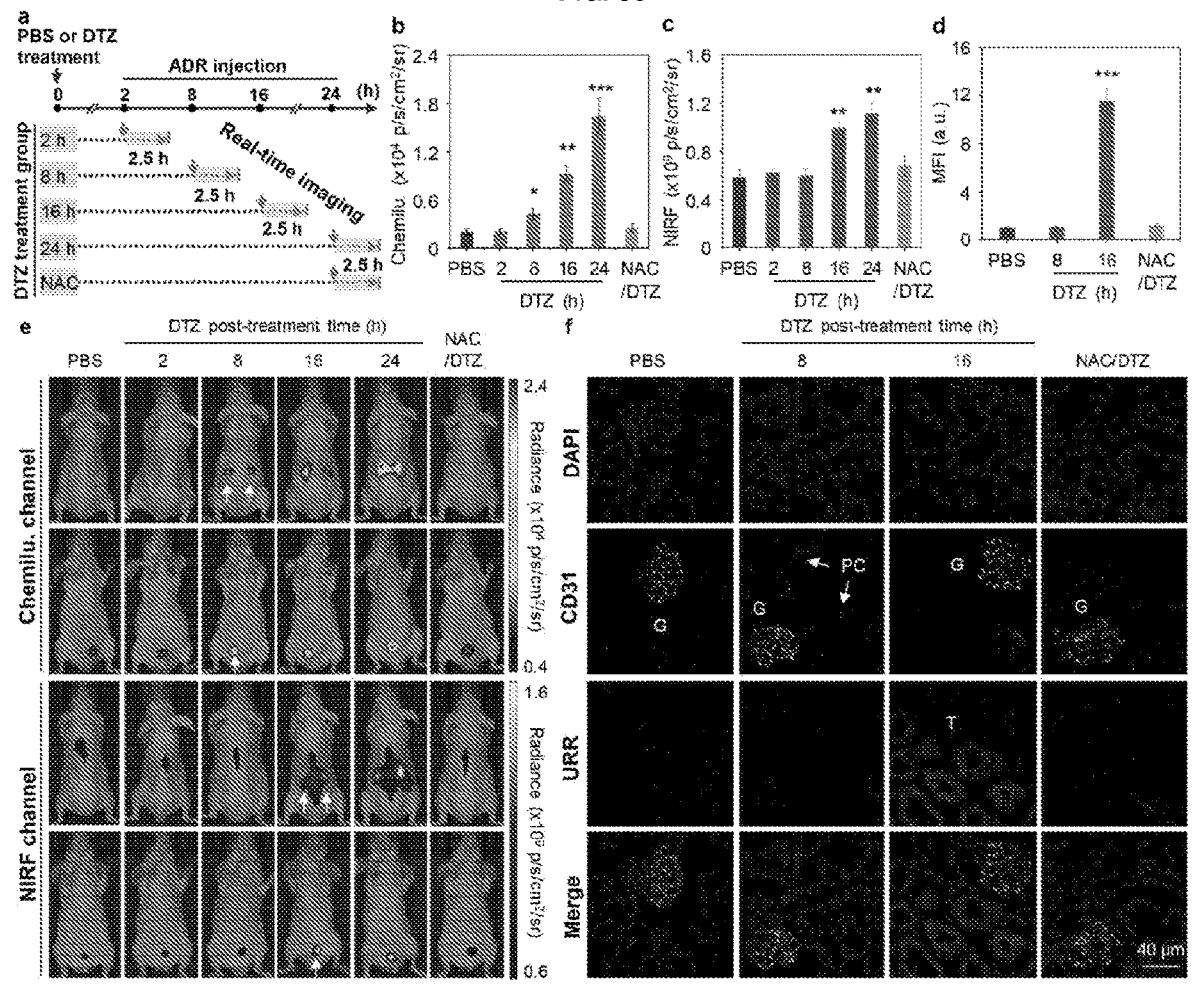

FIG. 60 Depicts in vivo real-time duplex imaging of CIAKI: (a) schematic illustration of development of CIAKI mouse model and imaging at different post-treatment timepoints. DTZ (1 g $kg^{-1}$ body weight) was intravenously administered into living mice, followed by i.v injection of ADR (30 μmol $kg^{-1}$ body weight) at different timepoints post-treatment of DTZ (2, 8, 16, or 24 h). The control groups were treated with PBS or a nephroprotective antioxidant NAC (10 mg $kg^{-1}$ $day^{-1}$, i.p. injection) 3 days prior to DTZ administration. Real-time chemiluminescence and NIRF imaging were performed for 2.5 h after i.v. injection of ADR; (b) chemiluminescent and (c) NIRF intensities of kidneys in living mice at t=8 or 60 min after injection of ADR at the different post-treatment timepoints. Data are the mean±SD. n=6 independent mice. Two-tailed student's t-test. PBS versus DTZ-treated groups, *p<0.05, p<0.01, *p<0.001; (d) mean fluorescence intensity (MFI) of fluorescence microscopy images of kidney sections from mice treated with PBS, 8 or 16 h post-treatment of DTZ, or NAC prior to DTZ administration in panel (f). Data are the mean±SD. n=3 independent samples. PBS versus DTZ-treated groups, ***p<0.001; (e) representative chemiluminescent and NIRF images of living mice at t=8 or 60 min after injection of ADR at different post-treatment timepoints. The white arrows indicate the kidneys and bladder in the dorsal and ventral side, respectively. Chemiluminescent images acquired under bioluminescence mode with the acquisition time of 180 s and NIRF images acquired at 720 nm upon excitation at 675 nm with IVIS spectrum imaging system; and (f) representative confocal fluorescence microscopy images of kidney sections from mice treated with PBS, 8 or 16 h post-treatment of DTZ, or NAC prior to DTZ administration. The blue and green signals are from 4', 6-diamidino-2-phenylindole (DAPI) and anti-CD31 antibody, which stain the nucleus and glomerulus (or other vasculatures), respectively. The red signal is from the activated ADR. Glomerulus (G), tubules (T), and peritubular capillaries (PC).

Figure 61:
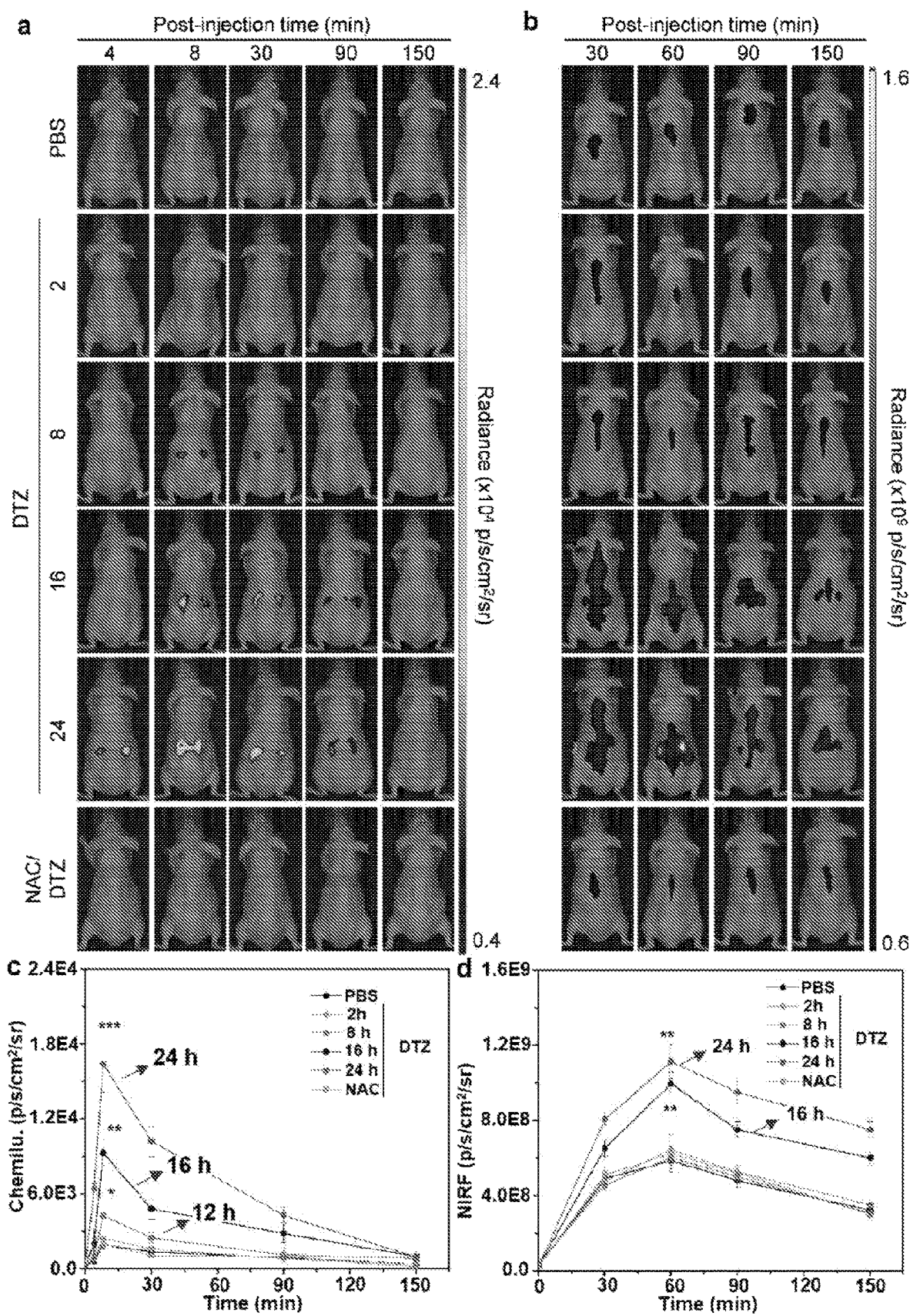

FIG. 61 Depicts representative (a) chemiluminescence and (b) NIRF images of living mice with i.v injection of ADR (30 μmol $kg^{-1}$ body weight) after treatment of DTZ (1 g $kg^{-1}$ body weight) for 2, 8, 16 or 24 h. The control groups were treated with PBS or a nephroprotective antioxidant NAC (10 mg $kg^{-1}$ $day^{-1}$, i.p. injection) 3 days prior to DTZ administration; (c) the dynamic chemiluminescence, and (d) NIRF intensities of kidneys as a function of time post-injection of ADR (30 μmol $kg^{-1}$ body weight) in living mice after treatment of DTZ for 2, 8, 16 or 24 h, PBS or NAC prior to DTZ administration. Data are the mean±SD. n=6 independent mice. PBS versus post-treatment groups. Two-tailed student's t-test. n.s: not significant, *p<0.05, p<0.01, *p<0.001.

Figure 62:
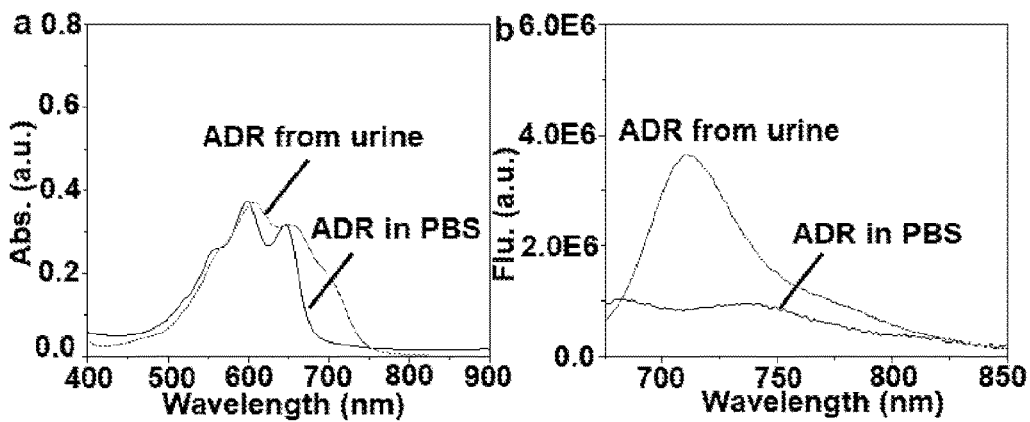

FIG. 62 Depicts: (a) absorption; and (b) fluorescence spectra of ADR (20 μM) in PBS buffer and the urine samples after 24 h i.v injection of ADR at 16 h post-treatment of DTZ. Urine samples were collected from living mice after i.v. injection of ADR (30 μmol $kg^{-1}$ body weight) at 24 h post-treatment with diatrizoate (1 g $kg^{-1}$ body weight). The collected urine samples were centrifuged at 4,500 r.p.m. for 8 min, filtered by a 0.22 μm syringe filter, and measured on a UV-vis absorption and fluorescence spectrophotometer. The fluorescence excitation was set at 650 nm.

Figure 63:
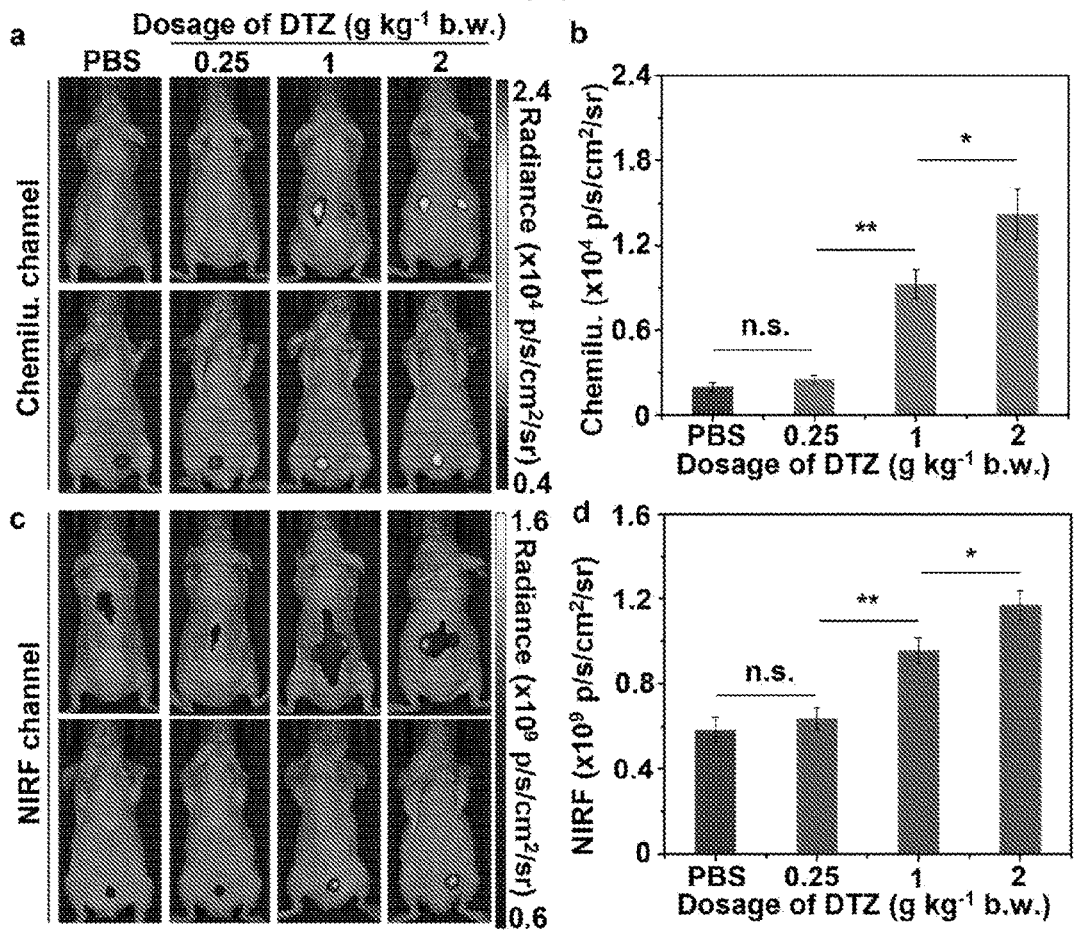

FIG. 63 Depicts: (a) representative chemiluminescent images of living mice at t=8 min after injection of ADR (30 μmol $kg^{-1}$ body weight) at 16 h post-treatment of DTZ; (b) chemiluminescent intensities of kidneys in living mice at t=8 min after injection of ADR at 16 h post-treatment of DTZ; and (c) representative NIRF images of living mice at t=60 min after injection of ADR at 16 h post-treatment of DTZ; and (d) NIRF intensities of kidneys in living mice at t=60 min after injection of ADR at 16 h post-treatment of DTZ. Data are the mean±SD. n=3 independent mice. Two-tailed student's t-test. *p<0.05, **p<0.01. Chemiluminescent images acquired under bioluminescence mode with the acquisition time of 180 s and NIRF images acquired at 720 nm upon excitation at 675 nm with IVIS spectrum imaging system. Note that the signals of ADR in the kidneys for 0.25 g $kg^{-1}$ DTZ-treated mice were as low as the background of PBS-treated control mice at 16 h post-treatment of DTZ, due to the fact such a low dosage of DTZ is below the nephrotoxicity level. However, both the chemiluminescence and NIRF signals of ADR in the kidneys were increased with the increasing of dosage of DTZ (1 and 2 g $kg^{-1}$ body weight), which was consistent with the literatures that DTZ caused a dose-dependent increase in ROS production and urinary NAG excretion.

Figure 64:
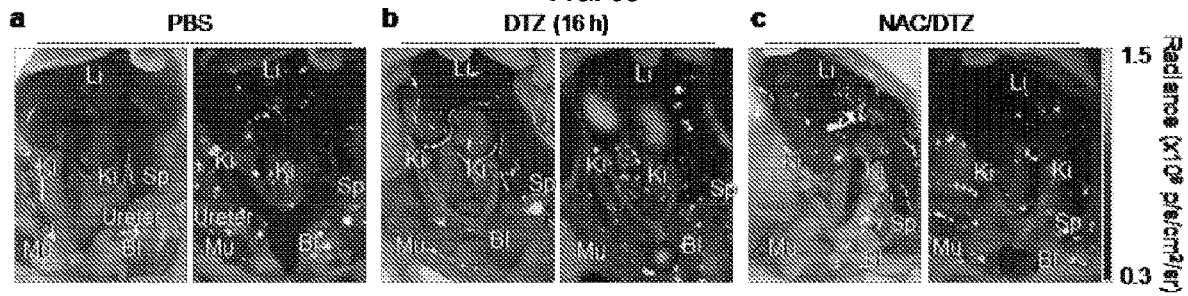

FIG. 64 Depicts representative NIRF images of the abdominal cavity of mice after treatment of: (a) PBS; (b) 16 h post-treatment of DTZ; and (c) NAC prior to DTZ administration, followed by i.v injection of ADR (30 μmol $kg^{-1}$ body weight). Liver (Li), muscle (Mu), spleen (Sp), kidneys (Ki), bladder (Bl). Mice were dissected after 3 h i.v.

injection of ADR. NIRF images acquired at 720 nm upon excitation at 675 nm with the IVIS spectrum imaging system.

Figure 65:
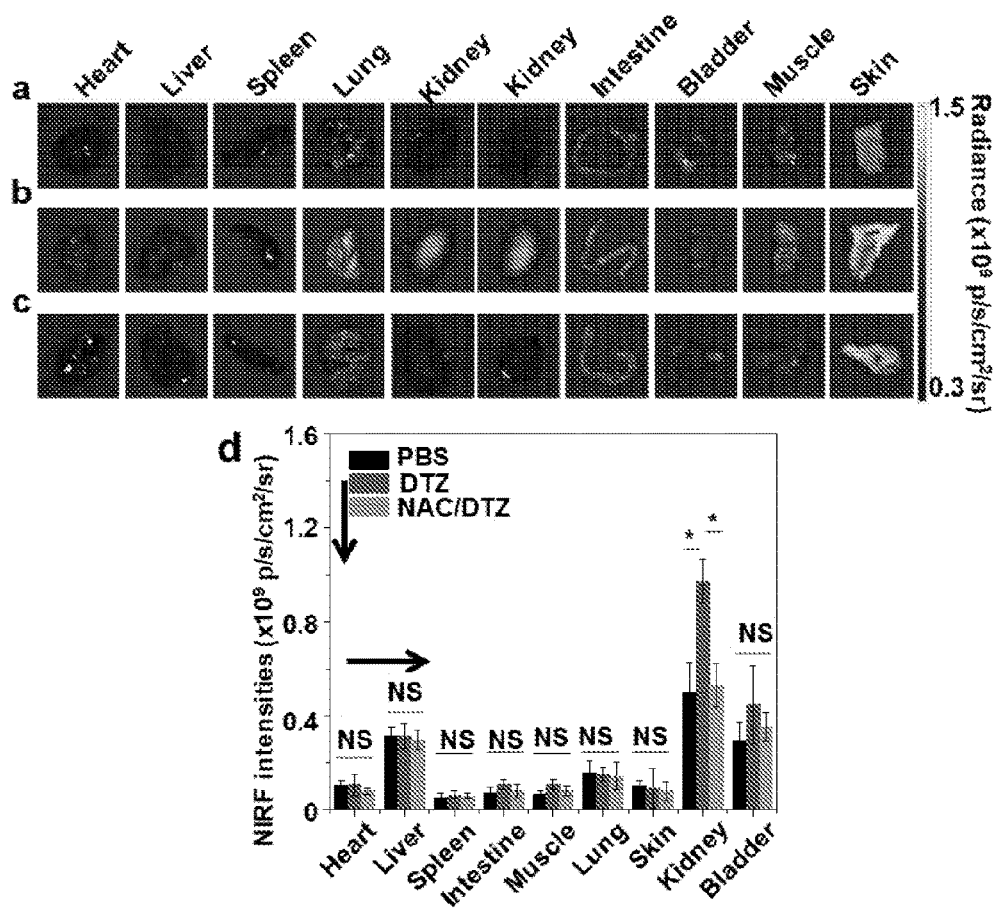

FIG. 65 Depicts ex vivo NIRF images of resected organs from mice after treatment of: (a) PBS; (b) 16 h post-treatment of DTZ; (c) NAC prior to DTZ administration, followed by i.v injection of ADR (30 μmol kg$^{-1}$ body weight); and (d) signal quantification of resected organs from mice after treatment of PBS, or 16 h post-treatment of DTZ, or NAC prior to DTZ administration, followed by i.v injection of ADR (30 μmol kg$^{-1}$ body weight). Mice were dissected, and major organs were resected after 3 h i.v. injection of ADR. NIRF images acquired at 720 nm upon excitation at 675 nm with the IVIS spectrum imaging system. The bladder from DTZ-treated mouse in the panel of b showed lower fluorescence intensity than that in FIG. 64b due to urinary incontinence and bladder emptying after resection. Data are the mean±SD, and represent mice treated with PBS, DTZ and NAC/DTZ, respectively, from the left to right charts of each organ. n=3 independent mice. PBS versus post-treatment groups. Two-tailed student's t-test. NS.: not significant, *p<0.05.

Figure 66:
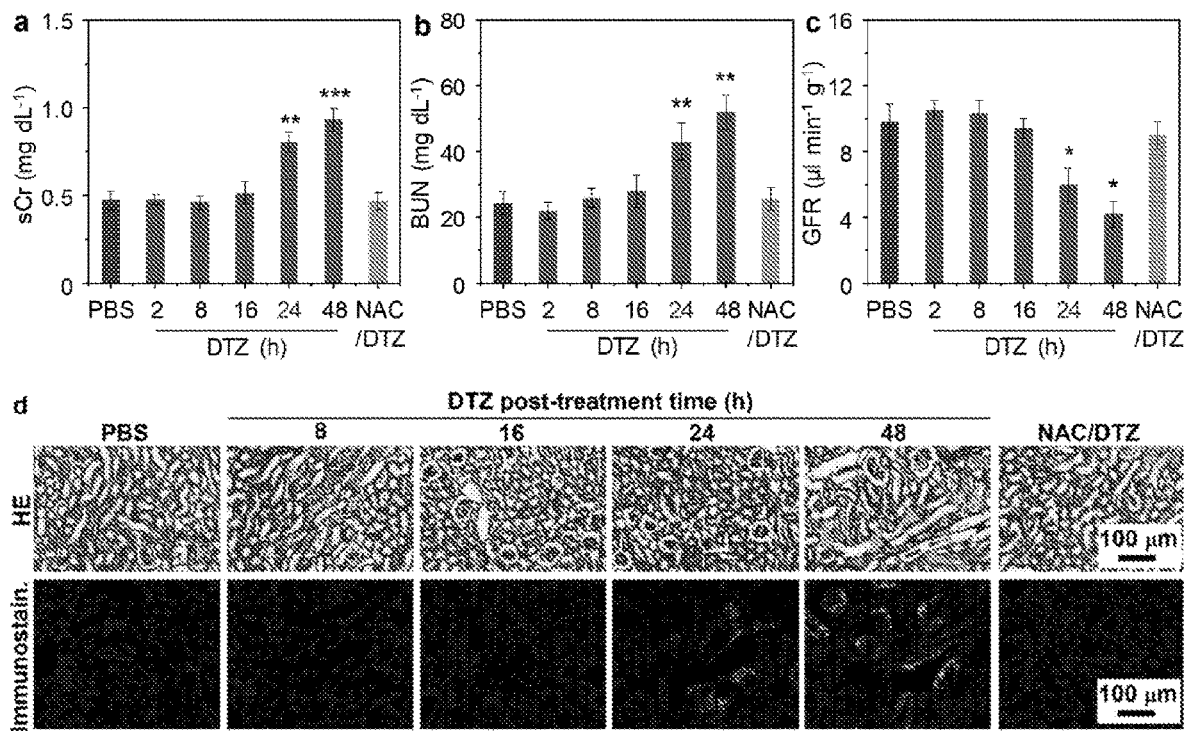
Figure 66:
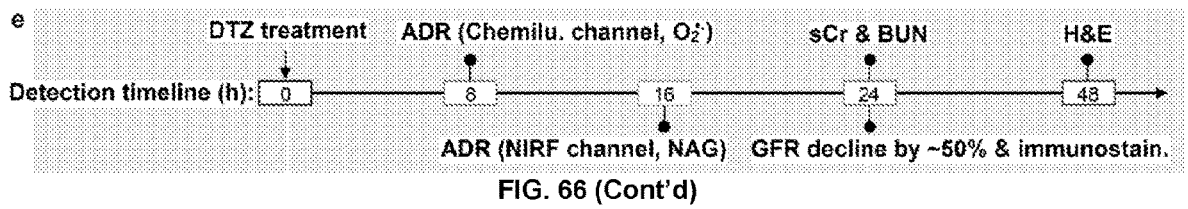

FIG. 66 Depicts in vitro detection of CIAKI with other assays: (a-b) change in sCr and BUN in living mice after treated with PBS, or NAC prior to DTZ administration, or at t=2, 8, 16, 24, or 48 h post-treatment of DTZ (1 g kg$^{-1}$ body weight). *Statistically significant differences between PBS and indicated statistically significant timepoints post-treatment of DTZ (*p<0.05, p<0.01, *p<0.001, n=3, mean±s.d.); (c) determination of GFR in the mouse model of CIAKI. GFR of living mice after treatment of PBS or NAC prior to DTZ administration, or at t=2, 8, 16, 24, or 48 h post-treatment of DTZ (1 g kg$^{-1}$ body weight), measured by the standard FITC-Inulin assay. *Statistically significant differences in GFR values between PBS and indicated statistically significant timepoints post-treatment of DTZ (*p<0.05, **p<0.01, n=3); (d) representative photomicrographs of H&E staining in paraffin embedded kidney sections from mice after treatment of PBS, or NAC prior to DTZ administration, or after treatment of DTZ for 8, 16, 24, 48 h. Green arrows and triangle indicate hyaline casts and loss of the brush border, respectively. (Scale bar=100 μm). Confocal fluorescence microscopy images of kidney slices from mice after treatment of PBS, or NAC prior to DTZ administration, or after treatment of DTZ for 8, 16, 24, 48 h. The blue and green signals come from DAPI and caspase-3 antibody staining, respectively (Scale bar=100 μm); and (e) detection timeline of CIAKI comparing ADR (chemiluminescence and NIRF imaging channel) to the clinical and preclinical assays.

Figure 67:
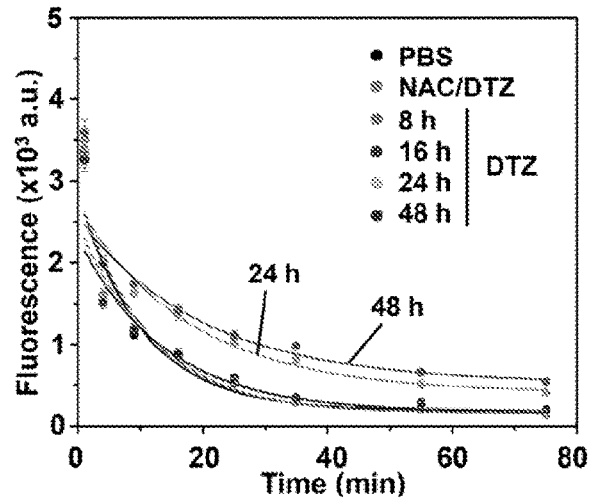

FIG. 67 Depicts plasma clearance kinetics of FITC-inulin in the living mice treated with PBS, or mice at t=8, 16, 24 or 48 h post-treatment of DTZ (1 g kg$^{-1}$ body weight), or NAC prior to DTZ administration (n=3, mean±s.d.).

Figure 68:
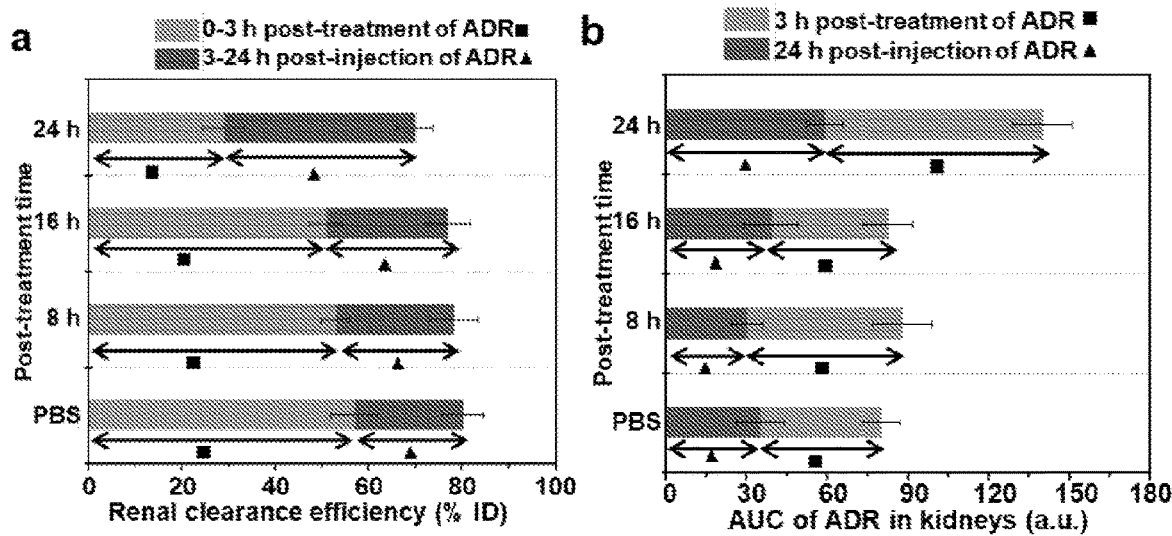

FIG. 68 Depicts: (a) renal clearance efficiency of ADR at 0-3 h and 3-24 h after i.v. injection of ADR (30 μmol kg$^{-1}$ body weight) in the living mice treated with PBS or mice at t=8, 16, or 24 h post-treatment of DTZ (1 g kg$^{-1}$ body weight) (n=3, mean±s.d.); and (b) HPLC analysis of residual ADR in kidneys in different treated groups after 3 h or 24 h injection of ADR. Kidneys were homogenised in PBS and centrifuged to remove insoluble components. The supernatant containing extracted probes were analysed by HPLC assay (n=3, mean±s.d.). The calculated AUC (area under curve) refers to ADR in kidneys. The renal clearance efficiencies of ADR in mice at 8 h and 16 h post-treatment of DTZ are similar to that in PBS-treated mice (50-60% ID in 3 h and 80% ID in 24 h). However, the renal clearance efficiency in mice at 24 h post-treatment of DTZ is lower than the PBS-treated mice (30% ID in 3 h and 70% ID in 24 h). Residual ADR in kidneys in different treated groups after 3 h or 24 h injection of ADR was analysed by HPLC assay. Residual ADR in kidneys (either 3 h or 24 h post-injection of ADR) in mice at 24 h post-treatment of DTZ is higher than PBS-treated mice and mice at 8 h and 16 h post-treatment of DTZ. This was due to the decline in kidney function at 24 h post-treatment of DTZ.

DESCRIPTION

In a first aspect of the invention, there is provided a compound of formula I:

$$(X)_a—Y—(Z)_b \qquad \text{I}$$

where:

X is selected from:

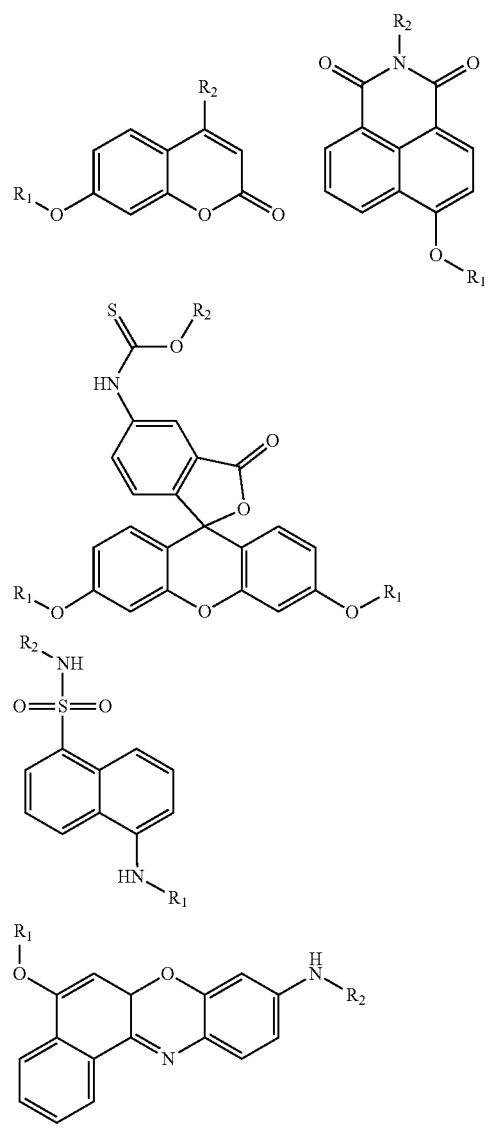

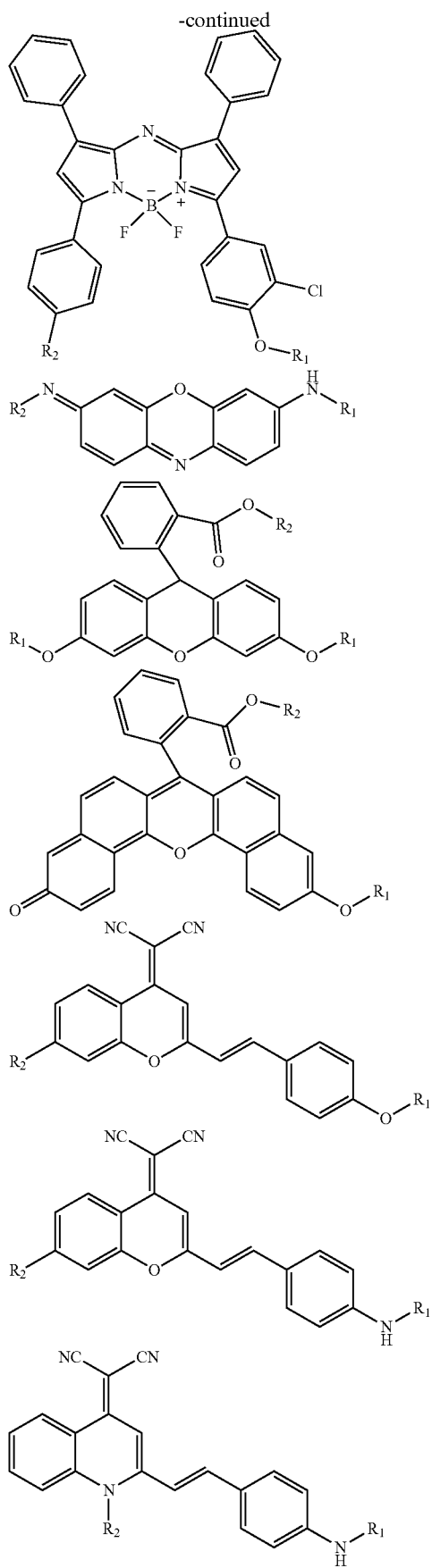
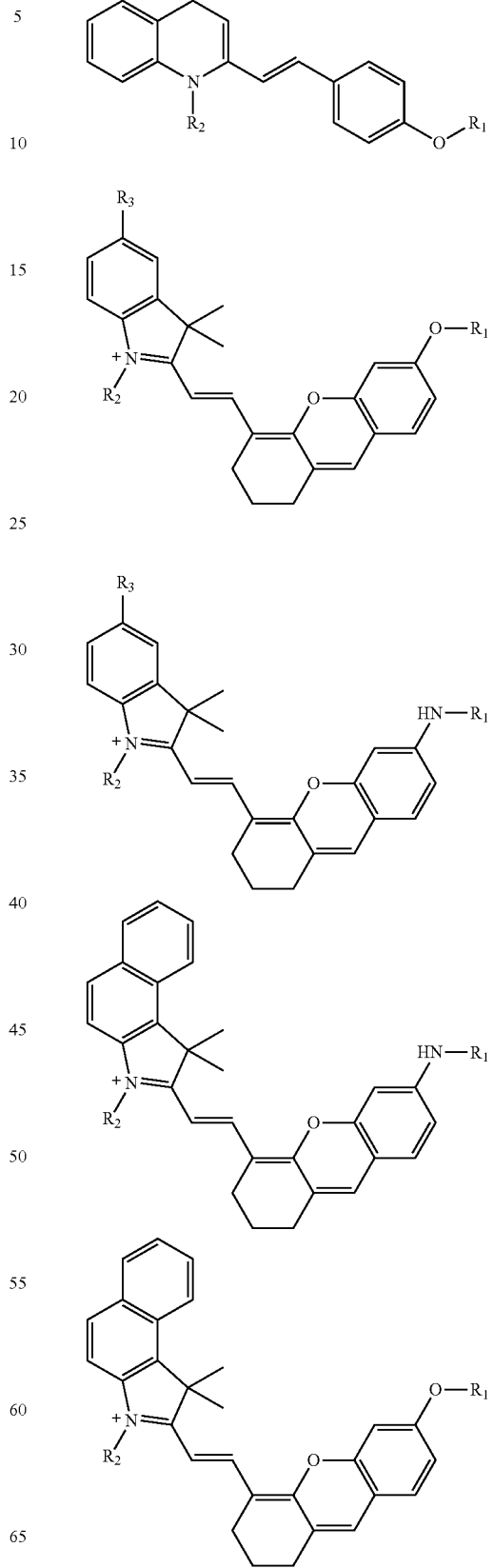

-continued

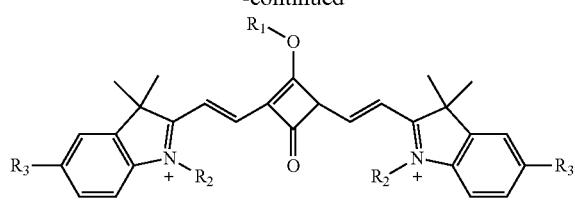

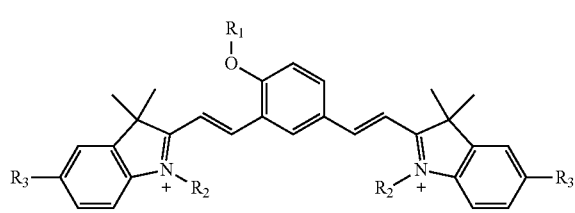

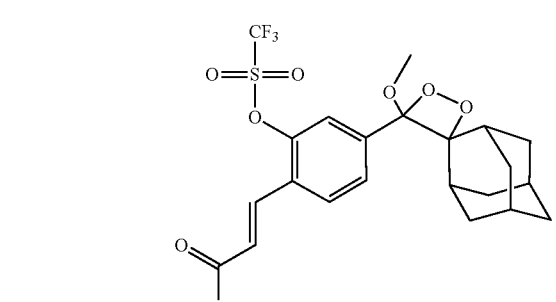

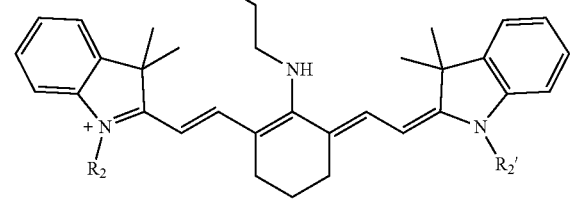

where R₁ represents a biomarker reactive moiety or a biomarker reactive moiety conjugated to a self-immolative moiety

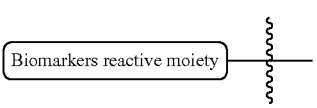    or

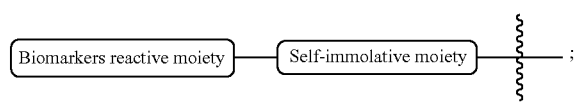;

R₂ represents a point of attachment to Y and R₂' represents another point of attachment to the same Y group or a point of attachment to a second Y group;

R₃ represents H, SO₃H or COOH;

Z is selected from:

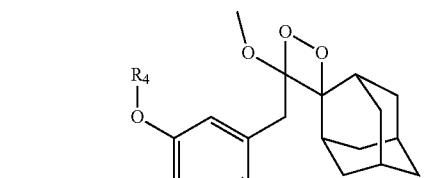, or

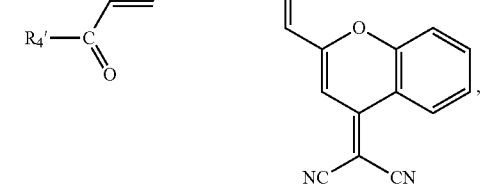

R₄ is selected from:

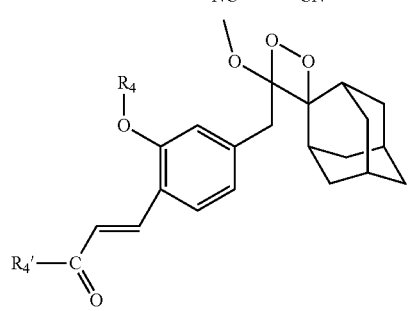, or

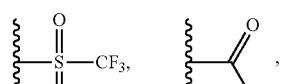

where the wavy line represents the point of attachment to the rest of the molecule;

R₄' represents the point of attachment to Y;

each Y is selected from:

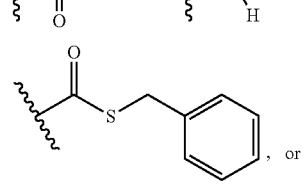

($1 \leq m \leq 50$, $10 \leq n \leq 500$) where the wavy line represents the point of attachment to X or Z,

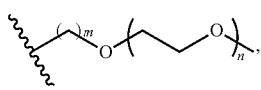

(1≤m≤50, 10≤n≤500) where the wavy line represents the point of attachment to X or Z,

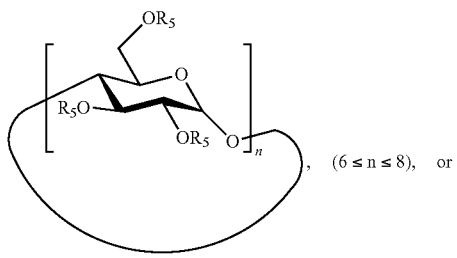, (6 ≤ n ≤ 8), or

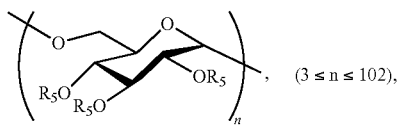, (3 ≤ n ≤ 102), where each $R_5$ is independently selected from H, $CH_2CHOHCH_3$, $CH_2CCH$, and

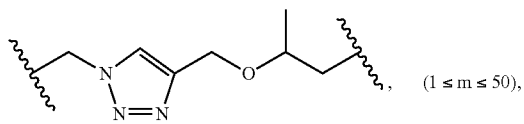 [SMILES: *CC(C)OCc1cn(C*)nn1], (1 ≤ m ≤ 50), where the left-hand wavy line (adjacent to m) represents the point of attachment to X or Z and the right-hand wavy line represents the point of attachment to the rest of the molecule;

a is 0 or 1 and b is 0 or 1, provided that:

at least one of a and b is 1; and when a and b are both 1, Y is selected from:

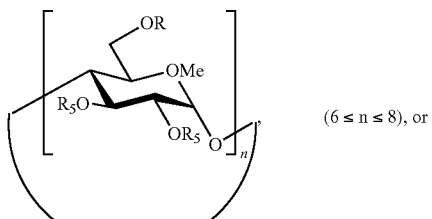, (6 ≤ n ≤ 8), or

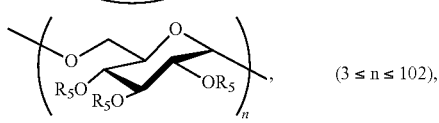, (3 ≤ n ≤ 102), or pharmaceutically acceptable salts and/or solvates thereof, provided that when X is

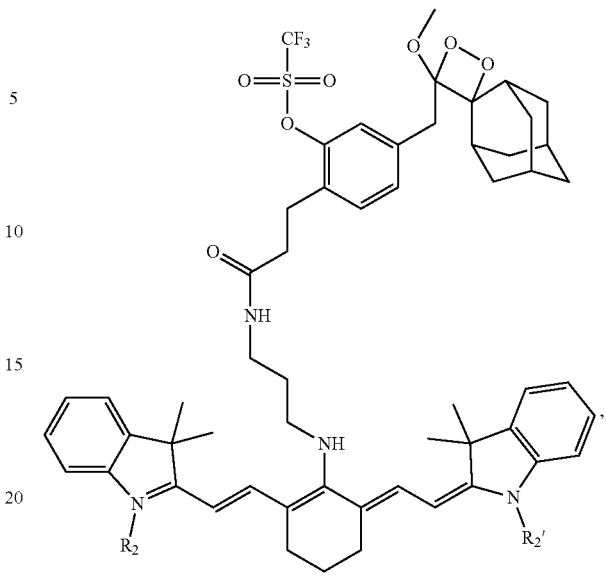

then Z is 0.

The compounds of formula I (and salts and/or solvates thereof) may be particularly suited to use in the in vivo diagnosis of kidney injury or kidney disease. In part, this is because the compounds of formula I contain at least one moiety that can be activated to provide fluoresence or chemiluminescence, as described in more detail below. In addition, the compounds of formula I are particularly suited to the above application because of the presence of a renal clearance moiety (Y), as described in more detail below. Without wishing to be bound by theory, it is believed that the compounds disclosed herein may be particularly useful in the diagnosis of early-stage kidney injury and disease. The addition of a renal clearance moiety (Y) provides enhanced renal clearance efficiencies, and at the same time allows selective delivery of the compounds to the kidneys with less uptake by other organs (see Example 3). This thereby improves the selectivity and efficacy of the compounds in detecting the relevant biomarkers in the kidneys.

Fluorescence imaging in the near-infrared (NIR) window has been widely used in biological and biomedical research because it drastically reduces the noise from the autofluorescence and increases tissue penetration. Fluorescence molecular reporters that change their signals in response to biomarkers have high signal-to-background ratio and thus are generally sensitive enough to detect diseases at the molecular level and relatively early stages. However, such molecular reporters have not been developed for diagnosing kidney injury. The compounds of formula I (particularly for in vivo use, though can be use in vitro too) and III (more suited to in vitro use) disclosed herein encompass a series of NIR fluorescent molecular renal probes (MRPs) for specific detection of kidney injury. These MRPs can turn on their NIR fluorescence in the presence of early biomarkers such as superoxide anion, NAG or caspase-3 (FIG. 7c), which are overexpressed in initial phases of kidney injury relative to normal kidneys (FIG. 7b). These compounds may be useful in detecting the response of the kidney to injury at the early stage of drug-induced nephrotoxic models, including cisplatin, gentamicin and diatrizoate induced AKI model and doxorubicin induced CKD model. Additionally, these MRPs may be used for the early detection of kidney injury by liquid biopsy in both animal models and CKD patients. Such MRPs allow one to identify biomarkers released by the diseased tissue and to quantify biomarkers changes at an earlier time than that of clinical diagnostic methods.

A series of MRPs (e.g. NIR MRPs) for optical imaging in a subject (e.g. living mice) have been developed. Due to their unique activatable mechanisms, MRPs can be used for specific detection of kidney injury at an earlier time than that of clinical diagnostic methods. Thus, the following advantages for MRPs are obtained.

(1) MRPs have the robustness and broad applicability in the early diagnosis of multiple drug-induced kidney injury, including cisplatin-, gentamicin- and diatrizoate-induced AKI model and doxorubicin-induced CKD model.

(2) MRPs have potential as an innovative preclinical nephrotoxicity screening method and could benefit in reducing nephrotoxicity during drug development.

(3) The feasibility of MRPs for early detection kidney injury by liquid biopsy in both animal models and CKD patients has been demonstrated (see examples below). The MRPs disclosed herein allow one to identify biomarkers released by the diseased tissue and to quantify biomarker changes at an earlier time than that of current clinical diagnostic methods. Given this, the MRPs can potentially quantify the biomarkers in a subject's (e.g. human) urine and therefore may be useful in the prediction of CKD in patients in clinical practice.

The compounds of formula I also encompass compounds that may make use of chemiluminescence in place of, or in addition to, the NIR fluoresence groups discussed above. When used in place of the NIR fluorescence groups, these compounds of formula I may be used in a similar way. However, when both types of groups are present, additional functionality may be observed. For example, when the probes described above rely on the respective activation of a single fluorescent (or chemiluminescent) moiety, the compound is not able to detect two interlinked molecular events in the kidneys, which may be useful for imaging of CIAKI. Although co-administration of two different single-channel probes has the potential to image two different molecular events simultaneously, the different pharmacokinetics of the injected single-channel probes could affect the resulting in vivo imaging studies. In contrast, real-time simultaneous imaging of dual biomarkers by using unimolecular duplex reporters can not only provide opportunities to investigate the fundamental correlation between different biomarkers in a certain pathological pathway in living organisms, but also can improve the accuracy of disease diagnosis.

Thus, compounds of formula I that contain both fluorescence and chemiluminescence moieties form a highly renal-clearable activatable duplex reporter (ADR) for real-time noninvasive chemiluminescence and near-infrared fluorescence (NIRF) imaging of CIAKI. This has been demonstrated in a murine model. Because oxidative stress has been well recognised as an early hallmark of CIAKI, superoxide anion ($O_2^{*-}$), the primary reactive oxygen species (ROS), may be chosen as one of the biomarkers. In addition, upregulation of ROS is known to trigger the pathways towards lysosomal damage and induce the release of the lysosomal enzyme (NAG: N-acetyl-β-D-glucosaminidase) from kidney proximal tubular cells, NAG may be chosen as the other biomarker. Thus, in certain embodiments disclosed herein, the ADR may be designed to comprise an $O_2^{*-}$-activatable chemiluminescent signal moiety and a NAG-activatable NIRF moiety, both of which are linked to a renal-clearance scaffold, e.g. (2-hydroxypropyl)-β-cyclodextrin (HPβCD) (FIG. 9b). After systemic administration of such an ADR in vivo (e.g. into living mice), it specifically goes to the kidneys and sends back its chemiluminescent and NIRF signals to report $O_2^{*-}$ and NAG levels, respectively. Such an independent duplex sensing capability of the ADRs disclosed herein avoids signal cross-talk, enabling real-time, noninvasive and simultaneous monitoring of two intercorrelated biomarkers in the kidneys of a living subject during the onset and progression of CIAKI.

The ADRs disclosed herein may also display all of the advantages attributed to MRPs herein. In addition, the ADRs disclosed herein may also enable one to conduct more sensitive and/or quicker and/or more specific detection of kidney damage and/or disease. For example, the use of the ADRs disclosed herein may enable one to detect CIAKI in real time.

References herein (in any aspect or embodiment of the invention) to compounds of formula I (and formulae II and III) includes references to such compounds per se, to tautomers of such compounds, as well as to pharmaceutically acceptable salts and/or solvates of such compounds. References to compounds of formula I (and formulae II or III) may also include reference to pharmaceutically functional derivatives of such compounds.

Pharmaceutically acceptable salts that may be mentioned include acid addition salts and base addition salts. Such salts may be formed by conventional means, for example by reaction of a free acid or a free base form of a compound of formula I, II or III with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I, II or III in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium.

Examples of acid addition salts include acid addition salts formed with acetic, 2,2-dichloroacetic, adipic, alginic, aryl sulphonic acids (e.g. benzenesulphonic, naphthalene-2-sulphonic, naphthalene-1,5-disulphonic and p-toluenesulphonic), ascorbic (e.g. L-ascorbic), L-aspartic, benzoic, 4-acetamidobenzoic, butanoic, (+) camphoric, camphor-sulphonic, (+)-(1 S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

As mentioned above, also encompassed by formula I, II and III are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particularly preferred solvates are hydrates, and examples of hydrates include hemihydrates, monohydrates and dihydrates.

For a more detailed discussion of solvates and the methods used to make and characterise them, see Bryn et al., *Solid-State Chemistry of Drugs*, Second Edition, published by SSCI, Inc of West Lafayette, IN, USA, 1999, ISBN 0-967-06710-3.

"Pharmaceutically functional derivatives" of compounds of formula I or formula III as defined herein includes ester derivatives and/or derivatives that have, or provide for, the same biological function and/or activity as any relevant compound of the invention. Thus, for the purposes of this invention, the term also includes prodrugs of compounds of formula I or formula III.

The term "prodrug" of a relevant compound of formula I or formula III includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

Prodrugs of compounds of formula I or III may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds of I or III wherein a hydroxyl, amino, sulfhydryl, carboxyl or carbonyl group in a compound of I or III is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, esters groups of carboxyl functional groups, N-acyl derivatives and N-Mannich bases. General information on prodrugs may be found e.g. in Bundegaard, H. "Design of Prodrugs" p. I-92, Elsevier, New York-Oxford (1985).

Compounds of formula I, as well as pharmaceutically acceptable salts, solvates and pharmaceutically functional derivatives of such compounds are, for the sake of brevity, hereinafter referred to together as the "compounds of formula I". Compounds of formula II, as well as pharmaceutically acceptable salts and/or solvates of such compounds are, for the sake of brevity, hereinafter referred to together as the "compounds of formula II". Compounds of formula III, as well as pharmaceutically acceptable salts, solvates and pharmaceutically functional derivatives of such compounds are, for the sake of brevity, hereinafter referred to together as the "compounds of formula III".

Compounds of formula I, II or III may contain double bonds and may thus exist as E (entgegen) and Z (zusammen) geometric isomers about each individual double bond. All such isomers and mixtures thereof are included within the scope of the invention.

Compounds of formula I, II or III may exist as regioisomers and may also exhibit tautomerism. All tautomeric forms and mixtures thereof are included within the scope of the invention.

Compounds of formula I, II or III may contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

Unless otherwise stated, the term "aryl" when used herein includes $C_{6-14}$ (such as $C_{6-10}$) aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like, such as 1,2,3,4-tetrahydronaphthyl, indanyl, indenyl and fluorenyl. Embodiments of the invention that may be mentioned include those in which aryl is phenyl.

Unless otherwise stated, the term "alkyl" refers to an unbranched or branched, cyclic, saturated or unsaturated (so forming, for example, an alkenyl or alkynyl) hydrocarbyl radical, which may be substituted or unsubstituted (with, for example, one or more halo atoms). Where the term "alkyl" refers to an acyclic group, it is preferably $C_{1-10}$ alkyl and, more preferably, $C_{1-6}$ alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably $C_{3-12}$ cycloalkyl and, more preferably, $C_{5-10}$ (e.g. $C_{5-7}$) cycloalkyl.

Further embodiments of the invention that may be mentioned include those in which the compound of formula I, II or III is isotopically labelled. However, other, particular embodiments of the invention that may be mentioned include those in which the compound of formula I, II or II is not isotopically labelled.

The term "isotopically labelled", when used herein includes references to compounds of formula I in which there is a non-natural isotope (or a non-natural distribution of isotopes) at one or more positions in the compound. References herein to "one or more positions in the compound" will be understood by those skilled in the art to refer to one or more of the atoms of the compound of formula I, II or III. Thus, the term "isotopically labelled" includes references to compounds of formula I, II or III that are isotopically enriched at one or more positions in the compound.

The isotopic labelling or enrichment of the compound of formula I, II or III may be with a radioactive or non-radioactive isotope of any of hydrogen, carbon, nitrogen, oxygen, sulfur, fluorine, chlorine, bromine and/or iodine. Particular isotopes that may be mentioned in this respect include $^{2}H$, $^{3}H$, $^{11}C$, $^{13}O$, $^{14}O$, $^{13}N$, $^{15}N$, $^{15}O$, $^{17}O$, $^{18}O$, $^{35}S$, $^{18}F$, $^{37}Cl$, $^{77}Br$, $^{82}Br$ and $^{125}I$).

When the compound of formula I, II or III is labelled or enriched with a radioactive or nonradioactive isotope, compounds of formula I, II or III that may be mentioned include those in which at least one atom in the compound displays an isotopic distribution in which a radioactive or non-radioactive isotope of the atom in question is present in levels at least 10% (e.g. from 10% to 5000%, particularly from 50% to 1000% and more particularly from 100% to 500%) above the natural level of that radioactive or non-radioactive isotope.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

When present, X may be selected from one of the groups defined above. Each of said groups contains at least one $R_1$ group, which represents a biomarker reactive moiety or a biomarker reactive moiety conjugated to a self-immolative moiety. In embodiments of the invention where X is present, X is a fluorophore. When used herein, the term "fluorophore" is intended to refer to a substituent group that does not fluoresce due to the presence of a biomarker reactive moiety or a biomarker reactive moiety conjugated to a self-immolative moiety by way of a covalent bond, but which is capable of fluorescence following cleavage of said covalent bond. In other words, the compounds of formula I contain a fluorophore that is initially nonfluorescent because the fluorophore is in a "caged" state due to a covalent bond reducing the donation of electrons to the fluorophore system. In the presence of a suitable biomarker the relevant covalent bond is cleaved (i.e. the covalent bond to the biomarker reactive moiety when bonded to it directly or the covalent bond to the self-immolative moiety when bonded to this directly), thereby providing a free fluorphore. This cleavage "uncages" the fluorophore and results in increased electron donation into the fluorophore system, thus making the fluorophore capable of fluorescence. Therefore, the compounds of formula I and III, when X is present, are able to selectively activate fluorescence in the presence of biomarker reactive moiety that is indicative of a kidney injury or a kidney disease.

As will be appreciated, the biomarkers referred to herein are intended to be ones that may be involved in kidney injury or a kidney disease. Such biomarkers may include enzymes, reactive oxygen species and reactive nitrogen species (RNS). Table 1 below provides a list of suitable biomarkers and the corresponding biomarker reactive moieties that can be cleaved from the compounds of formula I or formula III upon exposure to said biomarkers. It will be appreciated that other biomarker reactive moieties may be used in the compounds of formula I and III and so the compounds of formula I and III are not exclusively limited to the list of biomarker reactive moieties given below.

TABLE 1

| Biomarkers | | Biomarker reactive moieties |
|---|---|---|
| Enzymes | Alanine aminopeptidase | (structure: acyl group with CH-NH₂ side chain) |
| | Alkaline phosphatase | (structure: phosphate group -P(=O)(OH)₂) |
| | γ-Glutamyl transpeptidase | (structure: glutamyl group with NH₂ and COOH) |
| | Glutathione S-transferase | (structure: sulfonyl-2,4-dinitrophenyl group) |

TABLE 1-continued
| Biomarkers | | Biomarker reactive moieties |
|---|---|---|
| | N-acetyl-β-glucosaminidase | 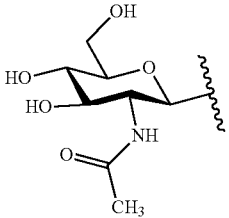 |
| | Caspase-3/7 | 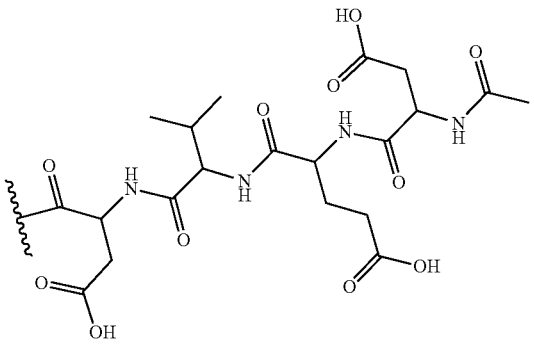 [SMILES: *C(=O)C(CC(=O)O)NC(=O)C(NC(=O)C(CCC(=O)O)NC(=O)C(CC(=O)O)NC(C)=O)C(C)C] |
| | Superoxide anion | 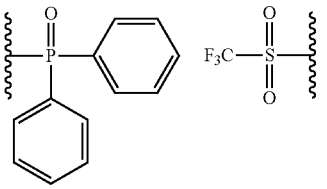 |
| ROS | Hydrogen peroxide | 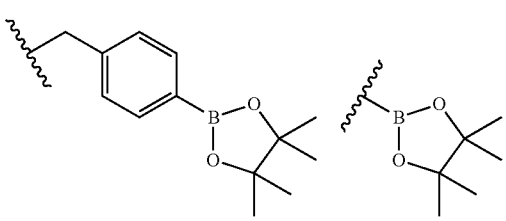 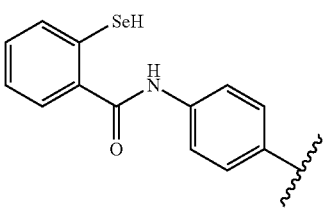 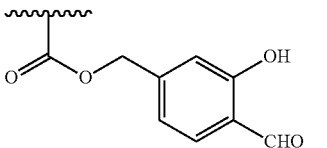 [SMILES: *C(=O)OCc1ccc(C=O)c(O)c1] |
| | Hydroxyl radical | 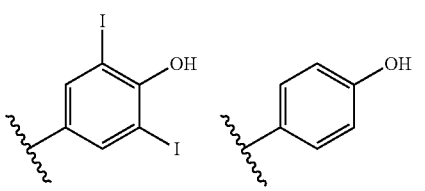 [SMILES: *c1cc(I)c(O)c(I)c1 ; *c1ccc(O)cc1] |

TABLE 1-continued
| Biomarkers | | Biomarker reactive moieties |
|---|---|---|
| | Hypochlorite | |
| | Glutathione | |
| RNS | Peroxynitrie | |
| | Nitric oxide | |
In particular embodiments that may be mentioned herein, the biomarker moiety $R_1$ may be selected from:
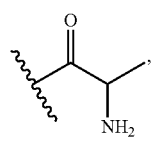
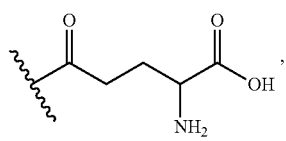
-continued
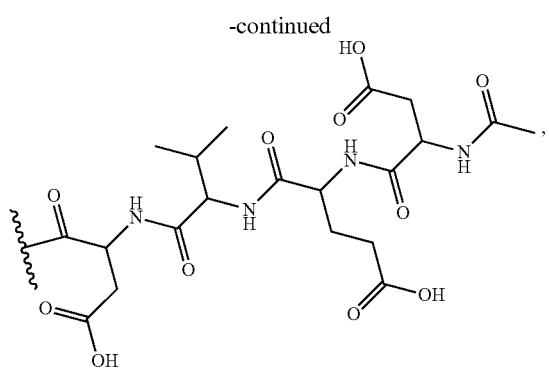

71
-continued
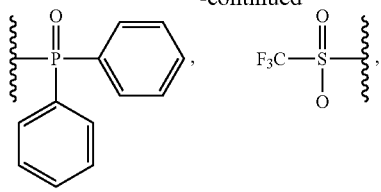
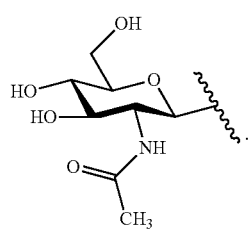
As will be appreciated, these moieties are reactive towards certain biomarkers and so the corresponding biomarkers are also inherently mentioned in said embodiments too.
In further embodiments of the first aspect of the invention, the compound or salts and/or solvates thereof may be one in which X may be selected from:
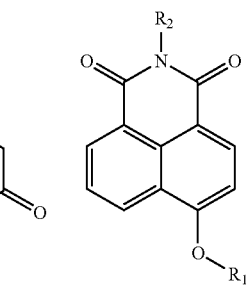
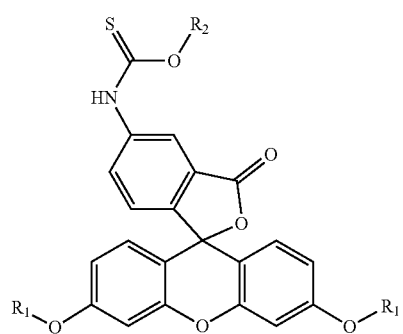
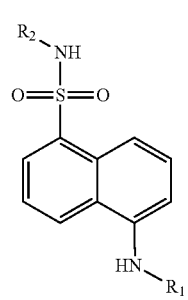
72
-continued
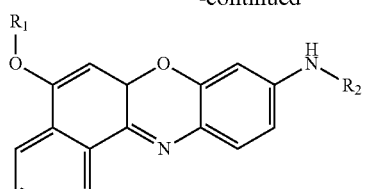
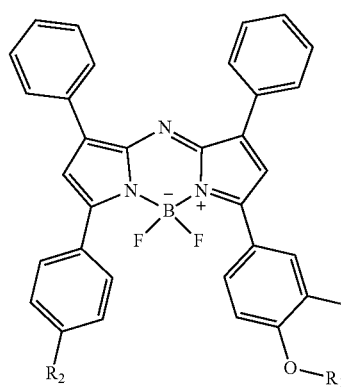
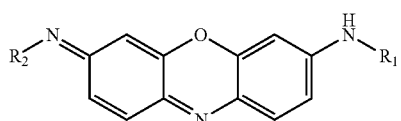
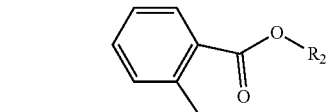
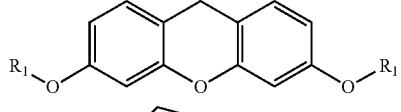
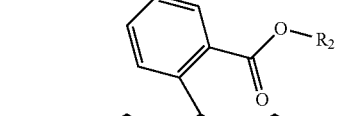
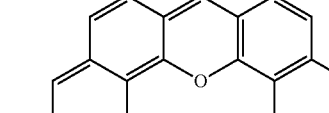
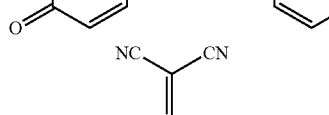
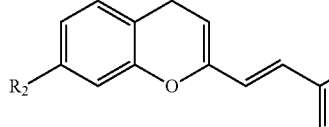
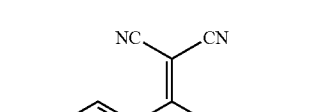
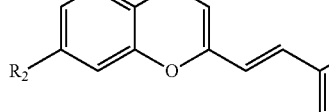

-continued
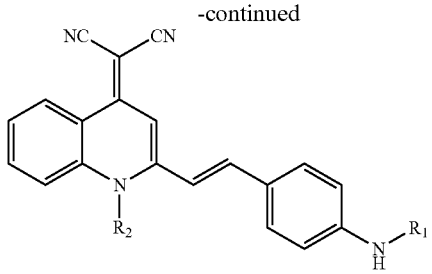
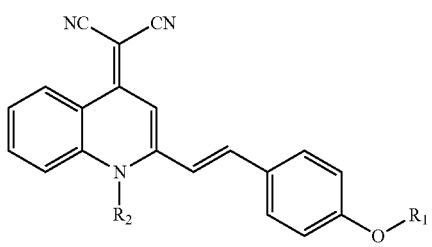
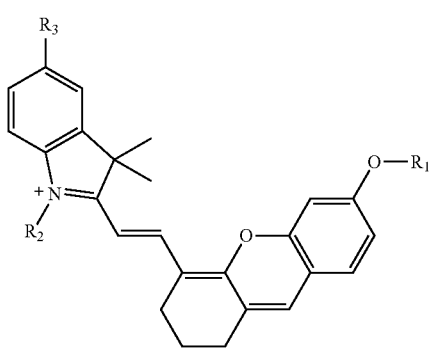
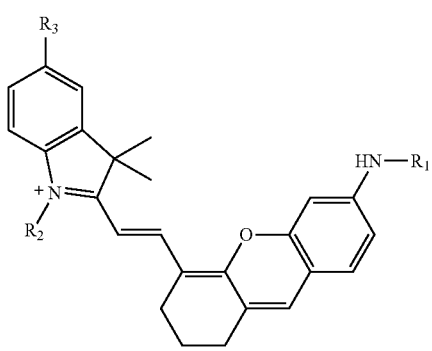
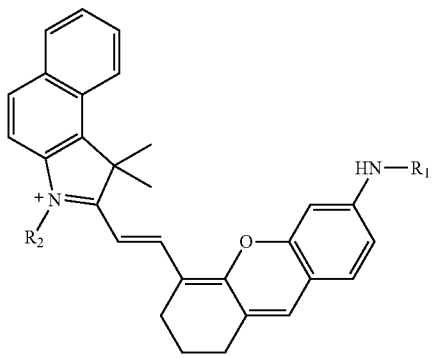
-continued
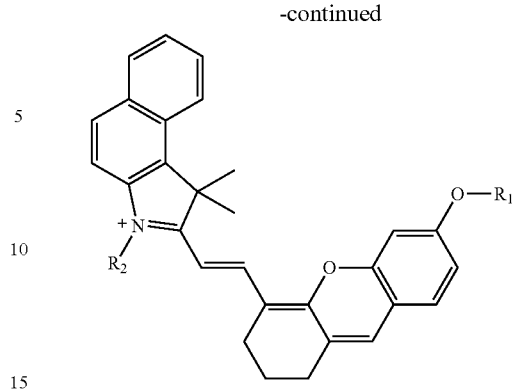
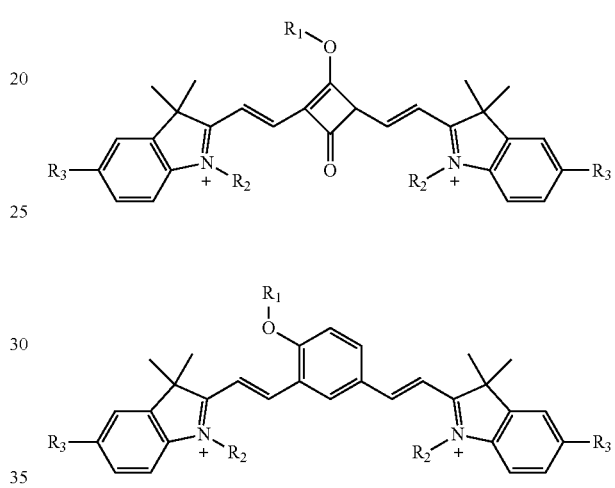
In particular embodiments of the invention that may be mentioned herein, X when present, may be selected from:
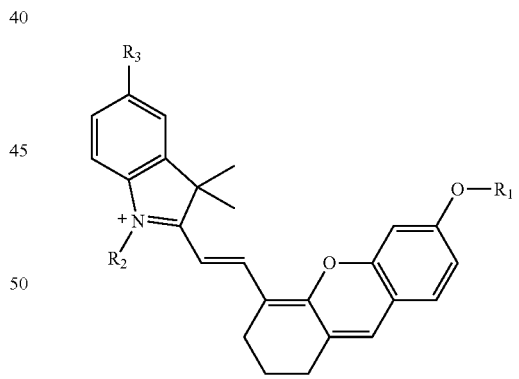
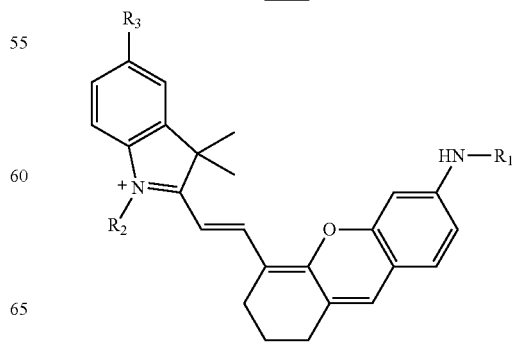

-continued

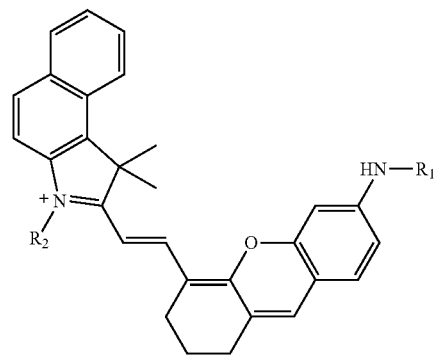

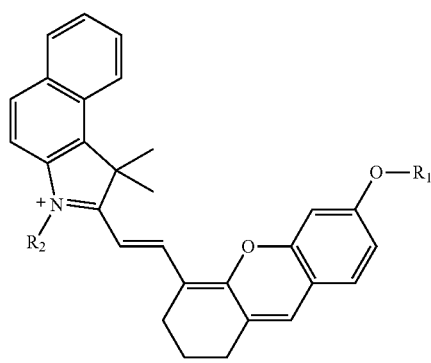

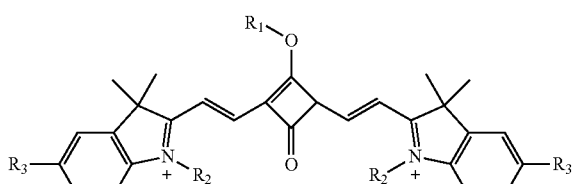

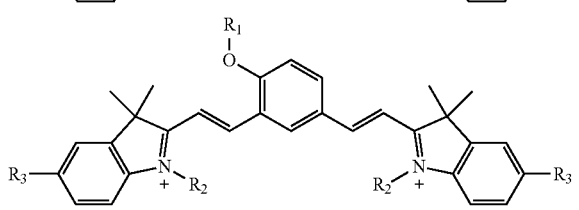

In yet further embodiments of the invention that may be mentioned herein, X, when present, may be selected from:

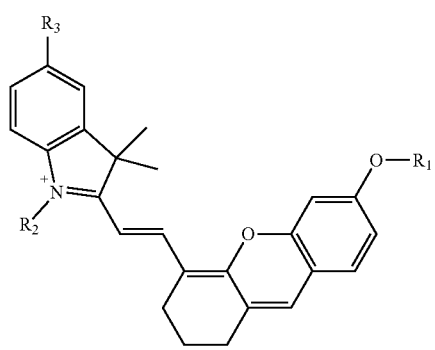

-continued

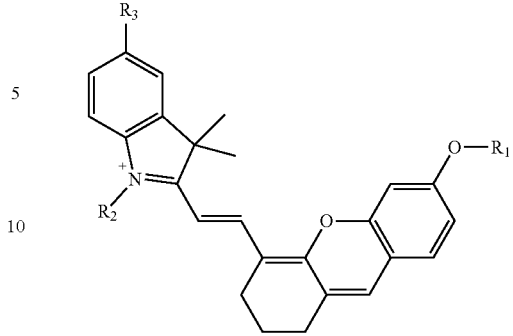

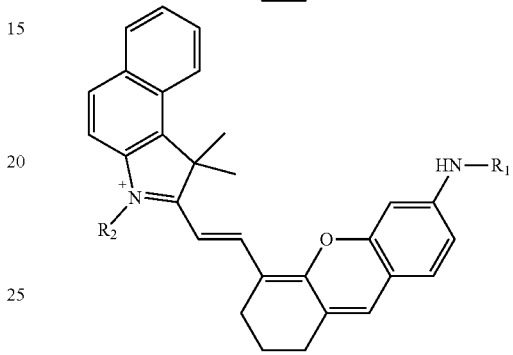

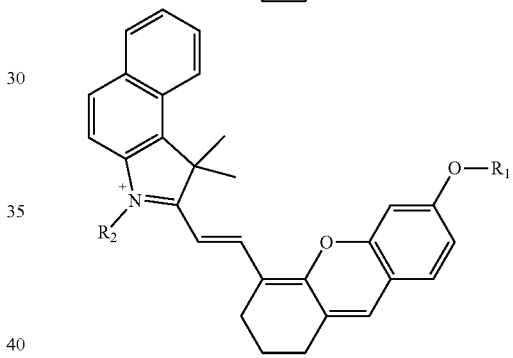

For example, X, when present, may be:

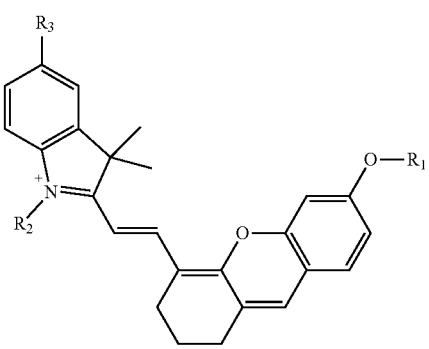

where $R_3$ is H.

When used herein, the term "self-immolative linker" is a bi-, tri- or tetra-functional chemical moiety which is capable of covalently linking together two to four spaced chemical moieties into a normally stable tri-, tetra or quintapartite molecule, that can release at least one of the spaced chemical moieties from the stable molecule by means of cleavage of a biomarker moiety, and following said cleavage, the self-immolative linker can spontaneously cleave from the remainder of the molecule to release the other spaced chemical moiety(ies). An example of this cleavage process is provided in FIGS. 7c, 8, 9b and 12 (see Example 2 for discussion on mechanism). Any suitable self-immolative linker may be used in the current invention. Examples of suitable self-immolative linkers include, but are not limited to those selected from:

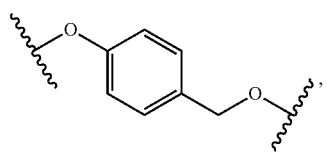

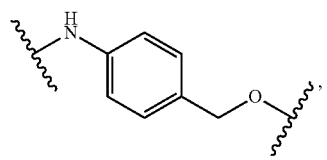

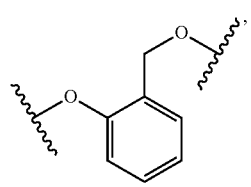

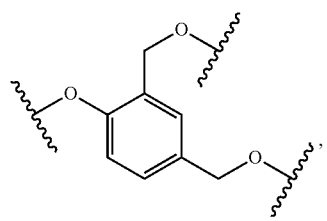

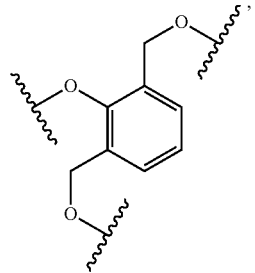

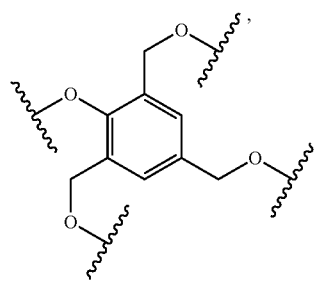

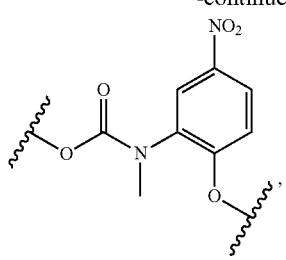

where the heteroatom directly bonded to the aromatic ring represents the point of attachment to Y and the other heteroatoms represent the point of attachment to a biomarker reactive moiety or are H, provided that at least one of the other heteroatoms is attached to a biomarker reactive moiety. As will be noted from the above, there may be one or more biomarker reactive moieties present in the compounds of formula I and III.

As noted above, Z (when it is present) may be selected from:

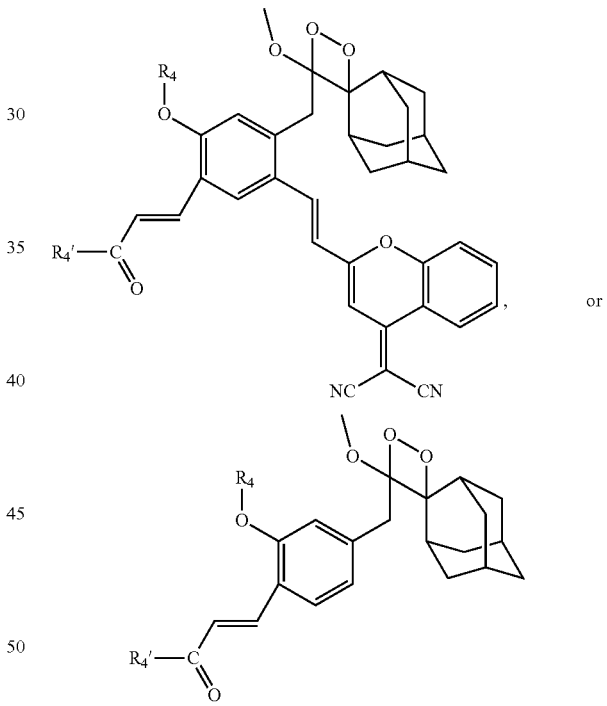

where $R_4$ may be selected from:

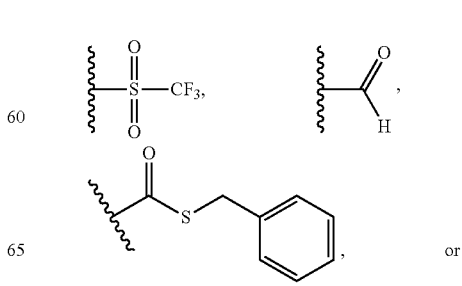

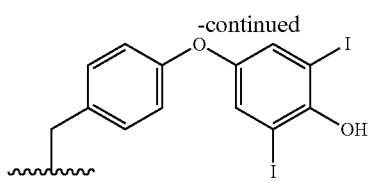

where the wavy line represents the point of attachment to the rest of the molecule and $R_{4'}$ represents the point of attachment to the rest of the molecule. As will be apparent, these fragments of the molecule provide chemiluminescence, with the maximum wavelength of the emission being controlled by the number of conjugated π atoms. Thus, compounds of formula I (and II) that contain the fragment:

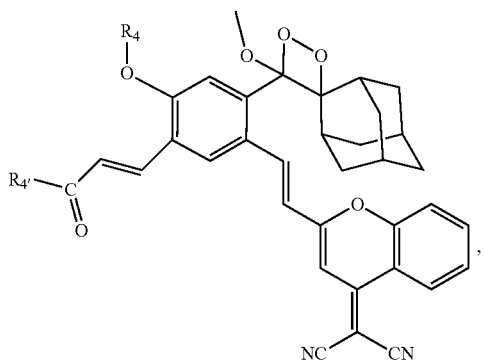

have a maximum emission at 700 nm, while compounds of formula I (II and III) have a maximum emission at 540 nm. The reactive moiety ($R_4$) attached to the conjugated system may be cleaved by a particular reactive species, which then initiates the chemiluminescence. Details of the reactive moiety (and the reactive species that cleaves it) are provided in Table 2 below.

TABLE 2

| Reactive Species | $R_4$ Moiety |
| --- | --- |
| Superoxide anion | 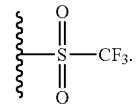 |
| Peroxynitrite | (structure: C(=O)H) |
| Hydrogen peroxide | (structure: C(=O)S-CH2-phenyl) |
| Hydroxyl radical | (structure: benzyl-O-diiodophenol-OH) |

In particular embodiments of the invention that may be mentioned herein, $R_4$ may be

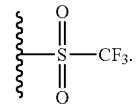

In order to ensure that the compounds of formula I are delivered to the desired site of diagnosis (the kidneys), the compounds contain a renal clearance moiety, designated as Y above, which also acts as the skeleton to which the fluorescent (X) and chemiluminescent moieties (Z) are attached to. For the compounds of formula I, a range of suitable renal clearance moieties are described hereinabove. It will be appreciated that when Y represents:

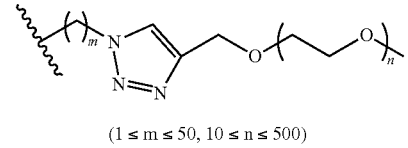

$(1 \leq m \leq 50, 10 \leq n \leq 500)$ where the wavy line represents the point of attachment to X or Z, or

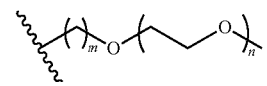

$(1 \leq m \leq 50, 10 \leq n \leq 500)$ where the wavy line represents the point of attachment to X or Z, then only one of X and Z may be present. However, when Y is selected from:

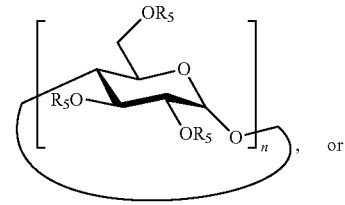

$(6 \leq n \leq 8)$

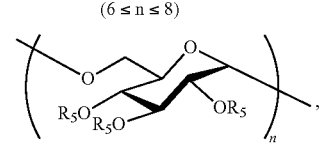

$(3 \leq n \leq 102)$ then both X and Z moieties may be present in a single molecule. Each $R_5$ may be independently selected from H, $CH_2CHOHCH_3$, $CH_2CCH$, and

81

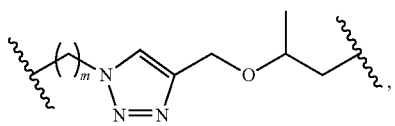

(1 ≤ m ≤ 50)

where the left-hand wavy line (adjacent to m) represents the point of attachment to X or Z and the right-hand wavy line represents the point of attachment to the rest of the molecule. As will be appreciated, both X and Z (when present) are attached to the rest of the molecule by way of the:

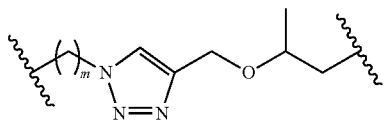

moiety. As such, this moiety is an essential component of the compounds of formula I, as it serves to link the fluorescent and chemiluminescent moieties to the rest of the molecule.

In addition, when Y is selected from:

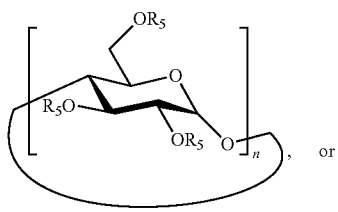

(6 ≤ n ≤ 8)

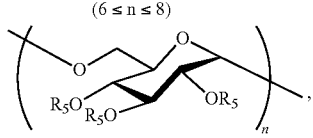

(3 ≤ n ≤ 102)

and X is selected from

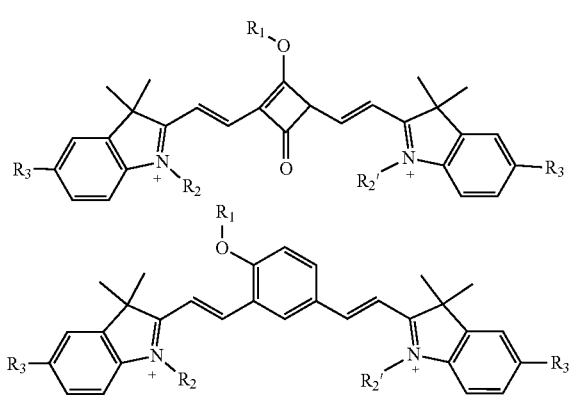

then each X can be attached to a single Y group by $R_2$ and $R_{2'}$ or each X can be attached to two Y groups. That is, the $R_2$ group and $R_{2'}$ group may be attached to a different Y group. In preferred embodiments that may be mentioned herein, the $R_2$ group and $R_{2'}$ group represents a point of attachment to the same Y group.

It will be appreciated that the discussion above also applies to embodiments of the invention there X is:

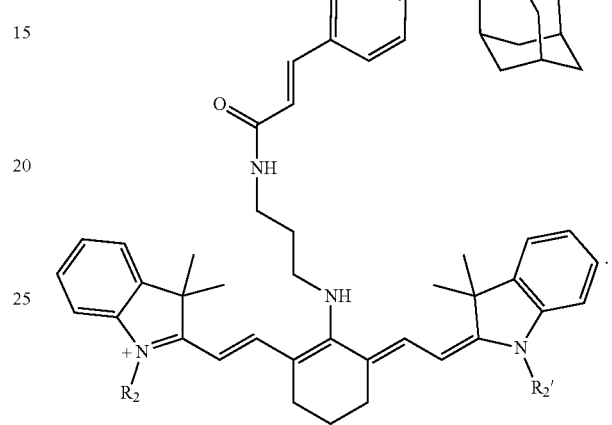

In particular embodiments of the invention that may be mentioned herein, each $R_5$ group, when present, may be independently selected from H, $CH_2CHOHCH_3$ and

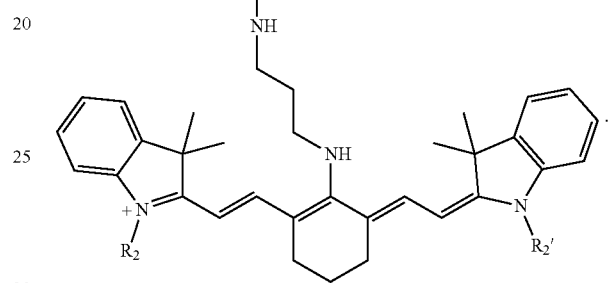

(1 ≤ m ≤ 50)

where the left-hand wavy line (adjacent to m) represents the point of attachment to X or Z and the right-hand wavy line represents the point of attachment to the rest of the molecule.

In particular embodiments of the invention that may be mentioned herein, a and b may each be 1 and Y may be

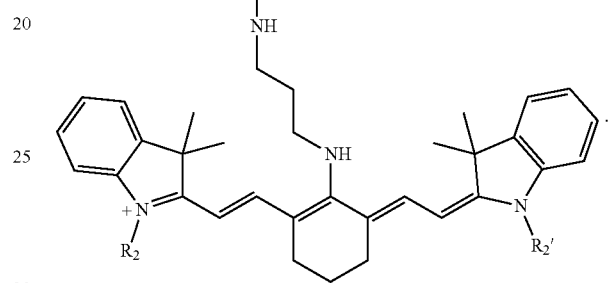

(6 ≤ n ≤ 8)

In particular embodiments, the compound formula I (and salts and/or solvates thereof) may be selected from:

(a) a is 1, b is 0, X is
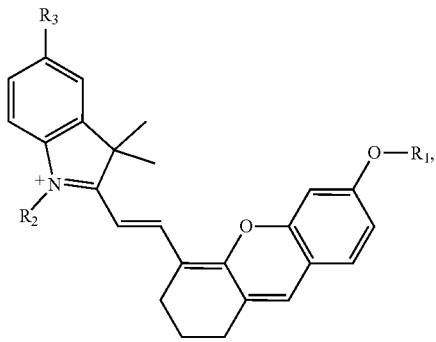
where $R_3$ is H, $R_1$ is a biomarker reactive moiety that is:
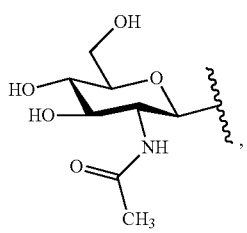
and Y is
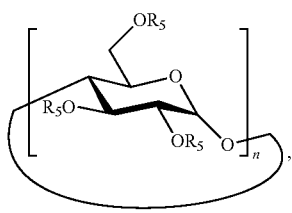
where n is 7; and
(b) a is 1, b is 1, X is
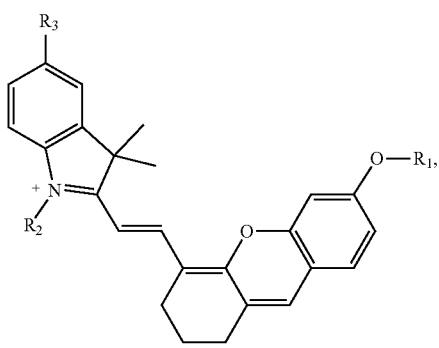
where $R_3$ is H, $R_1$ is a biomarker reactive moiety that is:
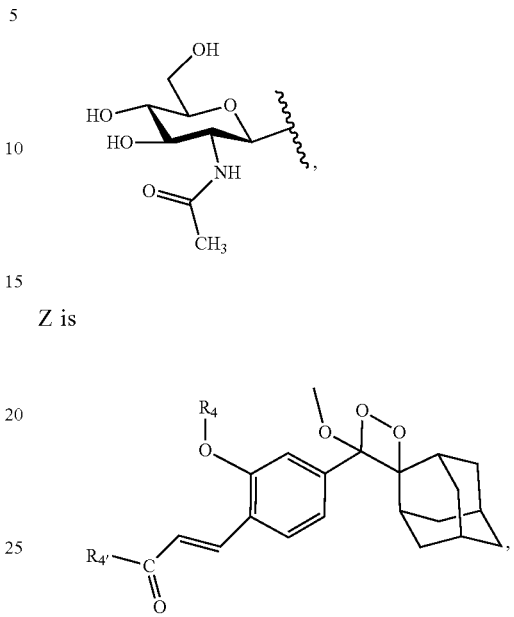
Z is
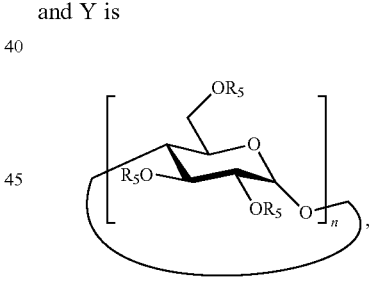
where $R_4$ is,
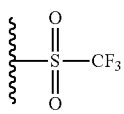
and Y is
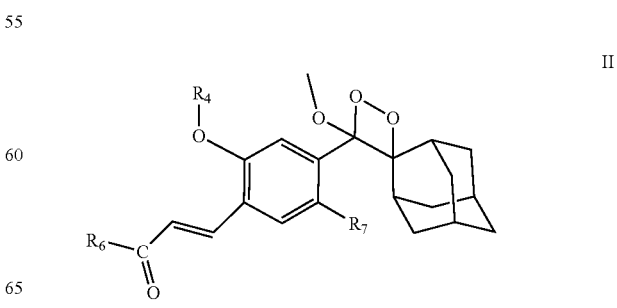
where n is 7.
In a further aspect of the invention, there is provided a compound of formula II:
II
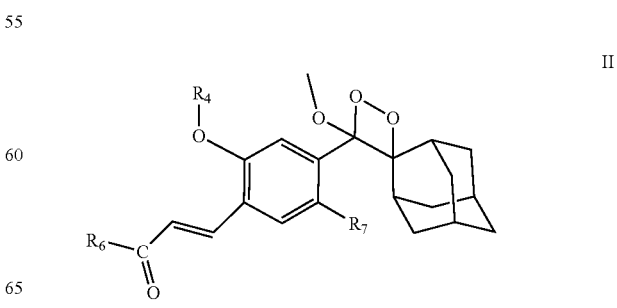

where:

$R_4$ is selected from:

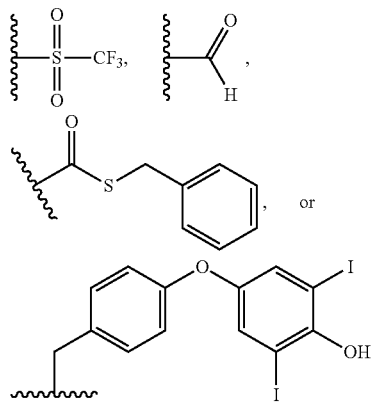

where the wavy line represents the point of attachment to the rest of the molecule;

$R_6$ is OH or $OC_1$-$C_6$ alkyl;

$R_7$ is:

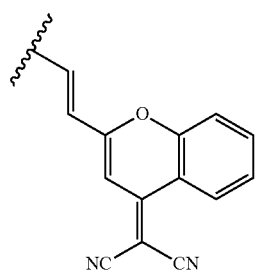 [SMILES: */C=C/C1=CC(=C(C#N)C#N)c2ccccc2O1]

or pharmaceutically acceptable salts and/or solvates thereof. Such compounds may display chemiluminescence when the $R_4$ group is cleaved (or is H).

As will be appreciated, it may also be possible to conduct a similar diagnosis in an in vitro setting. In this circumstance, there is not necessarily a need to make use of a renal clearance moiety. Thus, in further embodiments of the invention there are provided compounds of formula III:

X'—Y'    III where:

X' is selected from:

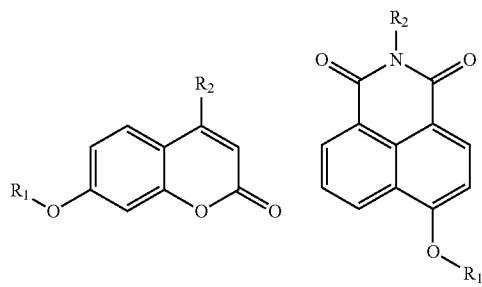

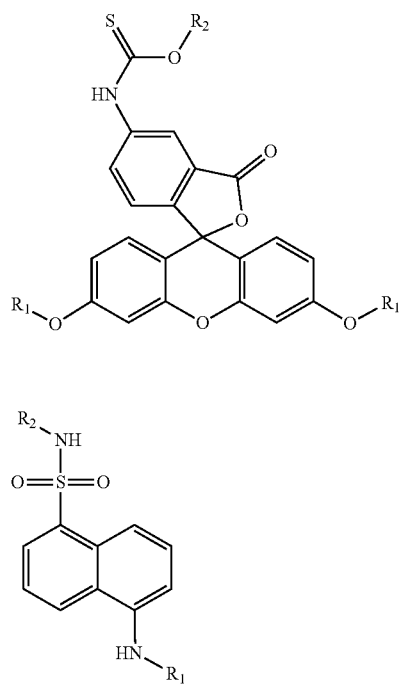

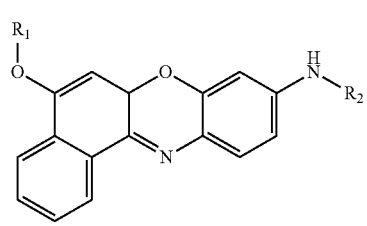

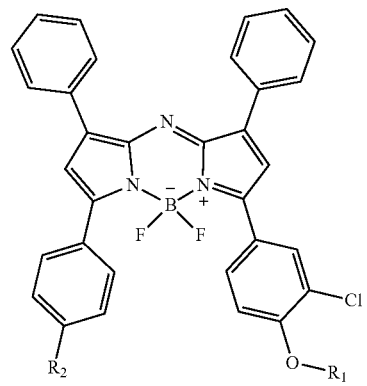

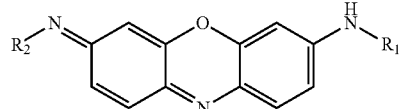

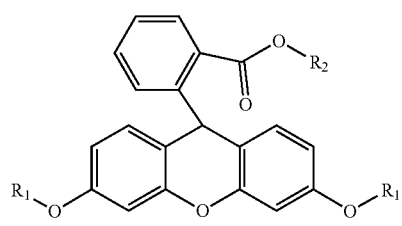

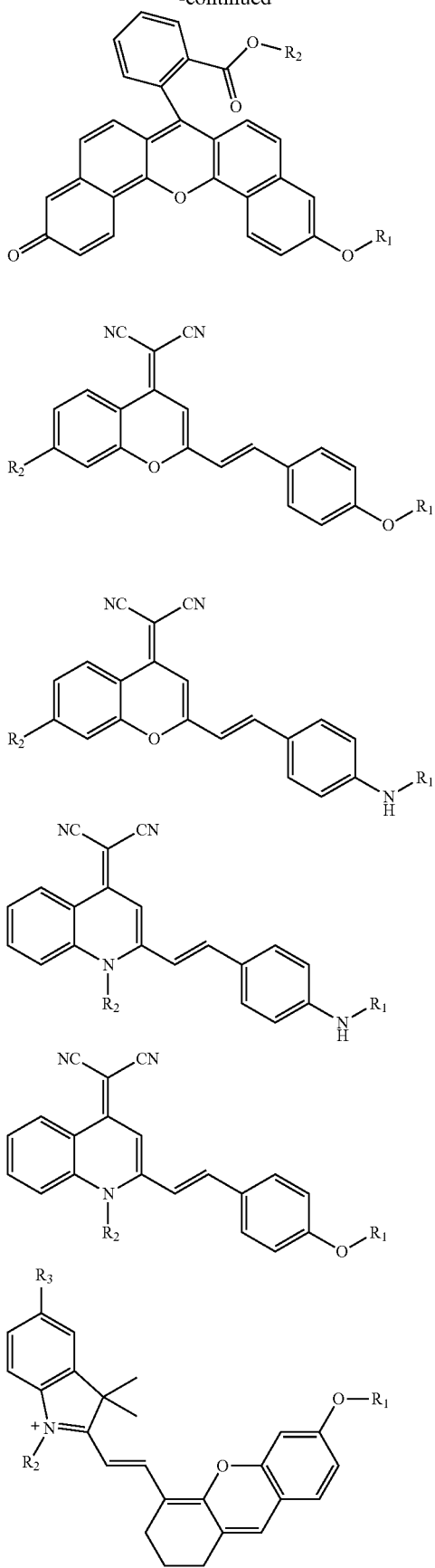
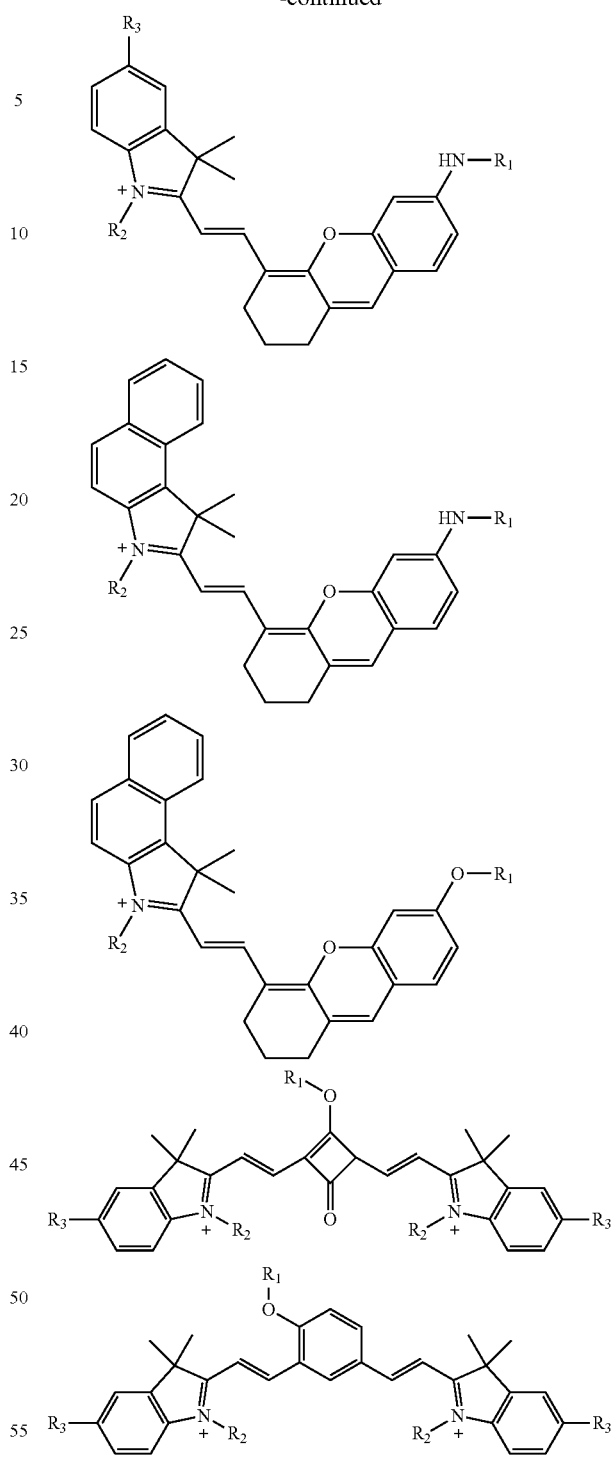
where $R_1$ represents a biomarker reactive moiety or a biomarker reactive moiety conjugated to a self-immolative moiety

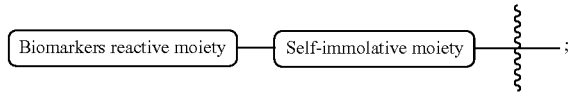

one $R_2$ represents the point of attachment to Y' and the other $R_2$ represents Y";
$R_3$ represents H, $SO_3H$ or COOH;
Y' and Y" are selected from H, $C_mH_{2m+1}$ (1≤m≤50),

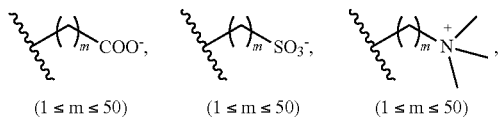

where the wavy line represents the point of attachment to X', or pharmaceutically acceptable salts and/or solvates thereof.

To avoid repetition, and for the avoidance of doubt, the terms used in respect of the compound of formula III are intended to be identical to those used in relation to the compounds of formula I. This includes the use of the same R group numbers, and the same general preferences noted above for X may also apply to X'.

The compound for use mentioned in the above-mentioned aspect of the invention may be utilised in a method of medical diagnosis. Thus, according to further aspects of the invention, there is provided:
(i) the use of a compound formula I or a salt and/or solvate thereof for the manufacture of a diagnostic agent for in vivo diagnosis of a kidney injury or a kidney disease;
(ii) a method of diagnosis of a kidney injury or a kidney disease, involving administering to a subject in need thereof a composition comprising a compound of formula I or a salt and/or solvate thereof and detecting a signal, the detection of which indicates a kidney injury or a kidney disease in said subject;
(iii) a compound of formula I or a salt and/or solvate thereof for use in the in vivo diagnosis of a kidney injury or a kidney disease.

In addition, there is also disclosed a method of in vitro diagnosis of a kidney injury or a kidney disease, using a compound of formula I, or a compound of formula III or a salt and/or solvate thereof comprising the steps of:
(a) providing a sample for detection;
(b) adding a compound of formula I or a salt or solvate thereof, or a compound of formula III or a salt or solvate thereof to the sample, allowing said compound to incubate for a period of time; and
(c) detecting a signal from the sample, the detection of which indicates a kidney injury or a kidney disease.

The sample may be prepared and used as described in the examples section below. As will be appreciated, the skilled person may adapt the protocols disclosed below in line with their knowledge and the condition under consideration.

The aspects of the invention described herein (e.g. the above-mentioned compounds, combinations, methods and uses) may have the advantage that, in the diagnosis of the conditions described herein, they may be more convenient for the physician and/or patient than, be more efficacious than, be less toxic than, have better selectivity over, be more selective than, be more sensitive than, produce fewer side effects than, or may have other useful pharmacological properties over, similar compounds, combinations, methods (treatments) or uses known in the prior art for use in the diagnosis of those conditions or otherwise.

Compounds of formula I and III may be administered by any suitable route, but may particularly be administered orally, intravenously, intramuscularly, cutaneously, subcutaneously, transmucosally (e.g. sublingually or buccally), rectally, transdermally, nasally, pulmonarily (e.g. tracheally or bronchially), topically, by any other parenteral route, in the form of a pharmaceutical preparation comprising the compound in a pharmaceutically acceptable dosage form. Particular modes of administration that may be mentioned include oral, intravenous, cutaneous, subcutaneous, nasal, intramuscular or intraperitoneal administration.

Compounds of formula I and III will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington *The Science and Practice of Pharmacy*, 19th ed., Mack Printing Company, Easton, Pennsylvania (1995).

For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, *Science* (1990) 249, 1527.

Otherwise, the preparation of suitable formulations may be achieved routinely by the skilled person using routine techniques and/or in accordance with standard and/or accepted pharmaceutical practice.

The amount of compound of formula I or II in any pharmaceutical formulation used in accordance with the present invention will depend on various factors, such as the condition to be diagnosed, the particular patient that is the subject of the diagnosis, as well as the compound(s) which is/are employed. In any event, the amount of compound of formula I or III in the formulation may be determined routinely by the skilled person.

For example, a solid oral composition such as a tablet or capsule may contain from 1 to 99% (w/w) diagnostic ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) diagnostic ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the condition to be diagnosed, and the patient to be diagnosed, as well as the route of administration, compounds of formula I or III may be administered at varying diagnostically effective doses to a subject in need thereof.

However, the dose administered to a mammal, particularly a human, in the context of the present invention should be sufficient to effect a therapeutic response in the mammal over a reasonable timeframe. One skilled in the art will recognise that the selection of the exact dose and composition and the most appropriate delivery regimen will also be influenced by inter alia the pharmacological properties of the formulation, the nature and severity of the condition being diagnosed, and the physical condition and mental acuity of the recipient, as well as the properties of the specific compound, the age, condition, body weight, sex and response of the patient to be diagnosed, and the suspected stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of formula I or III.

In any event, the medical practitioner, or other skilled person, will be able to determine routinely the actual dosage, which will be most suitable for an individual subject. The above-mentioned dosages are exemplary of the average case; there can, of course, be individual instances where higher or lower dosage ranges are merited, and such are within the scope of this invention.

When used herein "kidney injury" may refer to acute kidney injury. Acute kidney injury may be caused by low blood pressure, shock, blood loss, fluid loss (e.g. severe diarrhoea), heart attack, organ failure (e.g., heart, liver), overuse of pain medicines, severe allergic reactions, burns, major surgery, direct damage to the kidneys, sepsis, multiple myeloma, vasculitis, interstitial nephritis, scleroderma, tubular necrosis, thrombotic microangiopathy, glomerulonephritis, cancer (e.g. bladder, prostate, or cervical cancer), enlarged prostate and blood clots.

EXAMPLES

Materials and Methods

Chemicals. All chemicals were purchased from Sigma-Aldrich or Tokyo Chemical Industry (TCI) unless otherwise stated. Cisplatin, gentamicin, diatrizoate, alpha-naphthyl isothiocyanate (ANIT) and lipopolysaccharides (LPS, from *Escherichia coli* 0111:B4) were obtained from Sigma-Aldrich. N-acetyl-β-D-glucosaminidase, plasmin, β-galactosidase, nitroreductase and fibroblast activation protein-alpha were purchased from Sigma-Aldrich. Alanine aminopeptidase, furin and recombinant human caspase-3 were purchased from R&D Systems. Creatinine assay kit, urea assay kit and mouse cystatin C ELISA kit were purchased from Sigma-Aldrich, BioAssay Systems and RayBiotech, respectively. Mouse NGAL, osteopontin, KIM-1, TFF3 and clusterin ELISA kit were purchased from R&D Systems. Cleaved-caspase-3 antibody (9661 L) was purchased from Cell Signaling Technology. Mouse beta2-microglobulin ELISA kit, anti-CD31 antibody (ab28364), anti-CD11b antibody (ab133357) and Alexa Fluor 488 conjugated goat anti-rabbit IgG H&L (ab150077) were purchased from Abcam. Ultrapure water was supplied by Milli-Q Plus System (Millipore Corporation, Breford, USA).

Materials characterisation. Silica gel (Silicycle, 230-400 mesh) was used for column chromatography. Thin layer chromatography (TLC) was carried out on Merck Silica gel 60 F-254 Glass plates. UV-Vis spectra were recorded on a Shimadzu UV-2450 spectrophotometer using quartz cuvettes (1 cm path length). Fluorescence spectra were acquired with Fluorolog 3-TCSPC spectrofluorometer (Horiba Jobin Yvon) using quartz cuvettes (1 cm path length). Chemiluminescence was recorded on spectramax i3x (Molecular Devices, USA) or Luminometer (Promega, USA). HPLC analyses and purification were performed on an Agilent 1260 system with acetonitrile/water as the eluent. Proton-nuclear magnetic resonance ($^1$H NMR) spectra were conducted with a Bruker 300 MHz NMR instrument. Chemical shifts are reported in ppm relative to residual protic solvent resonances. Mestre Nova LITE v5.2.5-4119 software (Mestre lab Research S.L.) was used to analyse the NMR spectra. Multiplicities are reported as follows: s (singlet), d (doublet), t (triplet) or m (multiplet). Coupling constants are reported as a J value in hertz (Hz). The number of protons (n) for a given resonance is indicated nH, and based on the spectral integration values. Electrospray ionisation-mass spectrometry (ESI-MS) spectra were obtained on a Thermo Finnigan Polaris Q quadrupole ion trap mass spectrometer (ThermoFisher Corporation) equipped with a standard ESI source. Matrix-assisted laser desorption/ionisation time-of-flight (MALDI-TOF) analyses were conducted on a Bruker ultraflex TOF/TOF instrument. The pH values were tested by a digital pH-meter (SevenCompact S220, Zurich, Switzerland). Tissues were cut into sections using a cryostat (Leica, Germany). The tissue sections were examined using a Nikon ECLIPSE 80i microscope (Nikon Instruments Inc, USA). Confocal fluorescence microscopy images of tissue sections were acquired on a LSM800 confocal laser scanning microscope (Carl Zeiss, Germany). Fluorescence and chemiluminescence imaging were performed on the IVIS spectrum imaging system (PerkinElmer, Inc, USA). In silico calculation of the partition coefficients (Log D at pH 7.4) was calculated using Marvin and JChem calculator plug-ins (ChemAxon, Hungary). Blood samples were collected using heparinised capillary tubes (Paul Marienfeld, Germany). Urine samples were collected with metabolic cages (Lab Products Inc, USA).

Preparation of Components and/or Intermediates

Preparation 1: Synthesis of BrGlcNAc (FIG. 6a)

AcGlcNAc (0.78 g, 2.0 mmol) was dissolved in anhydrous dichloromethane (8 ml), followed by addition of hydrogen bromide (33% in acetic acid, 5 ml). The reaction mixture was stirred at 0° C. After 8 h, the reaction mixture was poured into distilled water (30 ml) and extracted by dichloromethane (60 ml). The organic layer was washed with sodium hydrogen carbonate (50 ml of a saturated aqueous solution), dried over anhydrous magnesium sulphate and concentrated under reduced pressure to afford compound BrGlcNAc (0.62 g, 75%) as a white crystalline solid. TLC (silica gel, ethyl acetate/petroleum ether, 1/3), $R_f$=0.4. $^1$H NMR (300 MHz, CDCl$_3$): δ 2.00 (s, 3H), 2.07 (s, 6H), 2.11 (s, 3H), 4.11 (d, J=3, 1H), 4.16 (t, 1H), 4.24 (t, 1H), 5.30 (m, 2H), 5.82 (d, J=9, 1H), 6.52 (d, J=6, 1H). ESI-MS (m/z): calcd: 409.04, found [M-Br]: 330.1.

Preparation 2: Synthesis of Br-Ph-DVED (FIG. 6b)

To a solution of Ac-DEVD (0.69 g, 1.0 mmol) in tetrahydrofuran (20 ml) were added (4-aminophenyl)methanol (0.49 g, 4.0 mmol) and N-ethoxycarbonyl-2-ethoxy-1,2-dihydroquinoline (0.99 g, 4.0 mmol). The reaction mixture was stirred for 12 h at room temperature before it was concentrated under reduced pressure. The residue was washed with distilled water and extracted with dichloromethane. The organic layer was further washed with brine, dried over anhydrous magnesium sulphate and concentrated under reduced pressure. The residue was purified by HPLC to give compound Ph-DVED (0.63 g, 80%). To a solution of compound Ph-DVED (0.40 g, 0.5 mmol) in tetrahydrofuran (25 ml) was added phosphorus tribromide (0.27 g, 1.0 mmol). The reaction mixture was stirred for 12 h at room temperature and then it was quenched with distilled water followed by extraction with dichloromethane. The organic layer was washed with brine, dried over anhydrous magnesium sulphate and concentrated under reduced pressure. The residue was purified by HPLC to afford compound Br-Ph-DVED (0.32 g, 76% yield). $^1$H NMR (300 MHz, CDCl$_3$): δ 0.95 (s, 6H), 1.43 (s, 27H), 2.08 (s, 3H), 2.22 (m, 3H), 2.53 (m, 3H), 2.85 (m, 4H), 4.35 (m, 3H), 4.76 (s, 3H), 7.11 (d, J=6 Hz, 1H), 7.31 (d, J=3 Hz, 1H), 7.52 (d, J=3 Hz, 1H), 7.92 (s, 1H). ESI-MS (m/z): calcd: 853.35, found [M-Br]: 774.21.

Preparation 3: Synthesis of propynyl-HPβCD (FIG. 6c)

A suspension of sodium hydride (0.80 g, 20 mmol, 60% dispersion in mineral oil) in anhydrous dimethylformamide (25 ml) was added to a solution of HPβCD (3.08 g, 2.0 mmol) and tetra-tert-butylammonium iodide (0.16 g, 0.44 mmol) in anhydrous dimethylformamide (15 ml) at 0° C. After stirring for 0.5 h at 0° C., a solution of propargyl bromide (0.30 g, 3.0 mmol) in anhydrous dimethylformamide (1 ml) was added. The reaction mixture was stirred at room temperature for additional 24 h before it was concentrated under reduced pressure. The residue was purified by silica gel column chromatography (methanol/ethylacetate=1/2 and methanol/H$_2$O=4/1) to afford propynyl-HPβCD (3.02 g, 94%) as a yellowish solid after freeze dry. $^1$H NMR (300 MHz, D$_2$O): δ 1.14 (d, J=6, 17H), 2.72 (s, 1H), 3.25-4.25 (m, 64H), 5.08-5.25 (m, 7H). MALDI-TOF MS found: 1400-1800.

Figure 3:
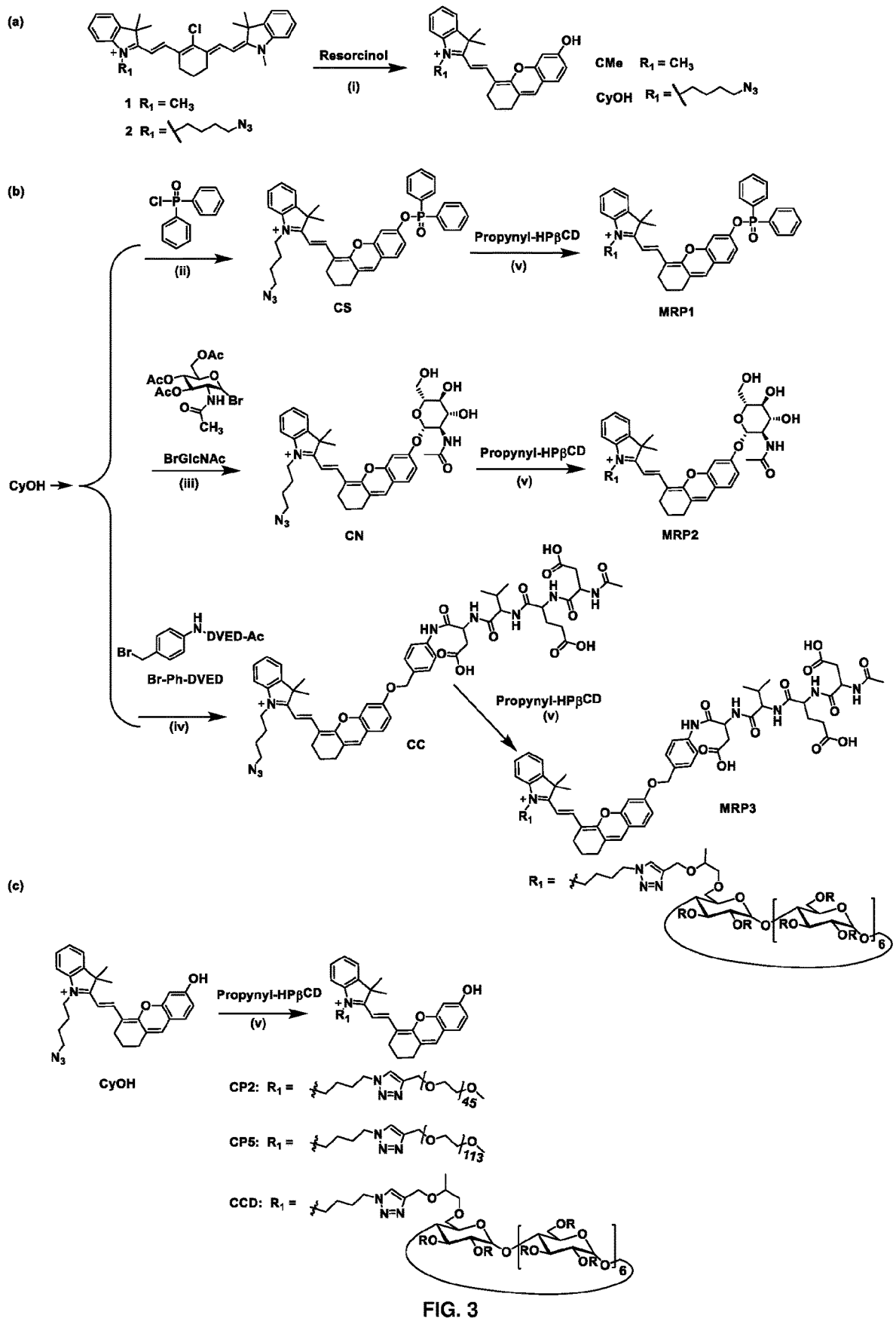
FIG. 3 Depicts the syntheses of MRPs1-3 and the uncaged fluorophores. (a) Syntheses of CMe and CyOH. Reagents and conditions: (i) Resorcinol, $K_2CO_3$, $CH_3CN$, 55° C., 3 h. (b) Syntheses of MRP1, MRP2 and MRP3, (R: H or $CH_2CHOHCH_3$). Reagents and conditions: (ii) diphenylphosphinic chloride, $CH_2Cl_2$, $Et_3N$, 15 min, rt; (iii)

Preparation 4: Synthesis of CMe and CyOH (FIG. 3a)

CMe and CyOH were synthesised according to our previous study (Q. Miao, et al., Angew. Chem. Int. Ed., 2018, 57, 1256-1260). $^1$H NMR of CMe (300 MHz, CDCl$_3$): δ 1.65 (s, 6H), 1.88 (m, 2H), 2.63 (m, 4H), 3.33 (s, 3H), 5.54 (d, J=15 Hz, 1H), 6.55 (s, 1H), 6.76 (m, 2H), 7.04-7.24 (m, 3H), 7.29 (m, 2H), 8.03 (t, 1H). ESI-MS of CMe (m/z): calcd: 384.19, found: 384.40.

$^1$H NMR of CyOH (300 MHz, CDCl$_3$): δ 1.76 (s, 6H), 1.96 (m, 8H), 2.71 (t, 2H), 3.47 (t, 2H), 4.21 (d, J=6 Hz, 2H), 5.30 (s, 1H), 6.11 (d, J=15 Hz, 1H), 7.17 (m, 3H), 7.44 (m, 4H), 7.71 (m, 1H), 8.50 (d, J=15 Hz, 1H). ESI-MS of CyOH (m/z): calcd: 467.2, found: 467.2.

Preparation 5: Synthesis of Compound 5 (FIG. 4)

A mixture of 3-hydroxybenzaldehyde (compound 4, 2.44 g, 20 mmol), trimethyl orthoformate (3.58 ml, 32 mmol), and tertrabutylammonium tribromide (0.49 g, 1.0 mmol) in methanol (30 ml) was stirred at room temperature under a nitrogen atmosphere. After 16 h, the reaction mixture was diluted with ethyl acetate (200 ml) and washed with sodium bicarbonate (200 ml). The organic layer was further washed with brine, dried over sodium sulfate and concentrated under reduced pressure. The residue was purified by silica gel column chromatography (ethyl acetate/petroleum ether=1/5) to afforded compound 5 (3.20 g, 95% yield) as colorless oil. TLC (silica gel, ethyl acetate/petroleum ether=1/5), $R_f$=0.42. $^1$H NMR (300 MHz, CDCl$_3$): 3.37 (s, 6H), 5.39 (s, 1H), 6.17 (s, 1H), 6.83 (m, 1H), 7.02 (m, 2H). ESI-MS (m/z): calcd: 168.08, found [M-Br]: 168.21.

Preparation 6: Synthesis of Compound 6 (FIG. 4)

A mixture of 3-hydroxybenzaldehyde dimethyl acetal (compound 5, 2.52 g, 15.0 mmol), imidazole (1.53 g, 22.5 mmol) and tert-butyldimethylsilyl chloride (2.70 g, 18.0 mmol) in dichloromethane (20 ml) was stirred at room temperature. After 16 h, the white precipitate was filtered off and the solvent was concentrated under reduced pressure. The residue was purified by silica gel column chromatography (ethyl acetate/petroleum ether=1/15) to afforded compound 6 (3.85 g, 91% yield) as colorless oil. TLC (silica gel, ethyl acetate/petroleum ether=1/15), $R_f$=0.45. $^1$H NMR (300 MHz, CDCl$_3$): δ 0.23 (s, 6H), 1.02 (s, 9H), 3.36 (s, 6H), 5.38 (s, 1H), 6.82 (d, J=3 Hz, 1H), 6.97 (s, 1H), 7.06 (d, J=9 Hz, 1H), 7.30 (m, 1H). ESI-MS (m/z): calcd: 282.17, found: 282.30.

Preparation 7: Synthesis of Compound 7 (FIG. 4)

A mixture of acetal (compound 6, 3.38 g, 12.0 mmol) and trimethyl phosphite (2.13 ml, 18.0 mmol) in dichloromethane (40 ml) was stirred in ice bath. Titanium (IV) chloride (2.38 ml, 18.0 mmol) was dropwise added and stirred for 16 h. The solution was poured into a saturated aqueous solution of sodium bicarbonate (200 ml) in ice bath. After stirring for 15 min, the mixture was extracted by dichloromethane (200 ml). The organic layer was dried with anhydrous sodium sulphate and concentrated under reduced pressure to yield crude product as colorless oil. The residue was purified by silica gel column chromatography (ethyl acetate/petroleum ether=2/1) to afforded compound 7 (3.24 g, 75% yield) as colorless oil. TLC (silica gel, ethyl acetate/petroleum ether=2/1), $R_f$=0.52. $^1$H NMR (300 MHz, CDCl$_3$): δ 0.21 (s, 6H), 0.99 (s, 9H), 3.38 (s, 3H), 3.69 (t, 6H), 4.48 (d, J=15 Hz, 1H), 6.81 (d, J=9 Hz, 1H), 6.94 (s, 1H), 7.01 (d, J=6 Hz, 1H), 7.24 (m, 1H). ESI-MS (m/z): calcd: 360.15, found: 360.81.

Preparation 8: Synthesis of Compound 8 (FIG. 4)

Phosphonate (compound 7, 3.24 g, 9.0 mmol) was dissolved in anhydrous tetrahydrofuran (20 ml) under a nitrogen atmosphere at −78° C. in a 50 ml round-bottom flask. Lithium di-isopropyl amide (2.0 M in tetrahydrofuran, 6 ml, 10.35 mmol) was added and the solution was stirred for 30 min. A solution of 2-adamantanone (1.62 g, 10.8 mmol) in anhydrous tetrahydrofuran (20 ml) was added and stirred for 30 min at −78° C., then stirred for additional 3 h. The reaction mixture was diluted with ethyl acetate (200 ml) and washed with brine (200 ml). The organic layer was dried over anhydrous sodium sulfate and concentrated under reduced pressure. The residue was purified by silica gel column chromatography (ethyl acetate/petroleum ether=1/15) to give compound 8 (2.94 g, 85% yield) as colorless oil. TLC (silica gel, ethyl acetate/petroleum ether=1/15), $R_f$=0.65. $^1$H NMR (300 MHz, CDCl$_3$): δ 0.20 (s, 6H), 0.98 (s, 9H), 1.78-1.97 (m, 13H), 3.25 (s, 1H), 3.38 (s, 3H), 6.75 (m, 2H), 6.79 (d, J=3 Hz, 1H), 7.20 (t, 1H). ESI-MS (m/z): calcd: 384.25, found [M-Br]: 384.40.

Preparation 9: Synthesis of Compound 9 (FIG. 4)

A mixture of compound 8 (2.94 g, 6.8 mmol) and tetrabutylammonium fluoride (1.0 M in tetrahydrofuran, 7.5 ml, 7.5 mmol) in anhydrous tetrahydrofuran (30 ml) was stirred for 12 h at room temperature in a 50 ml round-bottom flask. The reaction mixture was diluted with ethyl acetate (200 ml) and washed with hydrogen chloride (1M, 100 ml). The organic layer was dried over anhydrous sodium sulfate and concentrated under reduced pressure. The residue was purified by silica gel column chromatography (ethyl acetate/petroleum ether=1/15) to afforded compound 9 (1.74 g, 95% yield) as a white solid. TLC (silica gel, ethyl acetate/petroleum ether=1/15), $R_f$=0.30. $^1$H NMR (300 MHz, CDCl$_3$): δ 1.79-1.97 (m, 12H), 2.65 (s, 1H), 3.25 (s, 1H), 3.33 (s, 3H), 5.58 (s, 1H), 6.80 (m, 1H), 6.86 (t, 2H), 7.22 (t, 1H). ESI-MS (m/z): calcd: 270.16, found: 270.18.

Preparation 10: Synthesis of Compound 10 (FIG. 4)

Compound 9 (1.70 g, 6.3 mmol) was dissolved in toluene (150 ml) and cooled in ice bath. N-Iodosuccinimide (NIS, 1.42 g, 6.3 mmol) was added in portions and stirred for 12 h. The reaction was quenched with saturated sodium thiosulfate, diluted with ethyl acetate (200 ml) and washed with brine (150 ml). The organic layer was dried over anhydrous sodium sulfate and concentrated under reduced pressure. The residue was purified by silica gel column chromatography (ethyl acetate/petroleum ether=1/5) to afford compound 10 (1.97 g, 80% yield) as a white solid. TLC (silica gel, ethyl acetate/petroleum ether=1/5), $R_f$=0.70. $^1$H NMR (300 MHz, CDCl$_3$): δ 1.77-1.95 (m, 12H), 2.62 (s, 1H), 3.22 (s, 1H), 3.29 (s, 3H), 5.27 (s, 1H), 6.63 (d, J=3, 1H), 6.94 (s, 1H), 7.59 (d, J=9, 1H). ESI-MS (m/z): calcd: 396.06, found [M–I]: 269.10.

Preparation 11: Synthesis of CL (FIG. 4)

A mixture of iodophenol (compound 9, 1.78 g, 4.5 mmol), methyl acrylate (1.16 g, 13.5 mmol) and triethylamine (0.68 g, 6.75 mmol) was stirred in anhydrous acetonitrile (30 ml). Then palladium(II) acetate (Pd(OAc)$_2$) (50.50 mg, 0.225 mmol) and tri(o-tolyl)phosphine (P(o-tol)$_3$) (13.70 mg, 0.045 mmol) were added. The flask was sealed and the reaction was stirred at 90° C. After 12 h, the reaction mixture was diluted with ethyl acetate (200 ml) and washed with saturated ammonium chloride aqueous (200 ml). The organic layer was dried over anhydrous sodium sulfate and concentrated under reduced pressure. The residue was purified by silica gel column chromatography (ethyl acetate/petroleum ether=1/1) to give compound CL (1.27 g, 80% yield) as a pale-yellow solid. TLC (silica gel, ethyl acetate/petroleum ether=1/1), $R_f$=0.50. $^1$H NMR (300 MHz, CDCl$_3$): δ 1.79-1.96 (m, 12H), 2.69 (s, 1H), 3.23 (s, 1H), 3.33 (s, 3H), 3.81 (s, 3H), 6.38 (s, 1H), 6.58 (d, J=18 Hz, 1H), 6.86 (s, 2H), 7.41 (d, 1H), 7.95 (d, J=18 Hz, 1H). ESI-MS (m/z): calcd [(M+H)$^+$]: 355.18, found: 355.15.

Preparation 12: Synthesis of Compound 11 (FIG. 4)

A solution of compound CL (1.27 g, 3.6 mmol) was stirred in anhydrous pyridine (10 ml) and anhydrous dichloromethane (15 ml) at −78° C. Trifluoromethanesulfonic anhydride (1.22 ml, 7.2 mmol) was dropwise added to the solution under a nitrogen atmosphere. The mixture was kept stirring at −78° C. for 30 min and then at room temperature for additional 2 h. The reaction was quenched by sodium bicarbonate aqueous at room temperature and extracted by ethyl acetate (100 ml). The ethyl acetate layer was washed three times with hydrogen chloride (1 M, 150 ml) and brine (100 ml), dried over anhydrous sodium sulfate and concentrated under reduced pressure. The residue was purified by silica gel column chromatography (ethyl acetate/petroleum ether=1/6) to afford compound 11 (1.58 g, 90% yield) as a pale-yellow solid. TLC (silica gel, ethyl acetate/petroleum ether=1/6), $R_f$=0.60. $^1$H NMR (300 MHz, CDCl$_3$): δ 1.81-1.99 (m, 12H), 2.69 (s, 1H), 3.26 (s, 1H), 3.33 (s, 3H), 3.84 (s, 3H), 6.49 (s, J=15 Hz, 1H), 7.32 (t, 2H), 7.66 (d, J=9 Hz, 1H), 7.84 (d, J=18 Hz, 1H). ESI-MS (m/z): calcd [(M+H)$^+$]: 487.13, found: 487.09.

Preparation 13: Synthesis of Compound 12 (FIG. 4)

Compound 11 (1.50 g, 3.08 mmol) and sodium hydroxide (NaOH, 0.25 g, 6.16 mmol) were dissolved in tetrahydrofuran (20 ml) and H$_2$O (5 ml). Reaction mixture was stirred at 60° C. for 4 h and monitored by HPLC. Upon completion, the reaction mixture was diluted with ethyl acetate (150 ml) and washed with hydrogen chloride (0.5 M, 100 ml). The organic layer was separated, washed with brine, dried over anhydrous sodium sulfate and evaporated under reduced pressure. The residue was purified by silica gel column chromatography (ethyl acetate/petroleum ether=1/1) to afford compound 12 (1.38 g, 95% yield) as a pale-yellow solid. TLC (silica gel, ethyl acetate/petroleum ether=1/1), $R_f$=0.42. $^1$H NMR (300 MHz, CD$_3$OD): δ 1.76-1.92 (m, 12H), 2.69 (s, 1H), 3.22 (s, 1H), 3.25 (s, 3H), 6.54 (d, J=18 Hz, 1H), 7.23 (s, 1H), 7.35 (d, J=9 Hz, 1H), 7.74-7.86 (m, 2H). ESI-MS (m/z): calcd: 472.12, found [M-Br]: 472.16.

Preparation 14: Synthesis of CSCL (FIG. 4)

Compound 12 (1.30 g, 2.75 mmol) and methylene blue (32 mg, 0.1 mmol) were dissolved in a mixture of dichloromethane and methanol (20 ml, 1/1). Oxygen was bubbled through the solution while irradiating with yellow light for 2 h. The reaction mixture was concentrated under reduced pressure. The crude product was purified by preparative HPLC to afford CSCL (0.83 g, 60% yield) as a white solid. $^1$H NMR (300 MHz, CDCl$_3$): δ 0.86 (t, 1H), 1.25 (s, 1H), 1.75-1.92 (m, 10H), 2.92 (s, 1H), 3.26 (s, 3H), 6.32 (d, J=9 Hz, 1H), 7.19 (s, J=6 Hz, 1H), 7.37-7.65 (m, 3H). ESI-MS (m/z): calcd: 504.11, found [M–H]: 503.20.

Preparation 15: Synthesis of Cy7NH2 (FIG. 4)

A mixture of CyCl (0.26 g, 0.4 mmol) and N-Fmoc-1,3-diaminopropane hydrochloride (0.33 g, 1.0 mmol) in dimethylformamide (10 ml) was stirred at 65° C. for 4 h. After cooling down, distilled water (35 ml) was added. The mixture was extracted using dichloromethane. The organic layer was dried with anhydrous magnesium sulphate and concentrated under reduced pressure to yield crude product compound 13 as a blue solid. A mixture of compound 13 and piperidine (1 ml) in dichloromethane (4 ml) was stirred at room temperature for 1 h. The reaction was poured into distilled water (30 ml) and extracted by using dichloromethane. The organic layer was dried with anhydrous sodium sulphate and concentrated under reduced pressure. The residue was purified by silica gel column chromatography (dichloromethane/methanol=15/1) to afford compound Cy7NH2 (0.15 g, 55% yield) as a blue solid. TLC (silica gel, dichloromethane/methanol=15/1), $R_f$=0.46. $^1$H NMR (300 MHz, CDCl$_3$): δ 1.62 (m, 12H), 1.86 (m, 12H), 2.47 (t, 4H), 3.09 (t, 4H), 3.35 (m, 4H), 3.81-3.95 (m, 4H), 5.54 (d, J=12 Hz, 2H), 6.79-6.87 (m, 4H), 7.24 (m, 2H), 7.64 (m, 4H). ESI-MS (m/z): calcd: 687.46, found: 687.50.

Preparation 16: Synthesis of CySCL (FIG. 4)

A mixture of Cy7NH2 (0.14 g, 0.2 mmol), CSCL (0.11 mg, 0.2 mmol), N,N-diisopropylethylamine (12.90 mg, 0.1 mmol) and (2-(1H-benzotriazol-1-yl)-1,1,3,3-tetramethyluronium hexafluorophosphate (0.15 g, 0.4 mmol) in dimethylformamide (6 ml) was stirred at room temperature for 4 h. The reaction was poured into distilled water (40 ml) and extracted by dichloromethane. The organic layer was dried with anhydrous sodium sulphate and concentrated under reduced pressure. The residue was purified by silica gel column chromatography (dichloromethane/methanol=15/1) to afford compound CySCL (0.18 g, 75% yield) as a blue solid. TLC (silica gel, dichloromethane/methanol=15/1), $R_f$=0.65. $^1$H NMR (300 MHz, CDCl$_3$): δ 0.92 (m, 1H), 1.25 (s, 1H), 1.60-2.06 (m, 34H), 2.48 (m, 4H), 2.90 (t, 1H), 3.29 (s, 3H), 3.31 (m, 4H), 3.39 (m, 4H), 3.82-3.94 (m, 4H), 5.59 (d, J=9 Hz, 2H), 6.29 (t, 1H), 6.83 (m, 3H), 7.03 (m, 3H), 7.23 (m, 2H), 7.29 (m, 2H), 7.38 (m, 3H), 7.54 (m, 1H), 7.70 (m, 1H). ESI-MS (m/z): calcd: 1173.56, found: [M–H] 1172.40.

Synthesis of Compound 14 (FIG. 5)

A mixture of compound CyOH-2 (25.0 mg, 0.05 mmol) and cesium carbonate (0.07 g, 0.2 mmol) in anhydrous dichloromethane (5 ml) was stirred at room temperature for 30 min. BrGlcNAc (0.10 g, 0.25 mmol) was dissolved in anhydrous dichloromethane (3 ml) and added into the reaction mixture, and was stirred at room temperature for additional 16 h. The reaction mixture was then poured into distilled water (20 ml) and extracted by dichloromethane (80 ml). The organic layer was washed with brine, dried over anhydrous sodium sulfate and concentrated under reduced pressure to yield crude product. To a solution of above crude product (33 mg, 0.04 mmol) in methanol (5 ml), sodium methoxide solution (0.09 g, 0.4 mmol, 25% in methanol) was added. The reaction mixture was stirred at room temperature for 15 min. Then saturated ammonia chloride aqueous solution was added and the solvent was evaporated under reduced pressure. The crude product was purified by silica gel column chromatography (dichloromethane/methanol=10/1) for afford compound 14 as a blue solid. $^1$H NMR (300 MHz, CD$_3$OD): δ 1.49 (m, 4H), 1.51 (m, 2H), 1.81 (s, 6H), 1.99 (m, 4H), 2.71 (m, 4H), 3.62-3.74 (m, 5H), 3.92 (t, 2H), 4.35 (t, 2H), 5.19 (d, J=9 Hz, 2H), 6.56 (d, J=15 Hz, 1H), 7.01 (d, J=3 Hz, 1H), 7.12 (s, 1H), 7.36 (s, 1H), 7.46-7.55 (m, 3H), 7.66 (d, J=9 Hz, 1H), 8.76 (d, J=15 Hz, 1H). ESI-MS (m/z): calcd: 698.35, found: 698.30.

Synthesis of Compound 15 (FIG. 5)

Compound 14 (28 mg, 0.04 mmol) and propynyl-HPβCD (200 mg, 0.12 mmol) were dissolved in DMSO/water (3 ml/3 ml), followed by addition of a solution of sodium ascorbate (2.0 mg, 0.01 mmol) and cupric sulfate (2.5 mg, 0.01 mmol) in distilled water. After the reaction mixture was stirred at room temperature under a nitrogen atmosphere in dark for 2 h, it was precipitated in acetone (300 ml). The crude product was filtered and further purified by HPLC to afford compound 15 (60 mg, 85% yield) as a blue solid. $^1$H NMR (300 MHz, D$_2$O): δ 1.13 (m, 18H), 1.33 (m, 4H), 1.71 (m, 12H), 2.05 (m, 8H), 2.71 (s, 2H), 2.92 (m, 8H), 3.25-4.25 (m, 62H), 4.41 (m, 11H), 5.07-5.25 (m, 11H), 6.53 (d, J=15, 1H), 7.14 (d, J=3, 1H), 7.38 (s, 1H), 7.47 (s, 1H), 7.57 (m, 3H), 7.68 (d, J=3, 1H), 8.80 (d, J=15, 1H). MALDI-TOF MS found: 2100-2500 (Figure S1).

Synthesis of Compound 16 (FIG. 5)

Compound 12 (0.47 g, 1.0 mmol), 1-ethyl-3-(3-dimethylaminopropyl) carbodiimide (0.19 g, 1.0 mmol) and 4-dimethylamino-pyridine (0.12 g, 1.0 mmol) were stirred in anhydrous dichloromethane (20 ml) for 1 h. Then 3-azidopropan-1-ol (0.1 g, 1.0 mmol) was added and the reaction mixture was stirred at 25° C. for additional 24 h. Then the reaction mixture was diluted with ethyl acetate (100 ml) and washed with water (50 ml). The organic layer was separated, washed with brine, dried over anhydrous sodium sulfate and evaporated under reduced pressure. The residue was purified by silica gel column chromatography (ethyl acetate/petroleum ether=1/5) to afford compound 6 (0.44 g, 80% yield) as a pale-yellow solid. TLC (silica gel, ethyl acetate/petroleum ether=1/5), Rt=0.45. $^1$H NMR (300 MHz, CD$_3$OD): δ 1.81-1.94 (m, 12H), 2.15 (m, 2H), 2.68 (s, 1H), 3.21 (s, 1H), 3.31 (s, 3H), 3.55 (t, 2H), 4.12 (t, 2H), 6.57 (d, J=15 Hz, 1H), 6.78 (m, 2H), 7.47 (d, J=9 Hz, 1H), 7.96 (d, J=15 Hz, 1H). ESI-MS (m/z): calcd: 555.17, found: 555.26.

Preparation of stock solutions. MRPs, ADR and the uncaged fluorophores (CMe, CP2, CP5 and CCD) were dissolved in PBS buffer (10 mM, pH 7.4) to obtain stock solutions after filtration by using syringe filter (0.22 μm). 10% DMSO/PBS buffer are co-solvents for CMe. H$_2$O$_2$, HOCl, and O$_2$*$^-$ stock solutions were prepared by directly diluting commercially available H$_2$O$_2$, NaOCl, and KO$_2$, respectively. .OH was generated by Fenton reaction between H$_2$O$_2$ and Fe(ClO$_4$)$_2$. $^1$O$_2$ was produced by addition NaOCl to H$_2$O$_2$. ONOO$^-$ was generated from 3-morpholinosydnonimine hydrochloride. Stock solutions of histidine, glutathione, N-acetylcysteine, ascorbic acid, hydroquinone, caspase-3, fruin, nitroreductase, β-galactosidase, fibroblast activation protein-alpha, alanine aminopeptidase, N-acetyl-β-D-glucosaminidase, NaCl, KCl, MgSO$_4$, CaCl$_2$), FeSO$_4$ were prepared with distilled water.

Optical measurement. MRP1, MRP2, MRP3 and MRP$_D$ solutions (30 μM) were incubated with their respective biomarkers (60 μM KO$_2$, 40 mU NAG, 0.5 μg caspase-3 and 60 μM KO$_2$, respectively) in PBS buffer (10 mM, pH 7.4) at 37° C. The ADR solution (30 μM) was incubated with KO$_2$ (60 μM) and NAG (40 mU), respectively, in PBS (10 mM, pH 7.4) at 37° C. UV-Vis and fluorescence spectra of the solutions were measured on UV-Vis and fluorescence spectrophotometer after 60 min incubation (for MRP1, MRP2, MRP3 and MRP$_D$), or 120 min incubation (for ADR). Fluorescence images were acquired using the IVIS spectrum imaging system with excitation at 675±10 nm (640±10 nm for MRP$_D$) and emission at 720±10 nm (760±10 nm for MRP$_D$) and the acquisition time of 0.1 s. Chemiluminescence images were acquired under bioluminescence mode with open filter and the acquisition time of 1 s. The sensing capability of MRPs was analysed through HPLC. UV-Vis and fluorescence spectra of the uncaged fluorophores solution (30 μM) in PBS (10 mM, pH 7.4) were recorded on UV-Vis and fluorescence spectrophotometers.

In vitro selectivity studies. In initial studies, the compounds (CMe, CP2, CP5 and CCD) were dissolved in PBS buffer (10 mM, pH 7.4) to obtain stock solutions. The solutions were recorded on UV-Vis and fluorescence spectrofluorometer. MRP1 was incubated with $KO_2$ at 37° C. in PBS buffer (10 mM, pH 7.4). For selectivity study, the hydroxyl radical (—OH) was produced by treatment of $H_2O_2$ with $Fe^{2+}$; singlet oxygen ($^1O_2$) was obtained by addition of NaOCl to $H_2O_2$;

peroxynitrite was generated by using 3-morpholinosydnonimine hydrochloride; solutions of NaOCl (1.0 mM), $H_2O_2$ (1.0 mM), histidine (1.0 mM), GSH (1.0 mM), NAC (1.0 mM), NAC (1.0 mM), AA (1.0 mM), HQ (1.0 mM), NaCl (1.0 mM), KCl (1.0 mM), $MgSO_4$ (1.0 mM), $CaCl_2$ (1.0 mM), $FeSO_4$ (1.0 mM), were prepared with $H_2O$, and $KO_2$ were used as a solution (1.0 mM) in DMSO. MRP1 were treated with above analytes at 37° C. for 30 min.

MRP2 was incubated with NAG at 37° C. in PBS buffer (10 mM, pH 7.4). For selectivity study, MRP2 were treated with caspase-3 ($5.0 \times 10^{-1}$ U mL$^{-1}$) in HEPES buffer (50 mM, 50 mM NaCl, 0.1% Chaps, 10 mM EDTA, 5% Glycerol, 1 mM DTT, pH 7.4), furin (25 mM Tris, 1 mM $CaCl_2$), 0.5% (w/v) Brij-35, pH 9.0), nitroreductase (10 mM Tris-HCl, 1 mM NADH, 1 mM $K_2CrO_4$, pH 7.0), plasmin (100 mM Lysine Buffer, pH 7.5), β-Galactosidase (acetate buffer, pH 4.5), FAPα ($9.0 \times 10^{-4}$ U mL$^{-1}$) in HEPES buffer (50 mM, 1 mg mL$^{-1}$ BSA, 5% glycerol, pH=7.4), $KO_2$ (1.0 mM), NaOCl (1.0 mM), $H_2O_2$ (1.0 mM), NaCl (1.0 mM), KCl (1.0 mM), $MgSO_4$ (1.0 mM), $CaCl_2$ (1.0 mM), $FeSO_4$ (1.0 mM) and NAG ($4.0 \times 10^5$ U mL$^{-1}$) at 37° C. for 30 min. After incubation, the solutions were recorded on fluorescence spectrofluorometer.

MRP3 was incubated with Caspase 3 in PBS buffer (0.1% (w/v) CHAPS, 10 mM dithiothreitol (DTT), pH 7.5). For selectivity study, MRP3 were treated with alanine aminopeptidase ($1.0 \times 10^{-3}$ U mL$^{-1}$) in HEPES buffer (pH 7.4), furin (25 mM Tris, 1 mM $CaCl_2$), 0.5% (w/v) Brij-35, pH 9.0), nitroreductase (10 mM Tris-HCl, 1 mM NADH, 1 mM $K_2CrO_4$, pH 7.0), plasmin (100 mM Lysine Buffer, pH 7.5), β-Galactosidase (acetate buffer, pH 4.5), FAPα ($9.0 \times 10^{-4}$ U mL$^{-1}$) in HEPES buffer (50 mM, 1 mg mL$^{-1}$ BSA, 5% glycerol, pH=7.4), $KO_2$ (1.0 mM), NaOCl (1.0 mM), $H_2O_2$ (1.0 mM), NaCl (1.0 mM), KCl (1.0 mM), $MgSO_4$ (1.0 mM), $CaCl_2$ (1.0 mM), $FeSO_4$ (1.0 mM) and caspase-3 ($5.0 \times 10^{-1}$ U mL$^{-1}$) in HEPES buffer (50 mM, 50 mM NaCl, 0.1% Chaps, 10 mM EDTA, 5% Glycerol, 1 mM DTT, pH 7.4) at 37° C. for 30 min. After incubation, the solutions were recorded on fluorescence spectrofluorometer.

In subsequent studies, MRP1 and MRP$_D$ (30 μM) were treated with indicated ROS (150 μM) and other analytes (150 μM) in PBS buffer (10 mM, pH 7.4) at 37° C. for 60 min. MRP2 and MRP3 (30 μM) were incubated with indicated ROS (150 μM), metal ions (150 μM), and enzymes including caspase-3 (0.5 μg) in PBS buffer (10 mM, 50 mM NaCl, 0.1% Chaps, 10 mM EDTA, 5% Glycerol, 1 mM DTT, pH 7.4), alanine aminopeptidase (1.0 U) in HEPES buffer (10 mM, pH 7.4), furin (40 mU) in Tris buffer (25 mM, 1 mM $CaCl_2$), 0.5% (w/v) Brij-35, pH 9.0), nitroreductase (1.0 U) in Tris buffer (10 mM, 1 mM NADH, 1 mM $K_2CrO_4$, pH 7.0), plasmin (1.0 U) in lysine Buffer (100 mM, pH 7.5), β-Galactosidase (1.0 U) in acetate buffer (10 mM, pH 4.5), fibroblast activation protein-alpha (0.9 U) in HEPES buffer (50 mM, 1 mg mL$^{-1}$ BSA, 5% glycerol, pH 7.4), or NAG (40 mU) in PBS (10 mM, pH 7.4) at 37° C. for 60 min.

The ADR solution (30 μM) were incubated with indicated ROS (150 μM), metal ions (150 μM), and enzymes including furin (40 mU) in Tris buffer (25 mM, 1 mM $CaCl_2$), 0.5% (w/v) Brij-35, pH 9.0), plasmin (1.0 U) in lysine buffer (100 mM, pH 7.5), 6-galactosidase (1.0 U) in acetate buffer (10 mM, pH 4.5), fibroblast activation protein-alpha (0.9 U) in HEPES buffer (50 mM, 1 mg mL$^{-1}$ BSA, 5% glycerol, pH 7.4), or NAG (40 mU) in PBS (10 mM, pH 7.4) at 37° C. for 120 min.

Fluorescence or chemiluminescence enhancement of MRPs was measured on fluorescence spectrophotometer or spectramax after incubation. Unit definition: 1 U of enzyme will hydrolyse 1 μmol of the corresponding substrate per minute at optimized condition. PBS used for these experiments was purged with nitrogen gas for 35 min before the measurement.

Measurement of the limit of detection (LOD). Fluorescence intensities (720 nm) of MRP1 (30 μM) and chemiluminescence intensities (540 nm) of MRP$_D$ (30 μM) were measured upon addition of aliquots of micromolar concentration of $KO_2$. Chemiluminescence intensities (520 nm) of ADR (30 μM) were determined after addition of different concentrations of $KO_2$. The LOD was calculated using the equation (R. C. Benson, H. A. Kues, *J. Chem. Eng. Data* 1977, 22, 379-383): LOD=3σ/k, where σ is the standard deviation of blank, and k is the slope of the plot of emission intensities against the concentration of $KO_2$.

Enzyme kinetic assay. Various concentrations of MRP2 (5, 10, 15, 20, 25, 30, 35, 40, 45, 50 or 55 μM) or MRP3 (5, 10, 15, 20, 30, 40, 50 or 60 μM) were incubated with NAG (40 mU) or caspase-3 (0.5 μg) at 37° C. for 5-15 min in PBS buffer (10 mM, pH 7.4). Various concentrations of ADR (5, 10, 15, 30, 60, 90 or 120 μM) were incubated with NAG (40 mU) at 37° C. for 15 min in PBS buffer (10 mM, pH 7.4). After incubation, the mixtures were analysed using HPLC for quantification. The initial reaction velocity (nM s$^{-1}$) was calculated, plotted against the concentration of MRP2 or MRP3 or ADR, and fitted to a Michaelis-Menten curve. The kinetic parameters were calculated by use of the Michaelis-Menten equation (K. Gu, et al., *J. Am. Chem. Soc.* 2016, 138, 5334-5340): $V = V_{max} \cdot [S]/(K_m + [S])$, where V is the initial velocity, and [S] is substrate concentration.

Measurement of fluorescence quantum yields. ICG was used as a standard with a known fluorescence quantum yield (φ) value of 13% in DMSO (R. C. Benson, H. A. Kues, *J. Chem. Eng. Data* 1977, 22, 379-383). Fluorescence quantum yields were calculated using the following equation: $\phi_s/\phi_f = (A_s/A_f) \times (Abs_s/Abs_f) \times (\eta_s^2/\eta_f^2)$, Where $\phi_s$ and $\phi_f$ are the fluorescence quantum yields of the standard and the samples, respectively; $A_s$ and $A_f$ are the emission areas of the standard and the samples, respectively; $Abs_s$ and $Abs_f$ are the absorbance of the standard and the samples at the wavelength of excitation; $\eta_s$ and $\eta_f$ are the refractive indices of the standard and the samples, respectively.

Determination of chemiluminescence kinetic profiles. MRP$_D$ or ADR solution (30 μM) in PBS (10 mM, pH 7.4) was placed in a black 96-well plate. Chemiluminescence intensities were continuously acquired after addition of excess $KO_2$ (60 μM) using spectramax. The chemiluminescence intensities were plotted as a function of time.

Tissue-penetration studies. MRP$_D$ solution (30 μM) in PBS (10 mM, pH 7.4) was placed in a black 96-well plate. Chicken tissues with the desired thickness were overlaid on top of the wells. Chemiluminescence images were acquired after addition of $KO_2$ (60 μM) using the IVIS spectrum imaging system under bioluminescence mode with open filter and the acquisition time of 180 s. Fluorescence images were acquired with excitation at 640±10 nm and emission at 760±10 nm and the acquisition time of 0.1 s. The signal to background ratio (SBR) was calculated as SBR=fluorescence intensities (or chemiluminescence intensities)/background, where background is the signal intensity of neighboring tissues obtained over the imaging period[49]. The SBRs were plotted as a function of tissue depth.

In Vivo Biodistribution and Imaging Studies of MRPs

All animal studies were performed in compliance with the guidelines set by the Institutional Animal Care and Use Committee (IACUC), Sing Health. Female nude mice (Tac:Cr:(NCr)-Fox1nu, 8 weeks old) were obtained from InVivos Pte Ltd (Singapore). Aged female nude mice (25 weeks old) were obtained by feeding after receive at 8 weeks old. Female Balb/c mice (10 weeks old), male type 2 diabetic BKS-db mice (BKS-Lepr$^{em2Cd479}$ with a C57BLKS/J background, 12 weeks old) and male nondiabetic C57BLKS/J wild-type mice (12 weeks) were obtained from Nanjing Biomedical Research Institute of Nanjing University (Nanjing, China). NCr nude mice were i.v. injected with 0.2 ml saline (control), the uncaged fluorophores (CMe, CP2, CP5 and CCD, 8 μmol kg$^{-1}$ body weight) or MRP$_D$ (32 μmol kg$^{-1}$ body weight), and imaged using the IVIS spectrum imaging system at 30 and 60 min post-injection. The abdominal cavity and resected organs from mice were imaged after sacrifice at t=60 min post-injection. Fluorescence images were acquired using the IVIS spectrum imaging system with excitation at 675±10 nm (640±10 nm for MRP$_D$) and emission at 720±10 nm (760±10 nm for MRP$_D$). Fluorescence intensities for each organ were analysed by the region of interest (ROI) analysis using the Living Image 4.3 Software (3 mice were analysed for each sample).

Pharmacokinetic Studies

NCr nude mice were anesthetized by i.p. injection of ketamine/xylazine (50 mg kg$^{-1}$ body weight ketamine and 5 mg kg$^{-1}$ body weight xylazine) for the entire duration of the experiment. The end of the tail was cut for blood extraction. Blood was sampled in heparinised capillary tubes as a reference before injection. Mice were i.v. injected with the uncaged fluorophores (CP2, CP5 and CCD, 8 μmol kg$^{-1}$ body weight), MRPs1-3 (8 μmol kg$^{-1}$ body weight) or MRP$_D$ (32 μmol kg$^{-1}$ body weight) and blood was sampled at 1, 4, 9, 16, 25, 35, 55 and 75 min post-injection. For pharmacokinetic studies of MRPs1-3 and MRP$_D$ in cisplatin-treated mice, blood was sampled from living mice after 1, 4, 9, 16, 25, 35, 55, 75, 95 and 120 min injection of MRPs1-3 (8 μmol kg$^{-1}$ body weight) or MRP$_D$ (32 μmol kg$^{-1}$ body weight) at different timepoints post-treatment of cisplatin (8, 12, 16, 48 or 72 h). Collected blood samples were stored in an ice box to prevent clotting before centrifugation at 3500 r.p.m for 20 min. The uncaged fluorophores and MRPs were quantified using HPLC. Quantification results were presented as a bi-exponential decay curve to estimate elimination (t$_{1/2\beta}$) blood half-life values (3 mice were analysed for each sample).

Renal Clearance Efficiency Studies

NCr nude mice were i.v. injected with the uncaged fluorophores (CMe, CP2, CP5 and CCD, 8 μmol kg$^{-1}$ body weight), MRPs1-3 (8 μmol kg$^{-1}$ body weight) or MRP$_D$ (32 μmol kg$^{-1}$ body weight) and placed in metabolic cages (3 mice were analysed for each sample). For renal clearance efficiency studies of MRPs1-3 in cisplatin-treated mice, mice were i.v. injected with MRPs1-3 (8 μmol kg$^{-1}$ body weight) at t=8, 12, 16, 48 or 72 h post-treatment of cisplatin (20 mg kg$^{-1}$ body weight) and placed in metabolic cages (3 mice were analysed for each sample). Urine was collected at 1, 3, 6, 9 and 24 h post-injection, centrifuged at 4500 r.p.m. for 8 min and filtered by 0.22 μm syringe filter. Excretion of the uncaged fluorophores and MRPs in the urine was quantified using HPLC. Mice were sacrificed to image resected organs after 24 h urine collection. Fluorescence intensities for resected organs were analysed by the ROI analysis using the Living Image 4.3 Software. Major organs were collected, homogenised in PBS buffer (10 mM, pH 7.4) and centrifuged at 4500 r.p.m for 15 min to remove insoluble components. Fluorescence intensities of the final supernatants were measured on fluorescence spectrophotometer.

In Vivo Stability and Biocompatibility Studies

The collected urine in PBS buffer (10 mM, pH 7.4) were measured on UV-Vis and fluorescence spectrophotometer, imaged by the IVIS spectrum imaging system and analysed by HPLC as well as MALDI-TOF mass spectrometry. Heart, liver, spleen, lung and kidneys were collected from NCr nude mice after 24 h injection of CCD, MRPs1-3 (8 μmol kg$^{-1}$ body weight) or MRP$_D$ (32 μmol kg$^{-1}$ body weight) and placed into 4% paraformaldehyde for histological examination.

Establishment of Drug-Induced AKI Models in Living Mice

Mice were randomly selected and treated with cisplatin (5 mg kg$^{-1}$, 10 mg kg$^{-1}$ or 20 mg kg$^{-1}$ body weight, i.p. injection), gentamicin (100 mg kg$^{-1}$ day$^{-1}$, i.p. injection) or diatrizoate (1000 mg kg$^{-1}$ body weight, i.v injection, water deprivation for 24 h before treatment). The control groups were treated with saline (0.2 ml) or NAC (400 mg kg$^{-1}$ body weight, i.v injection) 30 min prior to cisplatin administration[50]. Body weights of all the mice were recorded during treatment. After drug administration, the weight of mice and signs of discomfort were monitored on a daily basis during the entire experiments (FIG. 46). Imaging, blood and urine sampling were conducted at different timepoints post-treatment of drug. At the end, mice were euthanized and major organs were placed into 4% paraformaldehyde for histological examination.

Real-Time In Vivo NIRF and Chemiluminescence Imaging of Drug-Induced AKI in Living Mice Real-time NIRF imaging was conducted every 30 min for 2.5 h after i.v injection of MRPs1-3 (8 μmol kg$^{-1}$ body weight) at t=8, 12, 16, 24, 48 or 60 h post-treatment of cisplatin, or i.v. injection of MRPs1-2 (8 μmol kg$^{-1}$ body weight) at t=24, 36, 48 or 72 h post-treatment of gentamicin, or i.v. injection of MRPs1-2 (8 μmol kg$^{-1}$ body weight) at t=2, 8, 16 or 48 h post-treatment of diatrizoate. Real-time dual-channel imaging was conducted every 30 min for 2 h after i.v injection of MRP$_D$ (32 μmol kg$^{-1}$ body weight) at t=8, 12, 48 or 72 h post-treatment of cisplatin, or at t=24, 36, 96 or 144 h post-treatment of gentamicin, or at t=2, 8, 16 or 48 h post-treatment of diatrizoate. The control groups were treated with saline (0.2 ml), and the negative control was treated NAC (400 mg kg$^{-1}$ body weight, i.v injection) 30 min prior to cisplatin administration. Fluorescence images were acquired using the IVIS spectrum imaging system with excitation at 675±10 nm (640±10 nm for MRP$_D$) and emission at 720±10 nm (760±10 nm for MRP$_D$) and the acquisition time of 0.1 s. Chemiluminescence images were acquired under bioluminescence mode with open filter and the acquisition time of 180 s. NIRF and chemiluminescence intensities of kidneys in living mice were analysed by the ROI analysis using the Living Image 4.3 Software (3 mice were analysed for each sample). Mice were euthanized after i.v injection of MRPs1-3 or MRP$_D$ at different timepoints post-treatment of saline or drugs. The abdominal cavity and resected organs from mice were imaged after sacrifice and NIRF intensities were analysed by the ROI analysis using the Living Image 4.3 Software. Major organs were placed into 4% paraformaldehyde for histological examination.

For the doxorubicin model, dose-finding studies were first carried out to define an optimal dose of 10 mg kg$^{-1}$ body weight of doxorubicin. Female BALB/c mice (8 weeks-old) were administered DOX (dissolved in 0.9% saline) intravenously by tail vein injection, while control mice received saline. All mice were weighed once daily. The corresponding MRP (40 mg kg$^{-1}$) was systematically injected through the tail vein at t=0, 2 d, 5 d, and 8 d post-treatment of DOX, and fluorescence images were acquired. Urine was collected using metabolic cages after intravenous injection of probes into mice. Fluorescence images of living mice and urine samples were acquired for 0.1 s with excitation at 675±20 nm, and emission at 720±20 nm. Fluorescence images were analysed by ROI analysis using the Living Image 4.0 Software.

Determination of GFR in Drug-Treated Living Mice

FITC-inulin (150 mg) was dissolved in 0.9% NaCl (3 ml) at 75° C. and dialysed in 0.9% NaCl (1000 ml) at room temperature for 24 h. Dialysed FITC-inulin (3.74 µl g$^{-1}$ body weight) was injected intravenously in living NCr nude mice at t=8, 12, 16, 24, or 48 h post-treatment of cisplatin (20 mg kg$^{-1}$ body weight), or at t=24, 36, 48, 96, or 144 h post-treatment of gentamicin (100 mg kg$^{-1}$ day$^{-1}$ body weight), or at t=2, 8, 16, 24, or 48 h post-treatment of diatrizoate (1000 mg kg$^{-1}$ body weight), or saline (0.2 ml) treated mice. Blood (approximately 20 µl) was collected via saphenous vein at 3, 7, 10, 15, 35, 55, and 75 min post-injection of FITC-inulin, and then centrifuged for 20 min at 3500 r.p.m. Serum sample (10 µl) was diluted with HEPES buffer (40 µl, 500 mM, pH 7.4) and fluorescence was measured using spectramax with excitation at 485 nm and emission at 538 nm. Serum fluorescence data were presented as a two-component exponential decay curve using nonlinear regression (3 mice were analysed for each sample). GFR was calculated according to the equation (Z. Qi, et al., *Am. J. Physiol. Renal. Physiol.* 2004, 286, F590-596): GFR=1/(A/α+B/β), where I is the amount of FITC-inulin delivered by the bolus injection, A and B are the y-intercept values of the two decay rates, and α and β are the decay constants for the distribution and elimination phases, respectively.

Online Urinalysis

Urine was collected from living mice after i.v. injection of MRPs1-3 (8 µmol kg$^{-1}$ body weight) at t=8, 12, 16, 24, 48 or 60 h post-treatment of cisplatin (10 mg kg$^{-1}$ or 20 mg kg$^{-1}$ body weight), or at t=24, 36, 48, 72, or 144 h post-treatment of gentamicin (100 mg kg$^{-1}$ day$^{-1}$ body weight), or at t=2, 8, 16, 24, or 48 h post-treatment of diatrizoate (1000 mg kg$^{-1}$ body weight), or saline (0.2 ml) treated mice. The collected urine samples were centrifuged at 4500 r.p.m. for 8 min, filtered by 0.22 µm syringe filter, and measured on fluorescence spectrophotometer (9 mice were analysed for each sample). Fluorescence images were acquired using the IVIS spectrum imaging system with excitation at 675±10 nm and emission at 720±10 nm. Activated MRPs were analysed by HPLC.

Offline Urinalysis

Urine was collected using metabolic cages from drug-treated mice at different timepoints post-treatment of drug. The collected urine samples were centrifuged at 4500 r.p.m. for 8 min and filtered by 0.22 µm syringe filter. MRPs1-3 solutions (30 µM) in PBS buffer (10 mM, pH 7.4) were incubated with the urine (100 µl) at 37° C., followed by fluorescence measurements on fluorescence spectrophotometer after 2 h incubation (9 mice were analysed for each sample). Urinary TFF3, osteopontin, NGAL, β2-Microglobulin, KIM-1, clusterin levels were quantified using ELISA kits according to the manufacturer's protocol (6 mice were analysed for each sample).

Blood Analysis

Blood was collected from the tail vein in living NCr nude mice under isoflurane anesthesia at t=8, 12, 16, 24, or 48 h post-treatment of cisplatin (20 mg kg$^{-1}$ body weight), or at t=24, 48, 72, 96, or 144 h post-treatment of gentamicin (100 mg kg$^{-1}$ day$^{-1}$ body weight), or at t=2, 8, 16, 24, or 48 h post-treatment of diatrizoate (1000 mg kg$^{-1}$ body weight), or saline (0.2 ml) treated mice. The collected blood samples were centrifuged for 20 min at 3500 r.p.m. Serum creatinine, BUN and cystatin C were determined using commercial kits according to the manufacturer's protocol (5 mice were analysed for each sample).

Specificity Studies in Living Mice with Local Skin Inflammation

NCr nude mice were intradermally injected with saline (15 µl) or LPS (5 µg in 15 µl PBS) on the left thigh[52], followed by i.v injection of MRP2 (8 µmol kg$^{-1}$ body weight) at 4 h post-treatment of saline or LPS. Real-time NIRF imaging of living mice was conducted using the IVIS spectrum imaging system. Urine was collected from a separate set of saline or LPS-treated mice at 4 h post-treatment. The collected urine samples were centrifuged at 4500 r.p.m. for 8 min and filtered by 0.22 µm syringe filter. MRP2 solutions (30 µM) in PBS buffer (10 mM, pH 7.4) were incubated with the urine (100 µl) at 37° C., followed by fluorescence measurement after 2 h incubation (3 mice were analysed for each sample). Sections of skin from the injection sites were resected after euthanasia for immunofluorescence staining. Note that such a low dosage of LPS does not induce organ injury (W. Wang, et al., *Am. J. Physiol. Renal. Physiol.* 2007, 293, F1131-1136).

Specificity Studies in Living Mice with ANIT-Induced Liver Injury

NCr nude mice were fasted overnight and intragastrically injected with olive oil (0.2 ml, control group) or ANIT (dissolved in olive oil, 75 mg kg$^{-1}$ body weight) (F. Dieterle, et al., *Nat. Biotechnol.* 2010, 28, 463-469), followed by i.v injection of MRPs1-3 (8 µmol kg$^{-1}$ body weight) at 24 h or 48 h post-treatment of olive oil or ANIT. Real-time NIRF imaging of living mice was conducted using the IVIS spectrum imaging system. For online urinalysis, urine was collected from control or ANIT-treated living mice after i.v injection of MRPs1-3 (8 µmol kg$^{-1}$ body weight) at 48 h post-treatment of ANIT. For offline urinalysis, urine was collected from a separate set of control or ANIT-treated mice at 48 h post-treatment. The collected urine samples were centrifuged at 4500 r.p.m. for 8 min and filtered by 0.22 µm syringe filter. MRPs1-3 solutions (30 µM) in PBS buffer (10 mM, pH 7.4) were incubated with the urine (100 µl) at 37° C., followed by fluorescence measurement after 2 h incubation (3 mice were analysed for each sample). Liver and kidneys were resected after euthanasia at 24 h or 48 h post-treatment of olive oil or ANIT for H&E and immunofluorescence staining. Note that ANIT does not induce kidney injury.

In Vivo Biodistribution and Imaging Studies of ADR

All mouse experimental procedures were approved by the Institutional Animal Care and Use Committee (IACUC), Nanyang Technological University (NTU). Female nude mice (Tac:Cr:(NCr)-Fox1nu, 4-6 weeks old) were obtained from InVivos Pte Ltd (Singapore).

Pharmacokinetic Studies

Mice were anesthetized by i.p. injection of ketamine/xylazine (50 mg kg$^{-1}$ body weight ketamine and 5 mg kg$^{-1}$ body weight xylazine) for the entire duration of the experiment. The end of the tail was cut for blood extraction. Blood was sampled in heparinised capillary tubes as a reference before injection. Mice were i.v. injected with ADR (30 µmol kg$^{-1}$ body weight) and blood was sampled at 1, 4, 9, 16, 25, 35, 55, 75, 95- and 115-min post-injection. Collected blood samples were stored in an ice box to prevent clotting before centrifugation at 4500 r.p.m for 15 min. ADR in the blood was quantified using HPLC and plotted as a function of time to calculate elimination half-life value ($t_{1/2\beta}$).

Renal Clearance Studies

Mice were i.v. injected with ADR (30 µmol kg$^{-1}$ body weight) and placed in metabolic cages. Urine was collected at 1, 3, 6, 9 and 24 h post-injection, diluted in PBS and centrifuged at 4500 r.p.m. for 10 min and filtered by 0.22 µm syringe filter. ADR in the urine was quantified using HPLC. The absorption and fluorescence spectra were measured for the urine samples. Mice were sacrificed and major organs were collected, homogenised in PBS buffer (10 mM, pH 7.4) and centrifuged at 4500 r.p.m for 15 min to remove insoluble components. The supernatant containing extracted molecules were taken for HPLC analysis.

Biocompatibility Studies

Major organs including heart, liver, spleen, lung and kidneys were collected from mice after 24 h injection of ADR and placed into 4% paraformaldehyde for histological examination.

Establishment of CIAKI Models in Living Mice Mice were randomly selected and treated with diatrizoate (DTZ, 1 g kg$^{-1}$ body weight, i.v injection, water deprivation for 24 h before treatment) (C. M. Erley, et al., *J. Am. Soc. Nephrol.* 1997, 8, 1125-1132). The control groups were treated with PBS (0.2 ml) or NAC (10 mg kg$^{-1}$ day$^{-1}$ during the study, i.p. injection) 3 days prior to DTZ administration (M. Colbay, et al., *Exp. Toxicol. Pathol.* 2010, 62, 81-89).

Real-Time In Vivo NIRF and Chemiluminescence Imaging of CIAKI in Living Mice

Real-time NIRF and chemiluminescence imaging were conducted every 30 min for 2.5 h after i.v injection of ADR (30 µmol kg$^{-1}$ body weight) at t=2, 8, 16 or 24 h post-treatment of DTZ (0.25, 1 or 2 g kg$^{-1}$ body weight). Fluorescence images were acquired using the IVIS spectrum imaging system with the excitation at 675±10 nm, the emission at 720±10 nm and the acquisition time of 0.1 s. Chemiluminescence images were acquired under bioluminescence mode with open filter and the acquisition time of 180 s. NIRF and chemiluminescence intensities of kidneys in living mice were analysed by the ROI analysis using the Living Image 4.3 Software. Mice were euthanized after imaging at different timepoints post-treatment of DTZ. Major organs were collected and placed into 4% paraformaldehyde for histological examination. Urine was collected from living mice after i.v. injection of ADR (30 µmol kg$^{-1}$ body weight) at 16 h post-treatment of DTZ (1 g kg$^{-1}$ body weight). The absorption and fluorescence spectra were measured.

Determination of GFR in Living Mice

FITC-inulin (150 mg) was dissolved in 0.9% NaCl (3 ml), heated at 75° C. and dialysed in 0.9% NaCl (1000 ml) at room temperature for 24 h. Dialysed FITC-inulin (3.74 µl g$^{-1}$ body weight) was i.v. injected into living mice at =2, 8, 16, 24, or 48 h post-treatment of diatrizoate (1 g kg$^{-1}$ body weight), or PBS (0.2 ml) treated mice, or NAC/DTZ co-treated mice. Blood (approximately 20 µl) was collected via tail vein at 3, 7, 10, 15, 35, 55, and 75 min post-injection of FITC-inulin, and then centrifuged for 15 min at 4500 r.p.m. Serum sample (10 µl) was diluted with PBS buffer (40 µl, 10 mM, pH 7.4) and fluorescence was measured using spectramax with excitation at 485 nm and emission at 538 nm. Serum fluorescence data were presented as a two-component exponential decay curve using nonlinear regression (3 mice were analysed for each sample). GFR was calculated according to the equation: $GFR=1/(A/\alpha+B/\beta)$, where 1 is the amount of FITC-inulin delivered by the bolus injection, A and B are the y-intercept values of the two decay rates, and $\alpha$ and $\beta$ are the decay constants for the distribution and elimination phases, respectively.

Serum Creatinine and BUN Assay

Blood was collected from the tail vein in living mice under isoflurane anesthesia at t=2, 8, 16, 24 or 48 h post-treatment of diatrizoate (1 g kg$^{-1}$ body weight), or PBS treated mice, or NAC/DTZ co-treated mice. The collected blood samples were centrifuged for 15 min at 4500 r.p.m. Serum creatinine and BUN were determined using commercial kits according to the manufacturer's protocol (3 mice were analysed for each sample).

Histology. All tissues were fixed with 4% paraformaldehyde, dehydrated in a series of ethanol solution, embedded in paraffin and cut into sections with a thickness of 10 µm for H&E staining.

The sections were washed with xylene and ethanol and then immersed in hematoxylin working solution for 4 min and eosin working solution for 2 min, followed by washing with distilled water. The stained sections were examined using a Nikon ECLIPSE 80i microscope. For immunofluorescence staining, heart, liver, spleen, lung, skin and kidney tissues were fixed with 4% paraformaldehyde, dehydrated using 30% sucrose solution, embedded in frozen optimal cutting temperature (O.C.T.) medium, and then cut into sections with a thickness of 10 µm or 15 µm (40 µm for the whole kidney sections). The sections were dried at room temperature for 60 min, washed three times using PBS containing 0.1% Triton X-100, and incubation with 3% BSA solution at room temperature for additional 60 min, followed by washing with PBS. The sections were then incubated with respective antibody (cleaved-caspase-3 antibody, anti-CD31 antibody, or anti-CD11b antibody) for 60 min at 37° C. After being washed three times with PBS to remove unbound antibody, the sections were counterstained with Alexa Fluor 488 conjugated goat anti-rabbit IgG H&L for 60 min at room temperature. Next, the cell nuclei were stained with DAPI. The stained sections were imaged using a LSM800 confocal laser scanning microscope.

Statistics and reproducibility. The in vivo fluorescence or chemiluminescence signals were quantified with ROI analysis using Living Image 4.3 Software. Data are mean±standard deviation (S.D.) unless stated otherwise. Investigators were blinded to group allocation during experiments. Statistical differences between two groups were tested with a two-tailed Student's t-test and more than three groups were determined by one-way analysis of variance followed by Tukey's post hoc test. For all tests, P values less than 0.05 were considered statistically significant. *P<0.05, P<0.01 and *P<0.001. All statistical calculations were performed using GraphPad Prism 6.0, including assumptions of tests used.

Figure 1:
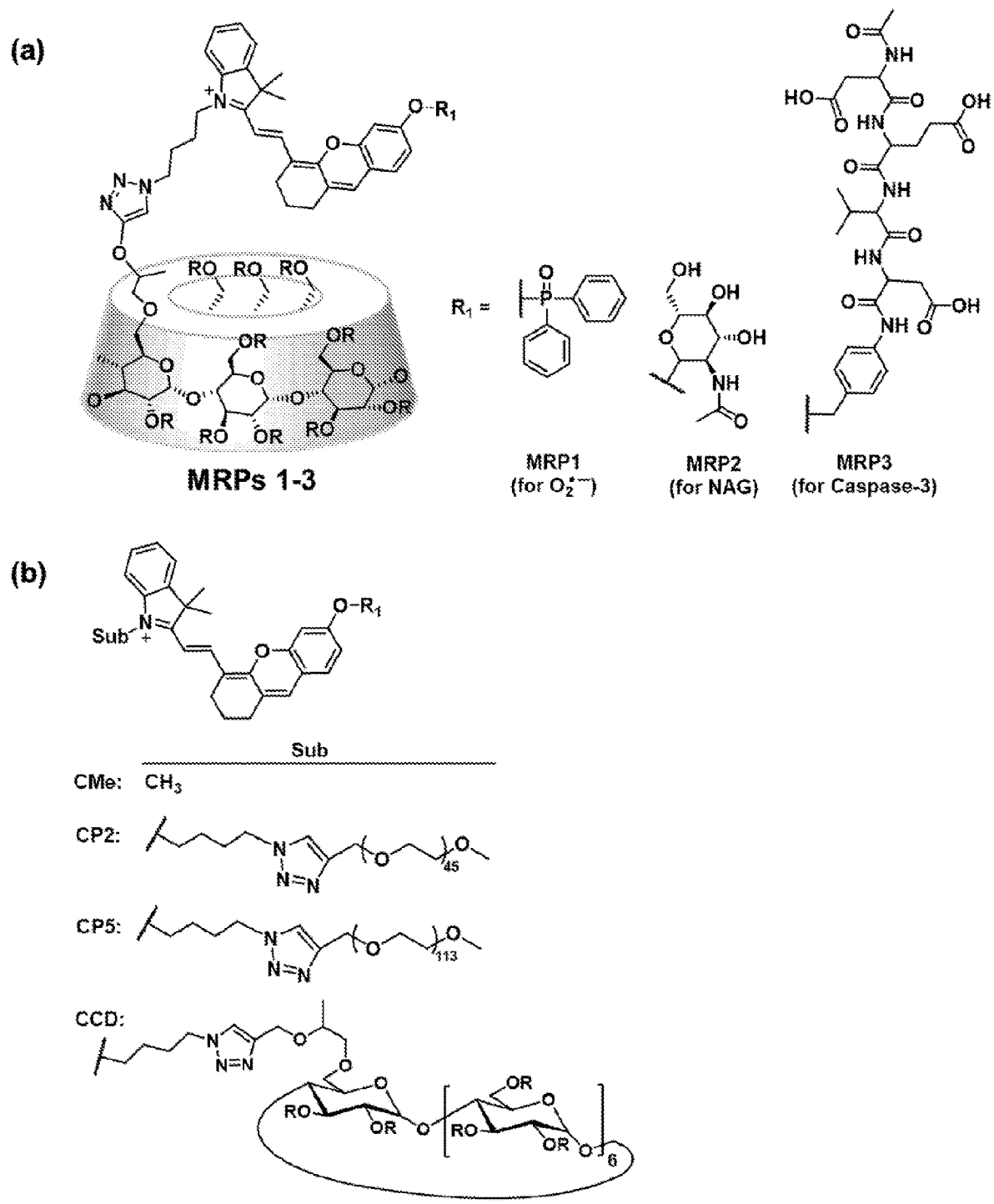
FIG. 1 Depicts the chemical structures of molecular renal probes of the current invention: (a) MRPs1-3; and (b) CMe, CP2, CP5 and CCD, where R=H or $CH_2CHOHCH_3$.
Figure 2:
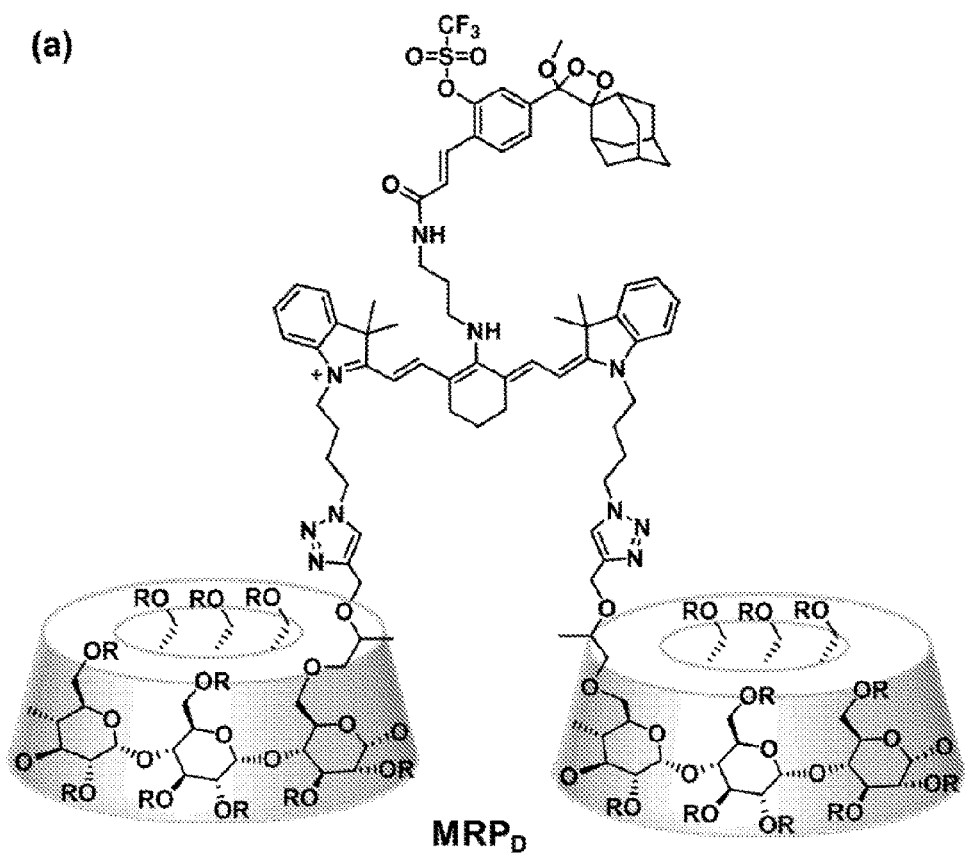
FIG. 2 Depicts the chemical structures of molecular renal probes of the current invention: (a) $MRP_D$, where R=H or $CH_2CHOHCH_3$; and (b) activatable duplex reporter (ADR), where R=H, $CH_2CHOHCH_3$ or $CH_2CCH$).
Figure 2:
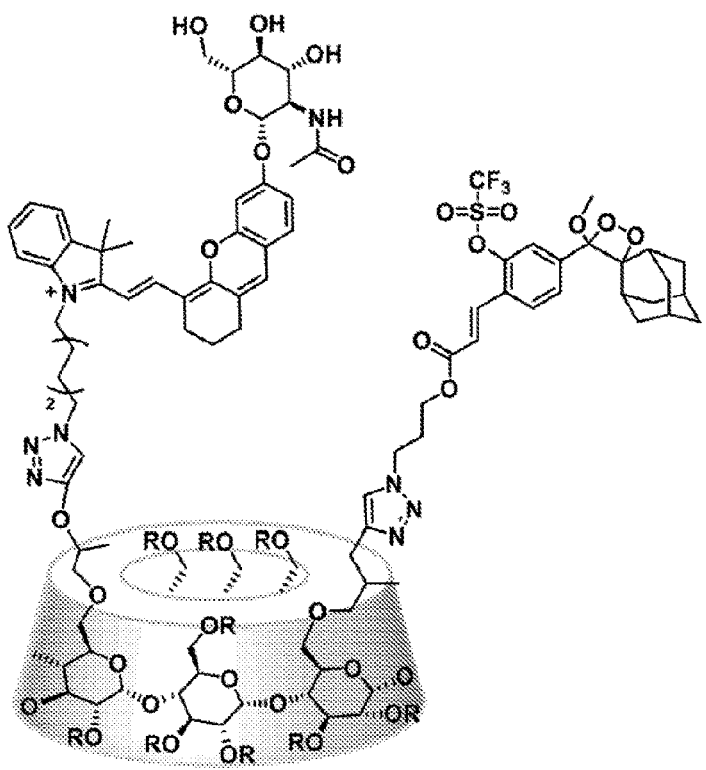

Example 1. Synthesis of Molecular Renal Probes of the Current Invention: MRPs1-3, CP2, CP5, CCD, MRP$_D$ and ADR Optical molecular renal probes (MRPs) of the current invention were synthesised for real-time near-infrared fluorescence (NIRF) imaging of early-stage biomarkers in the murine models of drug-induced AKI (FIGS. 1a and 2a). These probes comprise three key building blocks in general (FIGS. 7 and 8): renal clearance moiety, biomarker reactive moiety, and luminescent signaling moiety. Molecular screening found that (2-hydroxypropyl)-β-cyclodextrin (HPβCD) could dramatically facilitate probe renal clearance with the efficacy above 97%. Superoxide anion ($O_2^{*-}$), NAG, and caspase-3 are selected as the target AKI biomarkers because they are related to oxidative stress, lysosomal damage, and cellular apoptosis, respectively. MRPs1-3 (FIG. 7ai and c) are single-channel probes that turn-on their near-infrared fluorescence (NIRF) in the presence of these three respective biomarkers. $MRP_D$ (FIGS. 7aii and 8) is a dual-channel probe that is always fluorescent but only becomes chemiluminescent after reaction with $O_2^{*-}$. The fluorescent MRPs offer imaging of three interlinked molecular events in the kidneys to identify the earliest predictor for AKI. The $MRP_D$ enables simultaneous monitoring of $O_2^{*-}$ and probe clearance via the chemiluminescent and NIRF signals, respectively, providing the feasibility to directly compare the time between upregulation of $O_2^{*-}$ and changes in glomerular filtration after nephrotoxic exposure in living animals.

For independent detection of more than one biomarkers (also known as multiplex detection), a highly renal-clearable activatable duplex reporter (ADR) for real-time non-invasive chemiluminescence and NIRF imaging of CIAKI in murine model was synthesised (FIG. 2b). As oxidative stress has been recognised as an early hallmark of CIAKI, superoxide anion ($O_2^{*-}$), the primary reactive oxygen species (ROS), is chosen as one of the biomarkers (S. N. Heyman, et al., *Invest. Radiol.* 2010, 45, 188-195; A. Pisani, et al., *Biomed. Res. Int* 2013, 2013, 868321). In addition, upregulation of ROS is known to trigger the pathways towards lysosomal damage and induce the release of the lysosomal enzyme (NAG: N-acetyl-β-D-glucosaminidase) from kidney proximal tubular cells, NAG is chosen as the other biomarker (W. K. Han, et al., *Clin. J. Am. Soc. Nephrol.* 2009, 4, 873-882).

ADR is designed to comprise a $O_2^{*-}$-activatable chemiluminescent signal moiety and a NAG-activatable NIRF moiety, both of which are linked to a renal-clearance scaffold, (2-hydroxypropyl)-β-cyclodextrin (HPβCD) (FIG. 9b). After systemic administration of ADR into living mice, it specifically goes to the kidneys and send back its chemiluminescent and NIRF signals to report $O_2^{*-}$ and NAG levels, respectively. Such an independent duplex sensing capability of ADR avoids signal cross-talk, enabling real-time, non-invasive and simultaneous monitoring of two intercorrelated biomarkers in the kidneys of living mice during the onset and progression of CIAKI.

Experimental
Synthesis of MRP1 (FIG. 3b)

A mixture of CyOH (46.70 mg, 0.1 mmol), diphenylphosphinyl chloride (46.0 μl, 0.24 mmol) and triethylamine (56.0 μl, 0.4 mmol) in dichloromethane (10 ml) was stirred at room temperature. After 15 min, the reaction mixture was concentrated under reduced pressure to afford compound CS as a blue solid, which was used in the next step without further purification. ESI-MS (m/z): calcd: 667.2, found: 667.3.

Compound CS (83 mg, 0.125 mmol) was dissolved in distilled water (1 ml) and stirred at room temperature for 10 min. To above solution, propynyl-HPβCD (0.20 g, 0.125 mmol), sodium ascorbate (4.60 mg, 0.022 mmol) and cupric sulfate (7.50 mg, 0.03 mmol) in DMSO/water (1/1) was added. The mixture was stirred at room temperature under a nitrogen atmosphere in dark for 5 h, and then precipitated in acetone (350 ml). The crude product was filtered and further purified by HPLC to afford MRP1 (0.20 g, 80% yield) as a blue solid. $^1$H NMR (300 MHz, $D_2O$): δ 1.14 (m, 18H), 1.73-2.12 (m, 15H), 2.45 (m, 2H), 2.94 (m, 3H), 3.25-4.25 (m, 83H), 4.28 (m, 2H), 5.07-5.31 (m, 13H), 5.58 (m, 2H), 6.04 (s, 1H), 6.85-8.47 (m, 16H). MALDI-TOF MS found: 1600-2300.

Synthesis of MRP2 (FIG. 3b)

A mixture of compound CyOH (23.40 mg, 0.05 mmol) and cesium carbonate (0.07 g, 0.2 mmol) in anhydrous dichloromethane (3 ml) was stirred at room temperature under a nitrogen atmosphere for 15 min. Compound BrGlcNAc (0.08 g, 0.2 mmol) was added and the reaction mixture was further stirred at room temperature for 16 h. After that, the reaction was poured into distilled water (15 ml) and extracted by dichloromethane (60 ml). The organic layer was washed with brine, dried over anhydrous sodium sulfate and concentrated under reduced pressure to yield crude product. To a solution of above crude product (26.40 mg, 0.033 mmol) in methanol (4 ml), sodium methoxide solution (0.07 g, 0.33 mmol, 25% in methanol) was added. The reaction mixture was stirred at room temperature for 10 min. After that, the solvent was evaporated under reduced pressure. The crude product was purified by silica gel column chromatography (dichloromethane/methanol=8/1) for afford compound CN as a blue solid. $^1$H NMR (300 MHz, $CD_3OD$): δ 1.84 (d, 3H), 1.91 (s, 6H), 2.00 (m, 4H), 2.03 (s, 2H), 2.18 (m, 2H), 2.76 (m, 2H), 3.45 (m, 2H), 3.60-4.10 (m, 6H), 4.41 (s, 2H), 4.61 (d, J=9 Hz, 1H), 5.11 (d, J=3 Hz, 1H), 5.34 (t, 1H), 6.56 (d, J=15 Hz, 1H), 7.03 (d, J=3 Hz, 1H), 7.20 (s, 1H), 7.40-7.60 (m, 5H), 8.79 (d, J=15 Hz, 1H). ESI-MS (m/z): calcd: 670.3, found: 670.3.

Compound CN (23 mg, 0.033 mmol) and propynyl-HPβCD (53 mg, 0.033 mmol) were dissolved in DMSO/water (1/1), followed by addition of a solution of sodium ascorbate (2.0 mg, 0.01 mmol) and cupric sulfate (2.5 mg, 0.01 mmol) in distilled water. After the reaction mixture was stirred at room temperature under a nitrogen atmosphere in dark for 5 h, it was precipitated in acetone (350 ml). The crude product was filtered and further purified by HPLC to afford MRP2 (58 mg, 85% yield) as a blue solid. $^1$H NMR (300 MHz, $D_2O$): δ 1.20 (m, 18H), 1.80-2.13 (m, 15H), 2.70 (m, 3H), 3.00 (m, 3H), 3.25-4.25 (m, 70H), 4.32 (m, 3H), 5.15-5.31 (m, 9H), 5.60-5.75 (m, 2H), 6.57 (d, J=15, 1H), 7.04-7.72 (m, 7H), 8.80 (d, J=15, 1H). MALDI-TOF MS found: 1600-2300.

Synthesis of MRP3 (FIG. 3b)

To a solution of compound CyOH (23.40 mg, 0.05 mmol) in acetonitrile (10 ml) were added compound Br-Ph-DVED (0.13 g, 0.15 mmol) and N,N-diisopropylethylamine (79 μL, 0.62 mmol). After the reaction mixture was stirred for 4 h at 70° C., it was poured into distilled water (15 ml) and extracted by dichloromethane. The organic layer was washed with brine, dried over anhydrous sodium sulfate and concentrated under reduced pressure to yield crude product. Trifluoroacetic acid (1 ml) and dichloromethane (2 ml) were added to the residue, and the reaction mixture was stirred for additional 30 min at room temperature before being concentrated under reduced pressure. The residue was purified by HPLC to give compound CC as a blue solid (49 mg, 91%). $^1$H NMR (300 MHz, $CD_3OD$): δ 1.22 (s, 12H), 1.53 (m, 2H), 1.76 (m, 4H), 1.92 (t, 6H), 2.10 (t, 2H), 2.35 (t, 2H), 2.66 (m, 5H), 3.00 (m, 2H), 3.36 (m, 2H), 3.95 (t, 1H), 4.26 (t, 2H), 4.58 (t, 1H), 5.19 (m, 3H), 6.42 (d, J=15 Hz, 2H), 6.97 (s, 2H), 7.35 (m, 4H), 7.63 (m, 4H), 8.67 (d, J=15 Hz, 2H). ESI-MS (m/z): calcd: 1072.48, found: 1072.47.

Compound CC (22 mg, 0.02 mmol) and propynyl-HPβCD (32 mg, 0.02 mmol) was dissolved in DMSO/water (1/1). A solution of sodium ascorbate (4.10 mg, 0.02 mmol) and cupric sulfate (8.30 mg, 0.033 mmol) in distilled water was added. After the mixture was stirred at room temperature under a nitrogen atmosphere in dark for 5 h, it was precipitated in acetone (350 ml). The crude product was filtered and further purified by HPLC to afford MRP3 (45 mg, 84% yield) as a blue solid. $^1$H NMR (300 MHz, D$_2$O): δ 1.21 (m, 16H), 1.48-1.74 (m, 8H), 2.12-2.32 (m, 6H), 2.38 (s, 2H), 3.02 (m, 3H), 3.25-4.25 (m, 51H), 4.32-4.55 (m, 5H), 5.15-5.32 (m, 9H), 6.17 (d, J=12, 1H), 6.40 (d, J=9, 1H), 7.03-8.66 (m, 12H). MALDI-TOF MS found: 2350-2850.

Synthesis of CP2 and CP5 (FIG. 3c)

A mixture of CyOH (9.40 mg, 0.02 mmol) and methoxy-PEG-alkyne (MW: 2000 or 5000, 1.5 equiv to CyOH) was dissolved in DMSO/water (1/1), followed by addition of a solution of sodium ascorbate (1.05 mg, 0.005 mmol) and cupric sulfate (1.06 mg, 0.004 mmol) in distilled water. After the mixture was stirred at room temperature under a nitrogen atmosphere in dark for 5 h, it was precipitated in acetone (350 ml). The crude product was filtered and further purified by HPLC to afford CP2 (41 mg, 81% yield) and CP5 (92 mg, 83%) as a blue solid. $^1$H NMR of CP2 (300 MHz, D$_2$O): δ 1.60-1.82 (m, 8H), 1.83 (m, 2H), 2.48 (m, 4H), 3.37 (m, 2H), 3.4-4.0 (m, 177H), 4.54 (t, 4H), 6.00-8.21 (m, 10H). $^1$H NMR of CP5 (300 MHz, D$_2$O): δ 1.51 (m, 6H), 1.83 (m, 4H), 2.43 (s, 4H), 3.25-4.25 (m, 200H), 4.16-4.30 (m, 4H), 5.63-7.94 (m, 10H). MALDI-TOF MS found: 1400-3000 and 4000-7000 for CP2 and CP5, respectively.

Synthesis of CCD (FIG. 3c)

A mixture of CyOH (46.70 mg, 0.1 mmol), propynyl-HPβCD (0.20 g, 0.125 mmol), sodium ascorbate (4.60 mg, 0.022 mmol) and cupric sulfate (7.50 mg, 0.03 mmol) in DMSO/water (1/1, 5 ml) was stirred at room temperature under a nitrogen atmosphere in dark for 5 h. Then the reaction was precipitated in acetone (350 ml). The crude product was filtered and further purified by HPLC to afford CCD (0.22 g, 86%) as a blue solid. $^1$H NMR (300 MHz, D$_2$O): δ 1.23 (s, 18H), 1.85 (s, 6H), 1.99 (m, 6H), 2.72 (m, 2H), 3.05 (t, 2H), 3.25-4.25 (m, 74H), 4.34 (t, 1H), 4.57 (t, 2H), 5.18 (m, 9H), 5.62 (t, 2H), 6.59-7.72 (m, 10H). MALDI-TOF MS found: 1600-2180.

Synthesis of MRP$_D$ (FIG. 4)

A mixture of CySCL (0.18 g, 0.15 mmol), propynyl cyclodextrin (0.60 g, 0.375 mmol), sodium ascorbate (6.80 mg, 0.033 mmol) and cupric sulfate (8.30 mg, 0.033 mmol) in the solution of DMSO/water (1/1) was stirred in ice bath under a nitrogen atmosphere in dark. After 5 h, this mixture was precipitated in acetone (350 ml). The crude product was filtered and purified by HPLC to yield a blue solid MRP$_D$ (0.52 g, 80% yield). $^1$H NMR (300 MHz, D$_2$O): 0.90 (m, 1H), 1.26 (s, 21H), 1.64-2.10 (m, 34H), 2.58 (m, 4H), 2.83 (t, 2H), 3.20 (m, 4H), 3.25-4.25 (m, 100H), 4.24 (t, 4H), 4.37 (t, 2H), 4.48 (t, 2H), 5.00-5.16 (m, 14H), 5.65 (t, 2H), 6.86-7.11 (m, 10H), 7.47-7.79 (m, 6H). MALDI-TOF MS found: 3400-4400.

Synthesis of ADR (FIG. 5)

Compound 6 (0.28 g, 0.5 mmol) and methylene blue (32 mg, 0.1 mmol) were dissolved in a mixture of dichloromethane and methanol (30 ml, v/v=1/1). Oxygen was bubbled through the solution while irradiating with yellow light for 4 h. The reaction mixture was concentrated under reduced pressure. The product was washed three times with water (3×60 ml), exacted by dichloromethane (120 ml) and concentrated under reduced pressure in a water bath with temperature below 28° C., which was used in the next step without further purification. Compound 7 (12 mg, 0.02 mmol) and compound 2 (44 mg, 0.02 mmol) were dissolved in DMSO/water (5 ml/5 ml). A solution of sodium ascorbate (2.0 mg, 0.01 mmol) and cupric sulfate (2.5 mg, 0.01 mmol) in distilled water was added. After the reaction mixture was stirred at room temperature under a nitrogen atmosphere in dark for 2 h, it was precipitated in acetone (350 ml). The crude product was filtered and purified by HPLC to afford ADR after freeze drying (54 mg, 90% yield) as a blue solid. $^1$H NMR (300 MHz, D$_2$O): δ 1.12 (m, 18H), 1.20-1.75 (m, 15H), 1.77-2.10 (m, 11H), 2.71 (s, 1H), 2.93 (m, 8H), 3.25-4.25 (m, 60H), 4.25-4.41 (m, 10H), 5.07-5.25 (m, 9H), 6.03 (d, J=15, 1H), 6.38 (d, J=3, 2H), 6.41 (s, 1H), 6.95-7.26 (m, 5H), 7.26 (m, 1H), 7.28-7.31 (m, 4H), 7.43 (m, 2H), 8.54 (d, J=15, 1H). MALDI-TOF MS found: 2700-3200.

Results and Discussion

MRPs1-3 and MRP$_D$ were synthesised via a convergent approach (FIGS. 3b and 4). The fluorescent MRPs (MRPs1-3) were constructed on a hemi-cyanine precursor (CyOH) with an aromatic hydroxyl group and an azide group on the alky chain linked to the indole ring (FIG. 3b). The hydroxyl group of CyOH was first caged with diphenylphosphinyl, N-acetyl-β-D-glucosaminide, or a tetrapeptide sequence (Asp-Glu-Val-Asp: Ac-DEVD) (FIG. 6a), which could be specifically cleaved by O$_2$*$^-$, NAG and caspase-3, respectively. The azide group of CyOH was then conjugated with the alkyne-functionalised HPβCD via a click reaction.

MRP$_D$ was synthesised from an uncaged fluorescent heptamethine cyanine dye (Cy7NH2) (FIG. 4), which has two azide groups on the alky chain linked to the indole ring and an alkyl amine on the meso position. The amine group of Cy7NH2 was first coupled with the caged chemiluminescent phenoxy-dioxetane substrate stabilised by a O$_2$*$^-$-cleavable trifluoromethanesulfonate group on the phenol position. The azide groups were then reacted with the alkyne-functionalised HPβCD to afford MRP$_D$.

ADR was constructed through the following three main steps (FIG. 5): (i) synthesis of the N-acetyl-β-D-glucosamine-caged NIRF hemi-cyanine substrate 14; (ii) synthesis of the trifluoromethanesulfonate-caged chemiluminescent phenoxy-dioxetane substrate 17; and (iii) conjugation of these caged NIRF and chemiluminescent substrates (14 and 17) onto the alkyne-functionalised HPβCD. The hemi-cyanine precursor (CyOH-2) was synthesised by reacting a symmetric cyanine dye with resorcinol via a retro-knoevenagel reaction (similar to the synthesis of CyOH from CyCl; see FIG. 3a), followed by its reaction with a bromo-glucose derivative to afford the NIRF hemi-cyanine substrate 14. Synthesis of the chemiluminescent substrate 17 started from the phenol precursor CL by substituting a O$_2$*$^-$-cleavable trifluoromethanesulfonate group on the phenol position, followed by the hydrolysis of an ester bond to afford the carboxylic acid derivative 12 (see FIG. 4 for the synthesis of 12). Under ester coupling conditions, 12 was conjugated with 3-azido-1-propanol to give the enol ether precursor 16. This precursor underwent [2+2] cycloaddition with singlet oxygen ($^1$O$_2$) using a photosensitizer (methylene blue) to afford the 1,2-dioxetane chemiluminescent substrate 17. Finally, both the azide groups on the NIRF substrate 14 and chemiluminescent substrate 17 were consecutively reacted with the alkyne-functionalised HPβCD to afford ADR. MALDI-TOF-MASS assay confirmed that ADR had an average molecular weight of ~2950 Da, proving the conjugation of one NIRF moiety and one chemiluminescent moiety per HPβCD.

Example 2. Optical properties of MRPs1-3, MRP$_D$, CMe, CCD, CP2 and CP5 of the Current Invention To test the validity of the MRPs response to their corresponding biomarkers, the optical properties of the as-synthesised MRPs1-3, MRP$_D$, CMe, CCD, CP2 and CP5 (from Example 1) were investigated.

In the absence of O$_2$*$^-$, NAG and caspase-3, the MEPs1-3 showed a deep blue colour in PBS. In addition, the MRPs1-3 had similar optical profiles with an absorption maximum at ~600 nm and were barely fluorescent at the intrinsic state (FIG. 10a-c). This was because they were "caged" wherein the electron-donating ability of the aromatic hydroxyl group was inhibited by the substituents. The absorption spectra of MRPs1-3 changed in respond to their respective biomarkers with a peak shift to approximately 692-695 nm. The colour change from deep blue to green allows the colorimetric detection of O$_2$*$^-$, NAG and caspase-3 by the naked eye, which is attributed to the large red-shift of roughly 100-120 nm in the absorption spectra. Meanwhile, the fluorescence at 720 nm (FIG. 10e-g) increased by 21, ~17-19, and ~15-17 fold for MRP1, MRP2, and MRP3, respectively. The optical profiles of these probes resembled the uncaged derivative (CCD) (FIG. 11a), which had an unsubstituted hydroxyl group liberating the strong electron-donating ability of the phenolate group on the fluorophores.

The NIR fluorescent agents CMe, CCD, CP2 and CP5 had similar absorption with the peak at 690 nm and fluorescence spectra with the peak at 720 nm as shown in FIG. 11a, m-o. All of them have a similar fluorescent quantum yield of roughly 0.22 in phosphate buffer solution (PBS) (Table 3).

The mechanisms of the reaction of MRPs with their corresponding biomarkers were investigated, respectively. The deprotection of the diphenyl phosphinate group of MRP1 by O$_2$*$^-$ generates CCD (FIG. 12a). MRP2 can be hydrolysed by breaking the C—O bond through enzymatic reaction with NAG to release CCD (FIG. 12a). MRP3 was recognised by caspase-3 and cleaved to CCD, which possesses a distinct colorimetric change with a large spectral shift and emits light in the NIR region. To further confirm the sensing mechanisms, high performance liquid chromatography (HPLC) characterization were used to monitor the change of the MRPs from "caged" to "uncaged" state (FIG. 11g-i).

MRP1 (HPLC retention time, T$_R$=26.25 min, FIG. 11g) was converted into free CCD (T$_R$=22.18 min) after 15 min incubation with O$_2$*$^-$. Similarly, MRP2 (T$_R$=18.50 min) exhibits conversion to CCD after treatment with NAG (40 mU) (FIG. 11g). Lastly, CCD formation were confirmed after the enzymatic reaction of MRP3 (T$_R$=17.12 min) with recombinant caspase-3 (FIG. 11i).

The specificity of MRP1 was examined by measuring its fluorescence response after exposure to various ROS and other analytes in PBS. As shown in FIG. 10i, a 21-fold enhancement in fluorescence intensity was observed toward 1 equiv. of O$_2$*$^-$, while 5-10 equiv. of other analytes could only give negligible fluorescence increase. Further, the reaction of MRP1 with O$_2$*$^-$ in PBS was completed within 15 min (FIG. 11j), suggesting a very rapid reaction between MRP1 and O$_2$*$^-$. Additionally, FIG. 11p shows that the optimum pH range for O$_2$*$^-$ detection was from 7.0 to 8.0, which is very close to physiological environment. Notably, the plots of the fluorescence intensity against the concentration of O$_2$*$^-$ ranging from 0 to 2.5 µM displayed a good linear relationship, and the limit of detection (LOD) for MRP1 against O$_2$*$^-$ was estimated to be as low as ~11-11.4 nM (FIG. 11b-d), indicative of ultrasensitivity to changes in superoxide anion.

MRP2 and MRP3 showed increased the fluorescent signal at 720 nm with increased enzymes incubation time and plateaued at 45 and 60 min, respectively (FIG. 11e-f, k-l), indicating the complete conversion of MRP2 and MRP3 to free CCD. The kinetic results imply that the fluorescent response can be utilised for the rapid detection of NAG and caspase-3. In addition, MRP2 and MRP3 exhibited good selectivity to NAG and caspase-3, respectively, which are evidenced by the approximately 17- and 15-fold higher fluorescence changes than other enzymes, ROS and metal ions (FIGS. 10j and k). We further investigated the apparent steady-state kinetics of the enzymatic reaction between MRP2/MRP3 and their corresponding enzymes (FIG. 11e-f). The enzymatic Michaelis-Menten constants (K$_m$) of NAG towards MRP2 was calculated to be 11 µM, suggesting MRP2 has a high affinity to NAG. Additionally, the catalytic rate constants (K$_{cat}$) of NAG towards MRP2 was 1.87 S$^{-1}$. Therefore, the catalytic efficiency (K$_{cat}$/K$_m$) of NAG towards MRP2 was calculated to be 0.17 µM$^{-1}$ S$^{-1}$ (Table 4), indicating its rapid and quantitative fluorescence detection of NAG. Similarly, the K$_m$ and K$_{cat}$/K$_m$ of caspase-3 towards MRP3 were quantified to be 13.2 µM and 0.86 µM$^{-1}$ S$^{-1}$ (Table 4).

TABLE 3

Photophysical properties of the uncaged fluorophores and MRPs.

| Fluorophores/Probes | | $\lambda_{ab}$ (nm) | $\lambda_{em}$ (nm) | Stokes Shift (nm) | φ | Log D (pH = 7.4) |
|---|---|---|---|---|---|---|
| Uncaged fluorophores | CMe | 697 | 722 | 25 | 0.23 | 2.53 |
| | CP2 | 695 | 720 | 25 | 0.21 | -4.81 |
| | CP5 | 695 | 720 | 25 | 0.25 | -8.23 |
| | CCD | 692 | 720 | 28 | 0.21 | -10.07 |
| MRPs | MRP1 | 600 | 720 | 120 | 0.0031 | -6.97 |
| | MRP2 | 600 | 720 | 120 | 0.0034 | -13.12 |
| | MRP3 | 600 | 720 | 120 | 0.0035* (0.0038)^ | -16.94 |
| | MRP$_D$ | 640 | 760 | 120 | 0.038 | -18.44 |

Note:
$\lambda_{ab}$ and $\lambda_{em}$: wavelength of maximum absorbance and emission, respectively; φ: fluorescence quantum yield; Log D value: distribution coefficient.
*Initial reading.
^Subsequent reading.

TABLE 4

Enzyme kinetics parameters of MRP2 and MRP3

| | K$_m$ (µM) | V$_{max}$ (nM s$^{-1}$) | K$_{cat}$/K$_m$ (µM$^{-1}$s$^{-1}$) |
|---|---|---|---|
| MRP2 | 11 | 3.3 | 0.17 |
| MRP3 | 13.2 | 6.7 | 0.86 |

K$_m$ is the Michealis constant obtained from the Michaelis-Menten equation (V = V$_{max}$[S]/(K$_m$ + [S]), where V is the initial velocity, V$_{max}$ is the maximum velocity, [S] is substrate concentration, and K$_m$ is Michealis constant. K$_{ca\ t}$= V$_{max}$/[E], where [E] is enzyme concentration.

In contrast to the turn-on fluorescent response of MRPs1-3, the fluorescence of MRP$_D$ was always on and inert to the tested biological molecules (FIG. 10d). MRP$_D$ had a chemiluminescent phenoxy-dioxetane unit whose activity was initially inhibited due to the presence of trifluoromethanesulfonate substitution on its phenol group. In the presence of O$_2$*$^-$, nucleophilic attack occurred on the sulfonate ester group of MRP$_D$, leading to the cleavage of trifluoromethanesulfonate and formation of a phenolate dioxetane intermediate (FIG. 12b). This unprotected intermediate was unstable and spontaneously underwent a chemically initiated electron-exchange luminescence process[29], resulting in the chemiluminescence at 540 nm. Addition of O$_2$*$^-$ to MRP$_D$ led to a 3000-fold increase in chemiluminescent signal (FIG. 10h), which was not observed with other substances (FIG. 10l).

The LOD for MRP$_D$ against O$_2$*$^-$ (13 nM) was similar to MRP1, and its chemiluminescence half-life (8.9 min) was sufficient for in vivo imaging (FIG. 13). Note that despite the presence of the NIR-emissive unit in MRP$_D$, the chemiluminescence maximum was the same as the dioxetane unit itself (540 nm) suggesting little energy transfer between the chemiluminescent unit and the NIR unit probably because of their long distance. This chemiluminescence was detected through 1.5 cm of chicken tissue (FIG. 13e-h), confirming its utility for in vivo imaging.

Example 3. Renal Clearance and In Vivo Stability Studies of MRPs1-3 and MRP$_D$ in Comparison with CMe, CCD, CP2 and CP5

The biodistribution of MRPs was studied and compared with their uncaged derivatives including the methyl-substituted hemicyanine skeleton (CMe), the HPβCD-substituted CyOH (CCD), and the poly(ethylene glycol) (PEG) substituted CyOH (CP2 and CP5 with PEG2000 and PEG5000, respectively) (FIG. 1b). As the uncaged derivatives and MRP$_D$ were intrinsically fluorescent (Table 3), NIRF imaging was used to track their biodistribution after intravenous (i.v.) administration. As shown in FIG. 15a, no fluorescence signal can be observed at both dorsal and ventral side of mice before injection of NIR fluorescent agents. Fluorescence signals were quickly detected for CCD and MRP$_D$ in the kidneys (i.e. the kidneys were clearly delineated at the dorsal side of mice) and bladder 30 min post-injection (FIG. 15a), indicating an efficient accumulation of CCD and MRP$_D$ in kidneys. However, the kidneys cannot be observed on mice injected with CMe, CP2 and CP5 (FIG. 15a). Additionally, the NIR fluorescence signal at the ventral side was mainly located in the bladder region on mice with injection of CP2, CP5 and CCD, with CMe being undetectable in the bladder region but detectable in the liver region. Notably, CCD showed less nonspecific background in other tissues and organs than that of CP2 and CP5.

Ex vivo NIRF imaging of the abdominal cavity of mice (FIG. 14a) and biodistribution data (FIG. 15b-c) at 1 h post-injection showed that CCD and MRP$_D$ mainly accumulated in the kidneys and bladder. The signals in other organs were close to the background of saline-treated mice. In contrast, CP2 and CP5 had a relatively high accumulation in gallbladder, liver, lung and muscle in addition to kidneys and bladder; the hydrophobic agent CMe was trapped by the reticuloendothelial system (RES) and mainly accumulated in the liver, gallbladder, and intestine, resulting in high NIR fluorescence signal throughout the gastrointestinal tract (FIGS. 15b and c). Thus, the ex vivo data revealed that although both PEG and HPβCD-substituted CyOH could be excreted through the kidney, the relatively high uptake in other organs for CP2 and CP5 caused signal interference limiting kidney visualisation in the real-time whole-body images. These results demonstrate that HPβCD is superior to PEG for eluding nonspecific uptake by the reticuloendothelial system (RES) and exclusively excreting to the bladder. Minimizing off-target and non-specific background is critical to the sensitivity and specificity of kidney imaging, especially when the activation of MRPs reaches it threshold. Therefore, HPβCD was selected as renal clearance moiety to construct NIR fluorescent MRPs for the early diagnosis of kidney injury.

HPLC was used to study fluorophore pharmacokinetics by quantifying the fluorophores in the blood and urine of living mice as a function of time after i.v. injection. The probe concentration in blood decreased close to 0% injected doses (ID) g$^{-1}$ 75 min post-injection for all fluorophores (FIG. 14b), representing rapid elimination from the body by the systemic clearance. From the initial studies (FIG. 14bi and Table 5), the elimination half-life ($t_{1/2β}$) of CP2, MRP1, CP5, CCD, MRP2 and MRP3 in mice decreased from 17.6 to 13.6, 13.5, 12.95, 11.46 and 10.8 min with decreasing distribution coefficient (Log D) from -4.81 to -6.97, -8.23, -10.07, -13.12, -16.94, respectively. Among them, MRP3 showed relatively shorter half-life than other agents and MRPs, which might be due to its more hydrophilic feature (lower Log D value) and less non-specific interaction associated with plasma proteins. From the subsequent studies, the elimination half-lives ($t_{1/2β}$) of the HPβCD-substituted fluorophores (<17 min) were shorter than CP2 (20.8 min) (Table 5). Furthermore, the trend of $t_{1/2β}$ was generally consistent with their distribution coefficients (Log D) (FIG. 14c), implying that hydrophilicity played a role in their blood elimination.

An ideal molecular reporter for detecting kidney injury should be excreted completely into urine. Urine analysis showed that the renal clearance efficiencies of the HPβCD-substituted fluorophores were higher than others (FIG. 14e and FIG. 16). These were determined to be >80% ID at 3 h post-injection and >92% ID at 24 h post-injection (92±2.1, 94±2.2, 93±2.0, 94±3.0 and 97±2.7% ID for MRP1, MRP2, MRP3, MRP$_D$, and CCD, respectively). In contrast, CP2 and CP5 only reached 79±3 and 55±5% ID at 24 h post-injection, respectively, and CMe was nearly undetectable in urine due to RES uptake. The highly efficient renal clearance of MRPs is attributed to their relatively low molecular weights (<50 kDa, below glomerular filtration cutoff) and high hydrophilicity.

TABLE 5

Elimination half-life and renal clearance efficiency of the uncaged fluorophores and MRPs in living mice.

| Fluorophores/Probes | | $t_{1/2β}$ | Renal clearance efficiency (%) |
|---|---|---|---|
| Uncaged fluorophores | CMe | ND | <5 |
| | CP2 | 17.6* | 79.1 ± 2.9 |
| | | 20.79^ | |
| | CP5 | 13.5* | 55.2 ± 4.8 |
| | | 16.87^ | |
| | CCD | 12.95* | 97 ± 2.7 |
| | | 16.43^ | |
| MRPs | MRP1 | 13.6* | 91.7 ± 2.1 |
| | | 17.0^ | |
| | MRP2 | 11.46* | 93.5 ± 2.2 |
| | | 15.35^ | |
| | MRP3 | 10.8* | 92.5 ± 2.0 |
| | | 14.48^ | |
| | MRP$_D$ | 12.76 | 94.1 ± 3.0 |

Note:
$t_{1/2β}$: elimination blood half-life values; ND: not determined. Data are the mean ± SD. n = 3 independent mice. *Initial studies. ^Subsequent studies.

To determine in vivo stability, the optical and chemical profiles of MRPs recovered from the urine of living mice were measured and compared with the pure compounds. Except CMe (unable to be recovered from urine), none of fluorophores from urine had obvious changes to their absorption and fluorescence spectra after circulation in living mice (FIG. 17). CP2 and CCD had almost identical absorption and fluorescence spectra in PBS and urine samples, CP5 had subtle blue-shift in both its absorption and fluorescence spectra (FIGS. 17c, e and g). However, urine samples from mice injected with CMe had neither the absorption at 695 nm nor fluorescence at 720 nm (FIG. 17a), confirming non-renal clearance. Although matrix assisted laser desorption/ionisation (MALDI) analysis validated their intact chemical structures (FIG. 18), HPLC quantification (FIG. 14e) identified some CCDs and adamantanone (<6%) from the urine of MRPs1-3 and $MRP_D$-treated mice, respectively. This is likely due to probe activation by basal levels of biomarkers in healthy mice. These data not only showed that MRPs had minimal in vivo metabolism in healthy mice but also confirmed that their renal clearance efficiencies were near 100% ID for MRPs. In view of the undetectable signals in the major organs at 24 h post-injection of MRPs (FIGS. 16j and l), MRPs could be considered as fully renal clearable (>97% ID).

In addition, histological and immunofluorescence staining revealed that MRPs did not induce cellular apoptosis or cause any tissue damage. H&E staining of major organs including heart, liver, spleen, lung, and kidney from mice at 24 h after i.v injection of MRPs (8 µmol kg$^{-1}$ body weight for MRPs1-3, 32 µmol kg$^{-1}$ body weight for $MRP_D$) and double immunofluorescence staining of major organs with caspase 3 and DAPI from mice at 24 h after i.v injection of MRPs were carried out (repeated independently three times with similar results). No histological changes in H&E staining and no green fluorescence signals in immunofluorescence staining were observed for those major organs slides, suggesting that MRPs had good biocompatibility.

Example 4. Real-Time NIRF In Vivo Imaging Using MRPs1-3 on Mice Treated with Cisplatin, Gentamicin or Diatrizoate The ability of MRPs1-3 to detect drug-induced AKI was tested in living mice treated with cisplatin (an antineoplastic drug), gentamicin (an antibiotic), or diatrizoate (a radiocontrast agent)—all with known nephrotoxicity (R. Galgamuwa, et al., *J. Am. Soc. Nephrol* 2016, 27, 3331-3344; A. Otunctemur, et al., *Ren. Fail.*, 2014, 36, 925-931; C. M. Erley, et al., *J. Am. Soc. Nephrol.*, 1997, 8, 1125-1132). Cisplatin was intraperitoneally administered into living mice at a nephrotoxic dosage (FIG. 19a and Methods), followed by intravenous injection of MRPs at different timepoints post-treatment of cisplatin (8, 12, 16, 24, and 48 h). The control groups were treated with saline or a nephroprotective antioxidant (NAC) prior to cisplatin administration. Whole body longitudinal NIRF imaging was then conducted for those groups with different drug post-treatment times.

At 8 h post-treatment of cisplatin, the signals from MRPs1-3 in the kidneys were as low as the control mice (FIG. 19b-d and FIG. 20). However, at 12 h post-treatment of cisplatin, the injection of MRP1 led to a gradual signal increase in the kidneys with a signal maximum 30 min post-injection of MRP1 (FIG. 19e; 1.45-fold higher than control mice). The MRP1 signals in the kidneys and bladder decreased at later imaging timepoints due to its short elimination half-life. Similar trends were observed for MRP2 and MRP3, but the earliest timepoints that they showed a statistically significant signal increase were 16 and 48 h post-treatment of cisplatin for MRP2 (1.56-fold) and MRP3 (1.60-fold), respectively (FIG. 19f and FIG. 20). This sequential activation suggested that cisplatin first induced oxidative stress followed by lysosomal damage and cellular apoptosis. The maximum NIRF signals of MRPs1-2 in the kidneys increased with post drug treatment time (FIG. 19f), indicating the gradual upregulation of those biomarkers during the progression of AKI.

Consistent with the in vivo imaging data, whole kidney section imaging revealed that the NIRF signals (FIG. 19g and FIG. 21) were detected in the cortex and the outer medulla area for MRP1, MRP2, and MRP3 at 12, 16 and 48 h post-treatment of cisplatin, respectively. The caspase-3 signal was only detectable 48 h post-treatment of cisplatin, and the histological staining (FIG. 19h and FIG. 21k) showed normal tubular morphology at 48 h post-treatment of cisplatin, but loss of the brush border and hyaline casts at 72 h post-treatment of cisplatin. Magnified regional kidney section imaging further clarified that the NIRF signals of activated MRPs1-3 mainly came from the renal tubules rather than the glomeruli (FIG. 19i). This was because the tubules are at the frontline of nephrotoxin clearance; tubular injury is well reported for nephrotoxin exposure (D. P. Basile, et al., *Compr. Physiol.*, 2012, 2, 1303-1353). Thus, these data further validated that $O_2^{*-}$, NAG, and caspase-3 were sequentially upregulated prior to injury of kidney tissue. It also revealed that these molecular events occurred in renal tubules after nephrotoxin exposure. Note that similar trends were observed for the signal increases of MRPs1-2 in the mouse model of gentamicin or diatrizoate-induced AKI (FIG. 22-23 for gentamicin-induced AKI, and FIG. 24-25 for diatrizoate-induced AKI).

Example 5. Pharmacokinetics of $MRP_D$ and Real-Time Independent Dual-Channel In Vivo Imaging Using $MRP_D$ To confirm that MRPs could predict drug-induced AKI before the change in glomerular filtration, the dual-channel probe ($MRP_D$) was intravenously injected into living mice at different post drug treatment time (8, 12, 48 and 72 h). Longitudinal chemiluminescence and NIRF imaging were simultaneously conducted. At 8 h post-treatment of cisplatin, the chemiluminescent signal of $MRP_D$ in the kidneys was close to the background (FIG. 26a and FIG. 27), but the NIRF signal was detected (FIG. 26b; always-on signal). The NIRF signal reached maximum at 8 min post-injection of $MRP_D$ and then decreased with time (FIG. 26e). At 12 h post-treatment of cisplatin, the chemiluminescent signal was detected in the kidney, 14.6-fold higher than that of the control at 8 min post-injection of $MRP_D$. Moreover, similar chemiluminescent signal evaluation as a function of imaging time was observed for the mice groups at 12, 48 and 72 h post-treatment of cisplatin (FIG. 26d); however, the maximum chemiluminescent signal of the kidneys at 72 h post-treatment of cisplatin was 1.27 and 1.66-fold higher than that at 48 and 12 h, respectively. This proportional correlation between the maximum chemiluminescent signal and the post-treatment time was consistent with the data acquired with MRP1, confirming that the level of $O_2^{*-}$ was gradually upregulated after drug treatment. In contrast, the maximum NIRF signals of the kidneys had a non-linear relation with post-treatment time, and a threshold was observed. The profile for the signal as a function of imaging time remained similar when the post-treatment time was no more than 48 h; it changed dramatically at 72 h post-treatment. Instead of gradually decreasing signal 8 min after injection of $MRP_D$, the signal was stable, indicating the probe retention in the kidneys.

To gain insight into the origin of probe retention in the kidneys, the pharmacokinetics of $MRP_D$ (FIG. 26f) and GFR (FIG. 26c) were measured in the mice at different timepoints post-treatment of cisplatin. The blood elimination half-lives ($t_{1/2\beta}$) of $MRP_D$ in the mice after cisplatin treatment for 8, 12, and 48 h were similar (14.3 min), but it prolonged to 34.7 min for 72 h. This was ascribed to the significantly decreased GFR from 9.78 before treatment to 4.50 µl min$^{-1}$ g$^{-1}$ body weight at 72 h post-treatment. Thus, these data further proved that the probe retention was caused by declined glomerular filtration capability under nephrotoxic expose, consistent with the histological data showing renal tubular damage (FIG. 21). Moreover, the fact that the chemiluminescent signal of MRP$_D$ was detected at 12 h before the decrease in GFR indicated the ability of MRP$_D$ for early detection of drug-induced AKI. Similar trends of dual-channel imaging results and GFR changes were observed for MRP$_D$ in the mouse model of gentamicin or diatrizoate induced AKI (FIG. 28-30).

Example 6. In Vitro Detection of Drug-Induced AKI in Urine Samples Using MRPs1-3 (Via Liquid Biopsy)

Liquid biopsy provides an insight into the biology and genetics of systemic diseases by simply collecting blood, urine or other physiological fluids. Unlike tissue biopsies, sampling liquid biofluid is non-invasive, painless and represents no risk to the patient. NAG is normally secreted in very low concentrations to urine in healthy individuals but evaluated dramatically in the initial phases of ongoing kidney injury. The detection of urine allows to identify NAG released by the diseased tissue and to quantify its changes with respect to the healthy tissues. With this method, the early detection of pathology is made possible before the symptoms are manifested.

The increased plasma NAG activity was reported as a marker for inflammation as well as pulmonary and cardiac damage (M. P. Iqbal, et al., *J. Coll. Physicians Surg. Pak.*, 2008, 18(2), 74-77). To determine the effect of inflammation to the changes in activity of urinary NAG, the activity of urinary NAG was investigated in the mouse model of inflammation induced by lipopolysaccharide (LPS), a highly pro-inflammatory toxin found on the Gram-negative bacteria cell wall (F. A. Pinho-Ribeiro, et al., *J. Nutr. Biochem.* 2016, 33, 8-14). As depicted in FIG. 44*f*, urine were sampling on mice at 24 h post-treatment of either saline or LPS (i.p). Fluorescence enhancement of MRP2 was measured after the incubation of urine samples. We found that no fluorescence enhancement of MRP2 was observed between saline and LPS treated group (FIG. 44*f*). Hence the inflammation of extra-renal organs has no effect on the activity of urinary NAG.

To evaluate the translational potential of MRPs, drug-induced AKI was detected in urine and compared with existing assays. Two methods were used for MRP-based urinalysis (FIG. 31*a*): (i) direct NIRF measurement of excreted probes in urine after their intravenous injection into drug-treated mice (online urinalysis) and (ii) collection of urine samples from drug-treated mice followed by probe incubation and optical measurement (offline urinalysis).

In the initial online urinalysis studies showed the first statistically significant NIRF enhancement was respectively observed at 12 (2.39-fold), 36 (2.38-fold), and 8 h (2.36-fold) post-treatment of cisplatin, gentamicin, and diatrizoate for excreted MRP1, 16 (2.85-fold), 48 (2.27-fold) and 16 h (2.57-fold) for MRP2, and 48 (2.93-fold), 144 (3.05-fold) and 24 h (2.39-fold) for MRP3. In subsequent online urinalysis (FIG. 31*b-d* and FIGS. 32 and 33), the first statistically significant NIRF enhancement was respectively observed at 12 (2.0-fold), 36 (2.3-fold), and 8 h (2.1-fold) post-treatment of cisplatin, gentamicin, and diatrizoate for excreted MRP1, 16 (2.3-fold), 48 (2.3-fold) and 16 h (2.4-fold) for MRP2, and 48 (2.6-fold), 144 (2.8-fold) and 24 h (1.9-fold) for MRP3. Moreover, the NIRF signal continued increasing after these timepoints. The signal evolution behaviors of MRPs coincided with the real-time NIRF imaging data, as the excreted MRPs were activated in the renal clearance pathway. In offline urinalysis (FIG. 31*e-g* and FIG. 33), only MRP2 showed statistically significant NIRF enhancement after incubation in urine because $O_2^{*-}$ has a short half-life (<5 s), and caspase-3 is an intracellular enzyme that is excreted less in urine (M. Hayyan, et al., *Chem. Rev.* 2016, 116, 3029-3085; B. Zhivotovsky, et al., *Cell Death Differ.* 1999, 6, 644-651). The earliest timepoints for MRP2 to detect the upregulation of NAG in offline urinalysis were 24 (2.7-fold for subsequent studies, or 2.64-fold for initial studies), 72 (2.1-fold for subsequent studies, or 2.04-fold for initial studies) and 24 (2.7-fold for subsequent studies, or 2.97-fold for initial studies) for cisplatin-, gentamicin-, and diatrizoate-treated mice, respectively. These were slightly later (8-24 h) than those in online urinalysis, probably due to the diluted concentration of NAG in the urine relative to the kidneys.

Commercial assays were used to measure sCr, BUN, and Cystatin C in blood as well as NGAL, clusterin, KIM-1, osteopontin, β2-microglobulin and trefoil factor-3 in urine. The sCr and BUN had the statistically significant increase at 72 (2.4, 2.0-fold for subsequent studies, or 2.18, 1.89-fold for initial studies), 144 (2.9, 2.4-fold for subsequent studies, or 2.82, 2.23-fold for initial studies) and 24 h (1.8, 2.0-fold for subsequent studies, or 1.70, 1.76-fold for initial studies) after treatment of cisplatin, gentamicin and diatrizoate, respectively (FIG. 31*h-j*). At these timepoints, the GFRs were decreased by ~50% (FIG. 30). The serum Cystatin C behaved similarly in gentamicin and diatrizoate models but increased earlier at 48 h (2.0-fold for subsequent, or 1.80-fold for initial studies) in cisplatin model. Among the tested urinary biomarkers, KIM-1 and clusterin were most sensitive, showing their first statistically significant increases at 24 (1.9, 4.1-fold), 72 (2.2, 3.5-fold) and 24 h (3.7, 3.0-fold) after treatment of cisplatin, gentamicin, and diatrizoate, respectively. However, the first statistically significant changes of NGAL and trefoil factor-3 were observed at 48 (2.7 or 2.72, 0.4-fold), 96 (2.0 or 1.98, 0.3-fold) and 24 h (2.3 or 2.05, 0.5-fold) post-treatment of cisplatin, gentamicin, and diatrizoate, respectively. The statistically significant changes of osteopontin and β2-microglobulin after treatment of cisplatin, gentamicin, and diatrizoate occurred even later: 72 (2.3-fold) (cisplatin), 144 (2.3-fold) (gentamicin) and 24 h (2.3-fold) (diatrizoate) for osteopontin, and 72 (3.9-fold) (cisplatin), 144 (3.2-fold) (gentamicin) and 48 h (3.6-fold) (diatrizoate) for 132-microglobulin.

Comparison of the urinal/plasma analysis data (FIG. 31*k-m*) revealed that the MRPs1-2 based online urinalysis of upregulated $O_2^{*-}$/NAG was most sensitive to detect drug-induced AKI. The first statistically significant change of MRP1/MRP2 based online urinalysis detected drug-induced AKI at least 12/8 (cisplatin), 36/24 (gentamicin), and 16/8 h (diatrizoate) earlier than both MRP2-based offline urinalysis and KIM1- or clusterin-based urinalysis, and at least 36/32 (cisplatin), 60/48 (gentamicin) and 16/8 h (diatrizoate) earlier than the clinical methods and other tested preclinical assays.

As shown above, other than the use for clinical diagnosis (due to the non-toxicity and rapid renal clearance), MRPs1-3 can act as exogenous tracers for optical urinalysis. In MRP-based online urinalysis, the signals of the excreted probes were detected as early as the real-time imaging approach (FIG. 31*b-d* vs FIG. 14*b-d*)—these were again 16 to 108 h earlier than 50% decrease in GFR depending on the drugs. Additionally, the presence of urinary NAG allowed MRP2 to be valid for offline urinalysis simply by pre-incubation with mouse urine before optical analysis. Despite the slightly delayed detection timepoints relative to online urinalysis, MRP2-based offline urinalysis still outperformed most of the tested clinical assays and identified AKI 24-72 h earlier than the NAGL, Cyst C and β2-microglobulin assay (three assays better than sCr/BUN) in a cisplatin- or gentamicin-induced AKI mouse model (FIG. 31k). Moreover, NAG has a molecular weight (140 kDa) larger than the glomerular filtration cutoff (50 kDa) ensuring that plasma NAG produced from other organs cannot be filtered through the glomerulus and excreted into urine. Thereby, MRP2-based offline urinalysis should be specific to the AKI-induced renal NAG. Indeed, no signal enhancement was detected for MRP2 after incubation with urine from the mice with local inflammation (FIG. 44) or liver injury (FIG. 45).

Example 7. Comparison of the MRPs of the Current Invention with Existing Imaging Agents The fundamental limitation in molecular imaging of AKI is a lack of molecular probes that simultaneously possess high renal clearance efficiency and activatable signals specific to early AKI biomarkers. Upon substitution of HPβCD, MRPs1-3, MRP$_D$, and CCD had renal clearance efficiencies (>97% ID at 24 h post-injection) higher than all existing imaging agents regardless of their imaging modalities and compositions (Table 6) such as gold nanocluster (52% ID), quantum dots (75% ID), silica Cornell dots (73%), zwitterionic fluorophores (86% ID). Even in drug-treated mice, the renal clearance efficiencies of MRPs were >82% ID at 24 h post-injection (FIG. 34). The nearly complete renal clearance allowed the HPβCD-substituted fluorophore (CCD) to clearly delineate both kidneys of living mice through entire imaging course (FIG. 15a); in contrast, PEG-substituted CP2 and CP5 and other reported fluorophores failed to do so due to the signal interference from the fluorophore uptake by other organs.

TABLE 6

Summary of renal clearance efficiencies of imaging agents for kidney imaging.

| Imaging modalities | Agents | Renal clearance efficiency | Animal model | References |
|---|---|---|---|---|
| Optical | MRPs | >80% ID in 3 h ~97% ID in 24 h | NCr mice | Current invention |
| | CH1055-PEG | 90% ID in 24 h | Balb/c mice | Nat. Mater. 2016, 15, 235-242. |
| | Core: CdSe/ZnS Surface: Cys | 18.02-75.13% ID in 4 h | CD-1 mice | Nat. Biotechnol. 2007, 25, 1165-1170. |
| | ZW800-CDPL | 45-90% ID in 4 h | Health CD-1 mice | Adv. Mater. 2016, 28, 8162-8168. |
| | Porphyrin-PEG polymer | 80% ID at 24 h | ICR mice | Biomaterials. 2016, 76, 25-32. |
| | Carbon dots, ZW800 | 56% ID in 24 h | SCC-7 tumor bearing Balb/c mice | ACS Nano 2013, 7(7), 5684-5693 |
| | Carbon dots, PEG500Da | 73% ID in 48 h | NCr mice | Nano Lett 2008, 9, 442-448. |
| | InAs/ZnS | 0-47% ID in 4 h | S.D rats | Nano Lett 2009, 9, 2354-2359. |
| | Pd nanosheets | 6.6% ID in 24 h | BALB/c mice | Small 2014, 10(15), 3139-3144. |
| | Silica NPs (Cornell dots) | 73% ID in 48 h | NCr mice | Nano Lett 2009, 9(1), 442-448. |
| MRI | Gd-DTPA-BMA | 95% in 24 h | S.D Rats | Eur. J. Drug. Metab. Pharmacokinet. 1995, 20, 307-313. |
| | PAMAM-Gd-DTPA | NR | Cisplatin-induced AKI on BALB/c mice | Kidney Int. 2002, 61, 1980-1985. |
| PET | Au nanoclusters, $^{64}$Cu-alloy | ~30% ID in 24 h | PC3 tumor bearing C57BL/6 mice | Nanoscale 2014, 6, 13501-13509. |
| | CuNPs $^{64}$Cu-doped | 80% ID in 24 h | BALB/c mice | Bioconjugate Chem. 2015, 26, 511-519. |
| | VivoTag-680XL and $^{89}$Zr co-labelled dextran NPs | 75% ID g$^{-1}$ in 3 h | BALB/c mice | ACS Nano 2015, 9, 3641-3653. |
| | SWCNT-[([86Y]DOTA)(AF488)(AF680)] | 20% ID g$^{-1}$ in 60 min | NCr mice | Proc. Natl. Acad. Sci. USA 2010, 107, 12369-12374. |
| SPECT | $^{99m}$Tc-MAG$_3$ | 90% ID in 3 h | Patients | J. Nucl. Med.Technol. 2008, 36(3), 162-168. |
| | AuNPs, $^{111}$In | 64% ID in 24 h | FISHER rats | Nanoscale 2013, 5, 5930-5939. |
| | $^{111}$In-labeled MWNTs | 12% ID g$^{-1}$ in 24 h | Nude rats | Adv. Mater. 2008, 20, 225-230. |

TABLE 6-continued

Summary of renal clearance efficiencies of imaging agents for kidney imaging.

| Imaging modalities | Agents | Renal clearance efficiency | Animal model | References |
|---|---|---|---|---|
| X-ray | Iohexol | 59.7% in 4 h | S.D rats | *Acta. Radiol.* 1980, 362, 131-134. |
| | Core:Au nanoclusters Surface: GSH | 19.1-51.6% ID in 24 h | BALB/c mice | *Nat. Nanotechnol.* 2017, 12(11), 1096-1102. |
| | Core:Au NP Surface: GSH | 4-52.5% ID in 24 h | BALB/c mice | *Angew. Chem. Int. Ed. Engl.* 2011, 123, 3226-3230. |
| CT | Iothalamate | 93.5% ID in 24 h | S.D rat | *Biomed. Chromatogr.* 1994, 8(5), 224-229. |

The high sensing specificity and ideal in vivo stability of MRPs1-3 in association with their nearly same pharmacokinetics permitted the first longitudinal imaging of multiple biomarkers ($O_2^{*-}$, NAG and caspase-3) in the kidneys of drug-treated living mice. The real-time imaging results from three representative nephrotoxic drugs (cisplatin, gentamicin and diatrizoate) consistently showed that oxidative stress, lysosomal damage, and cellular apoptosis were prodromal molecular events occurring sequentially after nephrotoxic exposure.

In comparison with the fluorescent turn-on probe (MRP1), $MRP_D$ sensed the upregulation of $O_2^{*-}$ at the same timepoint but had a higher signal to background ratio (up 21-fold) due to minimized tissue autofluorescence in chemiluminescence imaging (FIG. 35). Moreover, $MRP_D$ is the first probe of its kind with always-on fluorescence but biomarker-activated chemiluminescence. Such an uncoordinated and intrinsically independent dual-channel imaging capability enabled $MRP_D$ to noninvasively validate that the chemiluminescence signal was activated by upregulated $O_2^{*-}$ prior to the retention-caused enhancement of NIRF signals (FIG. 26).

Comparison of the detection timelines of MRPs with the changes in GFR after nephrotoxic exposure (FIG. 31k-m) directly proved that MRPs1-2 and $MRP_D$ detected AKI before a decrease in glomerular filtration. Particularly, MRPs1-3 sequentially detected upregulated $O_2^{*-}$, NAG, and caspase-3 at 12, 16 and 48 h post-treatment in the cisplatin model of AKI. These timepoints were at least 36 h earlier than other real-time imaging methods based on the bioluminescent NGAL (168 h) or transcription factor Nuclear factor erythroid 2-related factor 2 (Nrf2) (a major regulator responding to oxidative stress) (48 h) reporter genes as well as the retention-based MRI, CT and SPECT contrast agents detecting the changes in glomerular filtration (>72 h) in the mouse model with the same drug dosage (20 mg kg$^{-1}$) (Tables 7 and 8).

TABLE 7

Summary of detection times of in vivo imaging for detection of drug-induced AKI.

| | Drug-induced AKI | | | | | |
|---|---|---|---|---|---|---|
| | Cisplatin | | Gentamicin | | Diatrizoate | |
| Imaging modalities/ Methods | Post-treatment time | Animal species | Post-treatment time | Animal species | Post-treatment time | Animal species |
| Optical (This study) | 12 h | mice | 36 h | mice | 8 h | mice |
| MRI | 72 h *Kidney Int.* 2002, 61, 1980 *Abdom. Imaging* 2006, 31, 224. | mice | 4-7 days *Int. J. Nephrol. Renovasc. Dis.* 2014, 7, 421. | rats | 48 h *Eur. Radiol.* 2016, 26, 1597. | rats |
| Ultrasound | 6 days *J. Vis. Exp.* 2016, 109, e52409. | rats | 5 days *Resbcal.* 2016, 4, 9. | rats | NR | |
| Multiphoton microscopy | NR | | 4 days *Kidney Int.* 2012, 83, 72. | rats | NR | |
| X-ray | 7 days *Int. J. Radiat. Biol.* 1989, 55, 661. | rats | NR | | NR | |
| SPECT | 5 days *Am. J. Physiol. Renal. Physiol.* 2010, 298, F454. | mice | 7 days *Mol. Cell. Biochem.* 2017, 434, 163. | rats | NR | |

TABLE 7-continued

Summary of detection times of in vivo imaging for detection of drug-induced AKI.

| | Drug-induced AKI | | | | | |
|---|---|---|---|---|---|---|
| | Cisplatin | | Gentamicin | | Diatrizoate | |
| Imaging modalities/ Methods | Post-treatment time | Animal species | Post-treatment time | Animal species | Post-treatment time | Animal species |
| Bioluminescence imaging | 48-168 h *Nat. Med.* 2011, 17, 216. *Sci. Rep.* 2017, 7, 16084. | mice | NR | | NR | |

NR: no report. Note that detection times in rats are presented in the case of no data reported in mice.

TABLE 8

Summary of detection times of in vitro methods for detection of drug-induced AKI.

| | Drug-induced AKI | | | | | |
|---|---|---|---|---|---|---|
| | Cisplatin | | Gentamicin | | Diatrizoate | |
| Imaging modalities/ Methods | Post-treatment time | Animal species | Post-treatment time | Animal species | Post-treatment time | Animal species |
| Optical urinalysis (This study) | Online (12 h) Offline (24 h) | mice | Online (36 h) Offline (72 h) | mice | Online (8 h) Offline (24 h) | mice |
| Creatinine | 72 h *Kidney Int.* 2007, 72, 1474. *Am. J. Physiol. Renal. Physiol.* 2012, 303, F437. *Inflamm. Res.* 2017, 66, 399. *J. Am. Soc. Nephrol.* 2016, 27, 3331. *J. Am. Soc. Nephrol.* 2009, 20, 1323. | mice | 5-9 days *Kidney Int.* 2008, 73, 578. *J. Pharmacol. Exp. Ther.* 2012, 341, 656. | mice | 24-48 h *Br. J. Radiol.* 2001, 74, 1103. *Curr. Vasc. Pharmacol.* 2017, 15, 174. | mice |
| BUN | 72 h *Kidney Int.* 2007, 72, 1474. *Am. J. Physiol. Renal. Physiol.* 2012, 303, F437. *Inflamm. Res.* 2017, 66, 399. *J. Am. Soc. Nephrol.* 2016, 27, 3331. *J. Am. Soc. Nephrol.* 2009, 20, 1323. | mice | 5-9 days *Kidney Int.* 2008, 73, 578. *J. Pharmacol. Exp. Ther.* 2012, 341, 656. | mice | 24-48 h *Br. J. Radiol.* 2001, 74, 1103. *Curr. Vasc. Pharmacol.* 2017, 15, 174. | mice |
| Cystatin C | 72 h *Clinical. Science.* 2018, 132, 825. | mice | 4-7 days *Biomed. Pharmacother.* 2018, 97, 1102. | mice | 24-48 h *Physiol. Rep.* 2013, 1, e00163. | mice |
| NGAL | 48-72 h *Proc. Natl. Acad. Sci. USA* 2015, 112, 5231. *BMC. Complement. Altern. Med.* 2017, 17, 544. *Ren. Fail.* 2018, 40, 314. | mice | 5 days *J. Pharmacol. Exp. Ther.* 2012, 341, 656. | mice | 24-48 h *BMC. Nephrol.* 2017, 18, 101. | mice |

TABLE 8-continued

Summary of detection times of in vitro methods for detection of drug-induced AKI.

| | Drug-induced AKI | | | | | |
|---|---|---|---|---|---|---|
| | Cisplatin | | Gentamicin | | Diatrizoate | |
| Imaging modalities/ Methods | Post-treatment time | Animal species | Post-treatment time | Animal species | Post-treatment time | Animal species |
| $\beta 2$-microglobulin | 72-168 h Nat. Biotechnol. 2010, 28, 463. Toxicol Pathol. 2012, 40, 1049. Biomarkers. 2011, 16, 553. | rats | 72 h Nat. Biotechnol. 2010, 28, 463. | rats | 24-48 h Toxicol Pathol. 2013, 41, 662. | rats |
| TFF3 | 72 h Nat. Biotechnol. 2010, 28, 470. | rats | 72 h Nat. Biotechnol. 2010, 28, 470 | rats | NR | |
| Osteopontin | 120-168 h Toxicol Pathol. 2012, 40, 1049. Toxicol Pathol. 2014, 42, 591. Biomarkers. 2011, 16, 553. | rats | 72 h Biomarkers. 2011, 16, 553. | rats | 24-48 h Toxicol Pathol. 2013, 41, 662. | rats |
| KIM-1 | 72 h Nat. Biotechnol. 2010, 28, 478. Toxicol Pathol. 2012, 40, 1049. Biomarkers. 2011, 16, 553. | rats | 72 h Nat. Biotechnol. 2010, 28, 478. Toxicol Sci. 2010, 116, 8. | rats | 24-48 h Toxicol Pathol. 2013, 41, 662. | rats |
| Clusterin | 48-72 h Nat. Biotechnol. 2010, 28, 463. Biomarkers. 2011, 16, 553. | rats | 72-96 h Nat. Biotechnol. 2010, 28, 463. Toxicol Rep, 2019, 6, 91. | rats | NR | |

NR: no report. Note that detection times in rats are presented in the case of no data reported in mice.

Such early detection capability of MRPs was also validated in other animal settings with the variation in drug dosages (FIG. 36-38), mouse strains (FIGS. 39 and 40) and mouse ages (FIG. 41). Thus, MRPs are by far the most sensitive probes that detect AKI at the incipient stage, which is imperative for timely initiation of renoprotective intervention to deter transition into severer complications and aid in recovery from AKI for hospitalised patients. Moreover, MRPs even could potentially detect drug-induced AKI on the backdrop of diabetes-related CKD (FIGS. 42 and 43), making them highly competent for drug development.

In FIG. 42, it was observed that the signals of kidneys in saline-treated diabetic mice were slightly higher (1.3-fold) than those in wild-type mice. This is reasonable because ROS are generated and lysosomes as well as caspase-3 are activated in the kidneys of diabetic mice (J. Y. C. Soo, et al., Nat. Rev. Nephrol. 2018, 14, 378-393; M. A. Perazella, S. G. Coca, Nat. Rev. Nephrol. 2013, 9, 484-490; M. Darmon, et al., Intensive Care. Med. 2017, 43, 829-840). In contrast, the signal of kidneys in cisplatin-treated diabetic mice significantly increased, which was 1.45 times higher than that of saline-treated diabetic mice, but 0.16-0.38 times lower than that cisplatin-treated NCr mice at the same drug dosage. In addition, as compared to those in cisplatin-treated NCr mice, the earliest timepoints of detectable signal increase in cisplatin-treated diabetic mice were delayed by 4-12 h to 16, 24 and 60 h post-treatment of cisplatin for MRP1, MRP2 and MRP3, respectively. This should be attributed to the fact that the expression of organic cation transporters (OCT) is reduced in the kidneys of diabetes, leading to lower cisplatin uptake in tubular cells (X. Wang et al., J. Am. Soc. Nephrol. 2006, 17, 2900-2909).

It was observed in FIG. 43 that the wild-type mice had normal renal morphology, while kidneys from saline-treated diabetic mice and diabetic mice at 60 h post-treatment of cisplatin exhibited features of chronic damage to the glomeruli, including expansion of the mesangial matrix and thickened glomerular basement membranes. In contrast, hyaline casts in tubules in addition to glomerulosclerosis were detected in diabetic mice at 72 h post-treatment of cisplatin, proving the acute tissue damage caused by cisplatin. Thus, these data validated that MRPs could detect drug-induced AKI in the mice with CKD.

Example 8. Real-Time Fluorescence Imaging for Early Detection of Drug-Induced Chronic Kidney Disease (CKD)

Other than for detecting AKI, MRPs1 and 2 were investigated for their potential in early detection of drug-induced chronic kidney disease (CKD). In this study, doxorubicin-induced nephropathy on BALB/c mice was chosen as test beds for monitoring kidney injury during progression to CKD.

The anthracycline antibiotic doxorubicin (DOX) primarily targets both glomerular endothelium and podocytes in rodents and is considered to be a robust experimental analogue of human focal glomerulosclerosis (Y. Wang, et al.,

*Kidney International*, 2000, 58(4), 1797-1804). Administration of a single dose of DOX in BALB/c mice leads to two phases of disease (M. Jeansson, et al., *J. Am. Soc. Nephrol.* 2009. 20(1), 114-122). In the first phase, glomeruli are grossly histologically intact but their ability to serve as a macromolecular barrier is severely compromised, as evidenced by heavy proteinuria. In the second phase, glomeruli become scarred and this leads to the loss of total glomeruli surface, and ultimately causes ESRD. This occurs in long-term observations and it exemplifies the 'progression of CKD' often observed in clinical practice.

Kidney injury was induced by a single dose of DOX (9 mg kg$^{-1}$) in female BALB/c mice while control group received saline injection. Sequential fluorescence images were acquired at t=2, 5 and 8 days after intravenously DOX injection, followed by MRP1 and MRP2 injection (FIG. 47a-c). Unlike the toxicity observed with AKI mice, DOX exhibited progressive nephrotoxicity on mice, as evidenced by the observation of fluorescence imaging of kidneys at t=day 5 DOX post-treatment, and the signal intensity was increased slightly at t=day 8 (FIG. 47). The fluorescence intensities in the kidney region of DOX-treated mice were 1.6 and 1.5 times, higher than that of saline-treated mice for MRP1 and MRP2, respectively (FIG. 48). In addition, a 4-fold and 2-fold increase in fluorescence intensity was observed in urine samples from mice at t=day 5 DOX post-treatment for MRP1 and MRP2, respectively (FIG. 47). However, urine samples in saline-treated mice exhibited very weak fluorescence, suggesting both MRP1 and MRP2 are intact in saline treated mice, but activated in DOX-treated mice. This was further confirmed by the changes in absorption at 692 nm (FIG. 49). Furthermore, fluorescence signal of kidneys and bladder in DOX treated mice was more than 2 times higher than that of in saline treated mice (FIG. 50).

Damage to the glomerular macromolecular barrier was confirmed by urinary albumin and histological analysis, albuminuria was significantly elevated in the DOX group at t=day 8 (FIG. 51). The weights of DOX-administered versus control mice reached their lowest point at t=day 8 DOX administration. Over the next 8 days, weights in the DOX group returned towards time matched control values but did not attain the initial weights (FIG. 51). By light microscopy, kidneys of DOX-treated mice showed tubular atrophy beginning at t=day 12 and collapsed glomerular capillary loops was observed at t=day 21. In control kidneys and t=day 5 DOX post-treatment, such glomerular lesions were rarely detected. Moreover, Immunofluorescent studies showed that no and relatively moderate fluorescence was presented in kidney tissue at t=day 5 and 12 DOX post-treatment, respectively. However, a high fluorescence was observed at t=day 21, suggest a chronic progressive renal disease. Thereby, the early detection of kidney injury can be realised on mice at t=day 5 DOX post-treatment, which is earlier than histology, immunofluorescence and proteinuria examination. Together, MRP1 and MRP2 have the robustness and broad applicability in the early diagnosis of multiple drug-induced kidney injury.

Example 9. Detection of NAG in DOX-Induced Chronic Kidney Disease (CKD) in Patients' Samples Using MRP2

The performance of MRP2 in sensing urinary NAG in DOX-induced chronic progressive kidney disease was further investigated. Significant increase was observed at t=day 5 DOX post-treatment (FIG. 52), whereas significant elevations in BUN and sCr were observed until t=12 day. These data suggest that MRP2 can be used to detect urinary NAG and monitor kidney injury through liquid biopsy in both AKI and CKD model.

A total of 38 patients were enrolled in this study. The mean age of the patients was 58 years, and 63% were males. A total of 10 healthy volunteers were enrolled as the control group in this study. Informed consent was collected at the time of blood and urine donation. sCr, BUN and the glomerular filtration marker Cys C were analysed in all CKD patients and healthy volunteers. The difference in the levels of sCr, BUN and Cys C between the cases and controls was highly significant (FIGS. 53b, c and d, p<0.001). Fluorescence enhancement of MRP2 triggered by urinary NAG was measured, which represents the NAG activity in human urine (FIG. 53a). As shown in FIG. 6e, a significantly higher fluorescence enhancement was observed in the urine of patients compared to the control group (p<0.001). Furthermore, the participants were divided into different CKD stages, which were defined according to the eGFR that calculated using MDRD equation.

Fluorescence enhancement of MRP2 in the urine of patients with different CKD stages was determined. The patients in CKD stage 5 (n=24) showed a higher fluorescence enhancement compared to that of in CKD stage 3 and 4 (FIG. 53d), implying that the production of urinary NAG in CKD stage 5 is higher than those in CKD stage 3 and 4. This suggests that the highest producers of NAG were those who had experienced the most severe in kidney impairment. Moreover, MRP2 is able to detect NAG in human urine for discriminating patients with declined eGFR and differentiation of the nature and severity of injury. A linear regression analysis was performed between Cys C and fluorescence enhancement of MRP2 (FIG. 53g). The fluorescence enhancement showed a positive correlation with Cys C ($r^2$=0.283, p<0.001, FIG. 53g). These data are in keeping with the conclusion that MRP2 permits the quantification of NAG in human urine and may perform well for the prediction of CKD in patients.

Example 10. Optical Properties of Activatable Duplex Reporter (ADR) of the Current Invention To study the optical properties and sensing ability of ADR of the current invention, its absorption, chemiluminescence and NIRF spectra were measured in the absence or presence of $O_2^{*-}$ or NAG.

ADR had an absorption maximum at 600 nm and was initially non-fluorescent with a low fluorescent quantum yield of 0.009 in PBS solution, because the fluorophore was in a "caged" state that the electron-donating ability of the oxygen atom was diminished. Upon the addition of NAG, the absorption peak at 600 nm decreased concomitant with the appearance of a new peak at 695 nm (FIG. 54a). Meanwhile, ADR showed a 10-fold enhancement in the fluorescence intensity at 720 nm (FIGS. 54b and 55) and an increased fluorescent quantum yield of 0.18 (Table 9) after incubation with NAG. This was due to the cleavage of glycosidic bond of N-acetyl-β-D-glucosamine moiety by NAG, which led to the formation of CyOH moiety with strong electron-donating phenolate group of the fluorophore and thus strong fluorescence.

The cleavage of glycosidic bond was further confirmed by observation of a new high-performance liquid chromatography (HPLC) peak at a retention time of 3.1 min corresponding to N-acetyl-β-D-glucosamine (FIG. 54c). Moreover, the catalytic efficiency ($k_{cat}/K_m$) of NAG towards ADR was calculated to be 0.025 μM$^{-1}$ s$^{-1}$ (FIG. 54d), suggesting its high sensitivity for detection of NAG.

TABLE 9

Photophysical properties of ADR.

| Probe | $\lambda_{ab}$ (nm) | $\lambda_{em}$ (nm) | Stokes shift (nm) | $\phi_1/\phi_2$ |
|---|---|---|---|---|
| ADR | 600 | 720 | 120 | 0.009/0.18 |

Upon addition of $O_2^{*-}$, the absorption and fluorescence spectra of ADR showed negligible change (FIGS. 54a and b), while the chemiluminescence at 520 nm increased ~12000-fold (FIG. 1e). Such an enhancement should be ascribed to the fact that $O_2^{*-}$ attacks the sulfonate ester group of ADR to cleave trifluoromethanesulfonate, leading to the formation of an unstable phenolate dioxetane intermediate. This intermediate is an active chemiluminescent substrate that spontaneously undergoes decomposition to emit photons. The cleavage of trifluoromethanesulfonate and subsequent release of 2-admantanone were confirmed by HPLC, showing a characteristic peak at a retention time of 26.1 min (FIG. 54c). Good linearity between the chemiluminescence signal at 520 nm and the $KO_2$ concentration was observed for ADR, showing an estimated limit of detection (LOD) of 12 nM (FIG. 54f). Moreover, the chemiluminescence half-life of ADR was approximately 7.8 min (FIG. 54g), and should be long enough for in vivo imaging. Note that incubation of ADR with both NAG and $O_2^{*-}$ led to the chemiluminescent spectrum with the maximum at 520 nm, the same as that after incubation with $O_2^{*-}$ alone (FIG. 56). This implied no energy transfer from the chemiluminescent moiety to the activated NIRF moiety probably due to their long distance. Nevertheless, ADR had negligible NIRF and chemiluminescence responses towards other interfering analytes including other enzymes, ROS, and metal ions (FIG. 54h), suggesting its high specificity of NIRF and chemiluminescence activation channels towards NAG and $O_2^{*-}$, respectively.

Example 11. Detection of $O_2^{*-}$ and NAG in Cultured Cells Using ADR of the Current Invention To study the ability of ADR to detect $O_2^{*-}$ and NAG in cultured cells, HK2 cells (an immortalised proximal tubule epithelial cell line from normal adult human kidney) treated with a radiocontrast medium, diatrizoate (DTZ), was used as the model.

Experimental

A human renal proximal tubular epithelial cell line (HK2 cells) was obtained from American ScienCell Research Laboratories (ScienCell, San Diego, CA). The HK2 cells were cultured in epithelial cell medium (ScienCell) supplemented with 2% fetal bovine serum (FBS; ScienCell), 1% epithelial cell growth factors (ScienCell), 20 U/ml of penicillin, and 100 μg/ml of streptomycin (ScienCell) at 37° C. and 5% humidified atmosphere.

For cell chemiluminescence imaging, HK2 cells (1×10$^5$ cells per well in 1 ml cell culture medium) were seeded into confocal cell culture dishes (dia. 35 mm) and incubated overnight. For DTZ treatment experiment, cells were treated with DTZ (100 mg/ml) in medium for indicated duration. For control groups, cells were treated with PBS or NAC (100 mM) for 1 h prior to co-incubation with mixture of DTZ (100 mg/ml) and NAC (100 mM) for indicated duration (G. L. Liu, et al., Exp. Ther. Med. 2017, 14, 3309-3313).

After incubation, the medium was removed, and the cells were washed three times with PBS buffer. Then the cells were incubated with ADR (10 μM) in medium for 15 min. Then the medium was removed, and the cells were washed with PBS buffer for three times. The cells were immediately taken for chemiluminescence imaging, and imaging was acquired within 20 min. Chemiluminescence images of living cells were acquired on LX71 inverted microscope (Olympus) equipped with infinity 3-1 (Lumenera) CCD camera. During imaging, the shutter for excitation light was closed, and exposure time was adjusted to 3000 ms.

For cell fluorescence imaging, HK2 cells (1×10$^5$ cells per well in 1 ml) were seeded into confocal cell culture dishes (dia. 35 mm) and incubated overnight. After incubation with DTZ above, the medium was removed, and the cells were washed three times with PBS buffer. Then the cells were incubated with ADR (10 μM) in medium for 30 min. Then the medium was removed, and the cells were washed with PBS buffer for three times. The cells were fixed with 4% polyformaldehyde solution and the stained with 4, 6-diamidino-2-phenylindole (DAPI). Fluorescence images of the live cells were acquired on a Laser Scanning Microscope LSM800 (Zeiss). The excitation and emission wavelengths for cell imaging were 640/655-710 nm for ADR and 405/410-470 nm for Hoechst. Cellular chemiluminescence and fluorescence intensities were quantified by using ImageJ software.

Results and Discussion

ADR was used to detect $O_2^{*-}$ and NAG in HK2 cells treated with a radiocontrast medium-diatrizoate (DTZ) (100 mg/ml) in medium for 1 h or 5 h. In control groups, the cells were treated with PBS or NAC (an antioxidant, N-acetyl L-cysteine, 100 mM) for 1 h prior to co-incubation with mixture of DTZ and NAC for 5 h. All groups were then incubated with ADR (10 μM) for chemiluminescence and fluorescence imaging. The chemiluminescence intensity of DTZ-treated cells was 110 and 240-fold higher than the PBS-treated cells at 1 h and 5 h post-treatment of DTZ, respectively. However, when the cells were pre-treated with NAC, chemiluminescence signals decreased to the basal levels (FIG. 57), because NAC could scavenge cellular ROS and prevent oxidative stress. In contrast, the NIRF intensity of DTZ-treated cells remained nearly the same as the control. This was due to the fact that although treatment of DTZ induced the release of NAG from lysosomes, the total amount of NAG remained nearly the same in the static cellular condition (D. Robic, et al., Toxicology 1995, 103, 37-44). Nevertheless, these results confirmed the feasibility of ADR to image $O_2^{*-}$ and NAG in living cells.

Example 12. Renal Clearance and In Vivo Stability Studies of ADR

To investigate the pharmacokinetics of ADR, the concentration of ADR in the blood was analysed by HPLC after a single i.v. injection into living mice. Blood concentration curves implied that ADR had a two-compartment profile of in vivo kinetics (FIG. 58b). The ADR concentration in blood was close to 0% injected doses (ID) g-1 at 115 min post-injection and its elimination half-lives (t1/2β) was estimated to be 22.02 min, indicating its rapid elimination from the body via systemic clearance. The renal clearance of ADR was also examined by HPLC analysis of mouse urine, showing 80.2±4.3% ID at 24 h post-injection in living mice (FIG. 58c).

After 24 h urinary recovery, the mice were dissected and the residual ADR in the body was determined by HPLC after homogenisation of major organs in PBS. The results revealed that the residual ADR (~20%) was mainly accumulated in liver and intestine (FIG. 58d), negligible ADR was found in other organs. Nevertheless, the renal clearance efficiency of ADR was higher than the ultra-small Pd nanosheets (6.6% ID at 24 h post-injection), gold nanoclusters (52% ID at 24 h post-injection) and silica Cornell dots (73% ID at 48 h post-injection), and similar to porphyrin-polyethylene glycol (PEG) (~80% ID at 24 post-injection) and ZW800-CDPL-(80% ID at 4 h post-injection) (S. Tang, et al., *Small* 2014, 10, 3139-3144; B. Du, et al., *Nat. Nanotechnol.* 2017, 12, 1096-1102; M. Yu, et al., *Angew. Chem. Int. Ed.* 2016, 55, 2787-2791; A. A. Burns, et al., *Nano lett.* 2008, 9, 442-448; H. Huang, et al., *Biomaterials* 2016, 76, 25-32; H. Kang, et al., *Adv. Mater.* 2016, 28, 8162-8168). Such an advantage of ADR was attributed to its high hydrophilicity and low molecular weight (~3 kDa) relative to the glomerular filtration molecular weight cutoff (50 kDa).

To determine in vivo stability of ADR, its optical profiles, NIRF images and mass distribution recovered from urine were measured and compared with its pure form in PBS. ADR had almost identical absorption (FIG. 58e), fluorescence (FIGS. 58f and g) and mass spectra (FIG. 59) in the urine and PBS, suggesting ADR had negligible in vivo metabolism in healthy mice. Moreover, histological and immunofluorescence staining revealed that neither tissue damage nor cellular apoptosis was observed after 24 h injection of ADR, proving its good biocompatibility.

Example 13. In Vivo Duplex Imaging of CIAKI Using ADR

The ability of ADR for real-time duplex imaging of CIAKI was evaluated in the mouse model using DTZ as the model drug, which was a radiocontrast medium with known nephrotoxicity. DTZ was i.v. injected into living mice at a nephrotoxic dosage (1 g kg$^{-1}$), followed by i.v. injection of ADR at different timepoints post-treatment of DTZ (2, 8, 16, and 24 h) (C. M. Erley, et al., *J. Am. Soc. Nephrol.* 1997, 8, 1125-1132). The control group mice were treated with PBS or a nephroprotective antioxidant NAC (10 mg kg$^{-1}$ day$^{-1}$, i.p. injection) 3 days prior to DTZ administration (M. Colbay, et al., *Exp. Toxicol. Pathol.* 2010, 62, 81-89).

Whole-body longitudinal chemiluminescence and NIRF imaging were simultaneously conducted at different post-treatment timepoints (FIG. 60a). At 2 h post-treatment of DTZ, the chemiluminescent signal of ADR in the kidneys was close to the control mice throughout the entire imaging course (FIGS. 60b and e). However, at 8 h post-treatment of DTZ, the injection of ADR led to a gradual signal increase in the kidneys with a maximum signal observed at 8 min post-injection of ADR (FIG. 61). At this timepoint, the kidneys of living mice were clearly delineated with chemiluminescence imaging (FIG. 60e), showing an ~2.2-fold signal increase relative to the control mice (FIG. 60b). The signal decrease of ADR in the kidneys at later imaging timepoints was caused by its rapid clearance and short elimination half-life (FIG. 61c).

At 16 h and 24 h post-treatment of DTZ, the chemiluminescence signal in the kidneys further increased to 4.6-fold and 8.2-fold relative to the control group, respectively (FIG. 60b), indicating the gradual upregulation of $O_2^{*-}$ during the progression of CIAKI. Similar trends were observed for NIRF imaging (FIGS. 60c and e), but the earliest timepoint of the first statistically significant signal increase was observed at 16 h post-treatment of DTZ after 60 min injection of ADR (1.7-fold higher than the control mice, FIGS. 60c and 61), which was 8 h later than chemiluminescence imaging. The NIRF signals of ADR in the kidneys further increased to 1.9-fold relative to the control group at 24 h DTZ post-treatment time, indicating the gradual upregulation of NAG after administration of DTZ. Such activated chemiluminescence and NIRF signals were also observed in the bladder at different post-treatment timepoints as well (FIG. 60e). The activation of ADR was further verified by the emergence of a new absorption peak at 700 nm and an ~3-fold enhancement of fluorescence intensity at 720 nm in the urine of living mice at 16 h post-treatment of DTZ (FIG. 62). The fact that ADR sensed the upregulation of $O_2^{*-}$ at an earlier timepoint relative to NAG proved that DTZ first induced oxidative stress followed by lysosomal damage, which coincided with the reported toxic mechanism of DTZ (Z. Z. Liu, et al., *Am. J. Physiol. Renal. Physiol.* 2014, 306, F864-F872). In addition, such early detection capability of ADR was validated in living mice treated with different dosages of DTZ (FIG. 63).

The ADR offers simultaneous imaging of two interlinked molecular events in the kidneys to detect CIAKI, while the previous single-channel molecular renal probes failed to do so. NAG is normally secreted at a low concentration (<0.03 unit/24 h) into urine in mice (X. Liu, et al., *PLoS One* 2017, 12, e0182558). However, NAG dramatically increased in renal tubules and urine (0.5 unit/24 h) after administration of nephrotoxic drugs (R. M. Franke, et al., *Clin. Cancer Res.* 2010, 16, 4198-4206). Note that the signals in NAC-treated mice were comparable to the PBS-treated mice because NAC had a superb ROS scavenging ability and protects the kidney against nephrotoxic insult (S. Fishbane, *Clin. J. Am. Soc. Nephrol.* 2008, 3, 281-287).

To confirm that the in-situ activation of ADR in the kidneys, ex vivo fluorescence images of kidneys and other extra-renal organs were recorded. Consistent with the NIRF imaging data observed in vivo, fluorescence signals were seen only in the resected kidneys and bladder from mice at 16 h post-treatment of DTZ (FIGS. 64 and 65), which was 2-fold higher than that of control mice. Moreover, kidney section imaging was performed at different post-treatment timepoints followed by i.v. injection of ADR. The NIRF signal of activated ADR was mainly observed at the kidney tubules rather than the glomeruli at 16 h post-treatment of DTZ (FIG. 60f). However, the NIRF signals were undetectable in kidney sections for control mice and mice at 8 h post-treatment of DTZ, which were 10-fold lower than that of 16 h post-treatment of DTZ (FIG. 60d). These results were consistent with the fact that DTZ is well known to induce tubular cell damage and result in the release of NAG into tubular lumen (R. Hofmeister, et al., *Toxicol. Lett.* 1990, 50, 9-15).

Example 14. Comparison of Detection Capability of ADR with Other Assays

To compare the detection ability of ADR with the clinical methods, sCr and BUN in the blood of living mice as well as GFR was measured using the commercial assays in DTZ-treated mice. The first statistically significant increase in sCr and BUN was observed at 24 h post-treatment of DTZ (FIGS. 66a and b), which was 1.7-fold and 1.8-fold higher than control groups, respectively. Such increased sCr and BUN levels were attributed to the decline in kidney function. This was further confirmed by the observation of ~40% and further ~60% decreases in GFR at 24 h and 48 h post-treatment of DTZ (FIGS. 66c and 67), respectively, and a reduced clearance rate of ADR at 24 h post-treatment of DTZ (FIG. 68). Histological hematoxylin and eosin (H&E) staining showed normal tubular morphology at 24 h post-treatment of DTZ, but the loss of the brush border and hyaline casts at 48 h post-treatment of DTZ (FIG. 66*d*). Moreover, immunofluorescence caspase-3 staining revealed that cell apoptosis was observed for the kidneys at 24 h and 48 h post-treatment of DTZ (FIG. 66*d*).

Comparison of ADR-based imaging and plasma/histological methods in terms of the earliest detection timepoints for CIAKI detection was summarised in FIG. 66*e*. The first statistically significant signal change of ADR-based chemiluminescence imaging occurred at least 16 h earlier than both sCr/BUN assays, GFR measurement, and immunofluorescence caspase-3 staining, and up to 40 h earlier than H&E staining assays. Moreover, ADR-based NIRF imaging outperformed those assays by at least 8 h and up to 32 h. Therefore, these data not only highlighted that ADR-based real-time imaging is more sensitive than sCr/BUN assays and histological analysis, but also validated that $O_2^{*-}$ and NAG were sequentially upregulated prior to GFR decline and kidney tissue damage.

The invention claimed is:

1. A compound of formula I:

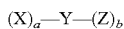

where:

X is selected from:

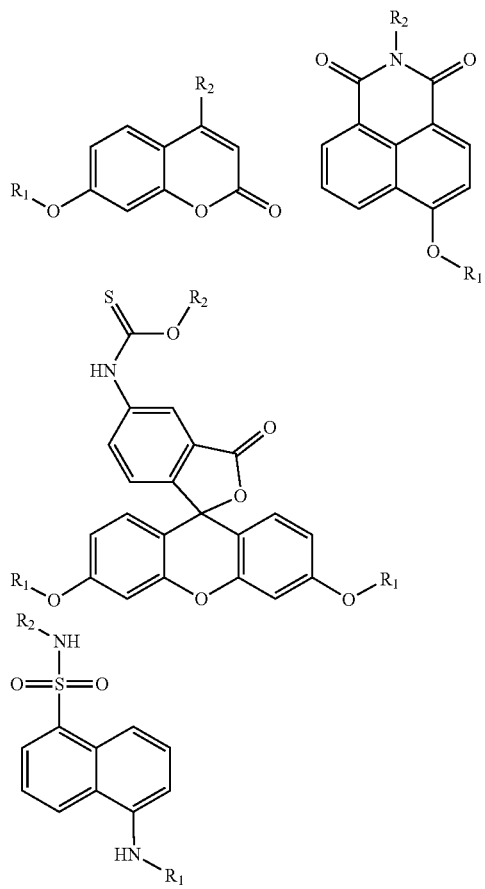

-continued

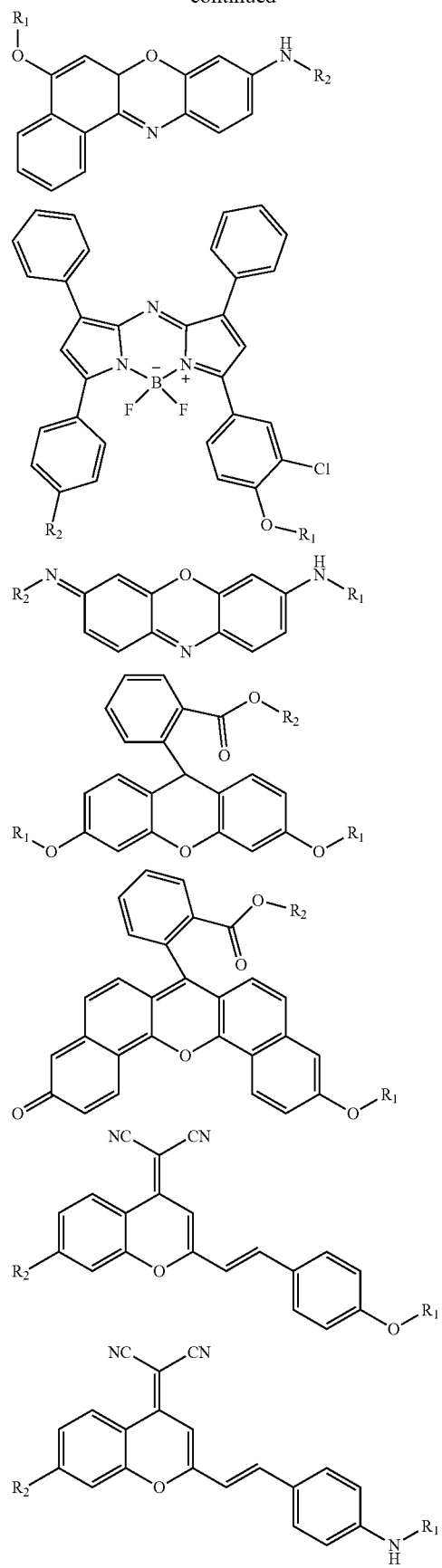

135
-continued
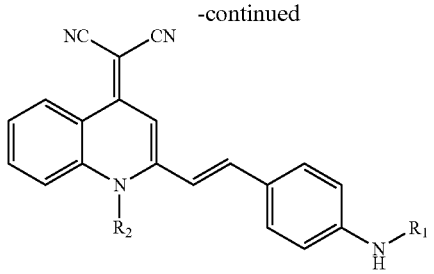
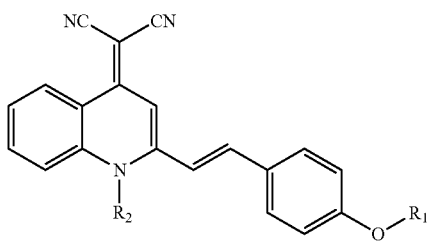
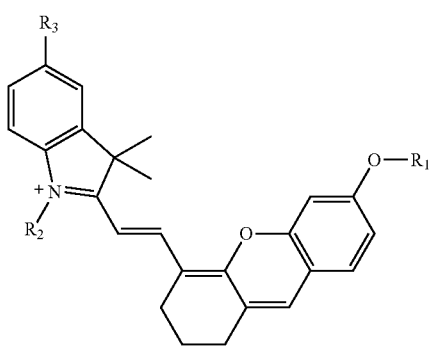
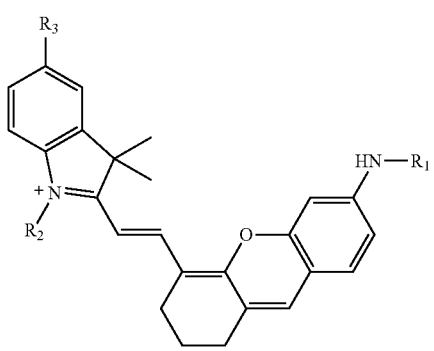
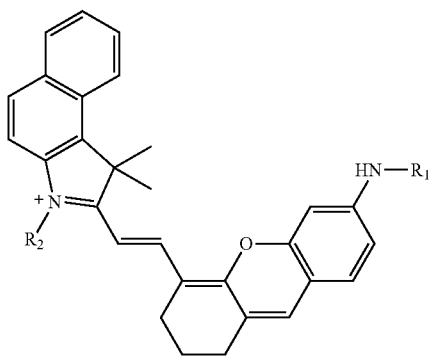
136
-continued
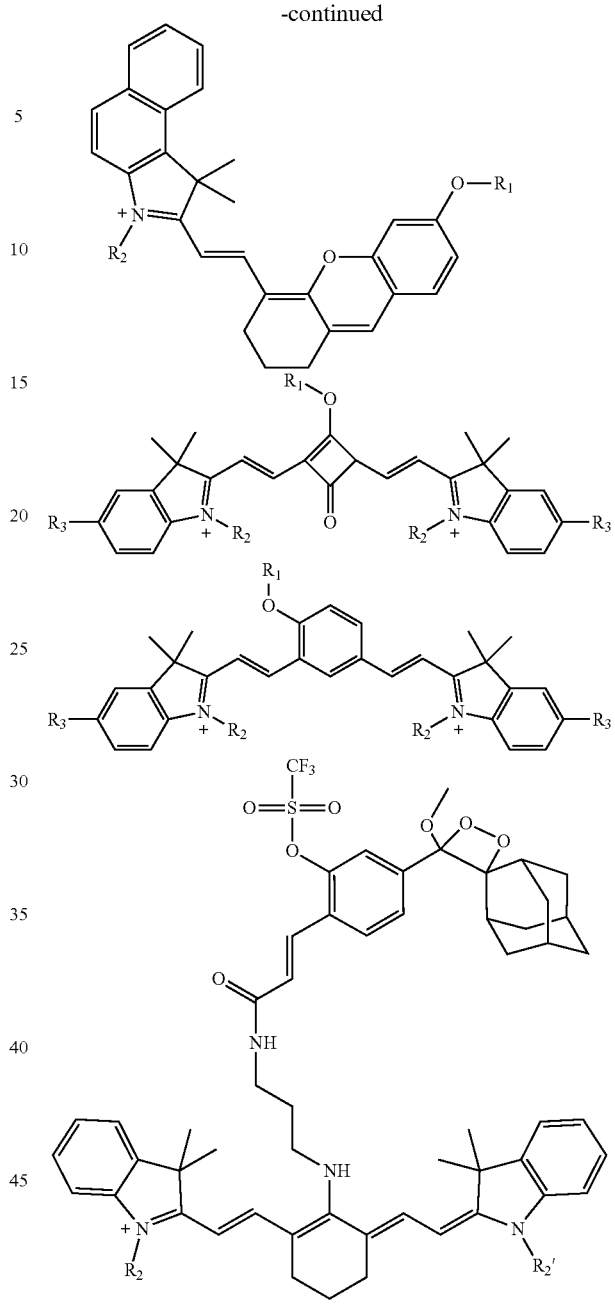
where $R_1$ represents a biomarker reactive moiety conjugated to a self-immolative moiety
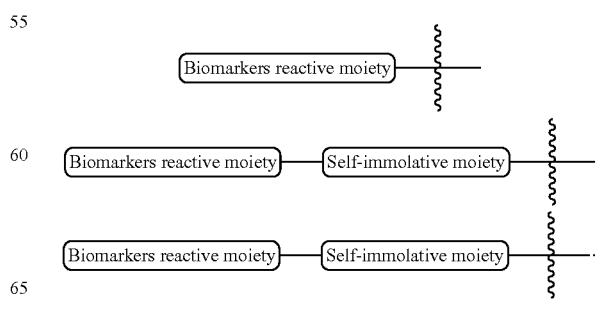

wherein the self-immolative moiety is selected from:

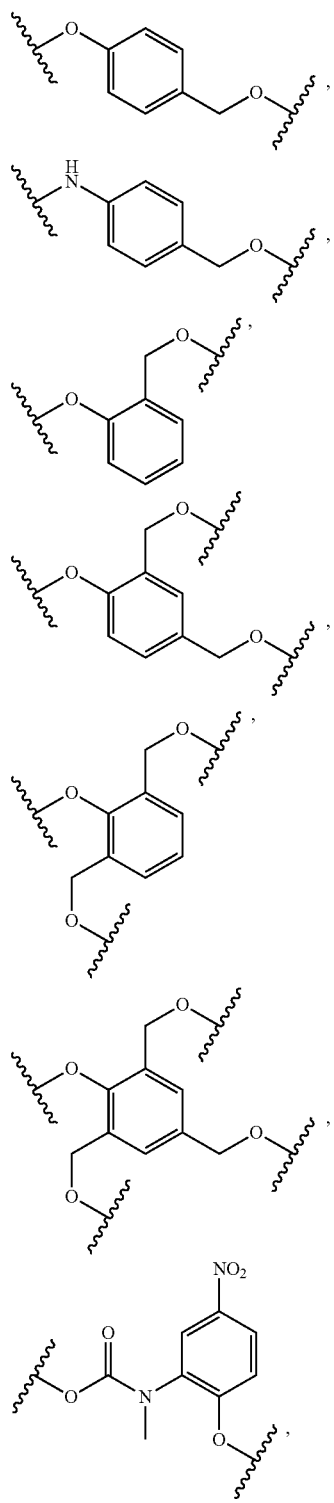

where the heteroatom directly bonded to the aromatic ring represents the point of attachment to Y and the other heteroatoms represent the point of attachment to a biomarker reactive moiety or are H, provided that at least one of the other heteroatoms is attached to a biomarker reactive moiety;

$R_2$ represents a point of attachment to Y and $R_{2'}$ represents another point of attachment to the same Y group or a point of attachment to a second Y group;

$R_3$ represents H, $SO_3H$ or COOH;

Z is selected from:

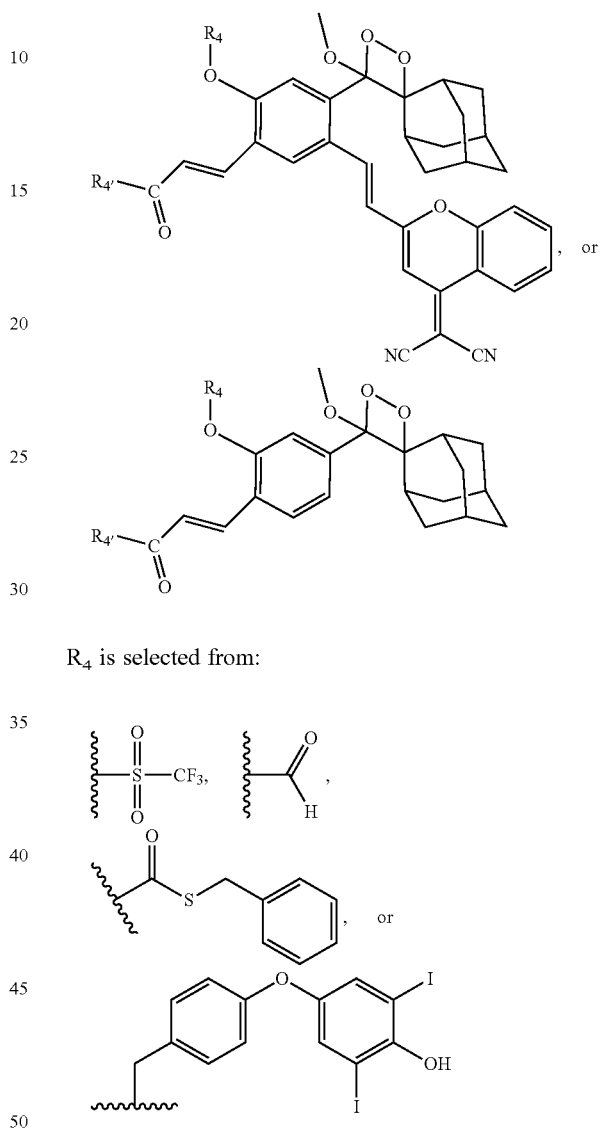

$R_4$ is selected from:

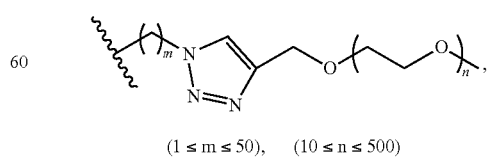

where the wavy line represents the point of attachment to the rest of the molecule;

$R_{4'}$ represents the point of attachment to Y;

each Y is selected from:

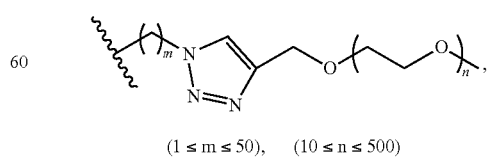

$(1 \leq m \leq 50)$, $(10 \leq n \leq 500)$ where the wavy line represents the point of attachment to X or Z,

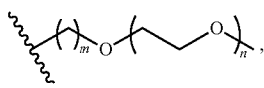

$(1 \leq m \leq 50)$, $(10 \leq n \leq 500)$ where the wavy line represents the point of attachment to X or Z,

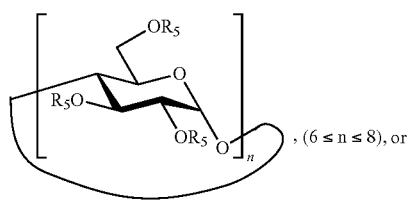

, $(6 \leq n \leq 8)$, or

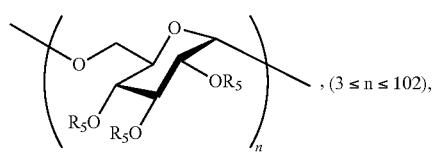

, $(3 \leq n \leq 102)$, where each $R_5$ is independently selected from H, $CH_2CHOHCH_3$, $CH_2CCH$, and

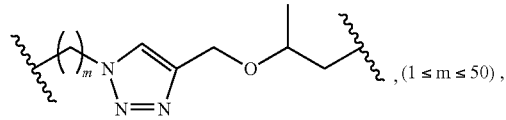

, $(1 \leq m \leq 50)$, where the left-hand wavy line (adjacent to m) represents the point of attachment to X or Z and the right-hand wavy line represents the point of attachment to the rest of the molecule;

a is 0 or 1 and b is 1, provided that:

at least one of a and b is 1; and when a and b are both 1, Y is selected from:

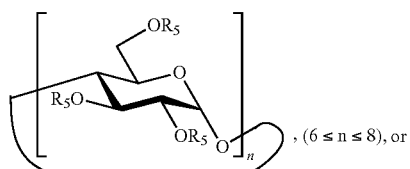

, $(6 \leq n \leq 8)$, or

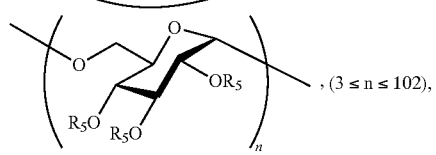

, $(3 \leq n \leq 102)$, or pharmaceutically acceptable salts and/or solvates thereof, provided that when X is

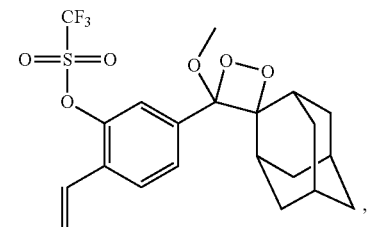

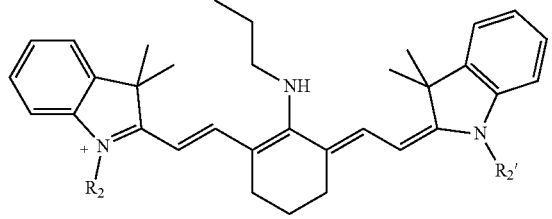

then Z is 0.

2. The compound or salts and/or solvates thereof according to claim 1, wherein the biomarker reactive moiety is selected from:

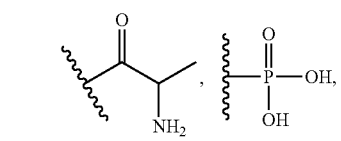

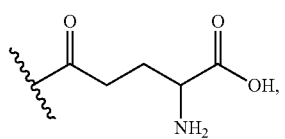

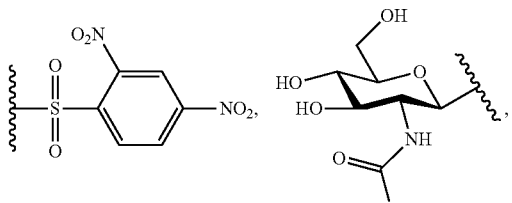

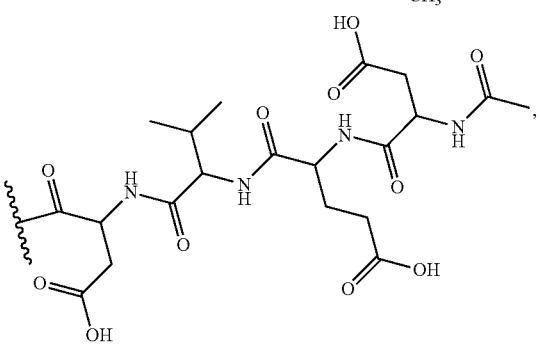

141
-continued
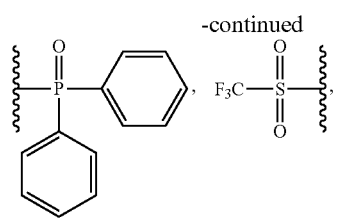
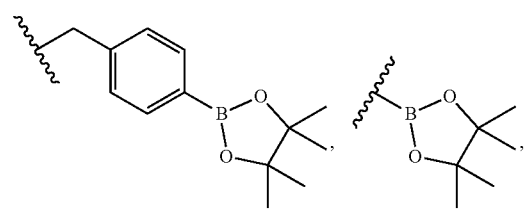
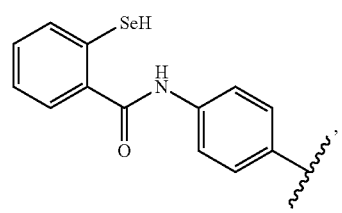
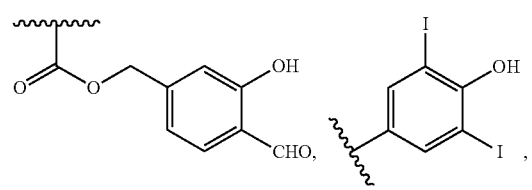
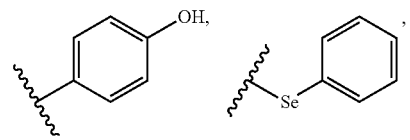
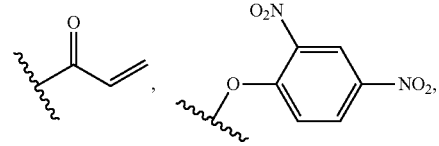
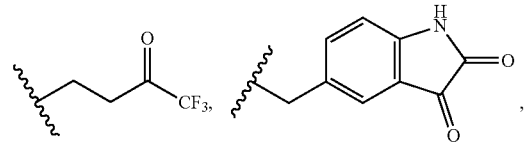
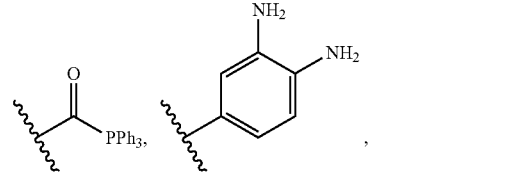
where the wavy line is the point of attachment to the rest of the molecule or, the self-immolative moiety.
3. The compound or salts and/or solvates thereof according claim 1, wherein X, when present, is selected from:
142
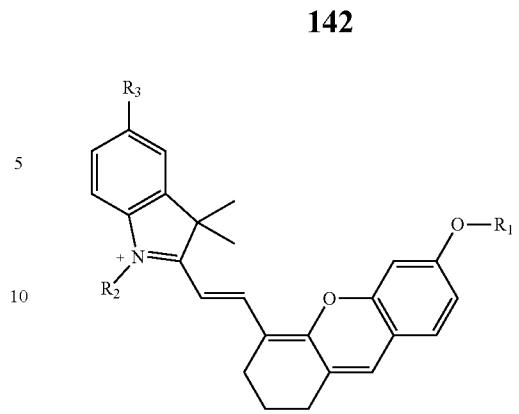
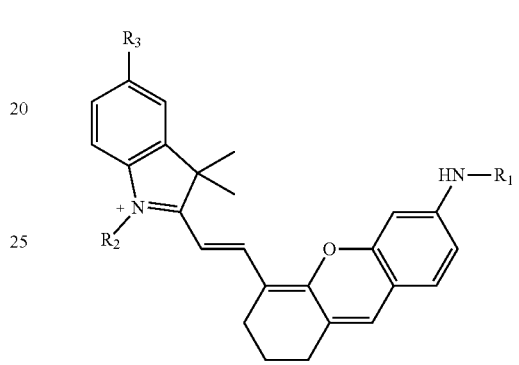
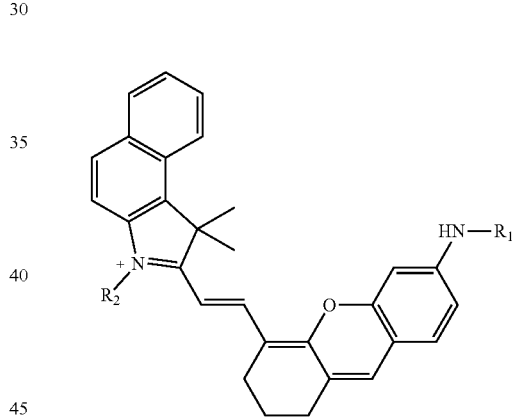
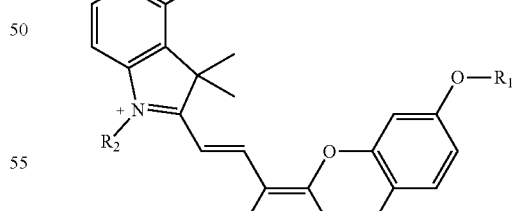
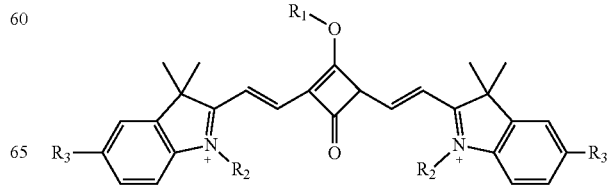

-continued

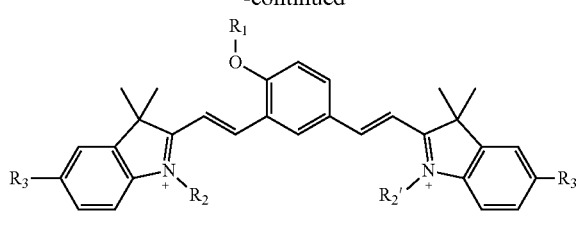

4. The compound or salts and/or solvates thereof according claim 1, wherein X, when present, is:

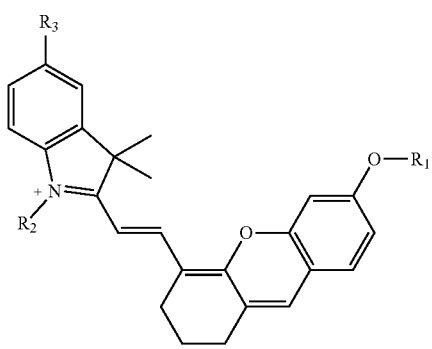

where R₃ is H.

5. The compound or salts and/or solvates thereof according to claim 1, wherein the biomarker reactive moiety is selected from:

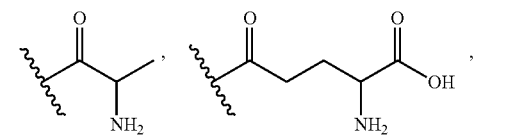

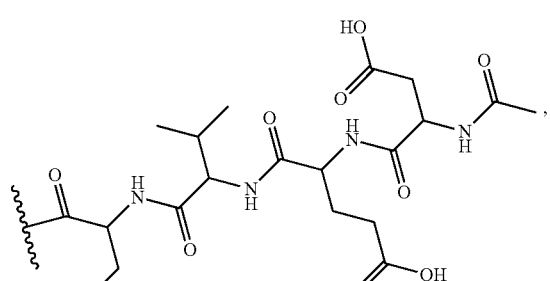

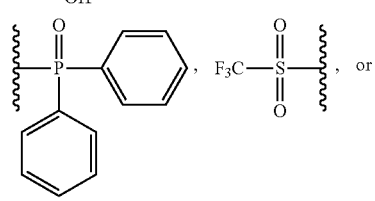

-continued

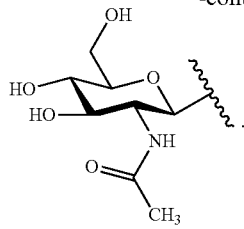

6. The compound or salts and/or solvates thereof according to claim 1 wherein Z is:

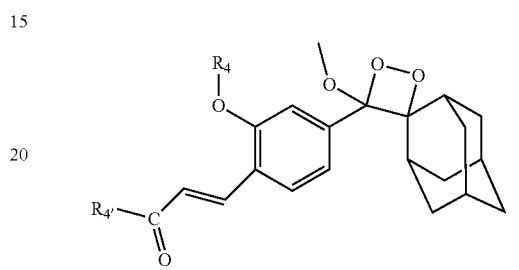

7. The compound or salts and/or solvates thereof according claim 1, wherein (ai) $R_4$, when present, is

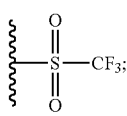

and/or (aii) each $R_5$, when present, is independently selected from H, $CH_2CHOHCH_3$ and

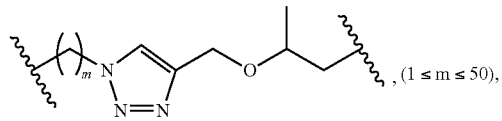, $(1 \leq m \leq 50)$, where the left-hand wavy line (adjacent to m) represents the point of attachment to X or Z and the right-hand wavy line represents the point of attachment to the rest of the molecule.

8. The compound or salts and/or solvates thereof according to claim 1, wherein a is 1 and Y is

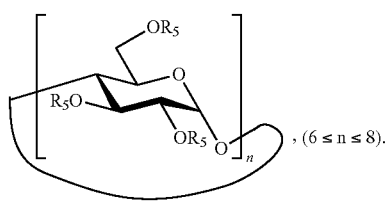, $(6 \leq n \leq 8)$.

9. The compound or salts and/or solvates thereof according to claim 1, wherein:

a is 1, X is
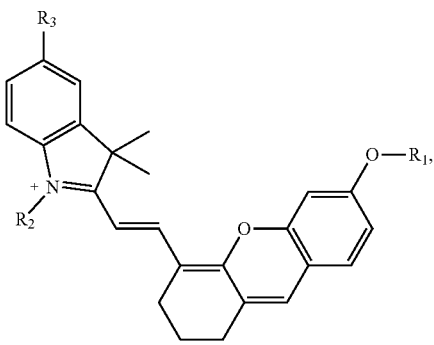
where R₃ is H, the biomarker reactive moiety is:
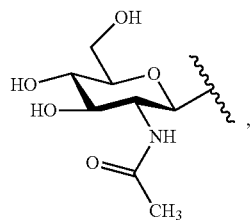
Z is
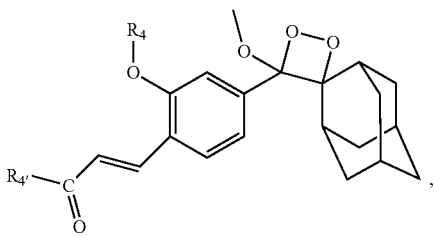
where R₄ is,
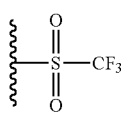
and Y is
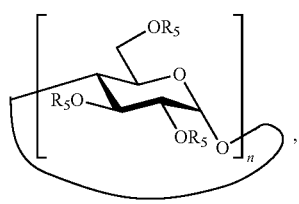
where n is 7.
10. A compound according to formula II:
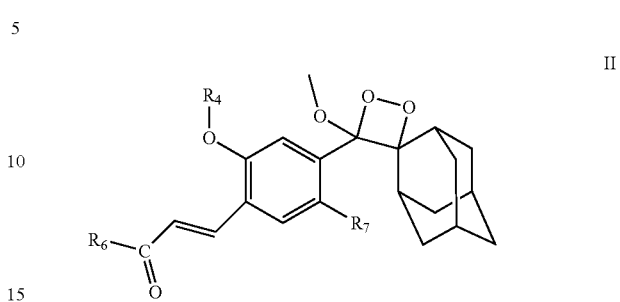
where:
R₄ is selected from:
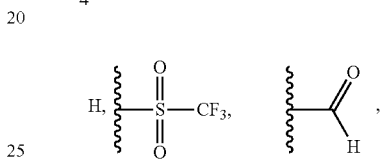
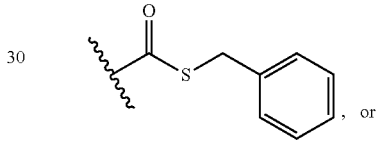
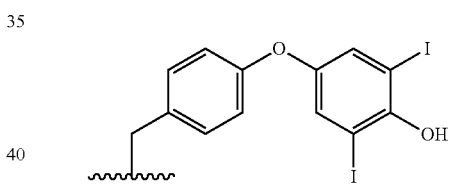
where the wavy line represents the point of attachment to the rest of the molecule;
R₆ is OH or OC₁-C₆ alkyl;
R₇ is:
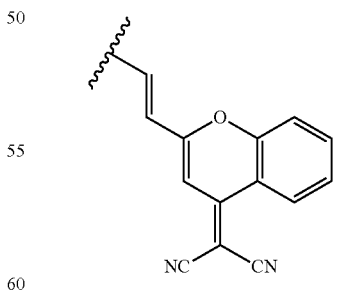
or pharmaceutically acceptable salts and/or solvates thereof.
* * * * *